(12) United States Patent
Mortlock et al.

(10) Patent No.: US 7,709,479 B1
(45) Date of Patent: *May 4, 2010

(54) QUINAZOLINE DERIVATIVES AND THEIR USE AS PHARMACEUTICALS

(75) Inventors: Andrew Austen Mortlock, Macclesfield (GB); Nicholas John Keen, Macclesfield (GB); Frederic Henri Jung, Reims (FR); Andrew George Brewster, Paris (FR)

(73) Assignee: AstraZeneca, Sodertalje (SE)

( * ) Notice: Subject to any disclaimer, the term of this patent is extended or adjusted under 35 U.S.C. 154(b) by 429 days.

This patent is subject to a terminal disclaimer.

(21) Appl. No.: 10/088,814

(22) PCT Filed: Sep. 18, 2000

(86) PCT No.: PCT/GB00/03580

§ 371 (c)(1),
(2), (4) Date: Sep. 4, 2002

(87) PCT Pub. No.: WO01/21596

PCT Pub. Date: Mar. 29, 2001

(30) Foreign Application Priority Data

Sep. 21, 1999 (GB) ................................ 9922154.1
Sep. 21, 1999 (GB) ................................ 9922170.7

(51) Int. Cl.
*A61K 31/517* (2006.01)
*A61K 31/535* (2006.01)
*C07D 239/72* (2006.01)
*C07D 413/12* (2006.01)

(52) U.S. Cl. ............ 514/235.8; 514/266.3; 514/266.31; 514/266.4; 544/287; 544/293; 544/116

(58) Field of Classification Search .............. 514/266.2, 514/266.21, 266.3, 266.31, 266.4, 235.8; 544/284, 287, 293, 116
See application file for complete search history.

(56) References Cited

U.S. PATENT DOCUMENTS

| 5,457,105 | A | * | 10/1995 | Barker ..................... 514/234.5 |
| 5,571,815 | A | * | 11/1996 | Schaper et al. ............. 514/269 |
| 5,616,582 | A | * | 4/1997 | Barker ..................... 514/234.5 |
| 5,710,158 | A | | 1/1998 | Myers et al. ................ 514/259 |
| 5,821,246 | A | * | 10/1998 | Brown et al. ........... 514/252.17 |
| 6,251,912 | B1 | * | 6/2001 | Wissner et al. ........... 514/228.2 |
| 6,593,333 | B1 | * | 7/2003 | Cumming ................ 514/266.1 |
| 6,716,847 | B2 | * | 4/2004 | Cumming .............. 514/253.06 |

FOREIGN PATENT DOCUMENTS

| EP | 0 860433 | | 8/1998 |
| JP | 10-7657 | * | 1/1998 |
| WO | WO 9609294 | | 3/1996 |
| WO | 96/15118 | * | 5/1996 |
| WO | 96-15118 | * | 5/1996 |
| WO | WO 9722596 | | 6/1997 |
| WO | WO 9722702 | | 6/1997 |
| WO | WO 9730035 | | 8/1997 |
| WO | WO 9732856 | | 9/1997 |
| WO | WO 9813354 | | 4/1998 |
| WO | WO 9935132 | | 7/1999 |
| WO | WO 9935146 | | 7/1999 |

OTHER PUBLICATIONS

PCT/GB00/03580 International Search Report, Dec. 2000.

* cited by examiner

*Primary Examiner*—James O Wilson
*Assistant Examiner*—Tamthom N Truong

(57) ABSTRACT

The use of a compound of formula (I) or a salt, ester, amide or prodrug thereof; where X is O, or S, S(O) or S(O)$_2$, NH or NR$^{12}$ where R$^{12}$ is hydrogen or C$_{1-6}$ alkyl; R$^5$ is selected from a group NHC(O)OR$^9$, NHC(O)R$^9$, NHS(O)$_2$R$^9$, C(O)R$^9$, C(O)OR$^9$, S(O)R$^9$, S(O)OR$^9$, S(O)$_2$OR$^9$, C(O)NR$^{10}$ R$^{11}$, S(O)NR$^{10}$R$^{11}$ S(O)ONR$^{10}$R$^{11}$, where R$^9$, R$^{10}$ or R$^{11}$ are various specified organic groups; R$^6$ is hydrogen, optionally substituted hydrocarbyl or optionally substituted heterocyclyl; R$^7$ and R$^8$ are various specified organic groups, and R$^1$, R$^2$, R$^3$, R$^4$ are independently selected from halogeno, cyano, nitro, C$_{1-3}$alkylsulphanyl, —N(OH)R$^{13}$— (wherein R$^7$ is hydrogen, or C$_{1-3}$alkyl), or R$^{15}$X$^1$— (wherein X$^1$ represents a direct bond, —O—, —CH$_2$—, —OCO—, carbonyl, —S—, —SO—, —SO$_2$—, —NR$^{16}$CO—, —CONR$^{16}$—, —SO$_2$NR$^{16}$—, —NR$^{17}$SO$_2$— or —NR$^{18}$— (wherein R$^{16}$, R$^{17}$ and R$^{18}$ each independently represents hydrogen, C$_{1-3}$alkyl or C$_{1-3}$alkoxy C$_{2-3}$alkyl), and R$^9$ is hydrogen, optionally substituted hydrocarbyl, optionally substituted heterocyclyl or optionally substituted alkoxy; in the preparation of a medicament for use in the inhibition of aurora 2 kinase.

3 Claims, No Drawings

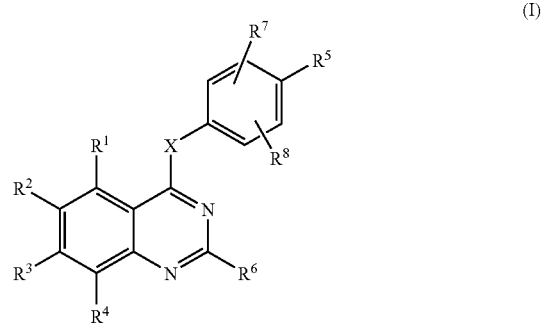

(I)

QUINAZOLINE DERIVATIVES AND THEIR USE AS PHARMACEUTICALS

CROSS-REFERENCE TO RELATED APPLICATIONS

This application is a national stage filing under 35 U.S.C. 371 of PCT application PCT/GB00/03580, filed Sep. 18, 2000, which claims priority from United Kingdom Application Nos. 9922170.7, filed Sep. 21, 1999, and 9922154.1, filed Sep. 21, 1999, the specifications of each of which are incorporated by reference herein. PCT Application PCT/GB00/03 580 was published under PCT Article 21(2) in English.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672-1677; Pines, 1995, Seminars in Cancer Biology 6: 63-72). Other studies (Loda et al., 1997, Nature Medicine 3(2): 231-234; Gemma et al., 1996, International Journal of Cancer 68(5): 605-11; Elledge et al. 1996, Trends in Cell Biology 6; 388-392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila aurora* and *S. cerevisiae* Ipl1 proteins. *Drosophila aurora* and *S. cerevisiae* Ipl1, which are highly homologous at the amino acid sequence level, encode serine/threonine protein kinases. Both aurora and Ipl1 are known to be involved in controlling the transition from the G2 phase of the cell cycle through mitosis, centrosome function, formation of a mitotic spindle and proper chromosome separation/segregation into daughter cells. The two human homologues of these genes, termed aurora1 and aurora2, encode cell cycle regulated protein kinases. These show a peak of expression and kinase activity at the G2/M boundary (aurora2) and in mitosis itself (aurora1). Several observations implicate the involvement of human aurora proteins, and particularly aurora2 in cancer. The aurora2 gene maps to chromosome 20q13, a region that is frequently amplified in human tumours including both breast and colon tumours. Aurora2 may be the major target gene of this amplicon, since aurora2 DNA is amplified and aurora2 mRNA overexpressed in greater than 50% of primary human colorectal cancers. In these tumours aurora2 protein levels appear greatly elevated compared to adjacent normal tissue. In addition, transfection of rodent fibroblasts with human aurora2 leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial overexpression of aurora2 leads to an increase in centrosome number and an increase in aneuploidy.

Importantly, it has also been demonstrated that abrogation of aurora2 expression and function by antisense oligonucleotide treatment of human tumour cell lines (WO 97/22702 and WO 99/3778) leads to cell cycle arrest in the G2 phase of the cell cycle and exerts an antiproliferative effect in these tumour cell lines. This indicates that inhibition of the function of aurora2 will have an antiproliferative effect that may be useful in the treatment of human tumours and other hyperproliferative diseases.

A number of quinazoline derivatives have been proposed hitherto for use in the inhibition of various kinases. For example, WO 96/09294, WO 96/33981 and EP 0837 063 describe the use of certain quinazoline compounds as receptor tyrosine kinase inhibitors, which may be useful in the treatment of proliferative disease.

The applicants have found a series of compounds which inhibit the effect of the aurora2 kinase and which are thus of use in the treatment of proliferative disease such as cancer, in particular in such diseases such as colorectal or breast cancer where aurora 2 kinase is known to be active.

The present invention provides the use of a compound of formula (I)

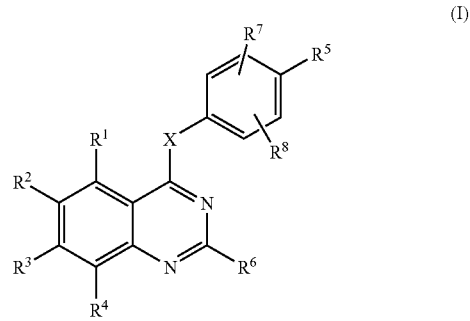

or a salt, ester, amide or prodrug thereof;

where X is O, or S, S(O) or $S(O)_2$, NH or $NR^{12}$ where $R^{12}$ is hydrogen or $C_{1-6}$alkyl;

$R^5$ is selected from a group $NHC(O)OR^9$, $NHC(O)R^9$, $NHS(O)_2R^9$, $C(O)R^9$, $C(O)OR^9$, $S(O)R^9$, $S(O)OR^9$, $S(O)_2OR^9$, $C(O)NR^{10}R^{11}$, $S(O)NR^{10}R^{11}$ $S(O)ONR^{10}R^{11}$ where $R^9$, $R^{10}$ or $R^{11}$ are independently selected from hydrogen, optionally substituted hydrocarbyl and optionally substituted heterocyclyl and $R^{10}$ and $R^{11}$ together with the nitrogen atom to which they are attached may additionally form an optionally substituted heterocyclic ring which optionally contains further heteroatoms;

$R^6$ is hydrogen, optionally substituted hydrocarbyl or optionally substituted heterocyclyl;

$R^7$ and $R^8$ are independently selected from hydrogen, halo, $C_{1-4}$alkyl, $C_{1-4}$ alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, $\underline{N}$—$C_{1-4}$alkylcarbamoyl, $\underline{N}$,$\underline{N}$-di($C_{1-4}$alkyl)carbamoyl, aminosulphonyl, $\underline{N}$—$C_{1-4}$alkylaminosulphonyl, $\underline{N}$,$\underline{N}$-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl; and $R^1$, $R^2$, $R^3$, $R^4$ are independently selected from halogeno, cyano, nitro, $C_{1-3}$alkylsulphanyl, —N(OH)$R^{13}$— (wherein $R^{13}$ is hydrogen, or $C_{1-3}$alkyl), or $R^{15}X^1$— (wherein $X^1$ represents a direct bond, —O—, —$CH_2$—, —OCO—, carbonyl, —S—, —SO—, —$SO_2$—, —$NR^{16}$CO—, —$CONR^{16}$—, —$SO_2NR^{16}$—, —$NR^{17}SO_2$— or —$NR^{18}$— (wherein $R^{16}$, $R^{17}$ and $R^{18}$ each independently represents hydrogen, $C_{1-3}$alkyl or $C_{1-3}$alkoxy$C_{2-3}$alkyl), and $R^{15}$ is hydrogen, optionally substituted hydrocarbyl, optionally substituted heterocyclyl or optionally substituted alkoxy;

in the preparation of a medicament for use in the inhibition of aurora 2 kinase.

In particular, such medicaments are useful in the treatment of proliferative disease such as cancer, and in particular cancers where aurora 2 is upregulated such as colon or breast cancers.

In this specification the term 'alkyl' when used either alone or as a suffix includes straight chained or branched structures. Unless otherwise stated, these groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocyclic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynyl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term "functional group" refers to reactive substituents such as nitro, cyano, halo, oxo, =$CR^{78}R^{79}$, $C(O)_xR^{77}$, $OR^{77}$, $S(O)_yR^{77}$, $NR^{78}R^{79}$, $C(O)NR^{78}R^{79}$, $OC(O)NR^{78}R^{79}$, =$NOR^{77}$, —$NR^{77}C(O)_xR^{78}$, —$NR^{77}CONR^{78}R^{79}$, —N=$CR^{78}R^{79}$, $S(O)_yNR^{78}R^{79}$ or —$NR^{77}S(O)_yR^{78}$ where $R^{77}$, $R^{78}$ and $R^{79}$ are independently selected from hydrogen, optionally substituted hydrocarbyl, optionally substituted heterocyclyl, or optionally substituted alkoxy, or $R^{78}$ and $R^{79}$ together form an optionally substituted ring which optionally contains further heteroatoms such as oxygen, nitrogen, S, S(O) or $S(O)_2$, where x is an integer of 1 or 2, y is 0 or an integer of 1-3.

Suitable optional substituents for hydrocarbyl, heterocyclyl or alkoxy groups $R^{77}$, $R^{78}$ and $R^{79}$ as well as rings formed by $R^{78}$ and $R^{79}$ include halo, perhaloalkyl such as trifluoromethyl, mercapto, thioalkyl, hydroxy, carboxy, alkoxy, heteroaryl, heteroaryloxy, cycloalkyl, cycloalkenyl, cycloalkynyl, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_yR^{90}$ where y is as defined above and $R^{90}$ is a hydrocarbyl group such as alkyl.

In particular, optional substituents for hydrocarbyl, heterocyclyl, or alkoxy groups $R^{77}$, $R^{78}$ and $R^{79}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_yR^{90}$ where y is as defined above and $R^{90}$ is a hydrocarbyl group such as alkyl.

Certain compounds of formula (I) may include a chiral centre and the invention includes the use of all enantiomeric forms thereof, as well as mixtures thereof including racemic mixtures.

In particular, $R^{15}$ is hydrogen or an alkyl group, optionally substituted with one or more groups selected from functional groups as defined above, or alkenyl, alkynyl, aryl, heterocyclyl, cycloalkyl, cycloalkenyl or cycloalkynyl, any of which may be substituted with a functional group as defined above, and where any aryl, heterocyclyl, cycloalkyl, cycloalkenyl, cycloalkynyl groups may also be optionally substituted with hydrocarbyl such as alkyl, alkenyl or alkynyl.

For example, $R^{15}$ is selected from one of the following twenty-two groups:

1) hydrogen or $C_{1-5}$alkyl which may be unsubstituted or which may be substituted with one or more functional groups;

2) —$R^a X^2 C(O)R^{19}$ (wherein $X^2$ represents —O— or —$NR^{20}$— (in which $R^{20}$ represents hydrogen, or alkyl optionally substituted with a functional group) and $R^{19}$ represents $C_{1-3}$alkyl, —$NR^{21}R^{22}$ or —$OR^{23}$ (wherein $R^{21}$, $R^{22}$ and $R^{23}$ which may be the same or different each represents hydrogen, or alkyl optionally substituted with a functional group));

3) —$R^b X^3 R^{24}$ (wherein $X^3$ represents —O—, —C(O)—, —S—, —SO—, —$SO_2$—, —OC(O)—, —$NR^{25}C(O)_s$—, —$C(O)NR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, or alkyl optionally substituted with a functional group and s is 1 or 2) and $R^{24}$ represents hydrogen, hydrocarbyl (as defined herein) or a saturated heterocyclic group, wherein the hydrocarbyl or heterocyclic groups may be optionally substituted by one or more functional groups and the heterocyclic groups may additionally be substituted by a hydrocarbyl group);

4) —$R^c X^4 R^{c'} X^5 R^{30}$ (wherein $X^4$ and $X^5$ which may be the same or different are each —O—, —C(O)—, —S—, —SO—, —$SO_2$—, —OC(O)—, —$NR^{31}C(O)_s$—, —$C(O)_x NR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen or alkyl optionally substituted by a functional group and s is 1 or 2) and $R^{30}$ represents hydrogen, or alkyl optionally substituted by a functional group;

5) $R^{36}$ wherein $R^{36}$ is a $C_{3-6}$ cycloalkyl or saturated heterocyclic ring (linked via carbon or nitrogen), which cycloalkyl or heterocyclic group may be substituted by one or more functional groups or by a hydrocarbyl or heterocyclyl group which hydrocarbyl or heterocyclyl group may be optionally substituted by one or more functional groups;

6) —$R^d R^{36}$ (wherein $R^{36}$ is as defined hereinbefore);

7) —$R^e R^{36}$ (wherein $R^{36}$ is as defined hereinbefore);

8) —$R^f R^{36}$ (wherein $R^{36}$ is as defined hereinbefore);

9) $R^{37}$ wherein $R^{37}$ represents a pyridone group, an aryl group or an aromatic heterocyclic group (linked via carbon or nitrogen) with 1-3 heteroatoms selected from O, N and S, which pyridone, aryl or aromatic heterocyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups;

10) —$R^g R^{37}$ (wherein $R^{37}$ is as defined hereinbefore);

11) —$R^h R^{37}$ (wherein $R^{37}$ is as defined hereinbefore);

12) —$R^i R^{37}$ (wherein $R^{37}$ is as defined hereinbefore);

13) —$R^j X^6 R^{37}$ (wherein $X^6$ represents —O—, —S—, —SO—, —$SO_2$—, —OC(O)—, —$NR^{42}C(O)$—, —$C(O)NR^{43}$—, —$SO_2NR^{44}$—, —$NR^{45}SO_2$— or —$NR^{46}$— (wherein $R^{42}$, $R^{43}$, $R^{44}$, $R^{45}$ and $R^{46}$ each independently represents hydrogen, or alkyl optionally substituted with a functional group) and $R^{37}$ is as defined hereinbefore);

14) —$R^k X^7 R^{37}$ (wherein $X^7$ represents —O—, —C(O)—, —S—, —SO—, —$SO_2$—, —OC(O)—, —$NR^{47}C(O)$—, —$C(O)NR^{48}$—, —$SO_2NR^{49}$—, —$NR^{50}SO_2$— or —$NR^{51}$— (wherein $R^{47}$, $R^{48}$, $R^{49}$, $R^{50}$ and $R^{51}$ each independently represents hydrogen, or alkyl optionally substituted with a functional group) and $R^{37}$ is as defined hereinbefore);

15) —$R^m X^8 R^{37}$ (wherein $X^8$ represents —O—, —C(O)—, —S—, —SO—, —$SO_2$—, —OC(O)—, —$NR^{52}C(O)$—, —$C(O)NR^{53}$—, —$SO_2NR^{54}$—, —$NR^{55}SO_2$— or —$NR^{56}$— (wherein $R^{52}$, $R^{53}$, $R^{54}$, $R^{55}$ and $R^{56}$ each independently represents hydrogen, or alkyl optionally substituted with a functional group) and $R^{37}$ is as defined hereinbefore);

16) —$R^n X^9 R^{n'} R^{37}$ (wherein $X^9$ represents —O—, —C(O)—, —S—, —SO—, —$SO_2$—, —OC(O)—, —$NR^{57}C(O)$—, —$C(O)NR^{58}$—, —$SO_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen or alkyl optionally substituted with a functional group) and $R^{37}$ is as defined hereinbefore);

17) —$R^p X^9$—$R^{p'} R^{36}$ (wherein $X^9$ and $R^{36}$ are as defined hereinbefore);

18) $C_{2-5}$alkenyl which may be unsubstituted or which may be substituted with one or more functional groups;

19) $C_{2-5}$alkynyl which may be unsubstituted or which may be substituted with one or more functional groups;

20) —$R^t X^9 R^{t'} R^{36}$ (wherein $X^9$ and $R^{36}$ are as defined hereinbefore);

21) —$R^u X^9 R^{u'} R^{36}$ (wherein $X^9$ and $R^{36}$ are as defined hereinbefore); and 22) —$R^v R^{62}(R^{v'})_q (X^9)_r R^{63}$ (wherein $X^9$ is as defined hereinbefore, q is 0 or 1, r is 0 or 1, and $R^{62}$ is a $C_{1-3}$alkylene group or a cyclic group selected from divalent cycloalkyl or heterocyclic group, which $C_{1-3}$alkylene group may be substituted by one or more functional groups and which cyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups; and $R^{63}$ is hydrogen, $C_{1-3}$alkyl, or a cyclic group selected from cycloalkyl or heterocyclic group, which $C_{1-3}$alkyl group may be substituted by one or more functional groups and which cyclic group may be substituted by one or more may be substituted by one or more functional groups or by a hydrocarbyl group optionally substituted by one or more functional groups or heterocyclyl groups, or by a heterocyclyl group optionally substituted by one or more functional groups or hydrocarbyl groups);

and wherein $R^a$, $R^b$, $R^c$, $R^{c'}$, $R^d$, $R^g$, $R^j$, $R^n$, $R^{n'}$, $R^p$, $R^{p'}$, $R^t$, $R^{u'}$, $R^v$ and $R^{v'}$ are independently selected from $C_{1-8}$alkylene groups optionally substituted by one or more substituents functional groups;

$R^e$ $R^h$, $R^k$ and $R^t$ are independently selected from $C_{2-8}$alkenylene groups optionally substituted by one or more functional groups, and $R^f$, $R^i$, $R^m$ and $R^u$ are independently selected from $C_{2-8}$alkynylene groups optionally substituted by one or more functional groups.

Particular example of the following twenty-two groups for $R^{15}$ are:

1) hydrogen or $C_{1-5}$alkyl which may be unsubstituted or which may be substituted with one or more groups selected from hydroxy, oxiranyl, fluoro, chloro, bromo and amino (including $C_{1-3}$alkyl and trifluoromethyl);

2) —$R^a X^2 C(O)R^{19}$ (wherein $X^2$ represents —O— or —$NR^{20}$— (in which $R^{20}$ represents hydrogen, $C_{1-3}$alkyl or $C_{1-3}$alkoxy$C_{2-3}$alkyl) and $R^{19}$ represents $C_{1-3}$alkyl, —$NR^{21}R^{22}$ or —$OR^{23}$ (wherein $R^{21}$, $R^{21}$ and $R^{23}$ which may be the same or different each represents hydrogen, $C_{1-5}$alkyl, hydroxy$C_{1-5}$alkyl or $C_{1-3}$alkoxy$C_{2-3}$alkyl));

3) —$R^b X^3 R^{24}$ (wherein $X^3$ represents —O—, —C(O)—, —S—, —SO—, —SO$_2$—, —OC(O)—, —$NR^{25}C(O)_s$—, —$NR^{25}C(O)NR^{26}$—, —C(O)$NR^{26}$—, —SO$_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl, hydroxy$C_{1-3}$alkyl or $C_{1-3}$alkoxy$C_{2-3}$alkyl and s is 1 or 2) and $R^{24}$ represents hydrogen, $C_{1-6}$alkyl, $C_{2-6}$alkenyl, or a cyclic groups selected from cyclopropyl, cyclobutyl, cyclopentyl, cyclohexyl, phenyl or a 5-6-membered saturated heterocyclic group with 1-2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, di-$C_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_4$alkyl, di($C_{1-4}$alkyl)amino$C_{1-4}$alkyl, $C_{1-4}$alkanoyl, $C_{1-4}$alkylamino$C_{1-4}$alkoxy, di($C_{1-4}$ alkyl)amino$C_{1-4}$alkoxy and a group —(—O—)$_f$($R^{b'}$)$_g$ D (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl));

4) —$R^c X^4 R^{c'} X^5 R^{30}$ (wherein $X^4$ and $X^5$ which may be the same or different are each —O—, —C(O)—, —S—, —SO—, —SO$_2$—, —$NR^{31}C(O)_s$—, —C(O)$NR^{32}$—, —SO$_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl, hydroxy$C_{1-3}$alkyl or $C_{1-3}$alkoxy$C_{2-3}$alkyl and s is 1 or 2) and $R^{30}$ represents hydrogen, $C_{1-3}$alkyl, hydroxy$C_{1-3}$alkyl or $C_{1-3}$alkoxy$C_{2-3}$alkyl);

5) $R^{36}$ (wherein $R^{36}$ is a 4-6-membered cycloalkyl or saturated heterocyclic ring (linked via carbon or nitrogen) with 1-2 heteroatoms, selected independently from O, S and N, which cycloalkyl or heterocyclic group may bear 1 or 2 substituents selected from oxo, hydroxy, halogeno, cyano, $C_{1-4}$alkyl, hydroxy$C_{1-4}$alkyl, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy nitro, amino, $C_{1-4}$alkoxy, $C_{1-4}$hydroxyalkoxy, carboxy, trifluoromethyl, —C(O)$NR^{38}R^{39}$, —$NR^{40}C(O)R^{41}$ (wherein $R^{38}$, $R^{39}$, $R^{40}$ and $R^{41}$, which may be the same or different, each represents hydrogen, $C_{1-4}$alkyl, hydroxy$C_{1-4}$ alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

6) —$R^d R^{36}$ (wherein $R^{36}$ is as defined hereinbefore);

7) —$R^e R^{36}$ (wherein $R^{36}$ is as defined hereinbefore);

8) —$R^f R^{36}$ (wherein $R^{36}$ is as defined hereinbefore);

9) $R^{37}$ (wherein $R^{37}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxy, carboxamido, trifluoromethyl, cyano, —C(O)$NR^{38}R^{39}$, —$NR^{40}C(O)R^{41}$ (wherein $R^{38}$, $R^{39}$, $R^{40}$ and $R^{41}$ which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

10) —$R^g R^{37}$ (wherein $R^{37}$ is as defined hereinbefore);

11) —$R^h R^{37}$ (wherein $R^{37}$ is as defined hereinbefore);

12) —$R^i R^{37}$ (wherein $R^{37}$ is as defined hereinbefore);

13) —$R^j X^6 R^{37}$ (wherein $X^6$ represents —O—, —C(O)—, —S—, —SO—, —SO$_2$—, —OC(O)—, —$NR^{42}C(O)$—, —C(O)$NR^{43}$—, —SO$_2NR^{44}$—, —$NR^{45}SO_2$— or —$NR^{46}$— (wherein $R^{42}$, $R^{43}$, $R^{44}$, $R^{45}$ and $R^{46}$ each independently represents hydrogen, $C_{1-3}$alkyl, hydroxy$C_{1-3}$alkyl or $C_{1-3}$alkoxy$C_{2-3}$alkyl) and $R^{37}$ is as defined hereinbefore);

14) —$R^k X^7 R^{37}$ (wherein $X^7$ represents —O—, —C(O)—, —S—, —SO—, —SO$_2$—, —$NR^{47}C(O)$—, —C(O)$NR^{48}$—, —SO$_2NR^{49}$—, —$NR^{50}SO_2$— or —$NR^{51}$— (wherein $R^{47}$, $R^{48}$, $R^{49}$, $R^{50}$ and $R^{51}$ each independently represents hydrogen, $C_{1-3}$alkyl, hydroxy$C_{1-3}$alkyl or $C_{1-3}$alkoxy$C_{2-3}$alkyl) and $R^{37}$ is as defined hereinbefore);

15) —$R^m X^8 R^{37}$ (wherein $X^8$ represents —O—, —C(O)—, —S—, —SO—, —SO$_2$—, —$NR^{52}C(O)$—, —C(O)$NR^{53}$—, —SO$_2NR^{54}$—, —$NR^{55}SO_2$— or $NR^{56}$— (wherein $R^{52}$, $R^{53}$, $R^{54}$, $R^{55}$ and $R^{56}$ each independently represents hydrogen, $C_{1-3}$alkyl, hydroxy$C_{1-3}$alkyl or $C_{1-3}$alkoxy$C_{2-3}$alkyl) and $R^{37}$ is as defined hereinbefore);

16) —$R^n X^9 R^{n'} R^{37}$ (wherein $X^9$ represents —O—, —C(O)—, —S—, —SO—, —SO$_2$—, —$NR^{57}C(O)$—, —C(O)$NR^{58}$—, —SO$_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen, $C_{1-3}$alkyl, hydroxy$C_{1-3}$alkyl or $C_{1-3}$alkoxy$C_{2-3}$alkyl) and $R^{37}$ is as defined hereinbefore);

17) —$R^p X^9$—$R^{p'} R^{36}$ (wherein $X^9$ and $R^{36}$ are as defined hereinbefore);

18) $C_{2-5}$alkenyl which may be unsubstituted or which may be substituted with one or more groups selected from hydroxy, fluoro, amino, $C_{1-4}$alkylamino, carboxy (and particularly alkyl esters thereof, <u>N,N</u>-di($C_{1-4}$alkyl)amino, aminosulphonyl, <u>N</u>—$C_4$alkylaminosulphonyl and <u>N,N</u>-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, $\underline{N},\underline{N}$-di($C_{1-4}$alkyl)amino, aminosulphonyl, $\underline{N}$—$C_{1-4}$alkylaminosulphonyl and $\underline{N},\underline{N}$-di($C_{1-4}$alkyl)aminosulphonyl;

20) —$R'X^9R'R^{36}$ (wherein $X^9$ and $R^{36}$ are as defined hereinbefore);

21) $R^u X^9 R^{u'}R^{36}$ (wherein $X^9$ and $R^{36}$ are as defined hereinbefore); and 22) —$R^v R^{62}(R^{v'})_q(X^9)_r R^{63}$ (wherein $X^9$ is as defined hereinbefore, q is 0 or 1, r is 0 or 1, and $R^{62}$ is a $C_{1-3}$alkylene group or a cyclic group selected from cyclopropylene, cyclobutylene, cyclopentylene, cyclohexylene or a 5-6-membered saturated heterocyclic group with 1-2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_4$alkylamino, di($C_{1-4}$ alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl); and $R^{63}$ is hydrogen, $C_{1-3}$alkyl, or a cyclic group selected from cyclopropyl, cyclobutyl, cyclopentyl, cyclohexyl and a 5-6-membered saturated or unsaturated heterocyclic group with 1-2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl) amino$C_{1-4}$alkyl, $C_{1-4}$alkylamino$C_{1-4}$alkoxy, di($C_{1-4}$alkyl) amino$C_{1-4}$alkoxy and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl));

and wherein $R^a$, $R^b$, $R^{b'}$, $R^c$, $R^{c'}$, $R^d$, $R^g$, $R^j$, $R^n$, $R^{n'}$, $R^p$, $R^{p'}$, $R^{t'}$, $R^{u'}$, $R^v$ and $R^{v'}$ are independently selected from $C_{1-8}$alkylene groups optionally substituted by one or more substituents selected from hydroxy, halogeno, and amino;

$R^e$ $R^h$, $R^k$ and $R^t$ are independently selected from $C_{2-8}$alkenylene groups optionally substituted by one or more substituents selected from hydroxy, halogeno, amino, and $R^t$ may additionally be a bond;

$R^f$, $R^i$, $R^m$ and $R^u$ are independently selected from $C_{2-5}$alkynylene groups optionally substituted by one or more substituents selected from hydroxy, halogeno, amino.

In particular $R^1$, $R^2$, $R^3$, $R^4$ are independently selected from, halo, cyano, nitro, trifluoromethyl, $C_{1-3}$alkyl, —$NR^{13}R^{14}$ (wherein $R^{13}$ and $R^{14}$, which may be the same or different, each represents hydrogen or $C_{1-3}$alkyl), or —$X^1R^{15}$ wherein $X^1$ represents a direct bond, —O—, —$CH_2$—, —OCO—, carbonyl, —S—, —SO—, —$SO_2$—, —$NR^{16}CO$—, —$CONR^{16}$—, —$SO_2NR^{16}$—, —$NR^{17}SO_2$— or —$NR^{18}$— (wherein $R^{16}$, $R^{17}$ and $R^{18}$ each independently represents hydrogen, $C_{1-3}$alkyl or $C_{1-3}$alkoxy$C_{2-3}$alkyl), and $R^{15}$ is selected from one of the following groups:

1') hydrogen or $C_{1-5}$alkyl which may be unsubstituted or which may be substituted with one or more groups selected from hydroxy, fluoro or amino;

2') $C_{1-5}$alkyl$X^2COR^{19}$ (wherein $X^2$ represents —O— or —$NR^{20}$— (in which $R^{20}$ represents hydrogen, $C_{1-3}$alkyl or $C_{1-3}$alkoxy$C_{2-3}$alkyl) and $R^{19}$ represents $C_{1-3}$alkyl, —$NR^{21}R^{22}$ or —$OR^{23}$ (wherein $R^{21}$, $R^{22}$ and $R^{23}$ which may be the same or different each represents hydrogen, $C_{1-3}$alkyl or $C_{1-3}$alkoxy$C_{2-3}$alkyl));

3') $C_{1-5}$alkyl$X^3R^{24}$ (wherein $X^3$ represents —O—, —S—, —SO—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_4$alkoxy);

4') $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);

5') $R^{36}$ (wherein $R^{36}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkyl$R^{36}$ (wherein $R^{36}$ is as defined in (5') above);

7') $C_{2-5}$alkenyl$R^{36}$ (wherein $R^{36}$ is as defined in (5') above);

8') $C_{2-5}$alkynyl$R^{36}$ (wherein $R^{36}$ is as defined in (5') above);

9') $R^{37}$ (wherein $R^{37}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{38}R^{39}$ and —$NR^{40}COR^{41}$ (wherein $R^{38}$, $R^{39}$, $R^{40}$ and $R^{41}$, which may be the same or different, each represents hydrogen, $C_{1-4}$alkyl or $C_{1-3}$alkoxy$C_{2-3}$alkyl));

10') $C_{1-5}$alkyl$R^{37}$ (wherein $R^{37}$ is as defined in (9') above);

11') $C_{2-5}$alkenyl$R^{37}$ (wherein $R^{37}$ is as defined in (9') above);

12') $C_{2-5}$alkynyl$R^{37}$ (wherein $R^{37}$ is as defined in (9') above);

13') $C_{1-5}$alkyl$X^6R^{37}$ (wherein $X^6$ represents —O—, —S—, —SO—, —SO$_2$—, —NR$^{42}$CO—, —CONR$^{43}$—, SO$_2$NR$^{44}$—, —NR$^{45}$SO$_2$— or —NR$^{46}$— (wherein $R^{42}$, $R^{43}$, $R^{44}$, $R^{45}$ and $R^{46}$ each independently represents hydrogen, $C_{1-3}$alkyl or $C_{1-3}$alkoxy$C_{2-3}$alkyl) and $R^{37}$ is as defined hereinbefore);

14') $C_{2-5}$alkenyl$X^7R^{37}$ (wherein $X^7$ represents —O—, —S—, —SO—, —SO$_2$—, —NR$^{47}$CO—, —CONR$^{48}$—, —SO$_2$NR$^{49}$—, —NR$^{50}$SO$_2$— or —NR$^{51}$— (wherein $R^{47}$, $R^{48}$, $R^{49}$, $R^{50}$ and $R^{51}$ each independently represents hydrogen, $C_{1-3}$alkyl or $C_{1-3}$alkoxy$C_{2-3}$alkyl) and $R^{37}$ is as defined in (9') above);

15') $C_{2-5}$alkynyl$X^8R^{37}$ (wherein $X^8$ represents —O—, —S—, —SO—, —SO$_2$—, —NR$^{52}$CO—, —CONR$^{53}$—, —SO$_2$NR$^{54}$—, —NR$^{55}$SO$_2$— or —NR$^{56}$— (wherein $R^{52}$, $R^{53}$, $R^{54}$, $R^{55}$ and $R^{56}$ each independently represents hydrogen, $C_{1-3}$alkyl or $C_{1-3}$alkoxy$C_{2-3}$alkyl) and $R^{37}$ is as defined hereinbefore);

16') $C_{1-3}$alkyl$X^9C_{1-3}$alkyl$R^{37}$ (wherein $X^9$ represents —O—, —S—, —SO—, —SO$_2$—, —NR$^{57}$CO—, —CONR$^{58}$—, —SO$_2$NR$^{59}$—, —NR$^{60}$SO$_2$— or —NR$^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl) and $R^{37}$ is as defined hereinbefore); and 17') $C_{1-3}$alkyl$X^9C_{1-3}$alkyl$R^{36}$ (wherein $X^9$ and $R^{36}$ are as defined in (5') above).

Preferably $R^1$ is hydrogen. Suitably $R^4$ is hydrogen or a small substituent such as halo, $C_{1-4}$ alkyl or $C_{1-4}$alkoxy such as methoxy.

Preferably both $R^1$ and $R^4$ are hydrogen.

In a preferred embodiment, at least one group $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Suitably $R^3$ is a group $X^1R^{15}$.

Preferably in this case, $X^1$ is oxygen and $R^{15}$ includes a methylene group directly adjacent $X^1$. Preferably where bridging alkylene, alkenylene or alkynylene groups $R^a$, $R^b$, $R^{b'}$, $R^c$, $R^{c'}$, $R^d$, $R^g$, $R^j$, $R^n$, $R^{n'}$, $R^p$, $R^{t'}$, $R^u$, $R^v$, $R^{v'}$, $R^e$, $R^h$, $R^k$, $R^l$, $R^i$, $R^m$ and $R^u$ are present, at least one such group includes a substituent and in particular a hydroxy substituent.

In particular $R^{15}$ is selected from a group of formula (1), (3), (6), (10) or (22) above and preferably selected from groups (1) or (10) above. Particular groups $R^{15}$ are those in group (1) above, especially alkyl such as methyl or halo substituted alkyl, or those in group (10) above. In one suitable embodiment, at least one of $R^2$ or $R^3$ is a group O$C_{1-5}$alkyl$R^{36}$ and $R^{36}$ is a heterocyclic ring such as an N-linked morpholine ring such as 3-morpholinopropoxy.

Other preferred groups for $R^3$ are groups of formula (3) above in particular those where $X^3$ is NR$^{29}$.

Suitably $R^2$ is selected from, halo, cyano, nitro, trifluoromethyl, $C_{1-3}$alkyl, —NR$^{13}$R$^{14}$ (wherein $R^{13}$ and $R^{14}$, which may be the same or different, each represents hydrogen or $C_{1-3}$alkyl), or a group —$X^1R^{15}$. Preferred examples of —$X^1R^{15}$ for $R^2$ include those listed above in relation to $R^3$.

Other examples for $R^2$ and $R^3$ include methoxy or 3,3,3-trifluoroethoxy.

Preferably X is NH or O and is most preferably NH.

Particular examples of $R^6$ include H or heterocyclic groups such as N-morpholino. Preferably however, $R^6$ is hydrogen.

In a particular embodiment, $R^5$ is a group NHC(O)$R^9$ or NHS(O)$_2R^9$ where $R^9$ is as defined above.

In an alternative embodiment, $R^5$ is a group C(O)$R^9$, C(O)OR$^9$, S(O)$R^9$, S(O)OR$^9$, S(O)$_2$OR$^9$, C(O)NR$^{10}R^{11}$, S(O)NR$^{10}R^{11}$ or S(O)O NR$^{10}R^{11}$ where $R^9$, $R^{10}$ and $R^{11}$ are as defined above.

Particular examples for $R^9$, $R^{10}$ or $R^{11}$ include:

aryl optionally substituted with one or more functional groups;

$C_{3-6}$cycloalkyl optionally substituted with one or more functional groups;

aralkyl optionally substituted with one or more functional groups and wherein the aryl portion may further comprise one or more alkyl substituents;

heterocyclyl optionally substituted with one or more functional, alkyl, alkenyl or alkynyl groups;

alkyl optionally substituted by a functional group or a cycloalkyl or heterocyclyl group wherein the cycloalkyl or heterocyclyl group may themselves be optionally substituted with one or more functional or alkyl groups;

alkenyl optionally substituted by a functional group or an aryl or heterocyclyl group wherein the aryl or heterocyclyl group may be optionally substituted with one or more functional or alkyl groups; and alkynyl optionally substituted by a functional group or an aryl or heterocyclyl group wherein the aryl or heterocyclyl group may be optionally substituted with one or more functional group or alkyl groups.

Particular examples of optionally substituted aryl groups $R^9$, $R^{10}$ or $R^{11}$ include phenyl optionally substituted with up to 5 groups selected from nitro, halo, carboxy, cyano, $C_{1-4}$alkyl, $C_{1-4}$alkoxy, $C_{1-4}$alkylthio, acetoxy, acetamido hydroxy, aminosulphonyl, $C_{1-4}$alkylsulphonyl, trifluoromethyl, aralkyl, or aralkyloxy wherein aryl rings in the substituents may themselves be substituted with for example halo, nitro or $C_{1-4}$alkyl.

Suitable optionally substituted $C_{3-6}$cycloalkyl groups $R^9$, $R^{10}$ and $R^{11}$ include optionally substituted cyclopropyl, cyclobutyl, cyclopentyl or cyclohexyl any of which may be optionally substituted with for example nitro, halo, carboxy, cyano, $C_{1-4}$alkyl, $C_{1-4}$alkoxy, $C_{1-4}$alkylthio, acetoxy, acetamido, hydroxy, aminosulphonyl, $C_{1-4}$alkylsulphonyl, trifluoromethyl, aralkyl, aralkyloxy, or aryl wherein aryl rings in the substituents may themselves be substituted with for example halo, nitro or $C_{1-4}$alkyl.

Suitable optionally substituted aralkyl groups $R^9$, $R^{10}$ and $R^{11}$ include optionally substituted benzyl, phenylethyl or phenylpropyl, wherein the phenyl ring is optionally substituted with for example up to 5 groups selected from nitro, halo, carboxy, cyano, $C_{1-4}$alkyl, $C_{1-4}$alkoxy, $C_{1-4}$alkylthio, acetoxy, acetamido, hydroxy, aminosulphonyl, $C_{1-4}$alkylsulphonyl, trifluoromethyl, aralkyl, or aralkyloxy wherein aryl rings in the substituents may themselves be substituted with for example halo, carboxy, trifluoromethyl, nitro or $C_{1-4}$alkyl and in particular nitro, $C_{1-4}$alkoxy, halo, hydroxy, trifluoromethyl or carboxy.

Suitable optionally substituted heterocyclyl groups $R^9$, $R^{10}$ and $R^{11}$ include pyridyl, pyrazine, pyrimidinyl, pyrrolidino, furyl, tetrahydrofuryl, oxazolyl, morpholino, thiadiazole, indolyl, quinolinyl, isoquinolinyl, pyrazolyl, methylenedioxybenzyl, thiophene, benzothiophene, all of which may be optionally substituted with, for example, one or more groups selected from nitro, halo, carboxy, cyano, $C_{1-4}$alkyl, $C_{1-4}$alkoxy, $C_{1-4}$alkylthio, acetoxy, acetamido hydroxy, aminosulphonyl, $C_{1-4}$alkylsulphonyl, trifluoromethyl, aralkyl, or aralkyloxy wherein aryl rings in the substituents may themselves be substituted with for example halo, carboxy, trifluoromethyl, nitro or $C_{1-4}$alkyl; and particularly with $C_{1-4}$alkyl, halo or nitro.

Suitable optional substituents for alkyl groups $R^9$, $R^{10}$ or $R^{11}$ include amino, mono- or di-$C_{1-4}$alkylamino, hydroxy, $C_{1-4}$alkoxy, heterocyclyl (such as thiophene, tetrahydrothiophene-1,1-dioxide, pyrrolidino, morpholino, furyl or tetrahydrofuryl) $C_{1-4}$alkoxy, acetamido, aryloxy such as phenyloxy, alkyl$C_{1-4}$thio, aroyl such as benzoyl where the aryl ring may itself be substituted with for example halo, carboxy, trifluoromethyl nitro, carboxy, trifluoromethyl, cycloalkyl (such as cyclohexyl) or cycloalkenyl (such as cyclohexenyl)

Suitable optional substituents for alkenyl or alkynyl groups $R^9$, $R^{10}$ or $R^{11}$ include nitro, halo, carboxy, cyano, $C_{1-4}$alkyl, $C_{1-4}$alkoxy, $C_{1-4}$alkylthio, acetoxy, acetamido, hydroxy, aminosulphonyl, $C_{1-4}$alkylsulphonyl, trifluoromethyl, aralkyl, or aralkyloxy wherein aryl rings in the substituents may themselves be substituted with for example halo, carboxy, trifluoromethyl, nitro or $C_{1-4}$alkyl. In particular such groups are substituted by aryl such as phenyl, where the aryl ring may itself be substituted with for example halo, nitro, carboxy, or trifluoromethyl.

with for example halo, nitro, carboxy, trifluoromethyl

Suitably $R^7$ and $R^8$ are independently selected from hydrogen halo, $C_{1-4}$alkoxy such as methoxy, or ethoxy, cyano, trifluoromethyl, or phenyl.

Preferably $R^7$ and $R^8$ are hydrogen.

Preferably X is NH or O and is most preferably NH.

In a particular embodiment, the present invention provides the use of a compound of formula (II)

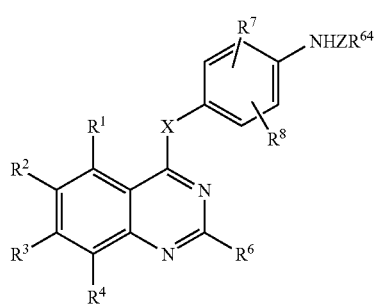

(II)

or a salt, ester, amide or prodrug thereof;

where X, $R^1$, $R^2$, $R^3$, $R^4$, $R^6$, $R^7$ and $R^8$ are as defined in relation to formula (I);

Z is C(O) or S(O)$_2$, and $R^{64}$ is optionally substituted hydrocarbyl or optionally substituted heterocyclyl;

in the preparation of a medicament for use in the inhibition of aurora 2 kinase.

In particular, there is provided the use of a compound of formula (IIC)

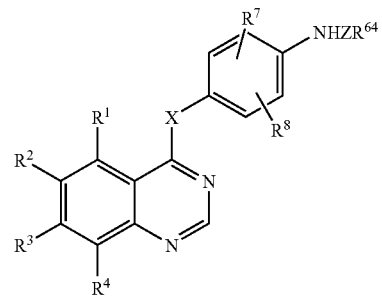

(IIC)

or a salt, ester or amide thereof;

where X is O, or S, S(O) or S(O)$_2$, or NR$^8$ where R$^8$ is hydrogen or $C_{1-6}$alkyl;

Z is C(O) or S(O)$_2$, $R^{64}$ is optionally substituted hydrocarbyl or optionally substituted heterocyclyl;

$R^7$ and $R^8$ are independently selected from hydrogen, halo, $C_{1-4}$alkyl, $C_{1-4}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, <u>N</u>—$C_{1-4}$alkylcarbamoyl, <u>N</u>, <u>N</u>-di($C_{1-4}$alkyl)carbamoyl, aminosulphonyl, <u>N</u>—$C_{1-4}$alkylaminosulphonyl, <u>N</u>, <u>N</u>-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl; and where $R^1$, $R^2$, $R^3$ and $R^4$ are independently selected from, halo, cyano, nitro, trifluoromethyl, $C_{1-3}$alkyl, —NR$^{13}$R$^{14}$ (wherein R$^{13}$ and R$^{14}$, which may be the same or different, each represents hydrogen or $C_{1-3}$alkyl), or —X$^1$R$^{15}$ wherein X$^1$ represents a direct bond, —O—, —CH$_2$—, —OCO—, carbonyl, —S—, —SO—, —SO$_2$—, —NR$^{16}$CO—, —CONR$^{16}$—, —SO$_2$NR$^{16}$—, —NR$^{17}$SO$_2$— or —NR$^{18}$— (wherein R$^{16}$, R$^{17}$ and R$^{18}$ each independently represents hydrogen, $C_{1-3}$alkyl or $C_{1-3}$alkoxy$C_{2-3}$alkyl), and R$^{15}$ is selected from one of the following groups:

1') hydrogen or $C_{1-5}$alkyl which may be unsubstituted or which may be substituted with one or more groups selected from hydroxy, fluoro or amino;

2') $C_{1-5}$alkylX$^2$COR$^{19}$ (wherein X$^2$ represents —O— or —NR$^{20}$— in which R$^{20}$ represents hydrogen, $C_{1-3}$alkyl or $C_{1-3}$alkoxy$C_{2-3}$alkyl) and $R^{19}$ represents $C_{1-3}$alkyl, —$NR^{21}R^{22}$ or —$OR^{23}$ (wherein $R^{21}$, $R^{22}$ and $R^{23}$ which may be the same or different each represents hydrogen, $C_{1-3}$alkyl or $C_{1-3}$alkoxy$C_{2-3}$alkyl));

3') $C_{1-5}$alkyl$X^3R^{24}$ (wherein $X^3$ represents —O—, —S—, —SO—, —$SO_2$—, —OCO—, —$NR^{25}$CO—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}$CO—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);

5') $R^{36}$ (wherein $R^{36}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkyl$R^{36}$ (wherein $R^{36}$ is as defined in (5') above);

7') $C_{2-5}$alkenyl$R^{36}$ (wherein $R^{36}$ is as defined in (5') above);

8') $C_{2-5}$alkynyl$R^{36}$ (wherein $R^{36}$ is as defined in (5') above);

9') $R^{37}$ (wherein $R^{37}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{38}R^{39}$ and —$NR^{40}COR^{41}$ (wherein $R^{38}$, $R^{39}$, $R^{40}$ and $R^{41}$, which may be the same or different, each represents hydrogen, $C_{1-4}$alkyl or $C_{1-3}$alkoxy$C_{2-3}$alkyl));

10') $C_{1-5}$alkyl$R^{37}$ (wherein $R^{37}$ is as defined in (9') above);

11') $C_{2-5}$alkenyl$R^{37}$ (wherein $R^{37}$ is as defined in (9') above);

12') $C_{2-5}$alkynyl$R^{37}$ (wherein $R^{37}$ is as defined in (9') above);

13') $C_{1-5}$alkyl$X^6R^{37}$ (wherein $X^6$ represents —O—, —S—, —SO—, —$SO_2$—, —$NR^{42}$CO—, —$CONR^{43}$—, —$SO_2NR^{44}$—, —$NR^{45}SO_2$— or —$NR^{46}$— (wherein $R^{42}$, $R^{43}$, $R^{44}$, $R^{45}$ and $R^{46}$ each independently represents hydrogen, $C_{1-3}$alkyl or $C_{1-3}$alkoxy$C_{2-3}$alkyl) and $R^{37}$ is as defined hereinbefore);

14') $C_{2-5}$alkenyl$X^7R^{37}$ (wherein $X^7$ represents —O—, —S—, —SO—, —$SO_2$—, —$NR^{47}$CO—, —$CONR^{48}$—, —$SO_2NR^{49}$—, —$NR^{50}SO_2$— or —$NR^{51}$— (wherein $R^{47}$, $R^{48}$, $R^{49}$, $R^{50}$ and $R^{51}$ each independently represents hydrogen, $C_{1-3}$alkyl or $C_{1-3}$alkoxy$C_{2-3}$alkyl) and $R^{37}$ is as defined in (9') above);

15') $C_{2-5}$alkynyl$X^8R^{37}$ (wherein $X^8$ represents —O—, —S—, —SO—, —$SO_2$—, —$NR^{52}$CO—, —$CONR^{53}$—, —$SO_2NR^{54}$—, —$NR^{55}SO_2$— or —$NR^{56}$— (wherein $R^{52}$, $R^{53}$, $R^{54}$, $R^{55}$ and $R^{56}$ each independently represents hydrogen, $C_{1-3}$alkyl or $C_{1-3}$alkoxy$C_{2-3}$alkyl) and $R^{37}$ is as defined hereinbefore);

16') $C_{1-3}$alkyl$X^9C_{1-3}$alkyl$R^{37}$ (wherein $X^9$ represents —O—, —S—, —SO—, —$SO_2$—, —$NR^{57}$CO—, —$CONR^{58}$—, —$SO_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl) and $R^{37}$ is as defined hereinbefore); and 17') $C_{1-3}$alkyl$X^9C_{1-3}$alkyl$R^{36}$ (wherein $X^9$ and $R^{36}$ are as defined in (5') above);

in the preparation of a medicament for use in the inhibition of aurora 2 kinase.

Preferably Z is C(O).

Suitably Preferably X is NH or O and is most preferably NH.

Particular examples of groups $R^{64}$ include groups listed above for $R^9$, and in particular are optionally substituted $C_{1-6}$alkyl, optionally substituted $C_{2-6}$ alkenyl, optionally substituted phenyl, naphthyl or benzyl, optionally substituted heterocyclyl such as pyridyl or furanyl.

Suitable substituents for hydrocarbyl or heterocyclyl groups $R^{64}$ include a functional group as defined above. Heterocyclyl groups may further be substituted with hydrocarbyl groups such as alkyl groups whilst alkyl, alkenyl or alkynyl.

In particular, the substituents for $R^{64}$ include halo, nitro, optionally substituted $C_{1-6}$ alkoxy, $C_{1-4}$alkoxymethyl, di($C_{1-4}$ alkoxy)methyl, $C_{1-4}$alkanoyl, trifluoromethyl, cyano, amino, $C_{2-5}$alkenyl, $C_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, $\underline{N}$—$C_{1-4}$alkylcarbamoyl, $\underline{N}$,$\underline{N}$-di($C_{1-4}$alkyl)carbamoyl, aminosulphonyl, $\underline{N}$—$C_{1-4}$alkylaminosulphonyl, $\underline{N}$,$\underline{N}$-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl.

A further particular substituent group for $R^{64}$ is a group of sub-formula (III)

where q' is 0, 1, 2, 3 or 4;

$R^{70}$ is hydrogen, hydroxy, $C_{1-6}$alkyl, $C_{1-6}$alkoxy, amino, N—$C_{1-6}$alkylamino, N,N—($C_{1-6}$alkyl)$_2$amino, hydroxy$C_{2-6}$alkoxy, $C_{1-6}$alkoxy$C_{2-6}$alkoxy, amino$C_{2-6}$alkoxy, N—$C_{1-6}$alkylamino$C_{2-6}$alkoxy, N,N—($C_{1-6}$alkyl)$_2$amino$C_{2-6}$ alkoxy or $C_{3-7}$cycloalkyl, or $R^{70}$ is of the Formula (IV):

—K—J  (IV)

wherein J is aryl, heteroaryl or heterocyclyl and K is a bond, oxy, imino, N—($C_{1-6}$alkyl)imino, oxy$C_{1-6}$alkylene, imino$C_{1-6}$alkylene, N—($C_{1-6}$alkyl)imino$C_{1-6}$alkylene, —NHC(O)—, —SO$_2$NH—, —NHSO$_2$— or —NHC(O)—$C_{1-6}$alkylene-, and any aryl, heteroaryl or heterocyclyl group in a $R^{70}$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)-O—, $C_{1-6}$alkylS(O)$_n$— (wherein n is 0-2), N—$C_{1-6}$alkylamino, N,N—($C_{1-6}$alkyl)$_2$amino, $C_{1-6}$alkoxycarbonyl, N—$C_{1-6}$alkylcarbamoyl, N,N—($C_{1-6}$alkyl)$_2$carbamoyl, $C_{2-6}$alkanoyl, $C_{1-6}$alkanoyloxy, $C_{1-6}$alkanoylamino, N—$C_{1-6}$alkylsulphamoyl, N,N—($C_{1-6}$alkyl)$_2$sulphamoyl, $C_{1-6}$alkylsulphonylamino and $C_{1-6}$alkylsulphonyl-N—($C_{1-6}$alkyl)amino, and suitably also oxo, or any aryl, heteroaryl or heterocyclyl group in a $R^{70}$ group may be optionally substituted with one or more groups of the Formula (V):

—B$^1$—(CH$_2$)$_p$—A$^1$  (V)

wherein A$^1$ is halo, hydroxy, $C_{1-6}$alkoxy, cyano, amino, N—$C_{1-6}$alkylamino, N,N—($C_{1-6}$alkyl)$_2$amino, carboxy, $C_{1-6}$alkoxycarbonyl, carbamoyl, N—$C_{1-6}$alkylcarbamoyl or N,N—($C_{1-6}$alkyl)$_2$carbamoyl, p is 1-6, and B$^1$ is a bond, oxy, imino, N—($C_{1-6}$alkyl)imino or —NHC(O)—, with the proviso that p is 2 or more unless B$^1$ is a bond or —NHC(O)—;

or any aryl, heteroaryl or heterocyclyl group in a $R^{70}$ group may be optionally substituted with one or more groups of the Formula (VA):

—E$^1$—D$^1$  (VA)

wherein D$^1$ is aryl, heteroaryl or heterocyclyl and E$^1$ is a bond, $C_{1-6}$alkylene, oxy$C_{1-6}$alkylene, oxy, imino, N—($C_{1-6}$alkyl)imino, imino$C_{1-6}$alkylene, N—($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N—($C_{1-6}$alkyl)-imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group in a substituent on R$^4$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N—$C_{1-6}$alkylcarbamoyl, N—($C_{1-6}$alkyl)$_2$carbamoyl, $C_{2-6}$alkanoyl, amino, N—$C_{1-6}$alkylamino and N,N—($C_{1-6}$alkyl)$_2$amino, and any $C_{3-7}$cycloalkyl or heterocyclyl group in a $R^{70}$ group may be optionally substituted with one or two oxo or thioxo substituents, and any of the $R^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N—$C_{1-6}$alkylamino, N,N—($C_{1-6}$alkyl)$_2$amino and heterocyclyl.

In yet a further alternative, $R^{70}$ may be cycloalkenyl or cycloalkynyl such as cyclohexenyl, alkenyl optionally substituted by aryl such as styryl or alkyl substituted by cycloalkenyl such as cyclohexenylethyl.

Examples of heterocyclyl groups for $R^{70}$ include pyridyl, methyledioxyphenyl, furyl, pyrrolyl, thiophene, quinolyl, isoquinolyl, thiazolyl, thiadiazolyl, pyrazolyl, tetrahydrothiophene-1,1-dioxide, dioxan, tetrahydrofuryl, pyrazinyl, imidazolyl, tetrahydropyran, indolyl, indanyl, pyrrolidine, or isoxazolyl.

A particular example of a group $R^{70}$ in formula (III) is phenyl. Preferably $R^{70}$ is halosubstituted phenyl and 2-chloro-4-fluorophenyl is a particularly preferred example.

Particular examples of $R^{70}$ in this instance include optionally substituted phenyl and especially, mono or di-halophenyl, or optionally substituted pyridyl such as nitropyridyl.

Preferably q' is 0.

Specific examples of $R^{64}$ include phenyl, 2-furan, (E)—CH═CH-phenyl, 3,4,5-trimethoxyphenyl, 2,4-difluorophenyl, 2-nitro-4,5-dimethoxyphenyl, 2,4-dinitrophenyl, 2-fluorobenzyl, cyclopentyl, 1-methylbut-3-enyl, CH$_2$CN n-heptyl, 2-(methylthio)ethyl, 2-ethoxyethyl, C(CH$_3$)═CH$_2$, 5-methyl-2-pyrazine 3-furyl, 3-cyanophenyl, 4-acetoxyphenyl, 2-nitro-3-methoxyphenyl, 2-methylthiophenyl, 3-acetoxyphenyl, 4-aminosulphonyl-1-hydroxy-2-naphthyl, 2-pyridyl, 2-quinolinyl, 1,5-dimethyl-1H-pyrazolyl, 2-fluoro-5-nitrophenyl, 3-pyridyl, 2-chloro-3-pyridyl, 2-fluorophenyl, 2,3-difluorophenyl, 2,5-difluorophenyl, 2,3-dimethoxyphenyl, 3,5-dimethoxy-4-hydroxy-phenyl, 3-chloro-4-carboxyphenyl, 3-nitro-4-(methylsulphonyl)-phenyl, 3-nitro-4-methoxyphenyl, (E)—CH═CH-(2-nitrophenyl), (E)—CH═CH-(3-nitrophenyl), (E)—CH═CH-(4-nitrophenyl), (E)—CH═CH-(4-chlorophenyl), (E)—CH═CH-(2,3,4-trifluoro-phenyl), (E)—CH═CH-(3-(trifluoromethyl)phenyl), (E)—CH═CH-(4-fluorophenyl), 2-indolyl, 5-fluoro-2-indolyl, 3-fluorophenyl, 3,5-dinitrophenyl, 3-(trifluoromethyl)benzyl, 3-fluorobenzyl, 4-chlorobenzyl, 4-methoxybenzyl, 4-(iso-propyl)benzyl, 3-nitrobenzyl, 2-phenoxyethyl, 2-(3,4-dimethoxyphenyl)ethyl, 2-(4-chlorobenzoyl)ethyl, 3-chloro-1-propyl 3-phenoxy-1-propyl, 3-phenyl-1-propyl, 3-benzylpropyl, dec-9-enyl, 1-methylbut-1-enyl, (2-thiophene)methyl, (3-thiophene)methyl, 2-(3-nitro-4-hydroxyphenyl)ethyl, 3,5-difluorobenzyl, 4-phenylbenzyl, 3,4-methylenedioxybenzyl, 2,6-difluorobenzyl, 4-(n-butoxy)benzyl, 3-methyl-1-butyl pent-4-ynyl, 3-phenoxybenzyl, 3-(5-bromo-4-methoxy)thiophene, 3-(5-chloro-4-methoxy)-thiophene, 3-methoxy-4-ethoxybenzyl, 4-(benzyloxy)benzyl 3-(2-thiophene)propyl, hex-5-ynyl, 1-(4-chlorophenyl)cyclopropyl, cyclopentylmethyl, 2-(cyclopentyl)ethyl, cyclohexylmethyl, 2-(cyclohexyl)ethyl, 3-(cyclohexyl)propyl 1-phenoxyethyl, (E)—C(CH$_3$)═CH-phenyl, 2-chloro-5-nitrophenyl, methyl. n-heptyl 2-furyl, 3-furyl, (2-thiophene)methyl, 2-indolyl, 2,4-difluorophenyl, (3-nitro-4-(methylsulphonyl))-phenyl, pent-4-ynyl, 5-methyl-2-pyrazinyl, cyclopentyl, (cyclohexyl)methyl, 3-nitro-4-methoxyphenyl, 2-tetrahydrofuryl, 2-pyridyl, 3-pyridyl, (E)—CH═CH-(4-nitrophenyl), 1,5-dimethyl-pyrazol-3-yl, cyclobutyl, 2-methoxyphenyl, 3-nitrophenyl, 4-nitrophenyl cyclohexyl, 4-nitropyrrole-2-yl, 3-nitro-4-methylphenyl, 3-nitro-4-fluorophenyl, (3-thiophene)methyl, 3-chloro-2-benzothiophene, 5-chloro-2-indolyl, (1-piperidine)ethyl, 3,4-methylenedioxyphenyl, but-3-ynyl, 3-cyanophenyl, 2-(acetamido)ethyl, 4-(trifluoromethyl)phenyl, 3-chloro-4-fluorophenyl, 4-fluoro-3-(trifluoromethyl)-phenyl, 4-fluorophenyl, 5-bromo-2-thiophene, 4-methoxyphenyl, 6-methyl-3-pyridyl, 5-nitro-2-furyl, 2-nitrophenyl, (E)—CH═CH-(3-chlorophenyl), 2-thiophene, cyclopropyl, -methylphenyl 2-chlorophenyl, 2-fluorophenyl, 2,5-dichlorophenyl, 3-fluorophenyl, 6-chloro-3-pyridyl, 5-bromo-2-furyl, 3-nitro-2-methylphenyl, 3-chlorophenyl, 3-(tetrahydrothiophene-1-1'-dioxide)methyl, 2-methoxyethyl, 2-(methylthio)phenyl.

Preferably $R^{64}$ is phenyl or halosubstituted phenyl and 2-chloro-4-fluorophenyl is a particularly preferred example.

In an alternative embodiment, the invention provides the use of a compound of formula (VI)

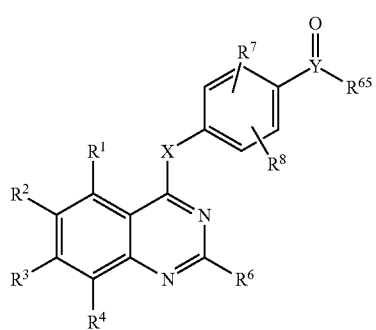

(VI)

or a salt, ester, amide or prodrug thereof;

where X, $R^1$, $R^2$, $R^3$, $R^4$, $R^6$, $R^7$ and $R^8$ are as defined in relation to formula (I);

Y is C, S or S(O)

$R^{65}$ is a group $R^9$, $OR^9$ or $NR^{10}R^{11}$ where $R^9$, $R^{10}$ and $R^{11}$ are as defined in relation to formula (I), in the preparation of a medicament for use in the inhibition of aurora 2 kinase.

For example, the compound of formula (VI) may be a compound of formula of formula (VIC)

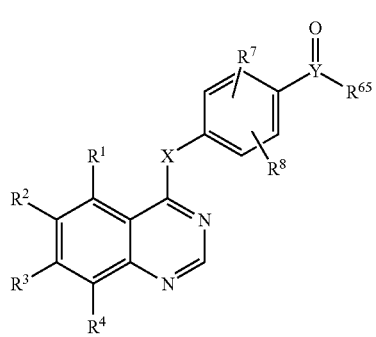

(VIC)

or a salt, ester or amide thereof;

where X, $R^7$ and $R^8$ are as defined in relation to formula (I);

Y is C, S or S(O), $R^{65}$ is a group $R^9$, $OR^9$ or $NR^{10}R^{11}$ where $R^9$, $R^{10}$ and $R^{11}$ are as defined in relation to formula (I), and $R^1$, $R^2$, $R^3$, $R^4$ are independently selected from, halo, cyano, nitro, trifluoromethyl, $C_{1-3}$alkyl, —$NR^{13}R^{14}$ (wherein $R^{13}$ and $R^{14}$, which may be the same or different, each represents hydrogen or $C_{1-3}$alkyl), or —$X^1R^{15}$ (wherein $X^1$ represents a direct bond, —O—, —$CH_2$—, —OCO—, carbonyl, —S—, —SO—, —$SO_2$—, —$NR^{16}CO$—, —$CONR^{16}$—, —$SO_2NR^{16}$—, —$NR^{17}SO_2$— or —$NR^{18}$— (wherein $R^{16}$, $R^{17}$ and $R^{18}$ each independently represents hydrogen, $C_{1-3}$alkyl or $C_{1-3}$alkoxy$C_{2-3}$alkyl), and $R^{15}$ is selected from one of the following groups:

1') hydrogen or $C_{1-5}$alkyl which may be unsubstituted or which may be substituted with one or more groups selected from hydroxy, fluoro or amino;

2') $C_{1-5}$alkyl$X^2COR^{19}$ (wherein $X^2$ represents —O— or —$NR^{20}$— in which $R^{20}$ represents hydrogen, $C_{1-3}$alkyl or $C_{1-3}$alkoxy$C_{2-3}$alkyl) and $R^{19}$ represents $C_{1-3}$alkyl, —$NR^{21}R^{22}$ or —$OR^{23}$ (wherein $R^{21}$, $R^{22}$ and $R^{23}$ which may be the same or different each represents hydrogen, $C_{1-3}$alkyl or $C_{1-3}$alkoxy$C_{2-3}$alkyl));

3') $C_{1-5}$alkyl$X^3R^{24}$ (wherein $X^3$ represents —O—, —S—, —SO—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);

5') $R^{36}$ (wherein $R^{36}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkyl$R^{36}$ (wherein $R^{36}$ is as defined in (5') above);

7') $C_{2-5}$alkenyl$R^{36}$ (wherein $R^{36}$ is as defined in (5') above);

8') $C_{2-5}$alkynyl$R^{36}$ (wherein $R^{36}$ is as defined in (5') above);

9') $R^{37}$ (wherein $R^{37}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{38}R^{39}$ and —$NR^{40}COR^{41}$ (wherein $R^{38}$, $R^{39}$, $R^{40}$ and $R^{41}$, which may be the same or different, each represents hydrogen, $C_{1-4}$alkyl or $C_{1-3}$alkoxy$C_{2-3}$alkyl));

10') $C_{1-5}$alkyl$R^{37}$ (wherein $R^{37}$ is as defined in (9') above);

11') $C_{2-5}$alkenyl$R^{37}$ (wherein $R^{37}$ is as defined in (9') above);

12') $C_{2-5}$alkynyl$R^{37}$ (wherein $R^{37}$ is as defined in (9') above);

13') $C_{1-5}$alkyl$X^6R^{37}$ (wherein $X^6$ represents —O—, —S—, —SO—, —$SO_2$—, —$NR^{42}CO$—, —$CONR^{43}$—, —$SO_2NR^{44}$—, —$NR^{45}SO_2$— or —$NR^{46}$— (wherein $R^{42}$, $R^{43}$, $R^{44}$, $R^{45}$ and $R^{46}$ each independently represents hydrogen, $C_{1-3}$alkyl or $C_{1-3}$alkoxy$C_{2-3}$alkyl) and $R^{37}$ is as defined hereinbefore);

14') $C_{2-5}$alkenyl$X^7R^{37}$ (wherein $X^7$ represents —O—, —S—, —SO—, —SO$_2$—, —NR$^{47}$CO—, —CONR$^{48}$—, —SO$_2$NR$^{49}$—, —NR$^{50}$SO$_2$— or —NR$^{51}$— (wherein $R^{47}$, $R^{48}$, $R^{49}$, $R^{50}$ and $R^{51}$ each independently represents hydrogen, $C_{1-3}$alkyl or $C_{1-3}$alkoxy$C_{2-3}$alkyl) and $R^{37}$ is as defined in (9') above);

15') $C_{2-5}$alkynyl$X^8R^{37}$ (wherein $X^8$ represents —O—, —S—, —SO—, —SO$_2$—, —NR$^{52}$CO—, —CONR$^{53}$—, —SO$_2$NR$^{54}$—, —NR$^{55}$SO$_2$— or —NR$^{56}$— (wherein $R^{52}$, $R^{53}$, $R^{54}$, $R^{55}$ and $R^{56}$ each independently represents hydrogen, $C_{1-3}$alkyl or $C_{1-3}$alkoxy$C_{2-3}$alkyl) and $R^{37}$ is as defined hereinbefore);

16') $C_{1-3}$alkyl$X^9C_{1-3}$alkyl$R^{37}$ (wherein $X^9$ represents —O—, —S—, —SO—, —SO$_2$—, —NR$^{57}$CO—, —CONR$^{58}$—, —SO$_2$NR$^{59}$—, —NR$^{60}$SO$_2$— or —NR$^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl) and $R^{37}$ is as defined hereinbefore); and 17') $C_{1-3}$alkyl$X^9C_{1-3}$alkyl$R^{36}$ (wherein $X^9$ and $R^{36}$ are as defined in (5') above).

Preferably Y is a carbon atom or an S(O) group, and is most preferably carbon.

Examples of $R^{65}$ include $R^9$ or $OR^9$ groups where $R^9$ is hydrogen, optionally substituted $C_{1-6}$alkyl or optionally substituted aryl such as optionally substituted phenyl. Suitable substituents for alkyl or aryl groups $R^9$ include functional groups as defined above but in particular nitro, halo such as fluoro or cyano.

Further examples of $R^{65}$ groups include $NR^{10}R^{11}$ where at least one of $R^{10}$ or $R^{11}$ is hydrogen and the other is selected from hydrogen, optionally substituted $C_{1-6}$alkyl, optionally substituted aryl or optionally substituted heterocyclyl. Suitable optional substituents for $R^{10}$ or $R^{11}$ include functional groups as defined above but in particular nitro, halo such as fluoro or cyano, haloalkyl such as trifluoromethyl, alkoxy such as methoxy. Alkyl groups $R^{10}$ or $R^{11}$ may also be substituted with aryl, cycloalkyl, cycloalkenyl, cycloalkynyl or heterocyclic groups, any of which may themselves be substituted with a functional group such as halo, or an alkyl group such as methyl. Aryl and heterocyclic groups $R^{10}$ and $R^{11}$ may be substituted with alkyl groups such as methyl.

In a particular embodiment, the group $Y(O)R^{65}$ is a group of sub-formula (VII)

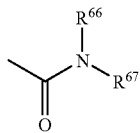

(VII)

where $R^{66}$ and $R^{67}$ are independently selected from hydrogen, optionally substituted hydrocarbyl or optionally substituted heterocyclyl, or $R^{66}$ and $R^{67}$ together with the nitrogen atom to which they are attached form an optionally substituted heterocyclic ring.

Examples of groups for $R^{66}$ and $R^{67}$ include the group —(CH$_2$)$_{q'}R^{70}$ where q' and $R^{70}$ are as defined above in relation to formula (III)

Suitably one of $R^{66}$ or $R^{67}$ is hydrogen, or methyl, ethyl or propyl optionally substituted with hydroxy and preferably one of $R^{66}$ or $R^{67}$ is hydrogen. In this case, the other is suitably a larger substituent for example of at least 4 carbon or heteroatoms, and is optionally substituted hydrocarbyl or optionally substituted heterocyclyl. Particular optionally substituted hydrocarbyl groups for $R^{66}$ or $R^{67}$ include alkyl, cycloalkyl, alkenyl, or aryl any of which is optionally substituted with a functional group as defined above, or in the case of aryl groups, with an alkyl group and in the case of alkyl group, with an aryl or heterocyclic group either of which may themselves be optionally substituted with alkyl or a functional group. Examples of optionally substituted aryl groups $R^{66}$ or $R^{67}$ include phenyl optionally substituted with one or more groups selected from $C_{1-6}$ alkyl group such as methyl or ethyl (either of which may be optionally substituted with a functional group such as hydroxy), or a functional group as defined above (such as halo like fluoro, chloro or bromo, hydroxy, alkoxy such as methoxy, trifluoromethyl, nitro, cyano, trifluoromethoxy, CONH$_2$, C(O)CH$_3$, amino, or dimethylamino).

When $R^{66}$ or $R^{67}$ is an optionally substituted alkyl group, it is suitably a $C_{1-6}$alkyl group, optionally substituted with one or more functional groups (such as cyano, hydroxy, alkoxy, in particular methoxy, COOalkyl such as COOCH$_3$), or aryl optionally substituted with a functional group as defined above (in particular in relation to $R^{66}$ or $R^{67}$ themselves, or an optionally substituted heterocyclic group such as N-methyl pyrrole.

When $R^{66}$ or $R^{67}$ is optionally substituted cycloalkyl, it is suitable cyclohexyl optionally substituted with a functional group such as hydroxy.

When $R^{66}$ or $R^{67}$ is optionally substituted alkenyl, it is suitably prop-2-enyl.

When $R^{66}$ or $R^{67}$ is optionally substituted heterocyclyl, or $R^{66}$ and $R^{67}$ together form a heterocyclic group, then this may be aromatic or non-aromatic and includes in particular, piperidine, piperazine, morpholino, pyrrolidine or pyridine any of which may be optionally substituted with a functional group such as hydroxy, alkoxy such as methoxy, or alkyl such as methyl which may itself be substituted with for instance a hydroxy group.

Suitable prodrugs of compounds of formula (I) are groups which enhance solubility and include phosphates and sulphates, in particular phosphates as well as alkyl, aryl or aralkyl derivatives thereof such as dibenzylphosphate. The prodrug moiety may be attached at any suitable position in the molecule, for example as a derivative of a hydroxy group, but in particular, may be advantageously present on one or more of groups $R^1$, $R^2$, $R^3$ or $R^4$, and preferably at $R^2$ or $R^3$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. Where the compound of formula (I) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-tnethoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of formula (I) which have a carboxy group which is derivatised into an amide such as a N—$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

Esters which are not in vivo hydrolysable may be useful as intermediates in the production of the compounds of formula (I).

Particular examples of compounds of formula (I) are set out in Tables 1-16 below

TABLE 1

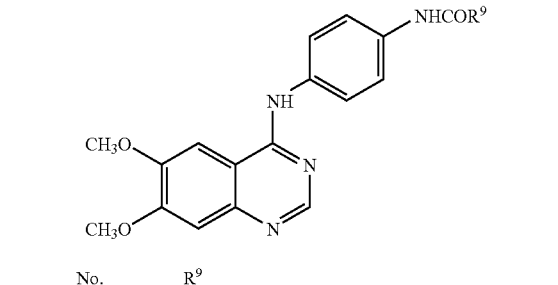

| No. | $R^9$ |
|---|---|
| 1 | phenyl |
| 2 | 2-furan |
| 3 | (E)-CH=2CH-phenyl |
| 4 | 3,4,5-trimethoxyphenyl |
| 5 | 2,4-difluorophenyl |
| 6 | 2-nitro-4,5-dimethoxyphenyl |
| 7 | 2,4-dinitrophenyl |
| 8 | 2-fluorobenzyl |
| 9 | cyclopentyl |
| 10 | 1-methylbut-3-enyl |
| 11 | $CH_2CN$ |
| 12 | n-heptyl |
| 13 | 2-(methylthio)ethyl |
| 14 | 2-ethoxyethyl |
| 15 | $C(CH_3)=CH_2$ |
| 16 | 5-methyl-2-pyrazine |
| 17 | 3-furyl |
| 18 | 3-cyanophenyl |
| 19 | 4-acetoxyphenyl |

TABLE 1-continued

| No. | $R^9$ |
|---|---|
| 20 | 2-nitro-3-methoxyphenyl |
| 21 | 2-methylthiophenyl |
| 22 | 3-acetoxyphenyl |
| 23 | 4-aminosulphonyl-1-hydroxy-2-naphthyl |
| 24 | 2-pyridyl |
| 25 | 2-quinolinyl |
| 26 | 1,5-dimethyl-1H-pyrazolyl |
| 27 | 2-fluoro-5-nitrophenyl |
| 28 | 3-pyridyl |
| 29 | 2-chloro-3-pyridyl |
| 30 | 2-fluorophenyl |
| 31 | 2,3-difluorophenyl |
| 32 | 2,5-difluorophenyl |
| 33 | 2,3-dimethoxyphenyl |
| 34 | 3,5-dimethoxy-4-hydroxyphenyl |
| 35 | 3-chloro-4-carboxyphenyl |
| 36 | 3-nitro-4-(methylsulphonyl)-phenyl |
| 37 | 3-nitro-4-methoxyphenyl |
| 38 | (E)-CH=CH-(2-nitrophenyl) |
| 39 | (E)-CH=CH-(3-nitrophenyl) |
| 40 | (E)-CH=CH-(4-nitrophenyl) |
| 41 | (E)-CH=CH-(4-chlorophenyl) |
| 42 | (E)-CH=CH-(2,3,4-trifluorophenyl) |
| 43 | (E)-CH=CH-(3-(trifluoromethyl)phenyl) |
| 44 | (E)-CH=CH-(4-fluorophenyl) |
| 45 | 2-indolyl |
| 46 | 5-fluoro-2-indolyl |
| 47 | 3-fluorophenyl |
| 48 | 3,5-dinitrophenyl |
| 49 | 3-(trifluoromethyl)benzyl |
| 50 | 4-fluorobenzyl |
| 51 | 4-chlorobenzyl |
| 52 | 4-methoxybenzyl |
| 53 | 4-(iso-propyl)benzyl |
| 54 | 3-nitrobenzyl |
| 55 | 2-phenoxyethyl |
| 56 | 2-(3,4-dimethoxyphenyl)ethyl |
| 57 | 2-(4-methoxybenzoyl)ethyl |
| 58 | 3-chloro-1-propyl |
| 59 | 3-phenoxy-1-propyl |
| 60 | 3-phenyl-1-propyl |
| 61 | 3-benzoylpropyl |
| 62 | dec-9-enyl |
| 63 | 1-methylbut-1-enyl |
| 64 | (2-thiophene)methyl |
| 65 | (3-thiophene)methyl |
| 66 | 2-(3-nitro-4-hydroxyphenyl)ethyl |
| 67 | 3,5-difluorobenzyl |
| 68 | 4-phenylbenzyl |
| 69 | 3,4-methylenedioxybenzyl |
| 70 | 2,6-difluorobenzyl |
| 71 | 4-(n-butoxy)benzyl |
| 72 | 3-methyl-1-butyl |
| 73 | pent-4-ynyl |
| 74 | 3-phenoxybenzyl |
| 75 | 3-(5-bromo-4-methoxy)thiophene |
| 76 | 3-(5-chloro-4-methoxy)thiophene |
| 77 | 3-methoxy-4-ethoxybenzyl |
| 78 | 4-(benzyloxy)benzyl |
| 79 | 3-(2-thiophene)propyl |
| 80 | hex-5-ynyl |
| 81 | 1-(4-chlorophenyl)cyclopropyl |
| 82 | cyclopentylmethyl |
| 83 | 2-(cyclopentyl)ethyl |

TABLE 1-continued

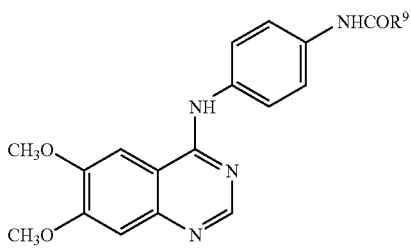

| No. | R⁹ |
|---|---|
| 84 | cyclohexylmethyl |
| 85 | 2-(cyclohexyl)ethyl |
| 86 | 3-(cyclohexyl)propyl |
| 87 | 1-phenoxyethyl |
| 88 | (E)-C(CH₃)=CH-phenyl |

TABLE 2

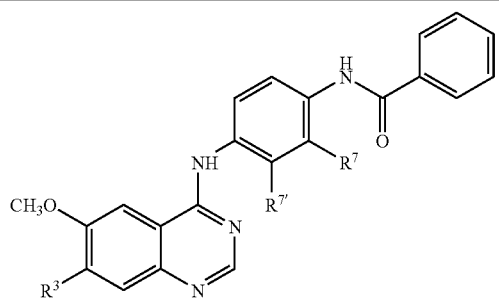

| Comp No. | R³ | R⁷ | R⁷' |
|---|---|---|---|
| 89 | OCH₃ | Cl | H |
| 90 | OCH₃ | CH₃ | H |
| 91 | OCH₃ | H | CH₃ |
| 92 | OCH₃ | OCH₃ | H |
| 93 | OCH₃ | CN | H |
| 94 | OCH₃ | H | CF₃ |
| 95 | benzyloxy | CH₃ | H |
| 96 | benzyloxy | CN | H |
| 97 | OCH₂CH₂CH₂-(4-morpholine) | CH₃ | H |
| 98 | OCH₂CH₂CH₂-(4-morpholine) | CF₃ | H |

TABLE 3

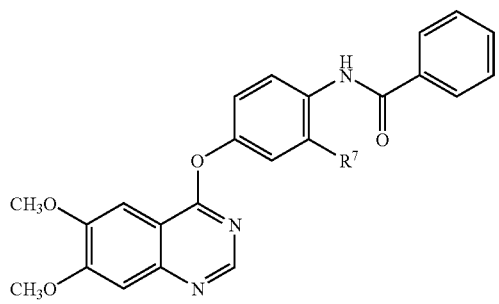

| Compound No | R⁷ | Compound No. | R⁷ |
|---|---|---|---|
| 99 | H | 100 | Cl |

TABLE 4

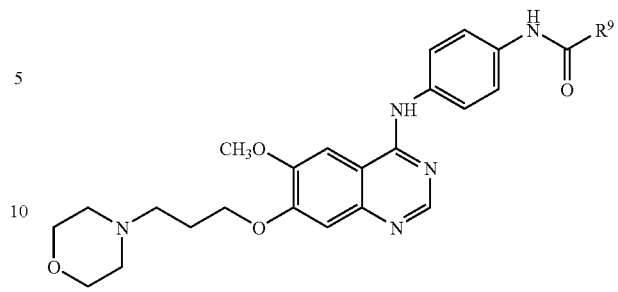

| No. | R⁹ |
|---|---|
| 101 | phenyl |
| 102 | tert-butoxy |
| 103 | 2-chloro-5-nitrophenyl |
| 104 | CH₃ |
| 105 | n-heptyl |
| 106 | 2-furyl |
| 107 | 3-furyl |
| 108 | (2-thiophene)methyl |
| 109 | 2-indolyl |
| 110 | 2,4-difluorophenyl |
| 111 | (3-nitro-4-(methylsulphonyl))-phenyl |
| 112 | pent-4-ynyl |
| 113 | 2-fluoro-5-nitrophenyl |
| 114 | 2-nitro-3-methoxyphenyl |
| 115 | 2-methylthio-phenyl |
| 116 | 5-methyl-2-pyrazinyl |
| 117 | hex-5-ynyl |
| 118 | cyclopentyl |
| 119 | (cyclohexyl)methyl |
| 120 | 3-nitro-4-methoxyphenyl |
| 121 | 2-tetrahydrofuryl |
| 122 | 2-pyridyl |
| 123 | 3-pyridyl |
| 124 | (E)-CH=CH-(4-nitrophenyl) |
| 125 | 2,4-dinitrophenyl |
| 126 | 3-acetoxyphenyl |
| 127 | 1,5-dimethyl-pyrazol-3-yl |
| 128 | cyclobutyl |
| 129 | 2-methoxyphenyl |
| 130 | 3-nitrophenyl |
| 131 | 4-nitrophenyl |
| 132 | cyclohexyl |
| 133 | 4-nitropyrrol-2-yl |
| 134 | 3-nitro-4-methylphenyl |
| 135 | 3-nitro-4-fluorophenyl |
| 136 | (3-thiophene)methyl |
| 137 | 3-chloro-2-benzothiophene |
| 138 | 5-chloro-2-indolyl |
| 139 | (1-piperidine)ethyl |
| 140 | 3,4-methylenedioxyphenyl |
| 141 | prop-3-ynyl |
| 142 | 3-cyanophenyl |
| 143 | 2-(acetamido)ethyl |
| 144 | 4-(trifluoromethyl)phenyl |
| 145 | 3-chloro-4-fluorophenyl |
| 146 | 4-fluoro-3-(trifluoromethyl)-phenyl |
| 147 | 4-fluorophenyl |
| 148 | 5-bromo-2-thiophene |
| 149 | 4-methoxyphenyl |
| 150 | 6-methyl-3-pyridyl |
| 151 | 5-nitro-2-furyl |
| 152 | 2-nitrophenyl |
| 153 | (E)-CH=CH-(3-chlorophenyl) |
| 154 | 2-thiophene |
| 155 | cyclopropyl |
| 156 | 3-methylphenyl |
| 157 | 2-chlorophenyl |
| 158 | 2-fluorophenyl |
| 159 | 2,5-dichlorophenyl |
| 160 | 3-fluorophenyl |
| 161 | 6-chloro-3-pyridyl |
| 162 | 5-bromo-2-furyl |
| 163 | 3-nitro-2-methylphenyl |
| 164 | 3-chlorophenyl |

TABLE 5

| No. | R⁹ |
|---|---|
| 165 | phenyl |
| 166 | 2-chloro-5-nitrophenyl |
| 167 | cyclopentyl |
| 168 | (cyclohexyl)methyl |
| 169 | 3-nitro-4-methoxyphenyl |
| 170 | n-heptyl |
| 171 | 2-furyl |
| 172 | 3-furyl |
| 173 | (2-thiophene)methyl |
| 174 | 2-indolyl |
| 175 | 2-tetrahydrofuryl |
| 176 | 2-pyridyl |
| 177 | 3-pyridyl |
| 178 | 2,4-dinitrophenyl |
| 179 | 2,4-difluorophenyl |
| 180 | pent-4-ynyl |
| 181 | 3-(tetrahydrothiophene-1,1'-dioxide)methyl |
| 182 | 2-methoxyethyl |
| 183 | 2-fluoro-5-nitrophenyl |
| 184 | 2-nitro-3-methoxyphenyl |
| 185 | 2-(methylthio)phenyl |
| 186 | 5-methyl-2-pyrazinyl |
| 187 | hex-5-ynyl |
| 188 | 3-acetoxyphenyl |
| 189 | 1,5-dimethyl-3-pyrazolyl |

TABLE 6

| Comp No | R⁶ | R² | R³ |
|---|---|---|---|
| 190 | H | acetoxy | OCH₃ |
| 191 | H | 2-methoxyethoxy | 2-methoxyethoxy |
| 192 | H | OCH₃ | benzyloxy |
| 193 | H | OCH₃ | (1-methyl-4-piperidine)methoxy |
| 194 | 4-morpholine | OCH₃ | OCH₃ |
| 195 | H | OH | OCH₃ |
| 196 | H | OCH₃ | OH |

TABLE 7

| Compd. No | R² |
|---|---|
| 197 | OCH₂CH₂(4-morpholine) |
| 198 | OCH₂CH₂CH₂(4-morpholine) |
| 199 | OCH₂CH₂CH₂(4-thiomorpholine-1,1'-dioxide) |
| 200 | 3-(methylsulphonyl)propoxy |
| 201 | (1-triazolyl)ethoxy |
| 202 | 2-(dimethylamino)ethoxy |
| 203 | (3-pyridyl)methoxy |
| 204 | 2-methoxyethoxy |
| 205 | 3-(dimethylamino)propoxy |
| 206 | benzyloxy |
| 207 | 2-hydroxyethoxy |

TABLE 8

| Comp No. | R³ |
|---|---|
| 208 | OCH₂CH₂CH₂(4-thiomorpholine-1,1'-dioxide) |
| 209 | OCH₂CH₂CH₂(4-morpholine) |
| 210 | OCH₂CH₂(4-morpholine) |
| 211 | 2-(dimethylamino)ethoxy |
| 212 | (1-triazolyl)ethoxy |
| 213 | 3-(methylsulphonyl)propoxy |
| 214 | N-(tert-butoxycarbonyl)-2-aminoethoxy |
| 215 | (3-pyridyl)methoxy |
| 216 | 2-methoxyethoxy |
| 217 | acetoxy |
| 218 | 3,4,5-trifluorobenzyl |
| 219 | OCH₂CH₂CH₂(1-(4,5-dihydro-1H-imidazolyl)) |
| 220 | (Z)-4-(1-pyrrolidine)but-2-enoxy |
| 221 | (E)-4-(1-pyrrolidine)but-2-enoxy |
| 222 | (Z)-4-(4-morpholine)but-2-enoxy |
| 223 | (E)-4-(4-morpholine)but-2-enoxy |
| 224 | (E)-4-(1-methyl-4-piperazine)but-2-enoxy |
| 225 | 2-hydroxyethoxy |
| 226 | 3-chloropropoxy |
| 227 | 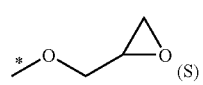 (S) |

TABLE 8-continued

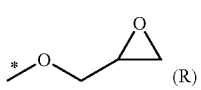

| Comp No. | $R^3$ |
|---|---|
| 228 | N-(tert-butoxycarbonyl)-3-pyrrolidinoxy |
| 229 | N-(iso-propyl)-3-azetidinoxy |
| 230 | (R) (epoxide methoxy structure) | where * indicates the point of attachment

TABLE 9

| Comp No. | $R^3$ |
|---|---|
| 231 | 2-(2,2,2-trifluoroethoxy)ethoxy |
| 232 | 2-aminoethoxy |
| 233 | O-(3-pyrrolidine) |
| 234 | 2-pyrrolidinomethoxy |
| 235 | O-(4-piperidine) |
| 236 | O-(1-methyl-4-piperidine) |
| 237 | (1-methyl-2-pyrrolidine)methoxy |
| 238 | O-(1-methyl-3-pyrrolidine) |
| 239 | $OCH_2CH_2CH_2$—$N(CH_3)$-(2-methoxyethyl) |
| 240 | $OCH_2CH_2CH_2$—$N(CH_3)$—$COCH_3$ |
| 241 | $OCH_2CH_2CH_2$—$N(CH_3)$—$CO$—$N(CH_3)_2$ |
| 242 | O-(1-(2-hydroxyethyl)-3-pyrrolidine) |
| 243 | O-(1-(2-methoxyethyl)-3-pyrrolidine) |
| 244 | O-(1-(cyanomethyl)-3-pyrrolidine) |
| 245 | O-(1-(2-hydroxyethyl)-4-piperidine) |
| 246 | O-(1-(cyanomethyl)-4-piperidine) |
| 247 | (1-(cyclopropyl)methyl-2-pyrrolidine)methoxy |
| 248 | (1-(cyclobutyl)methyl-2-pyrrolidine)methoxy |
| 249 | (1-(2-hydroxyethyl)-2-pyrrolidine)methoxy |
| 250 | (1-(2-thioethyl)ethyl)-2-pyrrolidine)methoxy |
| 251 | (1-(cyclopropyl)methyl-4-piperidine)methoxy |
| 252 | (1-(2-hydroxyethyl)-4-piperidine)methoxy |
| 253 | (1-(2-methoxyethyl)-4-piperidine)methoxy |
| 254 | (1-(cyanomethyl)-4-piperidine)methoxy |
| 255 | (4,5-dihydro-2-imidazolyl)methoxy |

TABLE 10

| No. | $R^B$ |
|---|---|
| 256 | NH-(2-thiophene)methyl |
| 257 | NH-(2-N-acetamido)ethyl |
| 258 | NH-(2-(di-iso-propylamino)ethyl) |
| 259 | NH-(2-methylthio)ethyl |
| 260 | NH-(1-carboxamido)ethyl |
| 261 | NH-(cyclopropyl) |
| 262 | NH-(cyclopropyl)methyl |
| 263 | NH-(cyclobutyl) |
| 264 | NH-(cyclopentyl) |
| 265 | NH-(1-imidazolyl)propyl |
| 266 | NH-cyclohexyl |
| 267 | NH-(4-hydroxy)cyclohexyl |
| 268 | NH-(cyclohexyl)methyl |
| 269 | NH-(1,3-dihydroxy-2-methyl-2-propyl) |
| 270 | tri(hydroxymethyl)-methylamino |
| 271 | NH-(3-(hydroxymethyl)-4-hydroxy-3-butyl) |
| 272 | NH-(1-hydroxy-4-methyl-2-pentyl) |
| 273 | NH-(1-ethyl-2-pyrrolidino)methyl |
| 274 | NH-(2-oxo-1-pyrroldino)propyl |
| 275 | NH-(2-tetrahydrofuryl)methyl |
| 276 | 4-(carboxamido)piperidine |
| 277 | NH-(2-(4-morpholino)ethyl) |
| 278 | NH-(3-(4-morpholino)propyl) |
| 279 | NH-(2-(1-piperidino)ethyl) |
| 280 | NH-(2-(1-pyrrolidino)ethyl) |
| 281 | NH-(3-hydroxy-2-methyl-2-hexyl) |
| 282 | NH-(2-methyl-1-hydroxy-2-propyl) |
| 283 | NH-(2-methyl-4-hydroxy-2-butyl) |
| 284 | NH-(iso-propyl) |
| 285 | NH-(1-hydroxy-2-propyl) |
| 286 | NH-(1-hydroxy-2-butyl) |
| 287 | NH-(2,3-dihydroxypropyl) |
| 288 | NH-(2-(dimethylamino)ethyl) |
| 289 | NH-(2-(diethylamino)ethyl) |
| 290 | NH-(2-methoxyethyl) |
| 291 | NH-(2-(2-hydroxyethoxy)ethyl) |
| 292 | NH-(2-hydroxyethyl) |
| 293 | NH-(2-mercaptoethyl) |
| 294 | NH-(2-(thioethyl)ethyl) |
| 295 | NH-(3-ethoxypropyl) |
| 296 | NH-(3-n-butoxypropyl) |
| 297 | NH-(3-hydroxypropyl) |
| 298 | NH-(5-hydroxypentyl) |
| 299 | NH-(1-methoxy-2-propyl) |
| 300 | NH-(4-hydroxybutyl) |
| 301 | NH-(3-methyl-5-pyrazolyl) |
| 302 | NH-(1-methyl-4-piperazinyl)-propyl |
| 303 | NH-(4-carboethoxy-4-piperidinyl) |
| 304 | NH-(2-(di-n-butyl)amino)ethyl |
| 305 | NH-(2-(di-n-propyl)amino)ethyl |
| 306 | NH-(tetrahydropyranyl)methyl |
| 307 | NH-(2-(2-thiopbene)ethyl) |
| 308 | NH-(1-hydroxy-2-hexyl) |
| 309 | NH-(1-hydroxy-4-(methylthio)-4-butyl) |
| 310 | NH-(2-(1-methyl-2-pyrrolidino)-ethyl) |
| 311 | NH-(5-methyl-2-furyl)methyl |
| 312 | NH-(3-tetrahydrothiophene-1,1'-dioxide) |
| 313 | NH-(2,2-dimethyl-3-hydroxy-1-propyl) |
| 314 | NH-(3-thiophene)methyl |
| 315 | 4-thiomorpholine |
| 316 | N(hydroxyethyl)-(2-(4-morpholino)ethyl) |
| 317 | di(2-hydroxyethyl)amino |

TABLE 10-continued

Structure: Quinazoline with 4-NH-(4-benzamidophenyl), 6-OCH₃, 7-O-CH₂CH₂-R^B

| No. | R^B |
|---|---|
| 318 | 1-piperidine |
| 319 | NH-(4-pyridyl)methyl |
| 320 | NH-(1,3-dihydroxy-2-propyl) |
| 321 | NH—CH₃ |
| 322 | N(CH₃)-(methylsulphonyl) |
| 323 | diethylamino |
| 324 | azepinyl |
| 325 | N(CH₃)-(2-hydroxyethyl) |
| 326 | 1-(2,5-dihydropyrrole) |
| 327 | N(CH₃)-(2-(dimethylamino)-ethyl) |
| 328 | 1-methyl-4-piperazine |
| 329 | 1-cyclopropyl-4-piperazine |
| 330 | 2-(hydroxymethyl)pyrrolidine |
| 331 | 4-hydroxypiperidine |
| 332 | 1-(2-(4-morpholino)ethyl)-4-piperazine |
| 333 | 1-(3-hydroxypropyl)-4-piperazine |
| 334 | N(CH₂CH₃)-(2-hydroxyethyl) |
| 335 | 3-hydroxypyrrolidine |
| 336 | N(CH₃)-(2-cyanoethyl) |
| 337 | (4-piperidino)piperidine |
| 338 | 2,6-dimethyl-4-morpholine |
| 339 | 1-acetyl-4-piperazine |
| 340 | N(CH₃)-allyl |
| 341 | 2-methylpyrrolidine |
| 342 | N(CH₂CH₃)-(iso-butyl) |
| 343 | N(CH₂CH₃)-(2-cyanoethyl) |
| 344 | N(CH₃)-(iso-butyl) |
| 345 | 4-ethyl-1-piperazine |
| 346 | 4-(4-fluorophenyl)-1-piperazine |
| 347 | 2-carboxy-3-thiazolidine |
| 348 | 4-(2-hydroxyethyl)-1-piperidine |
| 349 | N(CH₃)-(3-pyridyl)methyl |
| 350 | N(CH₃)-(2-pyridyl)methyl |
| 351 | 2,5-dimethylpyrrolidine |
| 352 | 1-(1,2,3,6-tetrahydropyridyl) |
| 353 | 4-methylpiperidine |
| 354 | 4-(2-hydroxyethyl)-1-piperazine |
| 355 | 2-(2-hydroxyethyl)piperidine |
| 356 | 2-ethyl-4,5-dihydro-1-imidazolyl |
| 357 | 4,5-dihydro-1-imidazolyl |

TABLE 11

Structure: Quinazoline with 4-NH-(4-benzamidophenyl), 6-OCH₃, 7-O-CH₂CH₂CH₂-R^B

| No. | R^B |
|---|---|
| 358 | NH-(2-acetamido)ethyl |
| 359 | NH-(1-carboxamido)ethyl |

TABLE 11-continued

| No. | R^B |
|---|---|
| 360 | NH-cyclopropyl |
| 361 | NH-(cyclopropyl)methyl |
| 362 | NH-cyclobutyl |
| 363 | NH-cyclopentyl |
| 364 | NH-(3-(1-imidazolyl)propyl |
| 365 | NH-cyclohexyl |
| 366 | NH-(4-hydroxy)cyclohexyl |
| 367 | NH-(cyclohexyl)methyl |
| 368 | NH-(1,1-di(hydroxymethyl)ethyl |
| 369 | NH-(tri(hydroxymethyl)-methyl) |
| 370 | NH-(3-(hydroxymethyl)-4-hydroxy-3-butyl) |
| 371 | NH-(1-hydroxy-4-methyl-2-pentyl) |
| 372 | NH-(2-tetrahydrofuryl)methyl |
| 373 | 4-(carboxamido)piperidine |
| 374 | NH-(2-(4-morpholine)ethyl) |
| 375 | NH-(2-methyl-3-hydroxy-2-propyl) |
| 376 | NH-(2-methyl-4-hydroxy-2-butyl) |
| 377 | NH-iso-propyl |
| 378 | NH-(1-hydroxy-2-propyl) |
| 379 | NH-(1-hydroxy-2-butyl) |
| 380 | NH-(2,3-dihydroxypropyl) |
| 381 | NH-(2-methoxyethyl) |
| 382 | NH-(2-hydroxyethoxy)ethyl |
| 383 | NH-(2-mercaptoethyl) |
| 384 | NH-(2-thioethyl)ethyl |
| 385 | NH-(3-(diethylamino)propyl) |
| 386 | NH-(3-ethoxypropyl) |
| 387 | NH-(3-hydroxypropyl) |
| 388 | NH-(5-hydroxypentyl) |
| 389 | 2-(carboxamido)pyrroldine |
| 390 | NH-(3-methyl-5-pyrazolyl) |
| 391 | NH-(2-tetrahydropyran)-methyl |
| 392 | NH-(1-hydroxy-6-hexyl) |
| 393 | NH-(5-methyl-2-furyl)-methyl |
| 394 | NH-(2-methyl-3-hydroxy-2-propyl) |
| 395 | NH-(3-thiophene)methyl |
| 396 | NH-2-hydroxyethyl |
| 397 | NH-(2-thiophene)methyl |
| 398 | piperidine |
| 399 | pyrrolidine |
| 400 | 4-methyl-1-piperazine |
| 401 | diethylamino |
| 402 | di-(2-hydroxyethyl)amino |
| 403 | N(CH₃)-(1-methyl-3-pyrrolidinyl) |
| 404 | N(CH₃)—CH₂CONH—CH₃ |
| 405 | 2-oxo-4-piperazine |
| 406 | NH-(4-hydroxy-3-tetrahydrofuryl) |
| 407 | 4-methylpiperidine |
| 408 | 3,5-dimethylpiperidine |
| 409 | N(CH₃)-(4-hydroxy-4-methyl-3-tetrahydropyranyl) |
| 410 | 1-(2,3-dihydropyrrolyl) |
| 411 | 2-(hydroxymethyl)-4-hydroxypyrrolidine |
| 412 | N(CH₃)-(3-hydroxy-4-tetrahydropyranyl) |
| 413 | N(CH₃)-(cyclobutyl)methyl |
| 414 | 3-hydroxyazetidine |
| 415 | N(CH₃)-(2-cyanoethyl) |
| 416 | N(CH₃)-(2-(4-morpholino)ethyl) |
| 417 | 1-(2-methoxyethyl)-4-piperazine |
| 418 | 2,6-dimethylmorpholine |
| 419 | thiomorpholine |
| 420 | 2-methylpiperidine |
| 421 | 2,6-dimethylpiperidine |
| 422 | 2-(hydroxymethyl)piperidine |
| 423 | 3-(hydroxy)piperidine |

TABLE 11-continued

| No. | R^B |
|---|---|
| 424 | 1-(2,5-dihydropyrrolyl) |
| 425 | di(2-methoxyethyl)amino |
| 426 | 4-hydroxypiperidine |
| 427 | 2-(carboxamido)pyrrolidine |
| 428 | 4-(iso-propyl)-1-piperazine |
| 429 | N(CH$_3$)-((2-tetrahydrofuryl)methyl) |
| 430 | 4-acetyl-1-piperidine |
| 431 | 3-hydroxypyrrolidine |
| 432 | N(CH$_3$)-(1-methyl-4-piperidinyl) |
| 433 | 4-pyrrolidino-1-piperidine |
| 434 | 4-methyl-1-diazepinyl |
| 435 | 2,2-dimethyl-4-tetrahydropyranyl |
| 436 | 1-(2-hydroxyethyl)-4-piperazine |
| 437 | N(CH$_3$)-(2-hydroxyethyl) |
| 438 | 2-(hydroxymethyl)-pyrrolidine |
| 439 | 3-(hydroxymethyl)piperidine |
| 440 | 2,5-dimethyl-1-piperazine |
| 441 | NH—CH$_3$ |

TABLE 12

| No. | R^B |
|---|---|
| 442 | NH-(3-dimethylamino)ethyl |
| 443 | NH-(3-diethylamino)ethyl |
| 444 | NH-(2-(2-hydroxyethoxy)ethyl) |
| 445 | NH-(2-hydroxyethyl) |
| 446 | NH-(2-(thioethyl)ethyl) |
| 447 | NH-(3-diethylamino)propyl |
| 448 | NH-(3-ethoxypropyl) |
| 449 | NH-(3-hydroxypropyl) |
| 450 | NH-(5-hydroxypentyl) |
| 451 | NH-(4-hydroxybutyl) |
| 452 | NH-(5-methyl-3-pyrazolyl) |
| 453 | NH-(1-hydroxycyclohexyl)methyl |
| 454 | NH-(2-(2-thiophene)ethyl) |
| 455 | NH-(1-hydroxy-2-hexyl) |
| 456 | NH-(2-(1-methyl-2-pyrrolidino)ethyl) |
| 457 | NH-(5-methyl-2-furyl)methyl |
| 458 | NH-(2,2-dimethyl-3-hydroxy-1-propyl) |
| 459 | NH-(3-thiophene)methyl |
| 460 | NH-(2,3-dihydroxypropyl) |
| 461 | NH-cyclobutyl |
| 462 | NH-cyclopentyl |
| 463 | NH-(3-(1-imidazolyl)propyl) |
| 464 | NH-cyclohexyl |

TABLE 12-continued

| No. | R^B |
|---|---|
| 465 | NH-(4-hydroxycyclohexyl) |
| 466 | NH-(cyclohexyl)methyl |
| 467 | NH-(1,3-dihydroxy-2-methyl-2-propyl) |
| 468 | NH-tri(hydroxymethyl)methyl |
| 469 | NH-(3-(hydroxymethyl)-4-hydroxy-3-butyl) |
| 470 | NH-(1-ethyl-2-pyrrolidino)methyl |
| 471 | NH-(2-tetrahydrofuryl)methyl |
| 472 | 4-(carboxamido)piperidine |
| 473 | NH-(2-(4-morpholino)ethyl) |
| 474 | NH-(2-methyl-3-hydroxy-2-propyl) |
| 475 | NH-(2-methyl-4-hydroxy-2-butyl) |
| 476 | NH-(iso-propyl) |
| 477 | NH-(1-methyl-2-hydroxyethyl) |
| 478 | NH-cyclopropyl |
| 479 | NH-(2-thiophene)methyl (S) |
| 480 | NH-(N-acetyl-2-aminoethyl) |
| 481 | NH-(2-(methylthio)ethyl) |
| 482 | NH-(2-(1-piperidino)ethyl) |
| 483 | 2-(carboxamido)pyrrolidine |
| 484 | NH-(1-hydroxy-4-methyl-2-pentyl) |
| 485 | NH-(1-hydroxy-2-butyl) |
| 486 | 2-(carboxamido)pyrrolidine |
| 487 | NH-(1-hydroxy-4-methyl-2-pentyl) |
| 488 | NH-(1-hydroxy-2-butyl) |
| 489 | NH-(3-dimethylamino)ethyl |
| 490 | NH-(2-(2-hydroxyethoxy)ethyl) |
| 491 | NH-(2-hydroxyethyl) |
| 492 | NH-(2-(thioethyl)ethyl) |
| 493 | NH-(3-diethylamino)propyl |
| 494 | NH-(3-ethoxypropyl) |
| 495 | NH-(3-hydroxypropyl) |
| 496 | NH-(5-hydroxypentyl) |
| 497 | NH-(4-hydroxybutyl) |
| 498 | NH-(5-methyl-3-pyrazolyl) |
| 499 | NH-(1-hydroxycyclohexyl)-methyl |
| 500 | NH-(2-(2-thiophene)ethyl) |
| 501 | NH-(1-hydroxy-2-hexyl) |
| 502 | NH-(2-(1-methyl-2-pyrrolidino)ethyl) |
| 503 | NH-(5-methyl-2-furyl)methyl |
| 504 | NH-(2,2-dimethyl-3-hydroxy-1-propyl) |
| 505 | NH-(3-thiophene)methyl |
| 506 | NH-cyclobutyl |
| 507 | NH-cyclopentyl |
| 508 | NH-cyclohexyl |
| 509 | NH-(4-hydroxy)cyclohexyl |
| 510 | NH-(cyclohexyl)methyl |
| 511 | NH-(1,3-dihydroxy-2-methyl-2-propyl) |
| 512 | NH-(3-(hydroxymethyl)-4-hydroxy-3-butyl) |
| 513 | NH-(1-ethyl-2-pyrrolidino)methyl |
| 514 | NH-(2-tetrahydrofuryl)methyl |
| 515 | 4-(carboxamido)piperidine |
| 516 | NH-(2-(4-morpholino)ethyl) |
| 517 | NH-(2-methyl-3-hydroxy-2-propyl) |
| 518 | NH-(2-methyl-4-hydroxy-2-butyl) |
| 519 | NH-(iso-propyl) |
| 520 | NH-(1-methyl-2-hydroxyethyl) |
| 521 | NH-cyclopropyl |
| 522 | NH-(2-thiophene)methyl (R) |

TABLE 12-continued

Structure: quinazoline with 6-OCH₃, 7-O-CH₂-CH(OH)-CH₂-R^B, 4-NH-C₆H₄-NHCO-C₆H₅

| No. | R^B |
|---|---|
| 523 | NH-(N-acetyl-2-aminoethyl) |
| 524 | NH-(2-(methylthio)ethyl) |
| 525 | di(2-hydroxyethyl)amino |

TABLE 13

Structure: quinazoline with 6-OCH₃, 7-O-CH₂-CH₂-O-P(=O)(OR^C)(OR^D), 4-NH-C₆H₄-NHCO-C₆H₅

| Compound No. | R^C | R^D |
|---|---|---|
| 526 | tert-butyl | tert-butyl |
| 527 | benzyl | benzyl |
| 528 | H | H |

TABLE 14

Structure: quinazoline with $R^2$ at 6-position, $R^3$ at 7-position, 4-NH-C₆H₄-NHCO-C₆H₅

| No. | $R^3$ | $R^2$ |
|---|---|---|
| 529 | (E)-CH=CH—CO—OCH₃ | OCH₃ |
| 530 | (E)-CH=CH—CO₂H | OCH₃ |
| 531 | 3-hydroxyprop-1-enyl | OCH₃ |
| 532 | (E)-CH=CH—CO-(1-piperidine) | OCH₃ |
| 533 | 3-hydroxypropyl | OCH₃ |
| 534 | (E)-CH=CH—CO-(4-(2-(dimethylamino)ethyl)-1-piperazine) | OCH₃ |
| 535 | 3-hydroxy-3-methylbut-1-ynyl | H |
| 536 | 3-hydroxy-prop-1-ynyl | OCH₃ |
| 537 | NH₂ | H |
| 538 | NHCO-(4-pyridyl) | H |
| 539 | NHCO-(2-(1-piperidino)ethyl) | H |
| 540 | NHCO-(acetoxymethyl) | H |

TABLE 15

| No. | X | R⁹ | Rᴱ |
|---|---|---|---|
| 541 | O | phenyl | H |
| 542 | NH | CH₃ | OCH₃ |

TABLE 16

| No. | R3 | X | R⁵ | Rᴱ | Rᶠ |
|---|---|---|---|---|---|
| 543 | OCH₃ | NH | CO-(n-butoxy) | H | H |
| 544 | OCH₃ | NH | CO-phenyl | H | H |
| 545 | OCH₃ | NH | SO₂NH₂ | H | H |
| 546 | OCH₃ | NH | SO₂-(4-nitrophenyl) | H | H |
| 547 | OCH₃ | NH | CONH-(2-cyanophenyl) | H | Cl |
| 548 | OCH₃ | NH | CO-(4-fluorophenyl) | H | F |
| 549 | OCH₃ | NH | SO₂NH-(4,5-dimethyl-2-oxazolyl) | H | H |
| 550 | OCH₃ | O | SO₂NH₂ | H | H |
| 551 | OCH₃ | O | CHO | H | OCH₃ |
| 552 | OCH₃ | O | methylsulphonyl | H | H |
| 553 | OCH₃ | O | CO-phenyl | H | H |
| 554 | OCH₃ | O | CHO | OEt | H |
| 555 | OCH₃ | NH | CONH-(n-heptyl) | H | H |
| 556 | OCH₃ | NH | CONH-(3-methoxypropyl) | H | H |
| 557 | OCH₃ | NH | CONH-(4-fluorobenzyl) | H | H |
| 558 | OCH₃ | NH | CONH-(2-(cyclohex-1-enyl)ethyl) | H | H |
| 559 | OCH₃ | NH | CONH-(2-thiophene)ethyl | H | H |
| 560 | OCH₃ | NH | CONH—CH₂CF₃ | H | H |
| 561 | OCH₃ | NH | CONH-(2-(methylthio)ethyl) | H | H |
| 562 | OCH₃ | NH | CONH-(1-indanyl) | H | H |
| 563 | OCH₃ | NH | CONH-cyclohexyl | H | H |
| 564 | OCH₃ | NH | CONH-(cyclohexyl)methyl | H | H |
| 565 | OCH₃ | NH | CONH-(6-chloro-3-pyridyl) | H | H |
| 566 | OCH₃ | H | CONH-(4-nitrobenzyl) | H | H |
| 567 | OCH₃ | NH | CONH-(2-(1,3,4-thiadiazole)) | H | H |
| 568 | OCH₃ | NH | CONH-(2-pyridyl) | H | H |
| 569 | OCH₃ | NH | CONH-(1-isoquinolyl) | H | H |
| 570 | OCH₃ | NH | CONH-(3-(trifluoromethyl)-4-nitrophenyl)) | H | H |
| 571 | OCH₃ | NH | CONH-(1,3-dimethylbuty-1-yl) | H | H |
| 572 | OCH₂CH₂CH₂(4-morpholine) | NH | CO₂H | H | H |
| 573 | OCH₂CH₂CH₂(4-morpholine) | NH | SO₂NH₂ | H | H |
| 574 | OCH₂CH₂CH₂(4-morpholine) | NH | SO₂NH-(5-methoxy-2-pyrimidinyl) | H | H |
| 575 | OCH₂CH₂CH₂(4-morpholine) | NH | SO₂NH-(4,5-dimethyl-2-oxazolyl) | H | H |
| 576 | OCH₂CH₂CH₂(4-morpholine) | NH | SO₂NH-(3,4-dimethyl-5-isoxazolyl) | H | H |
| 577 | benzyloxy | NH | CONH₂ | H | H |
| 578 | benzyloxy | NH | CO-phenyl | H | H |
| 579 | OCH₂CF₃ | NH | CO-(4-fluorophenyl) | H | Cl |
| 580 | OCH₂CH₂CH₂(4-morpholine) | NH | CONH-(cylopentyl) | H | H |
| 581 | OCH₂CH₂CH₂(4-morpholine) | NH | CONH-(cyclohexyl) | H | H |
| 582 | OCH₂CH₂CH₂(4-morpholine) | NH | CONH-(cyclohexyl)methyl | H | H |
| 583 | OCH₂CH₂CH₂(4-morpholine) | NH | CONH-(6-chloro-3-pyridyl) | H | H |
| 584 | OCH₂CH₂CH₂(4-morpholine) | NH | CONH-(2-furyl)methyl | H | H |
| 585 | OCH₂CH₂CH₂(4-morpholine) | NH | CONH-(2-tetrahydrofuryl)methyl | H | H |
| 586 | OCH₂CH₂CH₂(4-morpholine) | NH | CONH-(2-pyridyl) | H | H |
| 587 | OCH₂CH₂CH₂(4-morpholine) | NH | CONH-(3-pyridyl) | H | H |
| 588 | OCH₂CH₂CH₂(4-morpholine) | NH | CONH-(1,3-dimethylbuty-1-yl) | H | H |
| 589 | OCH₂CH₂CH₂(4-morpholine) | NH | CONH-CH₂CF₃ | H | H |
| 590 | OCH₂CH₂CH₂(4-morpholine) | NH | CONH-(3-ethoxypropyl) | H | H |
| 591 | OCH₂CH₂CH₂(4-morpholine) | NH | CONH-(3-(methylthio)propyl) | H | H |
| 592 | OCH₂CH₂CH₂(4-morpholine) | NH | CONH-(1-methyl-2-methoxyethyl) | H | H |
| 593 | OCH₂CH₂CH₂(4-morpholine) | NH | CONH-(3-methylcyclohexyl) | H | H |
| 594 | OCH₂CH₂CH₂(4-morpholine) | NH | CONH-(2-indanyl) | H | H |
| 595 | OCH₂CH₂CH₂(4-morpholine) | NH | CONH-(2-(cyclohex-1-enyl)ethyl) | H | H |
| 596 | OCH₂CH₂CH₂(4-morpholine) | NH | CONH-2-(2-thiophene)ethyl | H | H |
| 597 | OCH₂CH₂CH₂(4-morpholine) | NH | CONH-(5-methyl-2-furyl)methyl | H | H |
| 598 | OCH₂CH₂CH₂(4-morpholine) | NH | CONH-(3-(tetrahydrothiophene-1,1'-dioxide) | H | H |
| 599 | OCH₃ | NH | CONH-(2-methylpentyl) | H | H |
| 600 | OCH₃ | NH | CONH-(3-ethoxypropyl) | H | H |
| 601 | OCH₃ | NH | CONH-(3-(methylthio)propyl) | H | H |
| 602 | OCH₃ | NH | CONH-(n-hexyl) | H | H |
| 603 | OCH₂CF₃ | NH | CONH₂ | H | H |

TABLE 16-continued

[Structure: quinazoline with CH3O- at position 6, R3 at position 7, X linkage to a phenyl with R5, R^E, R^F substituents]

| No. | R3 | X | R5 | R^E | R^F |
|---|---|---|---|---|---|
| 604 | OCH₂CF₃ | NH | SO₂NH-(4,5-dimethyl-2-oxazolyl) | H | H |
| 605 | OCH₂CF₃ | NH | CO-(4-chlorophenyl) | H | Cl |
| 606 | OCH₂CF₃ | NH | SO₂NH-phenyl | H | H |
| 607 | OCH₂CF₃ | NH | CO-phenyl | H | H |
| 608 | OCH₂CF₃ | NH | SO₂-(4-nitrophenyl) | H | H |
| 609 | OCH₂CF₃ | NH | CONH-(3-(trifluoromethyl)phenyl) | H | H |
| 610 | OCH₂CF₃ | NH | CONH-2-(methylthio)ethyl | H | H |
| 611 | OCH₂CF₃ | NH | CONH-(cyclopentyl) | H | H |
| 612 | OCH₂CF₃ | NH | CONH-(cyclohexyl) | H | H |
| 613 | OCH₂CF₃ | NH | CONH-(6-chloro-3-pyridyl) | H | H |
| 614 | OCH₂CF₃ | NH | CONH-(2-tetrahydrofurylmethyl) | H | H |
| 615 | OCH₂CF₃ | NH | CONH-(2-(4-morpholino)ethyl) | H | H |
| 616 | OCH₂CF₃ | NH | CONH-(2-pyridyl) | H | H |
| 617 | OCH₂CF₃ | NH | CONH-(3-pyridyl) | H | H |
| 618 | OCH₂CF₃ | NH | CONH-(1,3-dimethylbuty-1-yl) | H | H |
| 619 | OCH₂CF₃ | NH | CONH—CH₂CF₃ | H | H |
| 620 | OCH₂CF₃ | NH | CONH-(2,3-dihydroxypropyl) | H | H |
| 621 | OCH₂CF₃ | NH | CONH-(2-methylpentyl) | H | H |
| 622 | OCH₂CF₃ | NH | CONH-(3-(dimethylamino)propyl) | H | H |
| 623 | OCH₂CF₃ | NH | CONH-(3-ethoxypropyl) | H | H |
| 624 | OCH₂CF₃ | NH | CONH-(3-methylcyclohexyl) | H | H |
| 625 | OCH₂CF₃ | NH | CONH-(2-indanyl) | H | H |
| 626 | OCH₂CF₃ | NH | CONH-(2-(cyclohex-1-enyl)ethyl) | H | H |
| 627 | OCH₂CF₃ | NH | CONH-2-(2-thiophene)ethyl | H | H |
| 628 | OCH₂CF₃ | NH | CONH-(2-(1-methyl-2-pyrrolidino)ethyl) | H | H |

In all the above Tables, Ph is phenyl, Me is methyl and Et is ethyl.

Certain compounds of formula (I) are novel and form a further aspect of the invention. Thus the invention further provides a compound of formula (IIA) which comprises a compound of formula (II) as defined above, or a salt, ester, amide or prodrug thereof, provided that (i) where $R^1$, $R^4$, $R^6$, $R^7$ and $R^8$ are all hydrogen and $R^2$ and $R^3$ are both hydrogen or both methoxy, $R^{64}$ is other than phenyl;

(ii) where $R^1$, $R^4$, $R^6$, $R^7$ and $R^8$ are all hydrogen and $R^2$ and $R^3$ are methoxy, and Z is C(O), $R^{64}$ is other than methyl; and (iii) where $R^1$, $R^2$, $R^3$, $R^4$, $R^6$, $R^7$ and $R^8$ are all hydrogen, X is oxygen, $R^6$ is 4-methyl-1-piperazinyl and Z is C(O), $R^{64}$ is other methyl.

Examples of such compounds are compounds of formula (IIC)

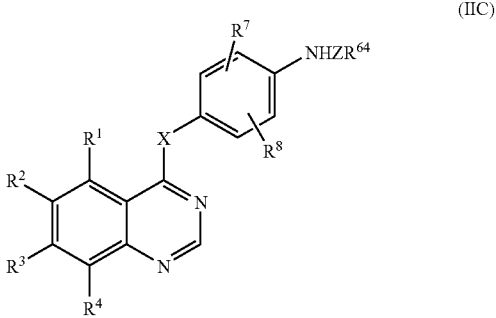

(IIC)

or a salt, ester or amide thereof;

where X is O, or S, S(O) or S(O)₂, or $NR^8$ where $R^8$ is hydrogen or $C_{1-6}$alkyl;

Z is C(O) or S(O)₂, $R^{64}$ is optionally substituted hydrocarbyl or optionally substituted heterocyclyl;

$R^7$ and $R^8$ are independently selected from hydrogen, halo, $C_{1-4}$alkyl, $C_{1-4}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_4$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl; and where $R^1$, $R^2$, $R^3$ and $R^4$ are independently selected from, halo, cyano, nitro, trifluoromethyl, $C_{1-3}$alkyl, —$NR^{13}R^{14}$ (wherein $R^{13}$ and $R^{14}$, which may be the same or different, each represents hydrogen or $C_{1-3}$alkyl), or —$X^1R^{15}$ wherein $X^1$ represents a direct bond, —O—, —CH₂—, —OCO—, carbonyl, —S—, —SO—, —SO₂—, —$NR^{16}$CO—, —$CONR^{16}$—, —SO₂$NR^{16}$—, —$NR^{17}$SO₂— or —$NR^{18}$— (wherein $R^{16}$, $R^{17}$ and $R^{18}$ each independently represents hydrogen, $C_{1-3}$alkyl or $C_{1-3}$alkoxy$C_{2-3}$alkyl), and $R^{15}$ is selected from one of the following groups:

1') hydrogen or $C_{1-5}$alkyl which may be unsubstituted or which may be substituted with one or more groups selected from hydroxy, fluoro or amino;

2') $C_{1-5}$alkylX$^2$COR$^{19}$ (wherein X$^2$ represents —O— or —NR$^{20}$— in which R$^{20}$ represents hydrogen, $C_{1-3}$alkyl or $C_{1-3}$alkoxy$C_{2-3}$alkyl) and R$^{19}$ represents $C_{1-3}$alkyl, —NR$^{21}$R$^{22}$ or —OR$^{23}$ (wherein R$^{21}$, R$^{22}$ and R$^{23}$ which may be the same or different each represents hydrogen, $C_{1-3}$alkyl or $C_{1-3}$alkoxy$C_{2-3}$alkyl));

3') $C_{1-5}$alkylX$^3$R$^{24}$ (wherein X$^3$ represents —O—, —S—, —SO—, —SO$_2$—, —OCO—, —NR$^{25}$CO—, —CONR$^{26}$—, —SO$_2$NR$^{27}$—, —NR$^{28}$SO$_2$— or —NR$^{29}$— (wherein R$^{25}$, R$^{26}$, R$^{27}$, R$^{28}$ and R$^{29}$ each independently represents hydrogen, $C_{1-3}$alkyl or $C_{1-3}$alkoxy$C_{2-3}$alkyl) and R$^{24}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_4$alkyl, $C_{1-4}$hydroxyalkyl and $C_{1-4}$alkoxy);

4') $C_{1-5}$alkylX$^4$$C_{1-5}$alkylX$^5$R$^{30}$ (wherein X$^4$ and X$^5$ which may be the same or different are each —O—, —S—, —SO—, —SO$_2$—, —NR$^{31}$CO—, —CONR$^{32}$—, —SO$_2$NR$^{33}$—, —NR$^{34}$SO$_2$— or —NR$^{35}$— (wherein R$^{31}$, R$^{32}$, R$^{34}$ and R$^{35}$ each independently represents hydrogen, $C_{1-3}$alkyl or $C_{1-3}$alkoxy$C_{2-3}$alkyl) and R$^{30}$ represents hydrogen or $C_{1-3}$alkyl);

5') R$^{36}$ (wherein R$^{36}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkylR$^{36}$ (wherein R$^{36}$ is as defined in (5') above);

7') $C_{2-5}$alkenylR$^{36}$ (wherein R$^{36}$ is as defined in (5') above);

8') $C_{2-5}$alkynylR$^{36}$ (wherein R$^{36}$ is as defined in (5') above);

9') R$^{37}$ (wherein R$^{37}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —CONR$^{38}$R$^{39}$ and —NR$^{40}$COR$^{41}$ (wherein R$^{38}$, R$^{39}$, R$^{40}$ and R$^{41}$, which may be the same or different, each represents hydrogen, $C_{1-4}$alkyl or $C_{1-3}$alkoxy$C_{2-3}$alkyl));

10') $C_{1-5}$alkylR$^{37}$ (wherein R$^{37}$ is as defined in (9') above);

11') $C_{2-5}$alkenylR$^{37}$ (wherein R$^{37}$ is as defined in (9') above);

12') $C_{2-5}$alkynylR$^{37}$ (wherein R$^{37}$ is as defined in (9') above);

13') $C_{1-5}$alkylX$^6$R$^{37}$ (wherein X$^6$ represents —O—, —S—, —SO—, —SO$_2$—, —NR$^{42}$CO—, —CONR$^{43}$—, —SO$_2$NR$^{44}$—, —NR$^{45}$SO$_2$— or —NR$^{46}$— (wherein R$^{42}$, R$^{43}$, R$^{44}$, R$^{45}$ and R$^{46}$ each independently represents hydrogen, $C_{1-3}$alkyl or $C_{1-3}$alkoxy$C_{2-3}$alkyl) and R$^{37}$ is as defined hereinbefore);

14') $C_{2-5}$alkenylX$^7$R$^{37}$ (wherein X$^7$ represents —O—, —S—, —SO—, —SO$_2$—, —NR$^{47}$CO—, —CONR$^{48}$—, —SO$_2$NR$^{49}$—, —NR$^{50}$SO$_2$— or —NR$^{51}$— (wherein R$^{47}$, R$^{48}$, R$^{49}$, R$^{50}$ and R$^{51}$ each independently represents hydrogen, $C_{1-3}$alkyl or $C_{1-3}$alkoxy$C_{2-3}$alkyl) and R$^{37}$ is as defined in (9') above);

15') $C_{2-5}$alkynylX$^8$R$^{37}$ (wherein X$^8$ represents —O—, —S—, —SO—, —SO$_2$—, —NR$^{52}$CO—, —CONR$^{53}$—, —SO$_2$NR$^{54}$—, —NR$^{55}$SO$_2$— or —NR$^{56}$— (wherein R$^{52}$, R$^{53}$, R$^{54}$, R$^{55}$ and R$^{56}$ each independently represents hydrogen, $C_{1-3}$alkyl or $C_{1-3}$alkoxy$C_{2-3}$alkyl) and R$^{37}$ is as defined hereinbefore);

16') $C_{1-3}$alkylX$^9$$C_{1-3}$alkylR$^{37}$ (wherein X$^9$ represents —O—, —S—, —SO—, —SO$_2$—, —NR$^{57}$CO—, —CONR$^{58}$—, —SO$_2$NR$^{59}$—, —NR$^{60}$SO$_2$— or —NR$^{61}$— (wherein R$^{57}$, R$^{58}$, R$^{59}$, R$^{60}$ and R$^{61}$ each independently represents hydrogen, $C_{1-3}$alkyl or $C_{1-3}$alkoxy$C_{2-3}$alkyl) and R$^{37}$ is as defined hereinbefore); and 17') $C_{1-3}$alkylX$^9$$C_{1-3}$alkylR$^{36}$ (wherein X$^9$ and R$^{36}$ are as defined in (5') above);

provided that i) where R$^1$, R$^4$, R$^7$ and R$^8$ are all hydrogen and R$^2$ and R$^3$ are both hydrogen or both methoxy, R$^{64}$ is other than phenyl; and (ii) where R$^1$, R$^4$, R$^6$, R$^7$ and R$^8$ are all hydrogen and R$^2$ and R$^3$ are methoxy, and Z is C(O), R$^{64}$ is other than methyl.

A particularly preferred group of novel compounds are compounds of formula (IIB)

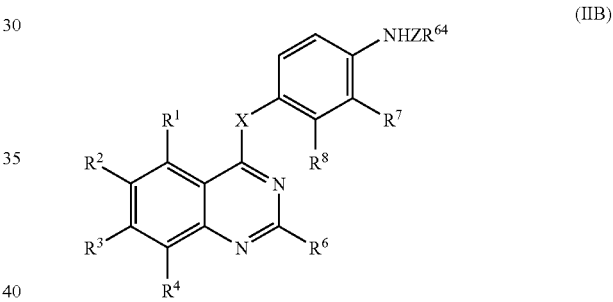

or a salt, ester, amide or prodrug thereof;

where X is O, or S, S(O) or S(O)$_2$ NH or NR$^{12}$ where R$^{12}$ is hydrogen or $C_{1-6}$alkyl;

Z is C(O) or S(O)$_2$;

R$^1$ and R$^4$ are independently selected from halogeno, cyano, nitro, $C_{1-3}$alkylsulphanyl, —N(OH)R$^{13}$— (wherein R$^{13}$ is hydrogen, or $C_{1-3}$alkyl), or R$^{15}$X$^1$— (wherein X$^1$ represents a direct bond, —O—, —CH$_2$—, —OCO—, carbonyl, —S—, —SO—, —SO$_2$—, —NR$^{16}$CO—, —CONR$^{16}$—, —SO$_2$NR$^{16}$—, —NR$^{17}$SO$_2$— or —NR$^{18}$— (wherein R$^{16}$, R$^{17}$ and R$^{18}$ each independently represents hydrogen, $C_{1-3}$alkyl or $C_{1-3}$alkoxy$C_{2-3}$alkyl), and R$^{15}$ is hydrogen, optionally substituted hydrocarbyl, optionally substituted heterocyclyl or optionally substituted alkoxy;

R$^{2'}$ and R$^{3'}$ are groups R$^2$ and R$^3$ respectively, provided that at least one of said groups and preferably R$^{3'}$ is a group of sub-formula X$^1$—R$^{15'}$ where X$^1$ is as defined above, and R$^{15'}$ is a group R$^{15}$, provided that it is other than methyl;

R$^6$ is hydrogen, optionally substituted hydrocarbyl or optionally substituted heterocyclyl;

R$^7$ and R$^8$ are independently selected from hydrogen, halo, $C_{1-4}$alkyl, $C_{1-4}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl; and $R^{64}$ is optionally substituted hydrocarbyl or optionally substituted heterocyclyl.

These include compounds of formula (IID)

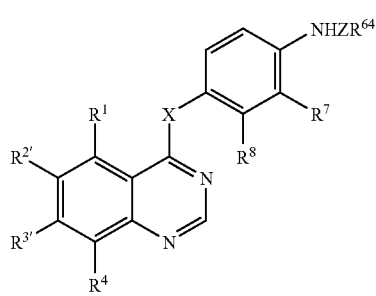

(IID)

or a salt, ester or amide thereof;

where $R^1$, $R^4$, $R^7$, $R^8$, X, Z and $R^{64}$ are as defined in relation to formula (IIC) and $R^{2'}$ and $R^{3'}$ are groups $R^2$ and $R^3$ as defined in relation to formula (IIC) respectively, provided that at least one of said groups and preferably $R^{3'}$ is a group of sub-formula $X^1$—$R^{15'}$ where $X^1$ is as defined in relation to formula (IIC), and $R^{15'}$ is a group $R^{15}$ as defined in relation to formula (IIC), provided that it is other than methyl.

Preferred variables as described above apply also to formula (IIA), (IIB), (IIC) and (IID) where possible.

Yet another embodiment of the invention provides a compound of formula (VIA)

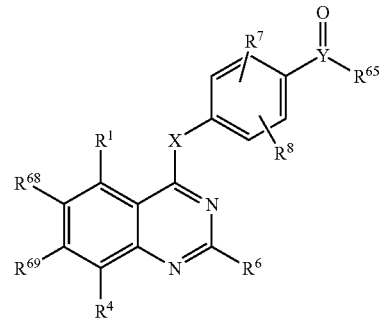

(VIA)

or a salt, ester, amide or prodrug thereof, where X, Y, $R^1$, $R^4$, $R^6$, $R^7$, $R^8$ are as defined in relation to formula (I), $R^{65}$ is as defined in relation to formula (VI), and $R^{68}$ and $R^{69}$ are equivalent to $R^2$ and $R^3$ as defined above in relation to formula (I) except that at least one of $R^{68}$ or $R^{69}$ is a group of sub-formula $X^1R^{15}$ where $R^{15}$ is as defined in relation to formula (I), provided that when said one of $R^{68}$ or $R^{69}$ is morpholinopropoxy, the other is not a group of sub-formula (18); and further provided that when said one of $R^{68}$ or $R^{69}$ is methoxyethoxy, the other is not methoxy.

Particular examples are compounds of formula (VIB)

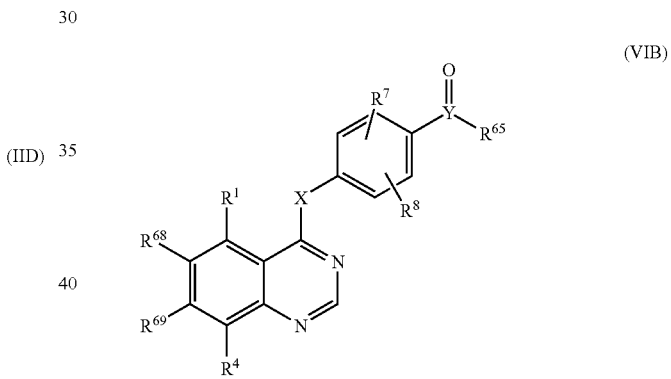

(VIB)

or a salt, ester or amide thereof, where X, Y, $R^1$, $R^4$, $R^7$, $R^8$ are as defined in relation to compound (VIC), $R^{65}$ is as defined in relation to compound (VIC), and $R^{68}$ and $R^{69}$ are equivalent to $R^2$ and $R^3$ in relation to compound (VIC), except that at least one of $R^{68}$ or $R^{69}$ is a group of sub-formula $X^1R^{15}$ where $R^{15}$ is as defined in relation to compound (VIC), provided that when said one of $R^{68}$ or $R^{69}$ is morpholinopropoxy, the other is not $C_{2-5}$alkenyl which may be unsubstituted or which may be substituted with one ore more functional groups; and further provided that when said one of $R^{68}$ or $R^{69}$ is methoxyethoxy, the other is not methoxy.

In another embodiment, the invention provides a compound of formula (VID) which is of similar structure to (VIA) above but in which X, Y, $R^1$, $R^4$, $R^6$, $R^7$, $R^8$ and $R^{65}$ are as defined in relation to formula (VI), $R^{68}$ is halo, cyano, nitro, trifluoromethyl, $C_{1-3}$alkyl, —$NR^{13}R^{14}$ wherein $R^{13}$ and $R^{14}$ are as defined above in relation to formula (I), or a group —$X^1R^{15}$ where $X^1$ and $R^{15}$ are as defined in relation to formula (I) and $R^{15}$ is particularly a group of sub group (1) or (10), and $R^{69}$ is $C_{1-6}$alkoxy optionally substituted by fluorine or a group $X^{12}R^{71}$ in which $X^{12}$ is selected from a group defined for $X^1$ above, and $R^{71}$ is a heterocyclic group, and in particular a 5-6-membered aromatic heterocyclic group (linked via nitrogen) with 1-3 heteroatoms selected from O, N and S; provided that at least one of $R^{68}$ and $R^{69}$ is other than unsubstituted methoxy.

Preferably at least one of $R^{68}$ or $R^{69}$ is selected from groups (1), (3), (6), (10) or (22) as defined in relation to formula (VIA).

A preferred example of $R^{69}$ is 3-morpholinopropoxy.

Preferably at least $R^{69}$ is other than unsubstituted alkoxy.

Where $R^{68}$ or $R^{69}$ is unsubstituted alkoxy, it is preferably methoxy.

Suitable halo substituents for $R^{68}$ and $R^{69}$ are fluoro.

Other examples for $R^{68}$ and/or $R^{69}$ include 3,3,3-trifluoroethoxy.

Again preferred variables defined above apply in respect of formula (VIA), (VIB), (VIC) or (VID) where possible.

Preferably in the novel compounds, X is NH.

Preferably also, $X^1$ is oxygen.

Compounds of formula (I) may be prepared by methods known in the art or by analogous methods. For example, a compound of formula (I) can be prepared by reacting a compound of formula (VIII)

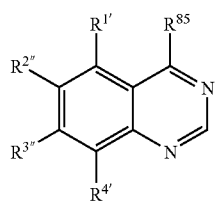

(VIII)

where $R^{1'}$, $R^{2''}$, $R^{3''}$, and $R^{4'}$ are equivalent to a group $R^1$, $R^2$, $R^3$ and $R^4$ as defined in relation to formula (I) or a precursor thereof, and $R^{85}$ is a leaving group, with a compound of formula (IX)

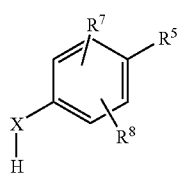

(IX)

where X, $R^5$, $R^7$ and $R^8$ are as defined in relation to formula (I), and thereafter if desired or necessary converting a group $R^{1'}$, $R^{2''}$, $R^{3''}$ or $R^{4'}$ to a group $R^1$, $R^2$, $R^3$ and $R^4$ respectively or to a different such group.

Suitable leaving groups for $R^{85}$ include halo such as chloro, mesylate and tosylate. The reaction is suitably effected in an organic solvent such as an alcohol like isopropanol, at elevated temperatures, conveniently at the reflux temperature of the solvent.

The conversion of a group $R^{1'}$, $R^{2''}$, $R^{3''}$ or $R^{4'}$ a group $R^1$, $R^2$, $R^3$ and $R^4$ respectively or to a different such group, may be particularly useful in connection with the preparation of compounds of formula (IIB) and examples of these preparations are provided hereinafter.

Compounds of formula (VIII) and (IX) are either known compounds or they can be derived from known compounds by conventional methods.

The use of such methods for producing novel compounds of the invention form a further aspect of the invention. Thus the invention further provides a method for preparing a compound of formula (IIA), (IIB), (IIC), (IID), (VIA) or (VIB), which method comprises reacting a compound of formula (VIII')

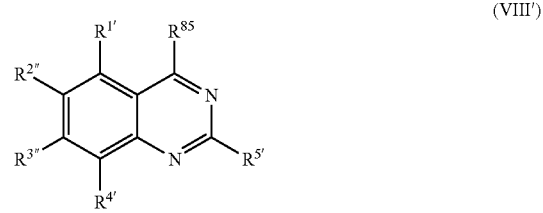

(VIII')

where $R^{1'}$ is equivalent to the corresponding group of formula $R^1$ as defined in relation to the said compound of formula (IIA), (IIB), (IIC), (IID), (VIA) or (VIB), or a precursor thereof;

$R^{2''}$ is equivalent to the corresponding group of formula $R^2$ or $R^{2'}$ or $R^{68}$ as defined in relation to the said compound of formula (IIA), (IIB), (IIC), (IID), (VIA) or (VIB), or a precursor thereof;

$R^{3''}$ is equivalent to the corresponding group of formula $R^3$ or $R^{3'}$ or $R^{69}$ as defined in relation to the said compound of formula (IIA), (IIB), (IIC), (IID), (VIA) or (VIB), or a precursor thereof;

$R^{4'}$ is equivalent to the corresponding group of formula $R^4$ as defined in relation to the said compound of formula (IIA), (IIB), (IIC), (IID), (VIA) or (VIB), or a precursor thereof, $R^{6'}$ is a group $R^6$ where present in the compound of any one of formula (IIA), (IIB), (IIC), (IID), (VIA) or (VIB), or is hydrogen where absent, and $R^{85}$ is a leaving group, with a compound of formula (IX')

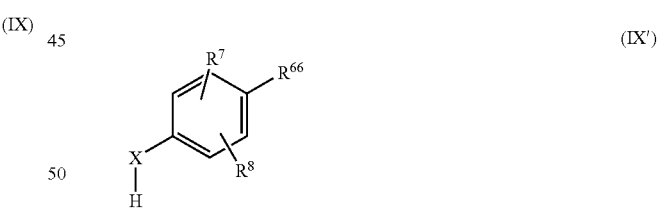

(IX')

where X, $R^7$ and $R^8$ are as defined for any one of formula (IIA), (IIB), (IIC), (IID), (VIA) or (VIB), and $R^{86}$ is a group of formula $NHZR^{64}$ or $Y(O)R^{65}$ where Z, $R^{64}$, Y and $R^{65}$ as are defined for any one of formula (IIA), (IIB), (IIC), (IID), (VIA) or (VIB); and thereafter if desired or necessary converting a group $R^{1'}$, $R^{2''}$, $R^{3''}$ or $R^{4'}$ to a group $R^1$, $R^2$ or $R^{2'}$ or $R^{68}$, $R^3$ or $R^{3'}$ or $R^{69}$ and $R^4$ respectively or to a different such group.

Compounds of formula (I) are inhibitors of aurora 2 kinase. As a result, these compounds can be used to treat disease mediated by these agents, in particular proliferative disease.

According to a further aspect of the present invention there is provided a method for inhibiting aurora 2 kinase in a warm blooded animal, such as man, in need of such treatment, which comprises administering to said animal an effective amount of a compound of formula (I), or a pharmaceutically acceptable salt, or an in vivo hydrolysable ester, or amide or prodrug thereof.

Novel compounds of formula (I) have not hitherto been proposed for use in therapy. Thus, according to a further aspect of the invention there is provided a compound of the formula (IIA), (IIB) or (VIA) as defined herein, or a pharmaceutically acceptable salt or an in vivo hydrolysable ester, or amide or prodrug thereof, for use in a method of treatment of the human or animal body by therapy. In particular, the compounds are used in methods of treatment of proliferative disease such as cancer and in particular cancers such as colorectal or breast cancer where aurora 2 is upregulated.

Compounds of formula (I) are suitably applied in the form of a pharmaceutical composition. Preferred compounds of formula (I) for use in the compositions of the invention are as described above.

Some of these are novel and form yet a further aspect of the invention. Thus, the invention also provides a pharmaceutical composition comprising a compound of formula (IIA), (IIB) or (VIA) as defined herein, or a pharmaceutically acceptable salt, or an in vivo hydrolysable ester thereof, in combination with at pharmaceutically acceptable carrier.

The compositions of compounds of formula (I) may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of aurora 2 kinase.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

The treatment defined hereinbefore may be applied as a sole therapy or may involve, in addition to the use of the compounds in accordance with the invention and/or compounds of the invention, one or more other substances and/or treatments. Such conjoint treatment may be achieved by way of simultaneous, sequential or separate administration of the individual components of the treatment. In the field of medical oncology it is normal practice to use a combination of different forms of treatment to treat each patient with cancer. The other components of such conjoint treatment may be, for example, surgery, radiotherapy or chemotherapy. Such chemotherapy may include one or more of the following categories of therapeutic agents:—

(i) anti-invasion agents (for example metalloproteinase inhibitors like marimastat and inhibitors of urokinase plasminogen activator receptor function);

(ii) anti-proliferative/anti-neoplastic drugs and combinations thereof, as used in medical oncology, such as platinum derivatives (for example cis-platin, carboplatin); alkylating agents (for example cyclophosphamide, nitrogen mustard, melphalan, chlorambucil, busulphan and nitrosoureas); antimetabolites (for example anti-folates such as fluoropyrimidines like 5-fluorouracil and tegafur, raltitrexed, methotrexate, cytosine arabinoside and hydroxyurea); anti-tumour antibiotics (for example anthracyclines like adriamycin, bleomycin, doxorubicin, daunomycin, epirubicin, idarubicin, mitomycin-C, dactinomycin and mithramycin); anti-mitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as anti-oestrogens (for example tamoxifen, toremifene, raloxifene, droloxifene and iodoxyfene); anti-androgens (for example bicalutamide, flutamide, nilutamide and cyproterone acetate); LHRH antagonists or LHRH agonists (for example goserelin, leuprorelin and buserelin); progestogens (for example megestrol acetate); aromatase inhibitors (for example as anastrozole, letrazole, vorazole and exemestane) and inhibitors of 5-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example EGFR tyrosine kinase inhibitors) for example inhibitors of the platelet-derived growth factor family and for example inhibitors of the hepatocyte growth factor family; and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such combination products employ the compounds of this invention within the dosage range described hereinbefore and the other pharmaceutically-active agent within its approved dosage range.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18-25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DMSOd$_6$ (unless otherwise stated) on the delta scale (ppm downfield from tetramethylsilane) using a Varian Gemini 2000 spectrometer operating at a field strength of 300 MHz, or a Bruker DPX300 spectrometer operating at a field strength of 300 MHz; and peak multiplicities are shown as follows: s, singlet; d, doublet; dd, double doublet; t, triplet; q, quartet; qu, quintet; m, multiplet; bs, broad singlet; mass spectrometry (MS) was performed by electrospray on a VG platform;

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Savant AES 2000; column chromatography was performed using either an Anachem Sympur MPLC or Jones Flashmaster MPLC systems on silica using Varian Mega Bond Elut cartridges; the structures of the final products were confirmed by LCMS on a Micromass OpenLynx system using the following and are quoted as retention time (RT) in minutes:

Column: 4.6 mm×3 cm Hichrom RPB

Solvent A: 5% Methanol in Water+0.1% formic acid

Solvent B: 5% Methanol in Acetonitrile+0.1% formic acid

Flow rate: 1.4 ml/min

Run time: 5 minutes with a 4.5 minute gradient from 0-100% B

Wavelength: 254 nm, bandwidth 10 nm

Mass detector: Micromass Platform LC

Injection volume 0.002 ml (vii) Analytical LCMS for compounds which had not been prepared by robotic synthesis was performed on a Waters Alliance HT system using the following and are quoted as retention time (RT) in minutes:

Column: 2.0 mm×5 cm Phenomenex Max-RP 80A

Solvent A: Water

Solvent B: Acetonitrile

Solvent C: Methanol+1% formic acid

Flow rate: 1.1 ml/min

Run time: 5 minutes with a 4.5 minute gradient from 0-95% B+constant 5% solvent C Wavelength: 254 nm, bandwidth 10 nm Injection volume 0.005 ml Mass detector: Micromass ZMD (viii) Preparative high performance liquid chromatography (HPLC) was performed on a Gilson instrument using the following and are quoted as retention time (RT) in minutes:

Column: 21 mm×10 cm Hichrom RPB

Solvent A: Water+0.1% trifluoroacetic acid,

Solvent B: Acetonitrile+0.1% trifluoroacetic acid

Flow rate: 18 ml/min

Run time: 15 minutes with a 10 minute gradient from 5-100% B

Wavelength: 254 nm, bandwidth 10 nm

Injection volume 2.0-4.0 ml (ix) intermediates were not generally fully characterised and purity was assessed by thin layer chromatography (TLC), HPLC, infra-red (IR), MS or NMR analysis;

The following Examples illustrate the invention.

EXAMPLE 1

Preparation of Compound No. 1 in Table 1

A solution of 4-chloro-6,7-dimethoxyquinazoline (3.176 g, 14.13 mmol) and N-benzoyl 4-aminoaniline (3.00 g, 14.13 mmol) in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded the title compound (5.66 g, 92% yield) as a pale-yellow solid:

$^1$H-NMR (DMSO d$_6$): 11.29 (s, 1H), 10.39 (s, 1H), 8.80 (s, 1H), 8.25 (s, 1H), 7.98 (d, 2H, J=8 Hz), 7.89 (d, 2H, J=8 Hz), 7.65 (d, 2H, J=8 Hz), 7.50-7.63 (m, 3H), 7.32 (s, 1H), 4.00 (s, 3H), 3.98 (s, 3H):

MS (+ve ESI): 401 (M+H)$^+$.

4-Chloro-6,7-dimethoxyquinazoline and N-benzoyl 4-aminoaniline, used as the starting materials were obtained as follows:

a) A mixture of 4,5-dimethoxyanthranilic acid (19.7 g, 100 mmol) and formamide (10 ml) was heated at 190° C. for 5 hours. The mixture was allowed to cool to approximately 80° C. and water (50 ml) was added. The mixture was then allowed to stand at ambient temperature for 3 hours. Collection of the solid by suction filtration, followed by washing with water (2×50 ml) and drying in vacuo, yielded 6,7-dimethoxy-3,4-dihydroquinazolin-4-one (3.65 g, 18% yield) as a white solid:

$^1$H-NMR (DMSO d$_6$): 12.10 (s, 1H), 7.95 (s, 1H), 7.42 (s, 1H), 7.11 (s, 1H), 3.88 (s, 3H), 3.84 (s, 3H):

MS (-ve ESI): 205 (M-H)$^-$.

b) Dimethylformamide (0.2 ml) was added dropwise to a solution of 6,7-dimethoxy-3,4-dihydro-quinazolin-4-one (10.0 g, 48.5 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6,7-dimethoxyquinazoline (10.7 g, 98% yield) as a white solid:
$^1$H-NMR (DMSO d$_6$): 8.86 (s, 1H), 7.42 (s, 1H), 7.37 (s, 1H), 4.00 (s, 3H), 3.98 (s, 3H):
MS (+ve ESI): 225 (M+H)$^+$.

c) Benzoyl chloride (10.7 ml, 92.5 mmol) was added to a stirred solution of 1,4-phenylenediamine (10.0 g, 92.5 mmol) and triethylamine (14.2 ml, 102 mmol) in dichloromethane (250 ml) at 0° C. The reaction was allowed to warm to ambient temperature over 3 hours, the solid was filtered off and water (100 ml) was added to the filtrate, causing precipitation of a second solid. Collection of this solid by suction filtration and drying in vacuo yielded N-benzoyl 4-aminoaniline (5.55 g, 28% yield) as a white solid:
$^1$H-NMR (DMSO d$_6$): 9.83 (s, 1H), 7.90 (d, 2H, J=7 Hz), 7.42-7.56 (m, 3H), 7.35 (d, 2H, J=8 Hz), 6.53 (d, 2H, J=8 Hz), 4.88 (s, 2H):
MS (−ve ESI): 211 (M−H)$^+$.

EXAMPLE 2

Preparation of Compound No. 2 in Table 1

2-Furoyl chloride (44 mg, 0.34 mmol) was added to a solution of 4-(4-aminoanilino)-6,7-dimethoxyquinazoline (100 mg, 0.34 mmol) and triethylamine (0.052 ml, 0.37 mmol) in dichloromethane at ambient temperature under an inert atmosphere. The reaction was stirred for 2 hours at ambient temperature, more furoyl chloride was added (15 mg, 0.11 mmol), the reaction was stirred for a further 30 minutes and then the volatiles were removed in vacuo. Purification of the crude product by flash chromatography on silica gel, eluting with 5% methanol in dichloromethane, yielded the title compound (70 mg, 53% yield) as a glassy yellow solid:
$^1$H-NMR (DMSO d$_6$): 10.15 (s, 1H), 9.43 (s, 1H), 8.41 (s, 1H), 7.92 (d, 1H, J=1 Hz), 7.82 (s, 1H), 7.73 (s, 4H), 7.30 (d, 1H, J=3 Hz), 7.15 (s, 1H), 6.68 (dd, 1H, J=1, 3 Hz), 3.95 (s, 3H), 3.90 (s, 3H):
MS (−ve ESI): 389 (M−H)$^-$.

EXAMPLE 3

Preparation of Compound No. 3 in Table 1

1-(3-dimethylaminopropyl)-3-ethylcarbodiimide hydrochloride (EDCI) (48.5 mg, 0.25 mmol) and 4-(dimethylamino)pyridine (3 mg, 0.025 mmol) were added to a solution of 4-(4-aminoanilino)-6,7-dimethoxyquinazoline (50 mg, 0.17 mmol) and cinnamic acid (28 mg, 0.19 mmol) in dimethylformamide (0.8 ml) and the reaction stirred at 50° C. for 18 hours. The reaction was cooled, poured into water (10 ml), treated with saturated aqueous sodium hydrogen carbonate solution (3 ml) and the solid material collected by suction filtration. Drying in vacuo yielded the title compound (60 mg, 83% yield) as a brown solid:
$^1$H-NMR (DMSO d$_6$): 10.18 (s, 1H), 9.42 (s, 1H), 8.41 (s, 1H), 7.83 (s, 1H), 7.72 (s, 4H), 7.61 (s, 2H), 7.58 (d, 1H, J=8 Hz), 7.35-7.50 (m, 3H), 7.17 (s, 1H), 6.83 (d, 1H, J=8 Hz), 3.95 (s, 3H), 3.91 (s, 3H):
MS (+ve ESI): 427.5 (M+H)$^+$.

EXAMPLE 4

Preparation of Compound No. 4 in Table 1

An analogous reaction to that described in example 3, but starting with 3,4,5-trimethoxybenzoic acid (39.4 mg, 0.186 mmol) yielded the title compound (69 mg, 83% yield) as a yellow solid:
$^1$H-NMR (DMSO d$_6$): 10.11 (s, 1H), 9.46 (s, 1H), 8.43 (s, 1H), 7.84 (s, 1H), 7.68-7.79 (m, 4H), 7.29 (s, 2H), 7.15 (s, 1H), 3.95 (s, 3H), 3.91 (s, 3H), 3.87 (s, 6H), 3.72 (s, 3H):
MS (−ve ESI): 489 (M−H)$^-$.

EXAMPLE 5

Preparation of Compound No. 5 in Table 1

An analogous reaction to that described in example 3, but starting with 2,4-difluorobenzoic acid (59 mg, 0.37 mmol), and performing the reaction at 80° C., yielded the title compound (70 mg, 48% yield) as a white solid:
$^1$H-NMR (DMSO d$_6$): 9.48 (bs, 1H), 8.41 (s, 1H), 7.84 (s, 1H), 7.66-7.78 (m, 5H), 7.35-7.45 (m, 1H), 7.15-7.26 (m, 1H), 7.14 (s, 1H), 3.95 (s, 3H), 3.90 (s, 3H):
MS (−ve ESI): 435 (M−H)$^-$.

EXAMPLE 6

Preparation of Compound No. 6 in Table 1

An analogous reaction to that described in example 3, but starting with 3,4-dimethoxy-6-nitrobenzoic acid (84 mg, 0.37 mmol), and performing the reaction at 80° C., yielded the title compound (57 mg, 33% yield) as a pale yellow solid:
$^1$H-NMR (DMSO d$_6$): 10.47 (s, 1H), 9.46 (s, 1H), 8.42 (s, 1H), 7.84 (s, 1H), 7.63-7.78 (m, 5H), 7.27 (s, 1H), 7.15 (s, 1H), 3.95 (s, 3H), 3.94 (s, 3H), 3.90 (s, 6H):
MS (−ve ESI): 504 (M−H)$^-$.

EXAMPLE 7

Preparation of Compound No. 7 in Table 1

O-(7-Azabenzotriazol-1-yl)-N,N,N',N'-tetramethyluronium hexafluorophosphate (HATU) (192 mg, 0.50 mmol) was added to a suspension of 2,4-dinitrobenzoic acid (71.5 mg, 0.337 mmol) in dimethylformamide (1.5 ml). After 5 minutes, 4-(4-aminoanilino)-6,7-dimethoxyquinazoline (100 mg, 0.17 mmol) was added and the reaction heated at 50° C. for 3 hours. The reaction was cooled, poured into water (15 ml) and diethyl ether (5 ml) was added. The solid which precipitated was collected by suction filtration and washed with water (10 ml) and diethyl ether (10 ml). Drying of the solid in vacuo yielded the title compound (57 mg, 34% yield) as a white solid:
$^1$H-NMR (DMSO d$_6$): 10.86 (s, 1H), 9.45 (s, 1H), 8.83 (d, 1H, J=1 Hz), 8.65 (dd, 1H, J=8, 1 Hz), 8.42 (s, 1H), 8.09 (d, 1H, J=8 Hz), 7.85 (s, 1H), 7.79 (d, 2H, J=8 Hz), 7.66 (d, 2H, J=8 Hz), 7.17 (s, 1H), 3.95 (s, 3H), 3.91 (s, 3H):
MS (+ve ESI): 491 (M+H)$^+$.

EXAMPLE 8

Preparation of Compound No. 8 in Table 1

An analogous reaction to that described in example 7, but starting with (2-fluorophenyl)acetic acid (57 mg, 0.37 mmol) yielded the title compound (116 mg, 60% yield) as a white solid:
$^1$H-NMR (DMSO d$_6$): 10.96 (bs, 1H), 10.34 (bs, 1H), 8.80 (s, 1H), 8.04 (s, 1H), 7.70 (d, 2H, J=8 Hz), 7.55 (d, 2H, J=8 Hz), 7.25-7.45 (m, 2H), 7.10-7.22 (m, 3H), 4.00 (s, 3H), 3.98 (s, 3H), 3.74 (s, 2H):
MS (+ve ESI): 433 (M+H)$^+$.

EXAMPLE 9

Preparation of Compound No. 9 in Table 1

An analogous reaction to that described in example 7, but starting with cyclopentane carboxylic acid (42 mg, 0.37 mmol) yielded the title compound (125 mg, 69% yield) as a white solid:
$^1$H-NMR (DMSO $d_6$): 10.96 (bs, 1H), 9.99 (s, 1H), 8.79 (s, 1H), 8.04 (s, 1H), 7.70 (d, 2H, J=8 Hz), 7.52 (d, 2H, J=8 Hz), 7.20 (s, 1H), 4.00 (s, 3H), 3.99 (s, 3H), 2.69-2.88 (m, 1H), 1.43-1.93 (m, 8H):
MS (+ve ESI): 393 (M+H)$^+$.

EXAMPLE 10

Preparation of Compound No. 10 in Table 1

An analogous reaction to that described in example 7, but starting with 2-methyl-4-pentenoic acid (42 mg, 0.37 mmol) yielded the title compound (85 mg, 47% yield) as a white solid:
$^1$H-NMR (DMSO $d_6$): 10.96 (s, 1H), 9.99 (s, 1H), 8.78 (s, 1H), 8.04 (s, 1H), 7.70 (d, 2H, J=8 Hz), 7.52 (d, 2H, J=8 Hz), 7.20 (s, 1H), 5.64-5.87 (m, 1H), 5.07 (dd, 1H, J=17, 1 Hz), 5.00 (dd, 1H, J=10, 1 Hz), 3.99 (s, 3H), 3.97 (s, 3H), 2.03-2.64 (m, 3H), 1.05 (d, 3H, J=7 Hz):
MS (+ve ESI): 393 (M+H)$^+$.

EXAMPLE 11

Preparation of Compound No. 11 in Table 1

An analogous reaction to that described in example 7, but starting with cyanoacetic acid (31.6 mg, 0.37 mmol) yielded the title compound (126 mg, 73% yield) as a white solid:
$^1$H-NMR (DMSO $d_6$): 10.85 (s, 1H), 10.41 (s, 1H), 8.76 (s, 1H), 8.02 (s, 1H), 7.55-7.68 (m, 4H), 7.20 (s, 1H), 4.00 (s, 3H), 3.99 (s, 3H), 3.91 (s, 2H):
MS (+ve ESI): 364 (M+H)$^+$.

EXAMPLE 12

Preparation of Compound No. 12 in Table 1

O-(7-Azabenzotriazol-1-yl)-N,N,N',N'-tetramethyluronium hexafluorophosphate (HATU) (192 mg, 0.50 mmol) was added to a solution of octanoic acid (53 mg, 0.371 mmol) in dimethylacetamide (1.0 ml). After 20 minutes, a solution of 4-(4-aminoanilino)-6,7-dimethoxyquinazoline (100 mg, 0.17 mmol) in dimethylacetamide (1.0 ml) was added and the reaction heated at 50° C. for 2 hours. The reaction was cooled and poured into water (10 ml). The solid which precipitated was collected by suction filtration and washed with water (10 ml) and diethyl ether (10 ml). (In some of the analogous reactions (described in examples 23-99), precipitation of a solid did not occur at this stage and it was necessary to neutralise the reaction mixture, by addition of saturated aqueous sodium bicarbonate solution, to cause precipitation of the free base instead of the hexafluorophosphate salt which was obtained in this example). Drying of the solid in vacuo yielded the title compound (133 mg, 69% yield) as a white solid:
$^1$H-NMR (DMSO $d_6$): 10.96 (s, 1H), 9.98 (s, 1H), 8.78 (s, 1H), 8.04 (s, 1H), 7.69 (d, 2H, J=8 Hz), 7.52 (d, 2H, J=8 Hz), 7.20 (s, 1 Hz), 4.00 (s, 3H), 3.99 (s, 3H), 2.30 (t, 2H, J=7 Hz), 1.52-1.65 (m, 2H), 1.27-1.36 (m, 8H), 0.86 (t, 3H, J=6 Hz):
MS (+ve ESI): 423 (M+H)$^+$.

EXAMPLE 13

Preparation of Compound No. 13 in Table 1

An analogous reaction to that described in example 12, but starting with 3-(methylthio)propanoic acid (45 mg, 0.37 mmol), yielded the title compound (151 mg, 82% yield) as a white solid:
$^1$H-NMR (DMSO $d_6$): 10.95 (s, 1H), 10.09 (s, 1H), 8.77 (s, 1H), 8.03 (s, 1H), 7.69 (d, 2H, J=8 Hz), 7.53 (d, 2H, J=8 Hz), 7.20 (s, 1H), 3.99 (s, 3H), 3.97 (s, 3H), 2.76 (t, 2H, J=7 Hz), 2.63 (t, 2H, J=7 Hz), 2.08 (s, 3H):
MS (+ve ESI): 399 (M+H)$^+$.

EXAMPLE 14

Preparation of Compound No. 14 in Table 1

An analogous reaction to that described in example 12, but starting with 3-ethoxypropanoic acid (44 mg, 0.37 mmol), yielded the title compound (139 mg, 76% yield) as a white solid:
$^1$H-NMR (DMSO $d_6$): 10.96 (s, 1H), 10.06 (s, 1H), 8.79 (s, 1H), 8.03 (s, 1H), 7.70 (d, 2H, J=8 Hz), 7.53 (d, 2H, J=8 Hz), 7.20 (s, 1H), 4.00 (s, 3H), 3.98 (s, 3H), 3.66 (t, 2H, J=6 Hz), 3.43 (q, 2H, J=7 Hz), 2.55 (t, 2H, J=6 Hz), 1.08 (t, 3H, J=7 Hz):
MS (+ve ESI): 397 (M+H)$^+$.

EXAMPLE 15

Preparation of Compound No. 15 in Table 1

An analogous reaction to that described in example 12, but starting with methacrylic acid (32 mg, 0.37 mmol), yielded the title compound (118 mg, 69% yield) as a white solid:
$^1$H-NMR (DMSO $d_6$): 10.96 (s, 1H), 9.90 (s, 1H), 8.80 (s, 1H), 8.04 (s, 1H), 7.79 (d, 2H, J=8 Hz), 7.55 (d, 2H, J=8 Hz), 7.20 (s, 1H), 5.81 (s, 1H), 5.52 (s, 1H), 4.00 (s, 3H), 3.99 (s, 3H), 1.95 (s, 3H): MS (+ve ESI): 365 (M+H)$^+$.

EXAMPLE 16

Preparation of Compound No. 16 in Table 1

An analogous reaction to that described in example 12, but starting with 5-methyl-2-pyrazine carboxylic acid (31 mg, 0.22 mmol) and 4-(4-aminoanilino)-6,7-dimethoxyquinazoline (60 mg, 0.20 mmol), yielded the title compound (94 mg, 83% yield) as a white solid:
$^1$H-NMR (DMSO $d_6$): 10.91 (s, 1H), 10.78 (s, 1H), 9.16 (s, 1H), 8.79 (s, 1H), 8.70 (s, 1H), 8.05 (s, 1H), 8.01 (d, 2H, J=8 Hz), 7.63 (d, 2H, J=8 Hz), 7.21 (s, 1H), 3.99 (s, 6H), 2.63 (s, 3H):
MS (+ve ESI): 417 (M+H)$^+$.

EXAMPLE 17

Preparation of Compound No. 17 in Table 1

An analogous reaction to that described in example 12, but starting with 3-furoic acid (25 mg, 0.22 mmol) and 4-(4-aminoanilino)-6,7-dimethoxyquinazoline (60 mg, 0.20 mmol), yielded the title compound (79 mg, 73% yield) as a white solid:

$^1$H-NMR (DMSO d$_6$): 10.99 (s, 1H), 10.04 (s, 1H), 8.81 (s, 1H), 8.38 (d, 1H, J=1 Hz), 8.06 (s, 1H), 7.78-7.86 (m, 3H), 7.60 (d, 2H, J=8 Hz), 7.21 (s, 1H), 7.00 (d, 1H, J=1 Hz), 4.00 (s, 3H), 3.99 (s, 3H):
MS (+ve ESI): 391 (M+H)$^+$.

EXAMPLE 18

Preparation of Compound No. 18 in Table 1

An analogous reaction to that described in example 12, but starting with 3-cyanobenzoic acid (55 mg, 0.37 mmol) and heating the reaction for 4 hours, yielded the title compound (159 mg, 83% yield) as a white solid:
$^1$H-NMR (DMSO d$_6$): 11.00 (s, 1H), 10.54 (s, 1H), 8.81 (s, 1H), 8.40 (s, 1H), 8.25 (d, 1H, J=8 Hz), 8.07 (d, 1H, J=8 Hz), 8.05 (s, 1H), 7.88 (d, 2H, J=8 Hz), 7.75 (t, 1H, J=8 Hz), 7.64 (d, 2H, J=8 Hz), 7.21 (s, 1H), 4.00 (s, 6H):
MS (+ve ESI): 426 (M+H)$^+$.

EXAMPLE 19

Preparation of Compound No. 19 in Table 1

An analogous reaction to that described in example 12, but starting 4-acetoxybenzoic acid (67 mg, 0.37 mmol) and heating the reaction for 3 hours, yielded the title compound (150 mg, 70% yield) as a white solid:
$^1$H-NMR (DMSO d$_6$): 10.93 (s, 1H), 10.38 (s, 1H), 8.79 (s, 1H), 8.03 (d, 2H, J=8 Hz), 7.99 (s, 1H), 7.88 (d, 2H, J=8 Hz), 7.62 (d, 2H, J=8 Hz), 7.30 (d, 2H, J=8 Hz), 7.21 (s, 1H), 3.99 (s, 6H), 2.30 (s, 3H):
MS (+ve ESI): 459 (M+H)$^+$.

EXAMPLE 20

Preparation of Compound No. 20 in Table 1

An analogous reaction to that described in example 12, but starting 3-methoxy-2-nitrobenzoic acid (73 mg, 0.37 mmol) and heating the reaction for 3 hours yielded the title compound (185 mg, 89% yield) as a white solid:
$^1$H-NMR (DMSO d$_6$): 10.96 (s, 1H), 10.79 (s, 1H), 8.79 (s, 1H), 8.04 (s, 1H), 7.78 (d, 2H, J=8 Hz), 7.76 (t, 1H, J=8 Hz), 7.62 (d, 2H, J=8 Hz), 7.53 (d, 1H, J=8 Hz), 7.44 (d, 1H, J=8 Hz), 7.21 (s, 1H), 4.00 (s, 3H), 3.99 (s, 3H), 3.93 (s, 3H):
MS (+ve ESI): 476 (M+H)$^+$.

EXAMPLE 21

Preparation of Compound No. 21 in Table 1

An analogous reaction to that described in example 12, but starting 2-(methylthio)benzoic acid (62 mg, 0.37 mmol) and heating the reaction for 3 hours yielded the title compound (134 mg, 67% yield) as a white solid:
$^1$H-NMR (DMSO d$_6$): 10.29 (bs, 1H), 9.45 (s, 1H), 8.42 (s, 1H), 7.83 (s, 1H), 7.71 (s, 4H), 7.37-7.53 (m, 3H), 7.21-7.29 (m, 1H), 7.15 (s, 1H), 3.95 (s, 3H), 3.90 (s, 3H), 2.44 (s, 3H):
MS (−ve ESI): 445 (M−H)$^−$.

EXAMPLE 22

Preparation of Compound No. 22 in Table 1

An analogous reaction to that described in example 12, but starting 3-acetoxybenzoic acid (67 mg, 0.37 mmol) and heating the reaction for 3 hours yielded the title compound (150 mg, 74% yield) as a white solid:
$^1$H-NMR (DMSO d$_6$): 11.00 (bs, 1H), 10.41 (s, 1H), 8.81 (s, 1H), 8.05 (s, 1H), 7.83-7.91 (m, 1H), 7.87 (d, 2H, J=8 Hz), 7.69-7.72 (m, 1H), 7.54-7.63 (m, 1H), 7.61 (d, 2H, J=8 Hz), 7.37 (dd, 1H, J=8, 1.5 Hz), 7.20 (s, 1H), 4.00 (s, 3H), 3.99 (s, 3H), 2.30 (s, 3H):
MS (+ve ESI): 459 (M+H)$^+$.

EXAMPLE 23

Preparation of Compound No. 23 in Table 1

An analogous reaction to that described in example 12, but starting 4-aminosulphonyl-1-hydroxy-2-naphthoic acid (94 mg, 0.37 mmol) and heating the reaction for 3 hours yielded the title compound (66 mg, 36% yield) as a white solid:
$^1$H-NMR (DMSO d$_6$): 14.05 (s, 1H), 9.39 (s, 1H), 8.62 (s, 1H), 8.44 (d, 1H, J=8 Hz), 8.28 (d, 1H, J=8 Hz), 8.01 (s, 1H), 7.84 (s, 1H), 7.75 (d, 2H, J=8 Hz), 7.67 (d, 2H, J=8 Hz), 7.40-7.50 (m, 1H), 7.25-7.32 (m, 1H), 7.15 (s, 1H), 6.79 (s, 2H), 3.95 (s, 3H), 3.91 (s, 3H):
MS (−ve ESI): 544 (M−H)$^−$.

EXAMPLE 24

Preparation of Compound No. 24 in Table 1

An analogous reaction to that described in example 12, but starting with 2-picolinic acid (27 mg, 0.22 mmol) and 4-(4-aminoanilino)-6,7-dimethoxyquinazoline (60 mg, 0.20 mmol), yielded the title compound (94 mg, 85% yield) as a white solid:
$^1$H-NMR (DMSO d$_6$): 10.92 (bs, 1H), 10.76 (s, 1H), 8.79 (s, 1H), 8.73 (d, 1H, J=5 Hz), 7.98-8.20 (m, 5H), 7.64-7.71 (m, 1H), 7.63 (d, 2H, J=8 Hz), 7.21 (s, 1H), 3.99 (s, 6H):
MS (+ve ESI): 402 (M+H)$^+$.

EXAMPLE 25

Preparation of Compound No. 25 in Table 1

An analogous reaction to that described in example 12, but starting with quinaldic acid (38 mg, 0.22 mmol) and 4-(4-aminoanilino)-6,7-dimethoxyquinazoline (60 mg, 0.20 mmol), yielded the title compound (108 mg, 89% yield) as a white solid:
$^1$H-NMR (DMSO d$_6$): 10.96 (bs, 1H), 10.86 (s, 1H), 8.82 (s, 1H), 8.64 (d, 1H, J=8 Hz), 8.26 (d, 2H, J=8 Hz), 8.03-8.14 (m, 4H), 7.88-7.96 (m, 1H), 7.75 (t, 1H, J=7 Hz), 7.67 (d, 2H, J=8 Hz), 7.22 (s, 1H), 4.00 (s, 6H):
MS (+ve ESI): 452 (M+H)$^+$.

EXAMPLE 26

Preparation of Compound No. 26 in Table 1

An analogous reaction to that described in example 12, but starting with 1,5-dimethyl-1H-pyrazole-3-carboxylic acid (31 mg, 0.22 mmol) and 4-(4-aminoanilino)-6,7-dimethoxyquinazoline (60 mg, 0.20 mmol), yielded the title compound (83 mg, 73% yield) as a white solid:
$^1$H-NMR (DMSO d$_6$): 10.97 (bs, 1H), 10.05 (s, 1H), 8.79 (s, 1H), 8.04 (s, 1H), 7.92 (d, 2H, J=8 Hz), 7.55 (d, 2H, J=8 Hz), 7.20 (s, 1H), 6.55 (s, 1H), 4.00 (s, 3H), 3.99 (s, 3H), 3.84 (s, 3H), 2.30 (s, 3H):
MS (+ve ESI): 419 (M+H)$^+$.

EXAMPLE 27

Preparation of Compound No. 27 in Table 1

An analogous reaction to that described in example 12, but starting with 2-fluoro-5-nitrobenzoic acid (69 mg, 0.37 mmol) and heating the reaction for 3 hours, yielded the title compound (140 mg, 68% yield) as a white solid:
$^1$H-NMR (DMSO d$_6$): 10.97 (bs, 1H), 10.78 (s, 1H), 8.80 (s, 1H), 8.51-8.58 (m, 1H), 8.42-8.50 (m, 1H), 8.06 (s, 1H), 7.82 (d, 2H, J=8 Hz), 7.61-7.72 (m, 3H), 7.22 (s, 1H), 4.00 (s, 6H):
MS (+ve ESI): 464 (M+H)$^+$.

EXAMPLE 28

Preparation of Compound No. 28 in Table 1

An analogous reaction to that described in example 12, but starting with nicotinic acid (27 mg, 0.22 mmol) and 4-(4-aminoanilino)-6,7-dimethoxyquinazoline (60 mg, 0.20 mmol), yielded the title compound (77 mg, 70% yield) as a white solid:
$^1$H-NMR (DMSO d$_6$): 10.99 (bs, 1H), 10.56 (s, 1H), 9.12 (d, 1H, J=1.5 Hz), 8.81 (s, 1H), 8.76 (dd, 1H, J=5, 1.5 Hz), 8.27-8.33 (m, 1H), 8.05 (s, 1H), 7.88 (d, 2H, J=8 Hz), 7.63 (d, 2H, J=8 Hz), 7.56-7.60 (m 1H), 7.21 (s, 1H), 4.00 (s, 6H):
MS (+ve ESI): 402 (M+H)$^+$.

EXAMPLE 29

Preparation of Compound No. 29 in Table 1

An analogous reaction to that described in example 12, but starting with 2-chloronicotinic acid (35 mg, 0.22 mmol) and 4-(4-aminoanilino)-6,7-dimethoxyquinazoline (60 mg, 0.20 mmol), yielded the title compound (44 mg, 50% yield) as a white solid:
$^1$H-NMR (DMSO d$_6$): 10.98 (bs, 1H), 10.86 (s, 1H), 8.49-8.54 (m, 1H), 8.41 (s, 1H), 8.07 (dd, 1H, J=8, 2 Hz), 7.83 (s, 1H), 7.66-7.78 (m, 4H), 7.51-7.58 (m, 1H), 7.15 (s, 1H), 3.95 (s, 3H), 3.91 (s, 3H):
MS (+ve ESI): 436 (M+H)$^+$.

EXAMPLE 30

Preparation of Compound No. 30 in Table 1

An analogous reaction to that described in example 12, but starting with 2-fluorobenzoic acid (52 mg, 0.37 mmol) and heating the reaction for 3 hours, yielded the title compound (52 mg, 37% yield) as a white solid:
$^1$H-NMR (DMSO d$_6$): 10.36 (s, 1H), 9.45 (s, 1H), 8.42 (s, 1H), 7.84 (s, 1H), 7.74 (s, 4H), 7.63-7.72 (m, 1H), 7.52-7.62 (m, 1H), 7.28-7.39 (m, 2H), 7.16 (m, 1H), 3.95 (s, 3H), 3.91 (s, 3H):
MS (+ve ESI): 419 (M+H)$^+$.

EXAMPLE 31

Preparation of Compound No. 31 in Table 1

An analogous reaction to that described in example 12, but starting with 2,3-difluorobenzoic acid (59 mg, 0.37 mmol) yielded the title compound (82 mg, 56% yield) as a white solid:
$^1$H-NMR (DMSO d$_6$): 8.42 (s, 1H), 7.83 (s, 1H), 7.68-7.79 (m, 4H), 7.52-7.66 (m, 1H), 7.44-7.51 (m, 1H), 7.29-7.39 (m, 1H), 7.15 (s, 1H), 3.95 (s, 3H), 3.91 (s, 3H):
MS (+ve ESI): 437 (M+H)$^+$.

EXAMPLE 32

Preparation of Compound No. 32 in Table 1

An analogous reaction to that described in example 12, but starting with 2,5-difluorobenzoic acid (59 mg, 0.37 mmol) yielded the title compound (75 mg, 51% yield) as a white solid:
$^1$H-NMR (DMSO d$_6$): 10.44 (bs, 1H), 9.47 (s, 1H), 8.42 (s, 1H), 7.84 (s, 1H), 7.67-7.78 (m, 4H), 7.49-7.57 (m, 1H), 7.36-7.45 (m, 2H), 7.15 (s, 1H), 3.95 (s, 3H), 3.91 (s, 3H):
MS (+ve ESI): 437 (M+H)$^+$.

EXAMPLE 33

Preparation of Compound No. 33 in Table 1

An analogous reaction to that described in example 12, but starting with 2,3-methoxybenzoic acid (68 mg, 0.37 mmol) yielded the title compound (154 mg, 75% yield) as a white solid:
$^1$H-NMR (DMSO d$_6$): 11.00 (bs, 1H), 10.36 (s, 1H), 8.79 (s, 1H), 8.06 (s, 1H), 7.84 (d, 2H, J=8 Hz), 7.58 (d, 2H, J=8 Hz), 7.08-7.24 (m, 4H), 4.00 (s, 6H), 3.85 (s, 3H), 3.81 (s, 3H):
MS (+ve ESI): 461 (M+H)$^+$.

EXAMPLE 34

Preparation of Compound No. 34 in Table 1

An analogous reaction to that described in example 12, but starting with 3,5-dimethoxy-4-hydroxybenzoic acid (73 mg, 0.37 mmol) yielded the title compound (42 mg, 26% yield) as a white solid:
$^1$H-NMR (DMSO d$_6$): 9.79 (s, 1H), 9.53 (bs, 1H), 8.41 (s, 1H), 7.88 (s, 1H), 7.71 (s, 4H), 7.25 (s, 2H), 7.15 (s, 1H), 3.95 (s, 3H), 3.91 (s, 3H), 3.77 (s, 6H):
MS (+ve ESI): 477 (M+H)$^+$.

EXAMPLE 35

Preparation of Compound No. 35 in Table 1

An analogous reaction to that described in example 12, but starting with 3-chloro-4-carboxybenzoic acid (75 mg, 0.37 mmol) yielded the title compound (164 mg, 78% yield) as a white solid:
$^1$H-NMR (DMSO d$_6$): 10.85 (s, 1H), 10.82 (bs, 1H), 8.75 (s, 1H), 8.43 (d, 1H, J=1.5 Hz), 8.30 (dd, 1H, J=8, 1.5 Hz), 8.03 (s, 1H), 7.91 (d, 1H, J=8 Hz), 7.80 (d, 2H, J=8 Hz), 7.65 (d, 2H, J=8 Hz), 7.21 (s, 1H), 3.98 (s, 6H):
MS (+ve ESI): 480 (M+H)$^+$.

EXAMPLE 36

Preparation of Compound No. 36 in Table 1

An analogous reaction to that described in example 12, but starting with 4-(methylsulphonyl)-3-nitrobenzoic acid (91 mg, 0.37 mmol) yielded the title compound (150 mg, 66% yield) as a white solid:

¹H-NMR (DMSO d₆): 10.97 (bs, 1H), 10.78 (s, 1H), 8.81 (s, 1H), 8.58 (d, 1H, J=1 Hz), 8.45 (dd, 1H, J=8, 1 Hz), 8.30 (d, 1H, J=8 Hz), 8.05 (s, 1H), 7.88 (d, 2H, J=8 Hz), 7.67 (d, 2H, J=8 Hz), 7.21 (s, 1H), 4.00 (s, 6H), 3.54 (s, 3H):

MS (+ve ESI): 524 (M+H)⁺.

EXAMPLE 37

Preparation of Compound No. 37 in Table 1

An analogous reaction to that described in example 12, but starting with 4-methoxy-3-nitrobenzoic acid (73 mg, 0.37 mmol), yielded the title compound (160 mg, 76% yield) as a white solid:

¹H-NMR (DMSO d₆): 10.98 (bs, 1H), 10.46 (s, 1H), 8.81 (s, 1H), 8.53 (d, 1H, J=1.5 Hz), 8.28 (dd, 1H, J=8, 1.5 Hz), 8.05 (s, 1H), 7.87 (d, 2H, J=8 Hz), 7.63 (d, 2H, J=8 Hz), 7.53 (d, 1H, J=8 Hz), 7.21 (s, 1H), 4.02 (s, 3H), 4.00 (s, 3H), 3.99 (s, 3H):

MS (+ve ESI): 476 (M+H)⁺.

EXAMPLE 38

Preparation of Compound No. 38 in Table 1

An analogous reaction to that described in example 12, but starting with 2-nitrocinnamic acid (73 mg, 0.37 mmol) and heating the reaction for 2.5 hours, yielded the title compound (75 mg, 79% yield) as a white solid:

¹H-NMR (DMSO d₆): 9.47 (bs, 1H), 8.43 (s, 1H), 8.07 (d, 1H, J=8 Hz), 7.90-7.62 (m, 9H), 7.17 (s, 1H), 6.85 (d, 1H, J=16 Hz), 3.95 (s, 3H), 3.92 (s, 3H):

MS (+ve ESI): 472 (M+H)⁺.

EXAMPLE 39

Preparation of Compound No. 39 in Table 1

An analogous reaction to that described in example 12, but starting with 3-nitrocinnamic acid (43 mg, 0.22 mmol), yielded the title compound (86 mg, 91% yield) as a white solid:

¹H-NMR (DMSO d₆): 10.31 (bs, 1H), 8.47 (m, 1H), 8.42 (s, 1H), 8.23 (dd, 1H, J=8, 1.5 Hz), 8.08 (d, 1H, J=8 Hz), 7.84 (s, 1H), 7.67-7.78 (m, 6H), 7.18 (s, 1H), 7.04 (d, 1H, J=16 Hz), 3.95 (s, 3H), 3.92 (s, 3H):

MS (+ve ESI): 472 (M+H)⁺.

EXAMPLE 40

Preparation of Compound No. 40 in Table 1

An analogous reaction to that described in example 12, but starting with 4-nitrocinnamic acid (43 mg, 0.22 mmol), yielded the title compound (66 mg, 69% yield) as a white solid:

¹H-NMR (DMSO d₆): 10.42 (bs, 1H), 9.48 (bs, 1H), 8.42 (s, 1H), 8.29 (d, 2H, J=8 Hz), 7.90 (d, 2H, J=8 Hz), 7.85 (s, 1H), 7.74 (s, 4H), 7.69 (d, 1H, J=16 Hz), 7.18 (s, 1H), 7.05 (d, 1H, J=16 Hz), 3.96 (s, 3H), 3.92 (s, 3H):

MS (+ve ESI): 472 (M+H)⁺.

EXAMPLE 41

Preparation of Compound No. 41 in Table 1

An analogous reaction to that described in example 12, but starting with 4-chlorocinnamic acid (40 mg, 0.22 mmol), yielded the title compound (55 mg, 59% yield) as a white solid:

¹H-NMR (DMSO d₆): 10.24 (bs, 1H), 9.46 (bs, 1H), 8.42 (s, 1H), 7.83 (s, 1H), 7.72 (s, 4H), 7.66 (d, 2H, J=8 Hz), 7.58 (d, 1H, J=16 Hz), 7.50 (d, 2H, J=8 Hz), 7.17 (s, 1H), 6.86 (d, 1H, J=16 Hz), 3.95 (s, 3H), 3.92 (s, 3H):

MS (+ve ESI): 461 (M+H)⁺.

EXAMPLE 42

Preparation of Compound No. 42 in Table 1

An analogous reaction to that described in example 12, but starting with 2,3,4-trifluorocinnamic acid (45 mg, 0.22 mmol), yielded the title compound (64 mg, 66% yield) as a white solid:

¹H-NMR (DMSO d₆): 10.33 (bs, 1H), 9.45 (s, 1H), 8.43 (s, 1H), 7.83 (s, 1H), 7.73 (s, 4H), 7.52-7.63 (m, 1H), 7.58 (d, 1H, J=16 Hz), 7.35-7.47 (m, 1H), 7.17 (s, 1H), 6.95 (d, 1H, J=16 Hz), 3.96 (s, 3H), 3.92 (s, 3H):

MS (+ve ESI): 481 (M+H)⁺.

EXAMPLE 43

Preparation of Compound No. 43 in Table 1

An analogous reaction to that described in example 12, but starting with 3-(trifluoromethyl)-cinnamic acid (48 mg, 0.22 mmol), yielded the title compound (104 mg, 81% yield) as a white solid:

¹H-NMR (DMSO d₆): 10.97 (bs, 1H), 10.38 (s, 1H), 8.79 (s, 1H), 8.04 (s, 1H), 7.98 (s, 1H), 7.93 (d, 1H, J=7 Hz), 7.81 (d, 2H, J=8 Hz), 7.63-7.80 (m, 3H), 7.60 (d, 2H, J=8 Hz), 7.20 (s, 1H), 6.96 (d, 1H, J=16 Hz), 4.00 (s, 6H):

MS (+ve ESI): 495 (M+H)⁺.

EXAMPLE 44

Preparation of Compound No. 44 in Table 1

An analogous reaction to that described in example 12, but starting with 4-fluorocinnamic acid (37 mg, 0.22 mmol), yielded the title compound (83 mg, 70% yield) as a white solid:

¹H-NMR (DMSO d₆): 10.94 (bs, 1H), 10.32 (s, 1H), 8.79 (s, 1H), 8.04 (s, 1H), 7.80 (d, 2H, J=8 Hz), 7.71 (d, 1H, J=8 Hz), 7.69 (d, 1H, J=8 Hz), 7.60 (d, 1H, J=16 Hz), 7.59 (d, 2H, J=8 Hz), 7.30 (d, 1H, J=8 Hz), 7.27 (d, 1H, J=8 Hz), 7.20 (s, 1H), 6.78 (d, 1H, J=16 Hz), 4.00 (s, 3H), 3.99 (s, 3H):

MS (+ve ESI): 445 (M+H)⁺.

EXAMPLE 45

Preparation of Compound No. 45 in Table 1

An analogous reaction to that described in example 12, but starting with indole-2-carboxylic acid (36 mg, 0.22 mmol), yielded the title compound (53 mg, 60% yield) as a white solid:

¹H-NMR (DMSO d₆): 11.72 (bs, 1H), 10.23 (bs, 1H), 9.48 (bs, 1H), 8.44 (s, 1H), 7.87 (s, 1H), 7.73-7.86 (m, 4H), 7.67 (d, 1H, J=7 Hz), 7.48 (d, 1H, J=7 Hz), 7.42 (s, 1H), 7.22 (t, 1H, J=7 Hz), 7.19 (s, 1H), 7.06 (t, 1H, J=7 Hz), 3.96 (s, 3H), 3.93 (s, 3H):

MS (+ve ESI): 440 (M+H)⁺.

EXAMPLE 46

Preparation of Compound No. 46 in Table 1

An analogous reaction to that described in example 12, but starting with 5-fluoroindole-2-carboxylic acid (40 mg, 0.22 mmol), yielded the title compound (58 mg, 63% yield) as a white solid:
¹H-NMR (DMSO d₆): 11.82 (bs, 1H), 10.25 (s, 1H), 9.48 (s, 1H), 8.44 (s, 1H), 7.86 (s, 1H), 7.72-7.84 (m, 4H), 7.39-7.50 (m, 3H), 7.18 (s, 1H), 7.03-7.13 (m, 1H), 3.96 (s, 3H), 3.93 (s, 3H):

MS (+ve ESI): 458 (M+H)⁺.

EXAMPLE 47

Preparation of Compound No. 47 in Table 1

An analogous reaction to that described in example 12, but starting with 3-fluorobenzoic acid (31 mg, 0.22 mmol), yielded the title compound (81 mg, 71% yield) as a white solid:
¹H-NMR (DMSO d₆): 11.00 (bs, 1H), 10.43 (s, 1H), 8.81 (s, 1H), 8.06 (s, 1H), 7.89 (d, 2H, J=8 Hz), 7.74-7.84 (m, 2H), 7.55-7.63 (m, 1H), 7.62 (d, 2H, J=8 Hz), 7.40-7.49 (m, 1H), 7.21 (s, 1H), 4.00 (s, 6H):

MS (+ve ESI): 419 (M+H)⁺.

EXAMPLE 48

Preparation of Compound No. 48 in Table 1

An analogous reaction to that described in example 12, but starting with 3,5-dinitrobenzoic acid (47 mg, 0.22 mmol), yielded the title compound (97 mg, 75% yield) as a white solid:
¹H-NMR (DMSO d₆): 10.98 (bs, 1H), 10.97 (s, 1H), 9.18 (d, 2H, J=1 Hz), 9.02 (t, 1H, J=1 Hz), 8.83 (s, 1H), 8.07 (s, 1H), 7.92 (d, 2H, J=8 Hz), 7.69 (d, 2H, J=8 Hz), 7.22 (s, 1H), 4.00 (s, 6H):

MS (+ve ESI): 491 (M+H)⁺.

EXAMPLE 49

Preparation of Compound No. 49 in Table 1

An analogous reaction to that described in example 12, but starting with 3-(trifluoromethyl)-phenylacetic acid (75.5 mg, 0.37 mmol) and heating the reaction for 18 hours, yielded the title compound (103 mg, 64% yield) as a white solid:
¹H-NMR (DMSO d₆): 10.20 (s, 1H), 9.40 (s, 1H), 8.40 (s, 1H), 7.82 (s, 1H), 7.69 (m, 3H), 7.54-7.63 (m, 5H), 7.15 (s, 1H), 3.94 (s, 3H), 3.91 (s, 3H), 3.78 (s, 2H):

MS (+ve ESI): 483 (M+H)⁺.

EXAMPLE 50

Preparation of Compound No. 50 in Table 1

An analogous reaction to that described in example 12, but starting with 4-fluorophenylacetic acid (57.0 mg, 0.37 mmol), yielded the title compound (141 mg, 73% yield) as a white solid:
¹H-NMR (DMSO d₆): 10.52 (s, 1H), 10.24 (s, 1H), 8.67 (s, 1H), 7.98 (s, 1H), 7.66 (d, 2H), 7.58 (d, 2H), 7.34-7.39 (m, 2H), 7.19 (d, 2H), 7.13 (m, 1H), 3.96 (s, 6H), 3.65 (s, 2H):

MS (+ve ESI): 433 (M+H)⁺.

EXAMPLE 51

Preparation of Compound No. 51 in Table 1

An analogous reaction to that described in example 12, but starting with 4-chlorophenylacetic acid (62.9 mg, 0.37 mmol), yielded the title compound (167 mg, 84% yield) as a white solid:
¹H-NMR (DMSO d₆): 10.43 (s, 1H), 10.24 (s, 1H), 8.65 (s, 1H), 7.96 (s, 1H), 7.66 (d, 2H), 7.59 (d, 2H), 7.35 (m, 4H), 7.19 (s, 1H), 3.96 (s, 6H), 3.66 (s, 2H):

MS (+ve ESI): 449 (M+H)⁺.

EXAMPLE 52

Preparation of Compound No. 52 in Table 1

An analogous reaction to that described in example 12, but starting with 4-methoxyphenylacetic acid (61.4 mg, 0.37 mmol), yielded the title compound (155 mg, 78% yield) as a white solid:
¹H-NMR (DMSO d₆): 10.41 (s, 1H), 10.17 (s, 1H), 8.64 (s, 1H), 7.96 (s, 1H), 7.66 (d, 2H), 7.59 (d, 2H), 7.25 (d, 2H), 7.19 (s, 1H), 6.89 (d, 2H), 3.96 (s, 6H), 3.72 (s, 3H), 3.56 (s, 2H):

MS (+ve ESI): 445 (M+H)⁺.

EXAMPLE 53

Preparation of Compound No. 53 in Table 1

An analogous reaction to that described in example 12, but starting with 4-isopropylphenylacetic acid (65.9 mg, 0.37 mmol), yielded the title compound (143 mg, 93% yield) as a white solid:
¹H-NMR (DMSO d₆): 10.09 (s, 1H), 9.39 (s, 1H), 8.40 (s, 1H), 7.81 (s, 1H), 7.67 (d, 2H), 7.59 (d, 2H), 7.25 (d, 2H), 7.19 (s, 1H), 7.16 (d, 2H), 3.93 (s, 3H), 3.91 (s, 3H), 3.58 (s, 2H), 2.80-2.85 (m, 1H), 1.91 (s, 3H), 1.68 (s, 3H):

MS (+ve ESI): 457 (M+H)⁺.

EXAMPLE 54

Preparation of Compound No. 54 in Table 1

An analogous reaction to that described in example 12, but starting with 3-nitrophenylacetic acid (67.0 mg, 0.37 mmol), yielded the title compound (104 mg, 67% yield) as a white solid:
¹H-NMR (DMSO d₆): 10.23 (s, 1H), 9.40 (s, 1H), 8.40 (s, 1H), 8.23 (s, 1H), 8.10-8.14 (m, 1H), 7.83 (d, 2H), 7.66-7.70 (m, 2H), 7.57-7.63 (m, 3H), 7.15 (s, 1H), 3.94 (s, 3H), 3.91 (s, 3H), 3.84 (s, 2H):

MS (+ve ESI): 460 (M+H)⁺.

EXAMPLE 55

Preparation of Compound No. 55 in Table 1

An analogous reaction to that described in example 12, but starting with 3-phenoxypropanoic acid (61.4 mg, 0.37 mmol), yielded the title compound (103 mg, 52% yield) as a white solid:

¹H-NMR (DMSO d₆): 10.93 (s, 1H), 10.19 (s, 1H), 8.78 (s, 1H), 8.04 (s, 1H), 7.73 (d, 2H), 7.56 (d, 2H), 7.29 (m, 2H), 7.21 (s, 1H), 6.93 (m, 3H), 4.30 (t, 2H), 3.99 (s, 3H), 3.98 (s, 3H), 2.80 (t, 2H):

MS (+ve ESI): 445 (M+H)$^+$.

EXAMPLE 56

Preparation of Compound No. 56 in Table 1

An analogous reaction to that described in example 12, but starting with 3-(3,4-dimethoxy-phenyl)propanoic acid (77.7 mg, 0.37 mmol), yielded the title compound (164 mg, 77% yield) as a white solid:

¹H-NMR (DMSO d₆): 10.89 (s, 1H), 10.01 (s, 1H), 8.77 (s, 1H), 8.04 (s, 1H), 7.69 (d, 2H), 7.54 (d, 2H), 7.20 (s, 1H), 6.85 (m, 2H), 6.76 (m, 1H), 3.99 (s, 3H), 3.98 (s, 3H), 3.71 (s, 3H), 3.70 (s, 3H), 2.86 (t, 2H), 2.61 (t, 2H):

MS (+ve ESI): 489 (M+H)$^+$.

EXAMPLE 57

Preparation of Compound No. 57 in Table 1

An analogous reaction to that described in example 12, but starting with 3-(4-methoxybenzoyl)-propanoic acid (77.0 mg, 0.37 mmol), yielded the title compound (61 mg, 37% yield) as a white solid:

¹H-NMR (DMSO d₆): 9.98 (s, 1H), 9.38 (s, 1H), 8.40 (s, 1H), 7.97 (d, 2H), 7.82 (s, 1H), 7.66 (d, 2H), 7.58 (d, 2H), 7.15 (s, 1H), 7.04 (d, 2H), 3.93 (s, 3H), 3.91 (s, 3H), 3.83 (s, 3H), 3.28 (t, 2H), 2.70 (t, 2H):

MS (+ve ESI): 487 (M+H)$^+$.

EXAMPLE 58

Preparation of Compound No. 58 in Table 1

An analogous reaction to that described in example 12, but starting with 4-chlorobutyric acid (45.1 mg, 0.37 mmol), yielded the title compound (132 mg, 72% yield) as a white solid:

¹H-NMR (DMSO d₆): 10.97 (s, 1H), 10.09 (s, 1H), 8.78 (s, 1H), 8.06 (s, 1H), 7.70 (d, 2H), 7.55 (d, 2H), 7.22 (s, 1H), 3.99 (s, 3H), 3.98 (s, 3H), 3.70 (t, 2H), 3.28 (t, 2H), 207-2.04 (m, 2H):

MS (+ve ESI): 401 (M+H)$^+$.

EXAMPLE 59

Preparation of Compound No. 59 in Table 1

An analogous reaction to that described in example 12, but starting with 4-phenoxybutyric acid (66.6 mg, 0.37 mmol), yielded the title compound (157 mg, 77% yield) as a white solid:

¹H-NMR (DMSO d₆): 10.92 (s, 1H), 10.07 (s, 1H), 8.77 (s, 1H), 8.04 (s, 1H), 7.74 (d, 2H), 7.53 (d, 2H), 7.28 (m, 2H), 7.20 (s, 1H), 6.93 (m, 3H), 4.02 (m, 2H), 3.99 (s, 3H), 3.98 (s, 3H), 2.49 (m, 2H), 2.05 (m, 2H):

MS (+ve ESI): 459 (M+H)$^+$.

EXAMPLE 60

Preparation of Compound No. 60 in Table 1

An analogous reaction to that described in example 12, but starting with 4-phenylbutyric acid (60.7 mg, 0.37 mmol), yielded the title compound (143 mg, 72% yield) as a white solid:

¹H-NMR (DMSO d₆): 10.92 (s, 1H), 10.0 (s, 1H), 8.77 (s, 1H), 8.04 (s, 1H), 7.70 (d, 2H), 7.53 (d, 2H), 7.28 (m, 2H), 7.10-7.20 (m, 4H), 3.99 (s, 3H), 3.98 (s, 3H), 2.6 (t, 2H), 2.35 (t, 2H), 1.91 (m, 2H):

MS (+ve ESI): 443 (M+H)$^+$.

EXAMPLE 61

Preparation of Compound No. 61 in Table 1

An analogous reaction to that described in example 12, but starting with 4-benzoylbutyric acid (71.0 mg, 0.37 mmol), yielded the title compound (174 mg, 85% yield) as a white solid:

¹H-NMR (DMSO d₆): 10.94 (s, 1H), 10.03 (s, 1H), 8.78 (s, 1H), 8.04 (s, 1H), 7.96 (d, 2H), 7.70 (d, 2H), 7.62 (d, 1H), 7.53 (m, 4H), 7.20 (s, 1H), 3.99 (s, 3H), 3.97 (s, 3H), 3.09 (t, 2H), 2.24 (t, 2H), 1.95 (m, 2H):

MS (+ve ESI) 471 (M+H)$^+$.

EXAMPLE 62

Preparation of Compound No. 62 in Table 1

An analogous reaction to that described in example 12, but starting with undec-10-enic acid (68.1 mg, 0.37 mmol), yielded the title compound (149 mg, 73% yield) as a white solid:

¹H-NMR (DMSO d₆): 10.92 (s, 1H), 9.97 (s, 1H), 8.77 (s, 1H), 8.04 (s, 1H), 7.75 (d, 2H), 7.52 (d, 2H), 7.20 (s, 1H), 6.70-6.85 (m, 1H), 4.90-5.00 (m, 2H), 3.99 (s, 3H), 3.97 (s, 3H), 2.31 (t, 2H), 1.99 (m, 2H), 1.60 (t, 2H), 1.20-1.40 (m, 10H):

MS (+ve ESI): 463 (M+H)$^+$.

EXAMPLE 63

Preparation of Compound No. 63 in Table 1

An analogous reaction to that described in example 12, but starting with trans-2-methylpent-2-enoic acid (42.2 mg, 0.37 mmol), yielded the title compound (47 mg, 36% yield) as a white solid:

¹H-NMR (DMSO d₆): 9.59 (s, 1H), 9.40 (s, 1H), 8.40 (s, 1H), 7.82 (s, 1H), 7.45-7.50 (m, 4H), 7.15 (s, 1H), 6.34 (t, 1H), 3.94 (s, 3H), 3.91 (s, 3H), 2.10-2.19 (m, 3H), 1.83 (s, 3H), 1.04 (m, 2H):

MS (+ve ESI): 393 (M+H)$^+$.

EXAMPLE 64

Preparation of Compound No. 64 in Table 1

An analogous reaction to that described in example 12, but starting with 2-thiopheneacetic acid (52.5 mg, 0.37 mmol), yielded the title compound (84 mg, 59% yield) as a white solid:

¹H-NMR (DMSO d₆): 10.18 (s, 1H), 9.43 (s, 1H), 8.39 (s, 1H), 7.82 (s, 1H), 7.67 (d, 2H), 7.57 (d, 2H), 7.38-7.36 (m, 1H), 7.15 (s, 1H), 6.97 (m, 2H), 3.93 (s, 3H), 3.91 (s, 3H), 3.86 (s, 2H):
MS (+ve ESI): 421 (M+H)⁺.

EXAMPLE 65

Preparation of Compound No. 65 in Table 1

An analogous reaction to that described in example 12, but starting with 3-thiopheneacetic acid (52.5 mg, 0.37 mmol), yielded the title compound (116 mg, 61% yield) as a white solid:
¹H-NMR (DMSO d₆): 10.89 (s, 1H), 10.25 (s, 1H), 8.78 (s, 1H), 8.03 (s, 1H), 7.70 (d, 2H), 7.51 (d, 2H), 7.47-7.54 (m, 1H), 7.33 (d, 1H), 7.20 (s, 1H), 7.09 (m, 1H), 3.98 (s, 3H), 3.97 (s, 3H), 3.70 (s, 2H):
MS (+ve ESI): 421 (M+H)⁺.

EXAMPLE 66

Preparation of Compound No. 66 in Table 1

An analogous reaction to that described in example 12, but starting with 3-(4-hydroxy-3-nitrophenyl)propanoic acid (78.1 mg, 0.37 mmol), yielded the title compound (156 mg, 73% yield) as a white solid:
¹H-NMR (DMSO d₆): 10.80 (s, 1H), 10.70 (s, 1H), 10.02 (s, 1H), 8.75 (s, 1H), 8.02 (s, 1H), 7.77 (d, 1H), 7.63-7.68 (m, 2H), 7.55 (m, 2H), 7.45-7.50 (m, 1H), 7.21 (s, 1H), 7.05 (d, 1H), 3.99 (s, 3H), 3.98 (s, 3H), 2.92 (m, 2H), 2.54-2.68 (m, 2H):
MS (+ve ESI): 490 (M+H)⁺.

EXAMPLE 67

Preparation of Compound No. 67 in Table 1

An analogous reaction to that described in example 12, but starting with 3,5-difluorophenyl-acetic acid (63.6 mg, 0.37 mmol), yielded the title compound (133 mg, 66% yield) as a white solid:
¹H-NMR (DMSO d₆): 10.88 (s, 1H), 10.32 (s, 1H), 8.77 (s, 1H), 8.04 (s, 1H), 7.70 (d, 2H), 7.56 (d, 2H), 7.21 (s, 1H), 7.14 (m, 1H), 7.05 (d, 2H), 3.99 (s, 3H), 3.98 (s, 3H), 3.74 (s, 2H):
MS (+ve ESI): 451 (M+H)⁺.

EXAMPLE 68

Preparation of Compound No. 68 in Table 1

An analogous reaction to that described in example 12, but starting with 4-biphenylacetic acid (78.4 mg, 0.37 mmol), yielded the title compound (108 mg, 65% yield) as a white solid:
¹H-NMR (DMSO d₆): 10.18 (s, 1H), 9.41 (s, 1H), 8.40 (s, 1H), 7.82 (s, 1H), 7.68 (m, 3H), 7.62 (m, 5H), 7.34-7.43 (m, 4H), 7.35 (m, 1H), 7.16 (s, 1H), 3.94 (s, 3H), 3.92 (s, 3H), 3.69 (s, 2H):
MS (+ve ESI): 491 (M+H)⁺.

EXAMPLE 69

Preparation of Compound No. 69 in Table 1

An analogous reaction to that described in example 12, but starting with (3,4-methylenedioxy-phenyl)acetic acid (66.6 mg, 0.37 mmol), yielded the title compound (155 mg, 76% yield) as a white solid:

¹H-NMR (DMSO d₆): 10.80 (s, 1H), 10.21 (s, 1H), 8.72 (s, 1H), 8.20 (s, 1H), 7.71 (d, 2H), 7.57 (d, 2H), 7.21 (s, 1H), 6.92 (s, 1H), 6.88 (d, 1H), 6.8 (d, 1H), 5.98 (s, 2H), 3.96 (s, 3H), 3.94 (s, 3H), 3.56 (s, 2H):
MS (+ve ESI): 459 (M+H)⁺.

EXAMPLE 70

Preparation of Compound No. 70 in Table 1

An analogous reaction to that described in example 12, but starting with 2,6-difluorophenyl-acetic acid (63.6 mg, 0.37 mmol), yielded the title compound (158 mg, 79% yield) as a white solid:
¹H-NMR (DMSO d₆): 10.92 (s, 1H), 10.42 (s, 1H), 8.78 (s, 1H), 8.05 (s, 1H), 7.71 (d, 2H), 7.58 (d, 2H), 7.40 (m, 1H), 7.20 (s, 1H), 7.12 (m, 2H), 3.98 (s, 3H), 3.96 (s, 3H), 3.82 (s, 2H):
MS (+ve EST): 451 (M+H)⁺.

EXAMPLE 71

Preparation of Compound No. 71 in Table 1

An analogous reaction to that described in example 12, but starting with 4-(n-butoxy)phenylacetic acid (77.2 mg, 0.37 mmol), yielded the title compound (110 mg, 67% yield) as a white solid:
¹H-NMR (DMSO d₆): 10.05 (s, 1H), 9.40 (s, 1H), 8.41 (s, 1H), 7.82 (s, 1H), 7.68 (d, 2H), 7.62 (d, 2H), 7.24 (d, 2H), 7.15 (s, 1H), 6.85 (d, 2H), 3.92 (m, 2H), 3.90 (s, 3H), 3.88 (s, 3H), 3.55 (s, 2H), 1.67 (m, 2H), 1.41 (m, 2H), 0.90 (t, 3H):
MS (+ve ESI): 487 (M+H)⁺.

EXAMPLE 72

Preparation of Compound No. 72 in Table 1

An analogous reaction to that described in example 12, but starting with 4-methylpentanoic acid (42.9 mg, 0.37 mmol), yielded the title compound (108 mg, 60% yield) as a white solid:
¹H-NMR (DMSO d₆): 10.95 (s, 1H), 9.98 (s, 1H), 8.80 (s, 1H), 8.05 (s, 1H), 7.71 (d, 2H), 7.55 (d, 2H), 7.22 (s, 1H), 3.98 (s, 3H), 3.96 (s, 3H), 2.33 (t, 2H), 1.58 (m, 1H), 1.52 (m, 2H), 0.88 (d, 6H):
MS (+ve ESI): 395 (M+H)⁺.

EXAMPLE 73

Preparation of Compound No. 73 in Table 1

An analogous reaction to that described in example 12, but starting with 5-hexynoic acid (41.4 mg, 0.37 mmol), yielded the title compound (144 mg, 80% yield) as a white solid:
¹H-NMR (DMSO d₆): 10.93 (s, 1H), 10.04 (s, 1H), 8.81 (s, 1H), 8.05 (s, 1H), 7.72 (d, 2H), 7.55 (d, 2H), 7.22 (s, 1H), 4.0 (s, 3H), 3.98 (s, 3H), 2.82 (t, 1H), 2.43 (t, 2H), 2.21 (m, 2H), 1.75 (m, 2H):
MS (+ve ESI): 391 (M+H)⁺.

EXAMPLE 74

Preparation of Compound No. 74 in Table 1

An analogous reaction to that described in example 12, but starting with 3-phenoxyphenylacetic acid (84.4 mg, 0.37 mmol), yielded the title compound (121 mg, 71% yield) as a white solid:

$^1$H-NMR (DMSO d$_6$): 10.10 (s, 1H), 9.40 (s, 1H), 8.41 (s, 1H), 7.82 (s, 1H), 7.70 (d, 2H), 7.62 (d, 2H), 7.35 (m, 3H), 7.17 (s, 1H), 7.13 (m, 2H), 7.03 (m, 3H), 6.95 (dd, 1H), 3.92 (s, 3H), 3.90 (s, 3H), 3.62 (s, 2H):
MS (+ve ESI): 507 (M+H)$^+$.

EXAMPLE 75

Preparation of Compound No. 75 in Table 1

An analogous reaction to that described in example 12, but starting with 2-bromo-3-methoxythiophene-4-carboxylic acid (87.3 mg, 0.37 mmol), yielded the title compound (190 mg, 86% yield) as a white solid:
$^1$H-NMR (DMSO d$_6$): 10.92 (s, 1H), 10.18 (s, 1H), 8.81 (s, 1H), 8.15 (s, 1H), 8.08 (s, 1H), 7.82 (d, 2H), 7.62 (d, 2H), 7.22 (s, 1H), 4.00 (s, 3H), 3.99 (s, 3H), 3.90 (s, 3H):
MS (+ve ESI): 515 (M+H)$^+$.

EXAMPLE 76

Preparation of Compound No. 76 in Table 1

An analogous reaction to that described in example 12, but starting with 2-chloro-3-methoxythiophene-4-carboxylic acid (71.0 mg, 0.37 mmol), yielded the title compound (166 mg, 80% yield) as a white solid:
$^1$H-NMR (DMSO d$_6$): 10.98 (s, 1H), 10.15 (s, 1H), 8.80 (s, 1H), 8.06 (s, 1H), 8.00 (s, 1H), 7.82 (d, 2H), 7.62 (d, 2H), 7.22 (s, 1H), 4.00 (s, 3H), 3.93 (s, 3H):
MS (+ve ESI): 471 (M+H)$^+$.

EXAMPLE 77

Preparation of Compound No. 77 in Table 1

An analogous reaction to that described in example 12, but starting with (4-ethoxy-3-methoxy-phenyl)acetic acid (77.7 mg, 0.37 mmol), yielded the title compound (54 mg, 33% yield) as a white solid:
$^1$H-NMR (DMSO d$_6$): 10.05 (s, 1H), 9.41 (s, 1H), 8.41 (s, 1H), 7.83 (s, 1H), 7.69 (d, 2H), 7.62 (d, 2H), 7.17 (s, 1H), 6.95 (s, 1H), 6.88 (d, 1H), 6.83 (d, 1H), 3.97 (q, 2H), 3.93 (s, 3H), 3.91 (s, 3H), 3.75 (s, 3H), 3.55 (s, 3H), 1.30 (t, 3H):
MS (+ve ESI): 489 (M+H)$^+$.

EXAMPLE 78

Preparation of Compound No. 78 in Table 1

An analogous reaction to that described in example 12, but starting with 4-benzyloxyphenyl-acetic acid (89.5 mg, 0.37 mmol), yielded the title compound (102 mg, 58% yield) as a white solid:
$^1$H-NMR (DMSO d$_6$): 10.08 (s, 1H), 9.41 (s, 1H), 8.40 (s, 1H), 7.82 (s, 1H), 7.68 (d, 2H), 7.59 (d, 2H), 7.40 (m, 5H), 7.26 (d, 2H), 7.15 (s, 1H), 6.95 (d, 2H), 5.08 (s, 2H), 3.92 (s, 3H), 3.90 (s, 3H), 3.53 (s, 2H):
MS (+ve ESI): 521 (M+H)$^+$.

EXAMPLE 79

Preparation of Compound No. 79 in Table 1

An analogous reaction to that described in example 12, but starting with 4-(2-thienyl)butyric acid (62.9 mg, 0.37 mmol), yielded the title compound (133 mg, 67% yield) as a white solid:

$^1$H-NMR (DMSO d$_6$): 10.95 (s, 1H), 10.05 (s, 1H), 9.80 (s, 1H), 8.05 (s, 1H), 7.70 (d, 2H), 7.55 (d, 2H), 7.31 (d, 1H), 7.22 (s, 1H), 6.95 (m, 1H), 6.88 (m, 1H), 4.00 (s, 3H), 3.98 (s, 3H), 2.88 (t, 2H), 2.41 (t, 2H), 1.93 (m, 2H):
MS (+ve ESI): 449 (M+H)$^+$.

EXAMPLE 80

Preparation of Compound No. 80 in Table 1

An analogous reaction to that described in example 12, but starting with 6-heptynoic acid (46.6 mg, 0.37 mmol), yielded the title compound (132 mg, 71% yield) as a white solid:
$^1$H-NMR (DMSO d$_6$): 10.95 (s, 1H), 10.05 (s, 1H), 8.78 (s, 1H), 8.05 (s, 1H), 7.71 (d, 2H), 7.55 (d, 2H), 7.20 (s, 1H), 4.01 (s, 3H), 3.99 (s, 3H), 2.78 (t, 1H), 2.35 (t, 2H), 2.20 (m, 2H), 1.71 (m, 2H), 1.50 (m, 2H):
MS (+ve ESI): 405 (M+H)$^+$.

EXAMPLE 81

Preparation of Compound No. 81 in Table 1

An analogous reaction to that described in example 12, but starting with 1-(4-chlorophenyl)-cyclopropane carboxylic acid (72.5 mg, 0.37 mmol), yielded the title compound (114 mg, 71% yield) as a white solid:
$^1$H-NMR (DMSO d$_6$): 9.41 (s, 1H), 9.07 (s, 1H), 8.41 (s, 1H), 7.81 (s, 1H), 7.65 (d, 2H), 7.50 (d, 2H), 7.43 (s, 4H), 7.18 (s, 1H), 3.92 (s, 3H), 3.89 (s, 3H), 1.48 (m, 2H), 1.10 (m, 2H):
MS (+ve ESI): 475 (M+H)$^+$.

EXAMPLE 82

Preparation of Compound No. 82 in Table 1

An analogous reaction to that described in example 12, but starting with cyclopentylacetic acid (47.4 mg, 0.37 mmol), yielded the title compound (139 mg, 75% yield) as a white solid:
$^1$H-NMR (DMSO d$_6$): 10.95 (s, 1H), 10.00 (s, 1H), 8.81 (s, 1H), 8.05 (s, 1H), 7.70 (d, 2H), 7.55 (d, 2H), 7.20 (s, 1H), 4.01 (s, 3H), 3.99 (s, 3H), 2.31 (m, 2H), 2.25 (m, 1H), 1.75 (m, 2H), 1.55 (m, 4H), 1.15 (m, 2H):
MS (+ve ESI): 407 (M+H)$^+$.

EXAMPLE 83

Preparation of Compound No. 83 in Table 1

An analogous reaction to that described in example 12, but starting with 3-(cyclopentyl)-propanoic acid (52.5 mg, 0.37 mmol), yielded the title compound (137 mg, 72% yield) as a white solid:
$^1$H-NMR (DMSO d$_6$): 10.95 (s, 1H), 10.02 (s, 1H), 8.80 (s, 1H), 8.05 (s, 1H), 7.71 (d, 2H), 7.52 (d, 2H), 7.21 (s, 1H), 3.99 (s, 3H), 3.87 (s, 3H), 2.35 (t, 2H), 1.75 (m, 3H), 1.55 (m, 6H), 1.10 (m, 2H):
MS (+ve ESI): 421 (M+H)$^+$.

EXAMPLE 84

Preparation of Compound No. 84 in Table 1

An analogous reaction to that described in example 12, but starting with cyclohexaneacetic acid (52.5 mg, 0.37 mmol), yielded the title compound (106 mg, 56% yield) as a white solid:

¹H-NMR (DMSO d₆) 10.90 (s, 1H), 10.01 (s, 1H), 8.78 (s, 1H), 8.05 (s, 1H), 7.71 (d, 2H), 7.55 (d, 2H), 7.22 (s, 1H), 4.01 (s, 3H), 3.99 (s, 1H), 2.2 (d, 2H), 1.71 (m, 6H), 1.20 (m, 3H), 0.98 (m, 2H):

MS (+ve ESI): 421 (M+H)⁺.

EXAMPLE 85

Preparation of Compound No. 85 in Table 1

An analogous reaction to that described in example 12, but starting with 3-(cyclohexyl)-propanoic acid (57.7 mg, 0.37 mmol), yielded the title compound (141 mg, 73% yield) as a white solid:

¹H-NMR (DMSO d₆): 10.95 (s, 1H), 10.00 (s, 1H), 8.81 (s, 1H), 8.05 (s, 1H), 7.70 (d, 2H), 7.55 (d, 2H), 7.20 (s, 1H), 4.01 (s, 3H), 3.99 (s, 3H), 2.35 (t, 2H), 1.71 (m, 6H), 1.51 (m, 2H), 1.15 (m, 5H), 0.90 (m, 2H):

MS (+ve ESI): 435 (M+H)⁺.

EXAMPLE 86

Preparation of Compound No. 86 in Table 1

An analogous reaction to that described in example 12, but starting with 4-(cyclohexyl)butyric acid (62.9 mg, 0.37 mmol), yielded the title compound (146 mg, 73% yield) as a white solid:

¹H-NMR (DMSO d₆): 10.95 (s, 1H), 10.00 (s, 1H), 8.81 (s, 1H), 8.05 (s, 1H), 7.71 (d, 2H), 7.52 (d, 2H), 7.20 (s, 1H), 3.99 (s, 3H), 3.97 (s, 3H), 2.31 (t, 2H), 1.60 (m, 7H), 1.18 (m, 6H), 0.85 (m, 2H):

MS (+ve ESI): 449 (M+H)⁺.

EXAMPLE 87

Preparation of Compound No. 87 in Table 1

An analogous reaction to that described in example 12, but starting with 2-phenoxypropanoic acid (61.4 mg, 0.37 mmol), yielded the title compound (140 mg, 93% yield) as a white solid:

¹H-NMR (DMSO d₆): 10.15 (s, 1H), 9.45 (s, 1H), 8.41 (s, 1H), 7.83 (s, 1H), 7.71 (d, 2H), 7.60 (d, 2H), 7.30 (m, 2H), 7.18 (s, 1H), 6.95 (m, 3H), 4.88 (q, 1H), 3.96 (s, 3H), 3.93 (s, 3H), 1.55 (d, 3H):

MS (+ve ESI): 445 (M+H)⁺.

EXAMPLE 88

Preparation of Compound No. 88 in Table 1

An analogous reaction to that described in example 21, but starting with α-methylcinnamic acid (59.9 mg, 0.37 mmol), yielded the title compound (44 mg, 30% yield) as a white solid:

¹H-NMR (DMSO d₆): 12.55 (s, 1H), 9.96 (s, 1H), 9.47 (s, 1H), 8.42 (s, 1H), 7.85 (s, 1H), 7.71 (s, 4H), 7.32-7.49 (m, 6H), 7.18 (s, 1H), 3.97 (s, 3H), 3.94 (s, 3H), 2.13 (s, 3H):

MS (+ve ESI): 441 (M+H)⁺.

EXAMPLE 89

Preparation of Compound No. 89 in Table 2

An analogous reaction to that described in example 1, but starting with N-benzoyl 2-chloro-4-aminoaniline (5.60 g, 22.7 mmol) and 4-chloro-6,7-dimethoxyquinazoline (5.10 g, 22.7 mmol), yielded the title compound (10.53 g, 98% yield) as a pale yellow solid:

¹H-NMR (DMSO d₆): 11.51 (s, 1H), 10.11 (s, 1H), 8.88 (s, 1H), 8.36 (s, 1H), 7.99 (m, 3H), 7.51-7.78 (m, 5H), 7.36 (s, 1H), 4.03 (s, 3H), 4.00 (s, 3H):

MS (+ve ESI): 435 (M+H)⁺.

N-Benzoyl 2-chloro-4-aminoaniline, used as the starting material was obtained as follows:

a) A mixture of 2-chloro-4-nitroaniline (15.0 g, 86.9 mmol), triethylamine (13.3 ml, 95.6 mmol) and benzoyl chloride (11.1 ml, 95.6 mmol) were heated in toluene (200 ml) at reflux for 2 hours under an inert atmosphere. The reaction was allowed to cool to ambient temperature overnight, causing precipitation of a white solid. The solid was collected by suction filtration, washed with toluene (3×50 ml) and dried in vacuo. The crude product was taken up in dichloromethane (300 ml) and washed with 2.0 N aqueous hydrochloric acid (3×100 ml), water (100 ml), saturated aqueous sodium bicarbonate solution (3×100 ml) and water (100 ml). Drying of the organic layer over magnesium sulphate, followed by solvent evaporation in vacuo, yielded N-benzoyl 2-chloro-4-nitroaniline (6.83 g, 28% yield) as a yellow crystalline solid:

¹H-NMR (DMSO d₆): 10.25 (s, 1H), 8.40 (d, 1H, J=2 Hz), 8.25 (dd, 1H, J=2, 8 Hz), 8.05 (d, 1H, J=8 Hz), 7.51-7.65 (m, 3H):

MS (−ve ESI): 275 (M−H)⁻,
MS (+ve ESI): 277 (M+H)⁺.

b) A mixture of N-benzoyl 2-chloro-4-nitroaniline (5.77 g, 20.8 mmol) and tin (II) chloride (23.5 g, 104 .mmol) were heated in ethyl acetate (250 ml) at reflux for 2 hours under an inert atmosphere. The reaction was allowed to cool to ambient temperature and concentrated aqueous ammonia (40 ml) was added. The reaction was filtered, the solid material was washed with ethyl acetate (3×30 ml) and the combined organic layers were evaporated in vacuo. Drying of the resultant solid in vacuo, yielded N-benzoyl 2-chloro-4-aminoaniline (4.63 g, 90% yield) as a cream-coloured crystalline solid:

¹H-NMR (DMSO d₆): 9.67 (s, 1H), 7.94 (d, 2H, J=8 Hz), 7.45-7.58 (m, 3H), 7.08 (d, 1H, J=8 Hz), 6.67 (d, 1H, J=2 Hz), 6.51 (dd, 1H, J=2, 8 Hz), 5.34 (s, 2H):

MS (−ve ESI): 245 (M−H)⁻,
MS (+ve ESI): 247 (M+H)⁺.

EXAMPLE 90

Preparation of Compound No. 90 in Table 2

An analogous reaction to that described in example 1, but starting with N-benzoyl 2-methyl-4-aminoaniline (111 mg, 0.50 mmol) and 4-chloro-6,7-dimethoxyquinazoline (100 mg, 0.45 mmol), yielded the title compound (188 mg, 94% yield) as a white solid:

¹H-NMR (DMSO d₆): 11.29 (s, 1H), 9.94 (s, 1H), 8.80 (s, 1H), 8.27 (s, 1H), 7.99 (d, 2H, J=8 Hz), 7.44-7.63 (m, 6H), 7.34 (s, 1H), 4.01 (s, 3H), 3.99 (s, 3H):

MS (−ve ESI): 413 (M−H)⁻,
MS (+ve ESI): 415 (M+H)⁺.

N-Benzoyl 2-methyl-4-aminoaniline, used as the starting material was obtained as follows:

a) A mixture of 2-methyl-4-nitroaniline (2.03 g, 13.3 mmol), triethylamine (2.00 ml, 14.6 mmol) and benzoyl chloride (1.70 ml, 14.6 mmol) were heated in toluene (50 ml) at reflux for 2 hours under an inert atmosphere. The reaction was allowed to cool to ambient temperature overnight, causing precipitation of a white solid. The solid was collected by suction filtration, washed with toluene (3×50 ml), dissolved in dichloromethane (100 ml) and washed with water (3×50 ml). Drying of the organic layer over magnesium sulphate, followed by solvent evaporation in vacuo, yielded N-benzoyl 2-methyl-4-nitroaniline (3.06 g, 90% yield) as a white solid:

$^1$H-NMR (DMSO $d_6$): 8.50 (d, 1H, J=8 Hz), 8.14-8.19 (m, 2H), 7.87-7.91 (m, 3H), 7.51-7.65 (m, 3H), 2.45 (s, 3H):
MS (−ve ESI): 255 (M−H)$^−$,
MS (+ve ESI): 257 (M+H)$^+$.

b) A mixture of N-benzoyl 2-methyl-4-nitroaniline (2.93 g, 11.4 mmol) and tin (II) chloride (12.9 g, 57.2 mmol) were heated in ethyl acetate (100 ml) at reflux for 2 hours under an inert atmosphere. The reaction was allowed to cool to ambient temperature and concentrated aqueous ammonia (20 ml) was added. The reaction was filtered, the solid material was washed with ethyl acetate (3×30 ml) and then the combined organic layers were evaporated in vacuo. Drying of the resultant solid in vacuo, yielded N-benzoyl 2-methyl-4-aminoaniline (1.03 g, 40% yield) as a white crystalline solid:

$^1$H-NMR (DMSO $d_6$): 9.51 (s, 1H), 7.94 (d, 2H, J=8 Hz), 7.44-7.56 (m, 3H), 6.88 (d, 1H, J=8 Hz), 6.44 (d, 1H, J=2 Hz), 6.39 (dd, 1H, J=2, 8 Hz), 4.91 (s, 2H), 2.05 (s, 3H):
MS (−ve ESI): 225 (M−H)$^−$,
MS (+ve ESI): 227 (M+H)$^+$.

EXAMPLE 91

Preparation of Compound No. 91 in Table 2

An analogous reaction to that described in example 1, but starting with N-(4-amino-3-methylphenyl)benzamide (90.8 mg, 0.40 mmol) and 4-chloro-6,7-dimethoxyquinazoline (90 mg, 0.40 mmol), yielded the title compound (145 mg, 81% yield) as a pale yellow solid:

$^1$H-NMR (DMSO $d_6$): 11.27 (s, 1H), 10.33 (s, 1H), 8.70 (s, 1H), 8.25 (s, 1H), 7.98 (d, 2H, J=8 Hz), 7.80 (d, 1H, J=2 Hz), 7.74 (dd, 1H, J=2, 8 Hz), 7.51-7.63 (m, 3H), 7.34 (s, 1H), 7.28 (d, 1H, J=8 Hz), 3.99 (s, 6H), 2.20 (s, 3H):
MS (−ve ESI): 413 (M−H)$^−$,
MS (+ve ESI): 415 (M+H)$^+$.

EXAMPLE 92

Preparation of Compound No. 92 in Table 2

An analogous reaction to that described in example 1, but starting with N-benzoyl 2-methoxy-4-aminoaniline hydrochloride (127 mg, 0.45 mmol) and 4-chloro-6,7-dimethoxyquinazoline (102 mg, 0.45 mmol), yielded the title compound (176 mg, 84% yield) as a pale yellow solid:

$^1$H-NMR (DMSO $d_6$): 11.43 (s, 1H), 9.48 (s, 1H), 8.80 (s, 1H), 8.35 (s, 1H), 7.96 (d, 2H, J=8 Hz), 7.83 (d, 1H, J=8 Hz), 7.48-7.61 (m, 4H), 7.36 (s, 1H), 7.34 (dd, 1H, J=2, 8 Hz), 4.03 (s, 3H), 3.99 (s, 3H), 3.85 (s, 3H)
MS (−ve ESI): 429 (M−H)$^−$,
MS (+ve ESI): 431 (M+H)$^+$.

N-Benzoyl 2-methoxy-4-aminoaniline, used as the starting material was obtained as follows:

a) A mixture of 2-methoxy-4-nitroaniline (2.23 g, 13.3 mmol), triethylamine (2.00 ml, 14.6 mmol) and benzoyl chloride (1.70 ml, 14.6 mmol) were stirred in toluene (50 ml) for 24 hours under an inert atmosphere at ambient temperature. The solid was collected by suction filtration and washed with toluene (3×50 ml) and diethyl ether (50 ml). Purification of the crude product by flash chromatography on silica gel, eluting with dichloromethane, yielded N-benzoyl 2-methoxy-4-nitroaniline (2.79 g, 77% yield) as a white solid:

$^1$H-NMR (DMSO $d_6$): 8.75 (s, 1H), 8.75 (d, 1H, J=8 Hz), 7.99 (dd, 1H, J=2, 8 Hz), 7.91 (d, 2H, J=8 Hz), 7.80 (d, 1H, J=2 Hz), 7.51-7.63 (m, 3H), 4.07 (s, 3H):
MS (−ve ESI): 271 (M−H)$^−$,
MS (+ve ESI): 273 (M+H)$^+$.

b) A mixture of N-benzoyl 2-methoxy-4-nitroaniline (2.63 g, 9.66 mmol) and tin (II) chloride (10.9 g, 48.3 mmol) were heated in ethyl acetate (200 ml) at reflux for 4 hours under an inert atmosphere. The reaction was allowed to cool to ambient temperature and concentrated aqueous ammonia (20 ml) was added. The reaction was filtered, the solid material was washed with ethyl acetate (3×30 ml) and then the combined organic layers were evaporated in vacuo. The orange solid was dissolved in ethyl acetate (45 ml) and a 1.0 N solution of hydrogen chloride in diethyl ether (25 ml) was added, causing precipitation of a white solid. Recrystallisation of this solid from methanol/ethyl acetate, yielded N-benzoyl 2-methoxy-4-aminoaniline hydrochloride (1.06 g, 39% yield) as a white crystalline solid:

$^1$H-NMR (DMSO $d_6$): 9.51 (s, 1H), 7.94 (d, 2H, J=8 Hz), 7.74 (d, 1H, J=8 Hz), 7.46-7.60 (m, 3H), 7.01 (d, 1H, J=2 Hz), 6.90 (dd, 1H, J=2, 8 Hz), 3.81 (s, 3H):
MS (−ve ESI): 225 (M−H)$^−$,
MS (+ve ESI): 227 (M+H)$^+$.

EXAMPLE 93

Preparation of Compound No. 93 in Table 2

An analogous reaction to that described in example 1, but starting with N-benzoyl 2-cyano-4-aminoaniline (107 mg, 0.45 mmol) and 4-chloro-6,7-dimethoxyquinazoline (101 mg, 0.45 mmol), yielded the title compound (21 mg, 10% yield) as a pale yellow solid:

$^1$H-NMR (DMSO $d_6$): 12.46 (s, 1H), 10.00 (s, 1H), 8.60 (s, 2H), 8.40 (dd, 1H, J=2, 8 Hz), 8.18 (d, 2H, J=8 Hz), 7.95 (s, 1H), 7.79 (d, 1H, J=8 Hz), 7.48-7.58 (m, 3H), 7.22 (s, 1H), 4.03 (s, 3H), 3.99 (s, 3H):
MS (−ve ESI): 424 (M−H)$^−$,
MS (+ve ESI): 426 (M+H)$^+$.

N-Benzoyl 2-cyano-4-aminoaniline, used as the starting material was obtained as follows:

a) A mixture of 2-cyano-4-nitroaniline (5.00 g, 30.6 mmol), triethylamine (4.70 ml, 33.7 mmol) and benzoyl chloride (3.90 ml, 33.7 mmol) were heated at reflux in toluene (50 ml) for 3 hours under an inert atmosphere. The reaction was allowed to cool to ambient temperature, the solid was collected by suction filtration and washed with toluene (3×50 ml). The product was dissolved in dichloromethane (100 ml) and washed with 2.0 N aqueous hydrochloric acid (2×50 ml), saturated aqueous sodium bicarbonate solution (50 ml) and water (2×50 ml). Drying of the organic layer over magnesium sulphate, followed by solvent evaporation in vacuo, yielded N,N-di(benzoyl)2-methyl-4-nitroaniline (3.90 g, 62% yield) as a yellow solid:

$^1$H-NMR (DMSO $d_6$): 8.61 (d, 1H, J=2 Hz), 8.40 (dd, 1H, J=2, 8 Hz), 7.76 (d, 4H, J=8 Hz), 7.34-7.51 (m, 7H):
MS (+ve ESI): 372 (M+H)$^+$.

b) Hydrogen peroxide (8.60 ml, 76.2 mmol) and lithium hydroxide (0.98 g, 23.4 mmol) were added to a stirred solution of N,N-di(benzoyl)2-methyl-4-nitroaniline (4.34 g, 11.7 mmol) in a mixture of water (70 ml) and tetrahydrofuran (210 ml) at 0° C. The reaction was allowed to warm to ambient temperature over 18 hours and then re-cooled to 0° C. before addition of 1.5 N aqueous sodium sulphate solution (60 ml, 90 mmol). The tetrahydrofuran was removed in vacuo and acidified to pH 6 by addition of 2.0 N aqueous hydrochloric acid. Collection of the precipitated solid by suction filtration yielded N-benzoyl 2-cyano-4-nitroaniline (3.04 g, 97% yield) as a pale yellow solid:

$^1$H-NMR (DMSO d$_6$): 12.94 (s, 1H), 8.80 (d, 1H, J=2 Hz), 8.54 (dd, 1H, J=2, 8 Hz), 8.19 (d, 2H, J=8 Hz), 7.90 (d, 1H, J=8 Hz), 7.54-7.65 (m, 4H):

MS (−ve ESI): 266 (M−H)$^-$,
MS (+ve ESI): 268 (M+H)$^+$.

c) A mixture of N-benzoyl 2-cyano-4-nitroaniline (3.38 g, 12.6 mmol) and tin (II) chloride (14.3 g, 63.2 mmol) were heated in ethyl acetate (200 ml) at reflux for 2.5 hours under an inert atmosphere. The reaction was allowed to cool to ambient temperature, concentrated aqueous ammonia (20 ml) added and the reaction was then filtered. Evaporation of the organic layer in vacuo yielded N-benzoyl 2-cyano-4-aminoaniline (2.64 g, 88% yield) as a yellow solid:

$^1$H-NMR (DMSO d$_6$): 12.07 (s, 1H), 8.09 (m, 2H), 7.43-7.50 (m, 4H), 7.20 (d, 1H, J=2 Hz), 7.10 (dd, 1H, J=2, 8 Hz), 5.63 (s, 3H):

MS (−ve ESI): 236 (M−H)$^-$,
MS (+ve ESI): 238 (M+H)$^+$.

EXAMPLE 94

Preparation of Compound No. 94 in Table 2

An analogous reaction to that described in example 1, but starting with N-benzoyl 3-(trifluoromethyl)-4-aminoaniline (154 mg, 0.55 mmol) and 4-chloro-6,7-dimethoxyquinazoline (112 mg, 0.50 mmol), yielded the title compound (157 mg, 62% yield) as a white solid:

$^1$H-NMR (DMSO d$_6$): 11.46 (s, 1H), 10.74 (s, 1H), 8.74 (s, 1H), 8.41 (d, 1H, J=2 Hz), 8.22 (m, 2H), 8.02 (d, 2H, J=8 Hz), 7.51-7.65 (m, 4H), 7.36 (s, 1H), 3.99 (s, 3H), 3.98 (s, 3H):

MS (−ve ESI): 467 (M−H)$^-$,
MS (+ve ESI): 469 (M+H)$^+$.

N-Benzoyl 3-(trifluoromethyl)-4-aminoaniline, used as the starting material was obtained as follows:

a) A mixture of 3-(trifluoromethyl)-4-nitroaniline (1.00 g, 4.85 mmol) and benzoyl chloride (0.62 ml, 5.34 mmol) were heated in pyridine (20 ml) at reflux for 3 hours under an inert atmosphere. The reaction was allowed to cool to ambient temperature, poured into water (200 ml) and basified by addition of 2.0 N aqueous sodium hydroxide solution. An oily liquid separated out which crystallised on standing at 4° C. overnight. The solid was collected by suction filtration, washed with water (3×20 ml) and then purified by flash chromatography on silica gel, eluting with dichloromethane. This yielded N-benzoyl 3-(trifluoromethyl)-4-nitroaniline (1.01 g, 67% yield) as a white solid:

$^1$H-NMR (DMSO d$_6$): 10.94 (s, 1H), 8.47 (d, 1H, J=2 Hz), 8.32 (dd, 1H, J=2, 8 Hz), 8.22 (d, 1H, J=8 Hz), 7.52-7.65 (m, 3H):

MS (−ve ESI): 309 (M−H)$^-$,
MS (+ve ESI): 311 (M+H)$^+$.

b) Platinum dioxide (100 mg, 0.44 mmol) was added to a solution of N-benzoyl 3-(trifluoromethyl)-4-nitroaniline (913 mg, 2.94 mmol) in ethanol (50 ml) at ambient temperature and the reaction stirred for 1.5 hours under an atmosphere of hydrogen. Filtration of the reaction through a pad of celite and solvent evaporation in vacuo, yielded N-benzoyl 3-(trifluoromethyl)-4-aminoaniline (750 mg, 91% yield) as an off-white solid:

$^1$H-NMR (DMSO d$_6$): 7.85 (d, 2H, J=8 Hz), 7.74 (s, 1H), 7.43-7.62 (m, 5H), 6.74 (d, 1H, J=8 Hz), 4.14 (s, 1H):

MS (−ve ESI): 279 (M−H)$^-$,
MS (+ve ESI): 281 (M+H)$^+$.

EXAMPLE 95

Preparation of Compound No. 95 in Table 2

A solution of 4-chloro-6-methoxy-7-benzyloxyquinazoline (150 mg, 0.50 mmol) and N-(4-amino-2-methylphenyl)benzamide (113 mg, 0.50 mmol), in isopropanol (5.0 ml) was heated at 40° C. for 30 minutes and then at 83° C. for 12 hours before the reaction was allowed to cool to ambient temperature. The solid which had precipitated was collected by suction filtration and washed with diethyl ether (2×10 ml). Drying of this material yielded the title compound (242 mg, 92% yield) as an off-white solid:

$^1$H-NMR (DMSO d$_6$): 11.32 (s, 1H), 9.98 (s, 1H), 8.82 (s, 1H), 8.32 (s, 1H), 8.04 (d, 2H), 7.37-7.66 (m, 12H), 5.35 (s, 2H), 4.04 (s, 3H), 2.32 (s, 3H):

MS (+ve ESI): 491 (M+H)$^+$.

EXAMPLE 96

Preparation of Compound No. 96 in Table 2

An analogous reaction to that described in example 95, but starting with N-(4-amino-2-cyanophenyl)benzamide (118 mg, 0.50 mmol) yielded the title compound (230 mg, 86% yield) as a white solid:

$^1$H-NMR (DMSO d$_6$): 12.56 (s, 1H), 10.91 (s, 1H), 8.80 (s, 1H), 8.59 (s, 1H), 8.35 (d, 1H), 8.15-8.26 (m, 3H), 7.83 (d, 1H), 7.34-7.65 (m, 9H), 5.32 (s, 2H), 4.05 (s, 3H):

MS (+ve ESI): 502 (M+H)$^+$.

EXAMPLE 97

Preparation of Compound No. 97 in Table 2

A solution of 1.0 N hydrochloric acid in ether (0.50 ml, 0.50 mmol) was added to a solution with N-(4-amino-2-methylphenyl)benzamide (113 mg, 0.50 mmol) and 4-chloro-6-methoxy-7-(3-morpholinopropoxy)quinazoline (168 mg, 0.50 mmol), in isopropanol (5.0 ml). The reaction was heated at 40° C. for 30 minutes and then at 83° C. for 12 hours. The reaction was allowed to cool to ambient temperature and the solid which had precipitated was collected by suction filtration and washed with diethyl ether (2×10 ml). Drying of this material yielded the title compound (275 mg, 98% yield) as a white solid:

$^1$H-NMR (DMSO d$_6$): 11.40 (s, 1H), 11.05 (s, 1H), 9.98 (s, 1H), 8.82 (s, 1H), 8.35 (s, 1H), 8.02 (d, 2H), 7.58 (m, 5H), 7.48 (d, 1H), 7.40 (s, 1H), 4.30 (t, 2H), 4.05 (s, 3H), 3.99 (m, 2H), 3.85 (m, 2H), 3.51 (m, 2H), 3.29 (m, 2H), 3.10 (m, 2H), 2.35 (m, 2H), 2.30 (s, 3H):

MS (+ve ESI): 528 (M+H)$^+$.

EXAMPLE 98

Preparation of Compound No. 98 in Table 2

An analogous reaction to that described in example 97, but starting with N-(4-amino-2-(trifluoromethyl)phenyl)benzamide (140 mg, 0.50 mmol) yielded the title compound (289 mg, 94% yield) as a white solid:

$^1$H-NMR (DMSO d$_6$): 11.70 (s, 1H), 11.05 (s, 1H), 10.20 (s, 1H), 8.90 (s, 1H), 8.48 (s, 1H), 8.25 (s, 1H), 8.18 (d, 1H), 7.95 (d, 2H), 7.65 (m, 2H), 7.55 (m, 2H), 7.45 (s, 1H), 4.35 (t, 2H), 4.10 (s, 3H), 4.00 (m, 2H), 3.85 (m, 2H), 3.50 (m, 2H), 3.30 (m, 2H), 3.10 (m, 2H), 2.35 (m, 2H):

MS (+ve ESI): 582 (M+H)$^+$.

EXAMPLE 99

Preparation of Compound No. 99 in Table 3

A solution of 4-chloro-6,7-dimethoxyquinazoline (224 mg, 1.00 mmol), potassium carbonate (152 mg, 1.10 mmol) and N-benzoyl 4-hydroxyaniline (235 mg, 1.10 mmol) in dimethylformamide (4 ml) was heated at 110° C. for 2 hours before the reaction was allowed to cool to ambient temperature. The reaction was poured into water and the solid which had precipitated was collected by suction filtration and washed with a mixture of diethyl ether (10 ml), ethyl acetate (10 ml) and isohexane (10 ml). Drying of this material yielded the title compound (325 mg, 81% yield) as a beige solid:

$^1$H-NMR (DMSO d$_6$): 10.33 (s, 1H), 8.55 (s, 1H), 7.95 (d, 2H, J=8 Hz), 7.85 (d, 2H, J=8 Hz), 7.50-7.60 (m, 4H), 7.40 (s, 1H), 7.25 (d, 2H, J=8 Hz), 4.00 (s, 6H):

MS (−ve ESI): 400 (M−H)$^−$,
MS (+ve ESI): 402 (M+H)$^+$.

N-benzoyl 4-hydroxyaniline, used as the starting material was obtained as follows:

A solution of benzoyl chloride (2.30 ml, 20.0 mmol) in tetrahydrofuran (25 ml) was added dropwise to a solution of 4-aminophenol (2.18 g, 20.0 mmol) and triethylamine (10 ml) in tetrahydrofuran (75 ml) at ambient temperature and the reaction allowed to stir for a further 18 hours. The reaction was poured into water and the solid material which formed was collected by suction filtration. Recrystallisation from ethyl acetate/isohexane (1:1), followed by solvent evaporation in vacuo, yielded N-benzoyl 4-hydroxyaniline (3.05 g, 72% yield) as a white solid:

$^1$H-NMR (DMSO d$_6$): 9.95 (s, 1H), 9.20 (s, 1H), 7.90 (d, 2H, J=8 Hz), 7.60-7.80 (m, 5H), 6.75 (d, 2H, J=8 Hz):

MS (−ve ESI): 212 (M−H)$^−$,
MS (+ve ESI): 214 (M+H)$^+$.

EXAMPLE 100

Preparation of Compound No. 100 in Table 3

An analogous reaction to that described in example 99, but starting with N-benzoyl 2-chloro-4-hydroxyaniline (199 mg, 0.80 mmol), yielded the title compound (172 mg, 54% yield) as a white solid:

$^1$H-NMR (DMSO d$_6$): 10.90 (s, 1H), 8.60 (s, 1H), 8.00 (d, 2H, J=8 Hz), 7.50-7.70 (m, 6H), 7.35-7.40 (m, 2H), 7.15 (d, 2H, J=8 Hz), 4.00 (s, 6H):

MS (−ve ESI): 434, 436 (M−H)$^−$,
MS (+ve ESI): 436, 438 (M+H)$^+$.

N-benzoyl 2-chloro-4-hydroxyaniline, used as the starting material was obtained as follows:

Triethylamine was added to a suspension of 3-chloro-4-aminophenol hydrochloride (1.80 g, 10.0 mmol) in tetrahydrofuran (200 ml), benzoyl chloride (3.00 ml, 20.0 mmol) was added and the reaction allowed to stir for 18 hours at ambient temperature. The reaction was filtered and the filtrate was evaporated in vacuo. The residue was dissolved in methanol (200 ml), treated with aqueous potassium carbonate solution (0.6 N, 25 ml, 15 mmol) and the mixture stirred for 4 hours at ambient temperature. Addition of saturated aqueous sodium hydrogen carbonate solution (100 ml) caused precipitation of an off-white solid which was collected by suction filtration. Drying in vacuo yielded N-benzoyl 2-chloro-4-hydroxyaniline (2.08 g, 83% yield) as a pale purple solid:

$^1$H-NMR (DMSO d$_6$): 9.80 (s, 1H), 7.95 (d, 2H, J=8 Hz), 7.45-7.60 (m, 3H), 7.25 (d, 1H, J=8 Hz), 6.90 (d, 1H, J=8 Hz), 6.75 (dd, 1H, J=2, 8 Hz):

MS (−ve ESI): 246, 248 (M−H)$^−$,
MS (+ve ESI): 248, 250 (M+H)$^+$.

EXAMPLE 101

Preparation of Compound No. 101 in Table 4

An analogous reaction to that described in example 1, but starting with 4-chloro-6-methoxy-7-(3-morpholinopropoxy)quinazoline (3.37 g, 10.0 mmol) yielded the title compound (3.00 g, 58% yield) as a white solid after purification by flash chromatography on silica gel, eluting with 10% methanol in dichloromethane:

$^1$H-NMR (DMSO d$_6$): 10.22 (s, 1H), 9.45 (s, 1H), 8.41 (s, 1H), 7.95 (d, 2H), 7.85 (s, 1H), 7.75 (dd, 4H), 7.55 (m, 3H), 7.15 (s, 1H), 4.20 (t, 3H), 3.95 (s, 3H), 3.60 (t, 4H), 2.45 (m, 2H), 2.41 (m, 4H), 1.95 (m, 2H):

MS (−ve ESI): 512 (M−H)$^−$,
MS (+ve ESI): 514 (M+H)$^+$.

4-Chloro-6-methoxy-7-(3-morpholinopropoxy)quinazoline, used as the starting material, was obtained as follows:

a) A mixture of morpholine (261 ml, 3.00 mol) and 1-bromo-3-chloropropene (148 ml, 1.50 mol) in toluene (900 ml) was stirred for 18 hours at ambient temperature. Additional 1-bromo-3-chloropropane (25 ml, 0.25 mol) was added, the reaction was stirred for a further 1 hour and then filtered to remove the precipitated solid before the filtrate was concentrated in vacuo. Distillation of the crude oil yielded N-(3-chloropropyl)-morpholine (119.3 g, 49% yield) as the fraction boiling at 70-80° C./2.6 mmHg:

$^1$H-NMR (DMSO d$_6$): 3.65 (t, 2H), 3.55 (m, 4H), 2.41 (t, 2H), 2.39 (m, 4H), 1.85 (m, 2H):

MS (+ve ESI): 164 (M+H)$^+$.

b) N-(3-Chloropropyl)morpholine (90 g, 0.55 mol) was added dropwise, over 30 minutes, to a solution of ethyl vanillate (98 g, 0.50 mol) and powdered potassium carbonate (104 g, 0.75 mol) in dimethylformamide (300 ml) at 80° C. The reaction was heated at 80° C. for 90 minutes, cooled to ambient temperature, filtered and the filtrate concentrated in vacuo. The crude product was taken up in diethyl ether (1000 ml), filtered and washed with water (2×200 ml) and brine (200 ml). Solvent evaporation in vacuo yielded ethyl 3-methoxy-4-(3-morpholinopropoxy)benzoate (161.5 g, 100% yield) as a pale yellow oil which crystallised on standing to afford a pale yellow solid:

$^1$H-NMR (DMSO d$_6$): 7.55 (dd, 1H), 7.41 (d, 1H), 7.05 (d, 1H), 4.30 (q, 2H), 4.05 (t, 2H), 3.80 (s, 3H), 3.55 (m, 4H), 2.41 (t, 2H), 2.35 (m, 4H), 1.92 (m, 2H), 1.32 (t, 3H):

MS (−ve ESI): 324 (M−H)$^−$, c) Concentrated sulphuric acid (110 ml) and concentrated nitric acid (19.0 ml, 0.289 mol) were added cautiously, over a 50 minute period, to a two-phase system containing a stirred solution of ethyl 3-methoxy-4-(3-morpholinopropoxy)benzoate (76.5 g, 0.237 mol) in dichloromethane (600 ml), acetic acid (300 ml) and water (70 ml) at 5° C. The reaction was allowed to warm to ambient temperature over 18 hours, the aqueous phase was separated, and the aqueous phase was taken to pH 9 by addition of 40% aqueous sodium hydroxide solution (775 ml). Extraction of the aqueous phase with dichloromethane (3×600 ml) and subsequent solvent evaporation in vacuo yielded ethyl 3-methoxy-4-(3-morpholinopropoxy)-6-nitrobenzoate (141.3 g, 86% yield) as a yellow gum:

$^1$H-NMR (CDCl$_3$): 7.50 (s, 1H), 7.11 (s, 1H), 4.41 (q, 2H), 4.22 (t, 2H), 4.0 (s, 3H), 3.70 (m, 4H), 2.50 (t, 2H), 2.45 (m, 4H), 2.05 (m, 2H), 1.41 (t, 3H):

MS (+ve ESI): 369 (M+H)$^+$.

d) A suspension of ethyl 3-methoxy-4-(3-morpholinopropoxy)-6-nitrobenzoate (132.2 g, 359 mmol) and 10% palladium on carbon (3.0 g) in a mixture of ethanol (200 ml) and ethyl acetate (2000 ml) was stirred under an atmosphere of hydrogen for 18 hours. Removal of the catalyst by filtration, followed by solvent evaporation in vacuo yielded ethyl 3-methoxy-4-(3-morpholinopropoxy)-6-aminobenzoate (122 g, 100% yield) as a brown oil:

$^1$H-NMR (DMSO d$_6$): 7.15 (s, 1H), 6.40 (s, 2H), 6.35 (s, 1H), 4.20 (q, 2H), 3.95 (t, 2H), 3.65 (s, 3H), 3.55 (m, 4H), 2.41 (t, 2H), 2.35 (m, 4H), 1.85 (m, 2H), 1.25 (t, 3H):

MS (−ve ESI): 337 (M−H)$^-$,
MS (+ve ESI): 339 (M+H)$^+$.

e) A solution of ethyl 3-methoxy-4-(3-morpholinopropoxy)-6-aminobenzoate (130 g, 384 mmol) in formamide (280 ml) was heated at 180° C. for 3 hours, during which time a small amount (25 ml) of liquid distilled out of the reaction. The reaction was cooled to 125° C. and the excess formamide was evaporated in vacuo. Trituration of the solid residue with isopropanol (100 ml), followed by drying in vacuo, yielded 6-methoxy-7-(3-morpholinopropoxy)-3,4-dihydroquinazolin-4-one (83.0 g, 68% yield) as a pale brown solid:

$^1$H-NMR (DMSO d$_6$): 12.0 (s, 1H), 7.95 (s, 1H), 7.45 (s, 1H), 7.10 (s, 1H), 4.15 (t, 2H), 3.85 (s, 3H), 3.61 (m, 4H), 2.45 (t, 2H), 2.35 (m, 4H), 1.92 (m, 2H):

MS (−ve ESI): 318 (M−H)$^-$,
MS (+ve ESI): 320 (M+H)$^+$.

f) Dimethylformamide (2.0 ml) was added dropwise to a solution of 6-methoxy-7-(3-morpholinopropoxy)-3,4-dihydro-quinazolin-4-one (83.0 g, 261 mmol) in thionyl chloride (700 ml) and the reaction was heated at reflux for 3.5 hours. The reaction was cooled, excess thionyl chloride was removed in vacuo, the residue was taken up in water (500 ml) and this aqueous solution was taken to pH 9 by addition of saturated aqueous sodium bicarbonate solution (300 ml). The aqueous phase was extracted with dichloromethane (2×400 ml), the organic solution was washed with brine (400 ml) and the solvents were removed in vacuo. Trituration of the solid residue with ethyl acetate (150 ml), followed by drying in vacuo, yielded 4-chloro-6-methoxy-7-(3-morpholinopropoxy)quinazoline (53 g, 60% yield) as a pale brown solid:

$^1$H-NMR (CDCl$_3$): 8.85 (s, 1H), 7.39 (s, 1H), 7.38 (s, 1H), 4.31 (t, 2H), 4.05 (s, 3H), 3.70 (m, 4H), 2.60 (t, 2H), 2.51 (m, 4H), 2.12 (m, 2H):

MS (+ve ESI): 338 (M+H)$^+$.

EXAMPLE 102

Preparation of Compound No. 102 in Table 4

An analogous reaction to that described in example 1, but starting with 4-chloro-6-methoxy-7-(3-morpholinopropoxy)quinazoline (8.44 g, 25.0 mmol) and N-(t-butoxycarbonyl)-4-aminoaniline (5.73 g, 27.5 mmol), yielded the title compound (13.79 g, 95% yield) as a white solid:

$^1$H-NMR (DMSO d$_6$): 11.30 (s, 1H), 9.45 (s, 1H), 8.75 (s, 1H), 8.30 (s, 1H), 7.55 (s, 4H), 7.41 (s, 1H), 4.32 (t, 2H), 4.0 (s, 3H), 3.95 (m, 2H), 3.85 (m, 2H), 3.51 (m, 2H), 3.3 (m, 2H), 3.10 (m, 2H), 2.31 (m, 2H), 1.50 (s, 9H):

MS (−ve ESI): 508 (M−H)$^-$,
MS (+ve ESI): 510 (M+H)$^+$.

EXAMPLE 103

Preparation of Compound No. 103 in Table 4

O-(7-Azabenzotriazol-1-yl)-N,N,N',N'-tetramethyluronium hexafluorophosphate (HATU) (143 mg, 0.375 mmol) was added to a solution of 2-chloro-5-nitrobenzoic acid (33 mg, 0.275 mmol) in dimethylacetamide (1.0 ml). After 20 minutes, a solution of 4-(4-aminoanilino)-6-methoxy-7-(3-morpholinopropoxy)quinazoline (102 mg, 0.25 mmol) in dimethylacetamide (1.0 ml) was added and the reaction heated at 50° C. for 18 hours. The reaction was cooled, water (10 ml) was added and the reaction mixture was neutralised by addition of saturated aqueous sodium bicarbonate solution. The aqueous phase was extracted with ethyl acetate. Solvent evaporation and drying of the solid in vacuo yielded the title compound (65 mg, 44% yield) as a white solid:

$^1$H-NMR (DMSO d$_6$): 9.45 (s, 1H), 8.45 (d, 1H, J=8 Hz), 8.40 (s, 1H), 8.32 (m, 1H), 7.88 (m, 2H), 7.75 (m, 4H), 7.19 (s, 1H), 4.20 (t, 3H), 3.99 (s, 3H), 3.61 (m, 4H), 2.45 (m, 6H), 1.95 (m, 2H):

MS (−ve ESI): 591, 593 (M−H)$^-$,
MS (+ve ESI): 593, 595 (M+H)$^+$.

4-(4-aminoanilino)-6-methoxy-7-(3-morpholinopropoxy) quinazoline used as starting material was prepared as follows:

Trifluoroacetic acid (1.00 ml, 13.1 mmol) was added to a suspension of 4-(4-(N-Boc-amino)anilino)-6-methoxy-7-(3-morpholinopropoxy)quinazoline dihydrochloride (100 mg, 0.172 mmol) in dichloromethane (2.0 ml) and the reaction stirred for 1 hour at ambient temperature. The solvents were removed in vacuo, the residue was suspended in water (2.0 ml) and saturated aqueous sodium bicarbonate solution (4.0 ml) was added. The aqueous phase was extracted with dichloromethane (3×10 ml) and the combined organic layers were washed with brine (25 ml) and evaporated in vacuo. Drying of the solid in vacuo yielded 4-(4-aminoanilino)-6-methoxy-7-(3-morpholinopropoxy)quinazoline (53 mg, 75% yield) as a white solid:

$^1$H-NMR (DMSO d$_6$): 9.19 (s, 1H), 8.31 (s, 1H), 7.79 (s, 1H), 7.25 (d, 2H), 7.10 (s, 1H), 6.61 (d, 2H), 5.0 (s, 2H), 4.15 (t, 2H), 3.91 (s, 3H), 3.60 (m, 4H), 2.45 (t, 2H), 2.40 (m, 4H), 1.95 (m, 2H):

MS (−ve ESI): 408 (M−H)$^-$,
MS (+ve ES): 410 (M+H)$^+$.

EXAMPLE 104

Preparation of Compound No. 104 in Table 4

An analogous reaction to that described in example 1, but starting with 4-chloro-6-methoxy-7-(3-morpholinopropoxy) quinazoline (74 mg, 0.22 mmol) and 4-aminoacetanilide (33 mg, 0.24 mmol) yielded the title compound (108 mg, 97% yield) as a white solid:

$^1$H-NMR (DMSO d$_6$): 10.09 (s, 1H), 8.75 (s, 1H), 8.21 (s, 1H), 7.65 (d, 2H), 7.58 (d, 2H), 7.35 (s, 1H), 4.30 (m, 2H), 4.00 (s, 3H), 3.95 (m, 2H), 3.80 (m, 2H), 3.50 (m, 2H), 3.30 (m, 2H), 3.11 (m, 2H), 2.30 (m, 2H), 2.03 (s, 3H):

MS (−ve ESI): 450 (M−H)⁻.

EXAMPLE 105

Preparation of Compound No. 105 in Table 4

An analogous reaction to that described in example 103, but starting with octanoic acid (72 mg, 0.50 mmol) and 4-(4-aminoanilino)-6-methoxy-7-(3-morpholinopropoxy)quinazoline (151 mg, 0.45 mmol), yielded the title compound (136 mg, 51% yield) as a white solid:

$^1$H-NMR (DMSO d$_6$): 9.82 (s, 1H), 9.40 (s, 1H), 8.38 (s, 1H), 7.81 (s, 1H), 7.64 (d, 2H), 7.57 (d, 2H), 7.14 (s, 1H), 4.16 (t, 2H), 3.94 (s, 3H), 3.57 (m, 4H), 2.42 (t, 2H), 2.36 (m, 4H), 2.28 (t, 2H), 1.90-2.00 (m, 2H), 1.50-1.65 (m, 2H), 1.20-1.27 (m, 8H), 0.85-0.80 (m, 3H).

EXAMPLE 106

Preparation of Compound No. 106 in Table 4

An analogous reaction to that described in example 103, but starting with furan-2-carboxylic acid (56 mg, 0.50 mmol), yielded the title compound (146.6 mg, 58% yield) as an off-white solid:

$^1$H-NMR (DMSO d$_6$): 9.45 (s, 1H), 8.41 (s, 1H), 7.91 (d, 1H), 7.83 (s, 1H), 7.70-7.80 (m, 4H), 7.31 (d, 1H), 7.15 (s, 1H), 6.68 (m, 1H), 4.17 (t, 2H), 3.95 (s, 3H), 3.57 (m, 4H), 2.42 (t, 2H), 2.36 (m, 4H), 1.90-1.99 (m, 2H):

MS (+ve ESI): 504 (M+H)⁺.

EXAMPLE 107

Preparation of Compound No. 107 in Table 4

An analogous reaction to that described in example 103, but starting with 3-furoic acid (56 mg, 0.50 mmol), yielded the title compound (135 mg, 54% yield) as an off-white solid:

$^1$H-NMR (DMSO d$_6$): 9.95 (s, 1H), 9.45 (s, 1H), 8.41 (s, 1H), 8.38 (d, 1H), 7.83 (s, 1H), 7.79 (m, 1H), 7.65-7.75 (m, 4H), 7.15 (s, 1H), 7.00 (d, 1H), 4.17 (t, 2H), 3.95 (s, 3H), 3.58 (m, 4H), 2.42 (t, 2H), 2.36 (m, 4H), 1.90-2.00 (m, 2H):

MS (+ve ESI): 504 (M+H)⁺.

EXAMPLE 108

Preparation of Compound No. 108 in Table 4

An analogous reaction to that described in example 103, but starting with 2-thiopheneacetic acid (71 mg, 0.50 mmol), yielded the title compound (149 mg, 56% yield) as an off-white solid:

$^1$H-NMR (DMSO d$_6$): 10.17 (s, 1H), 9.40 (s, 1H), 8.39 (s, 1H), 7.81 (d, 1H), 7.68 (d, 2H), 7.59 (d, 2H), 7.37 (m, 1H), 7.14 (s, 1H), 6.96 (m, 2H), 4.17 (t, 2H), 3.94 (s, 3H), 3.85 (s, 2H), 3.58 (m, 4H), 2.43 (t, 2H), 2.35-2.41 (m, 4H), 1.85-2.00 (m, 2H):

MS (+ve ESI): 534 (M+H)⁺.

EXAMPLE 109

Preparation of Compound No. 109 in Table 4

An analogous reaction to that described in example 103, but starting with indole-2-carboxylic acid (80 mg, 0.50 mmol), yielded the title compound (170 mg, 62% yield) as an off-white solid:

$^1$H-NMR (DMSO d$_6$): 11.78 (s, 1H), 10.28 (s, 1H), 9.45 (s, 1H), 8.42 (s, 1H), 7.85 (s, 1H), 7.80 (d, 2H), 7.76 (d, 2H), 7.65 (d, 1H), 7.45 (d, 1H), 7.40 (s, 1H), 7.17-7.22 (m, 1H), 7.15 (s, 1H), 7.05 (d, 1H), 4.17 (t, 2H), 3.95 (s, 3H), 3.57 (m, 4H), 2.45 (t, 2H), 2.37 (m, 4H), 1.90-2.00 (m, 2H):

MS (+ve ESI): 553 (M+H)⁺.

EXAMPLE 110

Preparation of Compound No. 110 in Table 4

An analogous reaction to that described in example 103, but starting with 2,4-difluorobenzoic acid (79 mg, 0.50 mmol), yielded the title compound (140 mg, 51% yield) as an off-white solid:

$^1$H-NMR (DMSO d$_6$): 8.41 (s, 1H), 7.83 (s, 1H), 7.70-7.80 (m, 5H), 7.35-7.45 (m, 1H), 7.16-7.25 (m, 1H), 7.15 (s, 1H), 4.19 (t, 2H), 3.95 (s, 3H), 3.57 (m, 4H), 2.45 (t, 2H), 2.37 (m, 4H), 1.92-1.97 (m, 2H):

MS (+ve ESI): 550 (M+H)⁺.

EXAMPLE 111

Preparation of Compound No. 111 in Table 4

An analogous reaction to that described in example 103, but starting with 4-methylsulphonyl-3-nitrobenzoic acid (122 mg, 0.50 mmol), yielded the title compound (199 mg, 63% yield) as an off-white solid:

$^1$H-NMR (DMSO d$_6$): 8.58 (s, 1H), 8.47 (d, 1H), 8.42 (s, 1H), 8.25 (d, 1H), 7.83 (s, 1H), 7.75-7.80 (m, 4H), 7.16 (s, 1H), 4.17 (t, 2H), 3.95 (s, 3H), 3.57 (m, 4H), 3.53 (s, 3H), 2.44 (t, 2H), 2.37 (m, 4H), 1.92-2.00 (m, 2H):

MS (+ve ESI): 637 (M+H)⁺.

EXAMPLE 112

Preparation of Compound No. 112 in Table 4

An analogous reaction to that described in example 103, but starting with 5-hexynoic acid (56 mg, 0.50 mmol), yielded the title compound (146 mg, 58% yield) as an off-white solid:

$^1$H-NMR (DMSO d$_6$): 9.90 (s, 1H), 9.40 (s, 1H), 8.38 (s, 1H), 7.81 (s, 1H), 7.66 (d, 2H), 7.58 (d, 2H), 7.14 (s, 1H), 4.17 (t, 2H), 3.95 (s, 3H), 3.57 (m, 4H), 3.53 (s, 3H), 2.80 (m, 1H), 2.45-2.50 (m, 2H), 2.44 (t, 2H), 2.37 (m, 4H), 2.20-2.25 (m, 2H), 1.95-2.00 (m, 2H), 1.70-1.80 (m, 2H):

MS (+ve ESI): 504 (M+H)⁺.

EXAMPLE 113

Preparation of Compound No. 113 in Table 4

An analogous reaction to that described in example 103, but starting with 2-fluoro-5-nitrobenzoic acid (92 mg, 0.50 mmol), yielded the title compound (180 mg, 62% yield) as an off-white solid:

$^1$H-NMR (DMSO d$_6$): 9.50 (s, 1H), 8.50-8.57 (m, 1H), 8.42 (m, 1H), 8.40 (s, 1H), 7.84 (s, 1H), 7.75 (d, 2H), 7.70 (d, 2H), 7.67 (d, 1H), 7.16 (s, 1H), 4.17 (t, 2H), 3.95 (s, 3H), 3.57 (m, 4H), 2.44 (t, 2H), 2.37 (m, 4H), 1.95 (m, 2H):

MS (+ve ESI): 577 (M+H)⁺.

EXAMPLE 114

Preparation of Compound No. 114 in Table 4

An analogous reaction to that described in example 103, but starting with 3-methoxy-2-nitrobenzoic acid (99 mg, 0.50 mmol), yielded the title compound (168 mg, 57% yield) as an off-white solid:
$^1$H-NMR (DMSO d$_6$): 8.41 (s, 1H), 7.83 (s, 1H), 7.75 (m, 2H), 7.67 (m, 3H), 7.50 (d, 1H), 7.45 (d, 1H), 7.15 (s, 1H), 4.17 (t, 2H), 3.95 (s, 3H), 3.93 (s, 3H), 3.57 (m, 4H), 2.44 (t, 2H), 2.37 (m, 4H), 1.95-2.00 (m, 2H):
MS (+ve ESI): 589 (M+H)$^+$.

EXAMPLE 115

Preparation of Compound No. 115 in Table 4

An analogous reaction to that described in example 103, but starting with 3-(methylthio)-benzoic acid (84 mg, 0.50 mmol), yielded the title compound (72 mg, 26% yield) as a white solid:
$^1$H-NMR (DMSO d$_6$): 9.45 (s, 1H), 8.40 (s, 1H), 7.83 (s, 1H), 7.71 (m, 4H), 7.40-7.51 (m, 3H), 7.24 (m, 1H), 7.15 (s, 1H), 4.17 (t, 2H), 3.95 (s, 3H), 3.57 (m, 4H), 2.45-2.50 (m, 5H), 2.37 (m, 4H), 1.95-2.00 (m, 2H):
MS (+ve ESI): 560 (M+H)$^+$.

EXAMPLE 116

Preparation of Compound No. 116 in Table 4

An analogous reaction to that described in example 103, but starting with 2-methylpyrazine-5-carboxylic acid (69 mg, 0.50 mmol), yielded the title compound (117 mg, 44% yield) as a white solid:
$^1$H-NMR (DMSO d$_6$): 9.16 (s, 1H), 8.69 (s, 1H), 8.42 (s, 1H), 7.90 (d, 2H), 7.83 (s, 1H), 7.74 (d, 2H), 7.15 (s, 1H), 4.19 (t, 2H), 3.95 (s, 3H), 3.57 (m, 4H), 2.63 (s, 3H), 2.45 (t, 2H), 2.37 (m, 4H), 1.95 (m, 2H):
MS (+ve ESI): 530 (M+H)$^+$.

EXAMPLE 117

Preparation of Compound No. 117 in Table 4

An analogous reaction to that described in example 103, but starting with 6-heptynoic acid (63 mg, 0.50 mmol), yielded the title compound (146 mg, 56% yield) as an off-white solid:
$^1$H-NMR (DMSO d$_6$): 9.86 (s, 1H), 9.40 (s, 1H), 8.38 (s, 1H), 7.81 (s, 1H), 7.66 (d, 2H), 7.60 (d, 2H), 7.14 (s, 1H), 4.16 (t, 2H), 3.94 (s, 3H), 3.57 (m, 4H), 2.77 (m, 1H), 2.45 (t, 2H), 2.37 (m, 4H), 2.31 (t, 2H), 2.15-2.22 (m, 2H), 1.90-2.00 (m, 2H), 0.60-0.70 (m, 2H), 0.40-0.55 (m, 2H):
MS (+ve ESI): 518 (M+H)$^+$.

EXAMPLE 118

Preparation of Compound No. 118 in Table 4

An analogous reaction to that described in example 103, but starting with cyclopentane-carboxylic acid (57 mg, 0.50 mmol), yielded the title compound (150 mg, 59% yield) as an off-white solid:
$^1$H-NMR (DMSO d$_6$): 9.85 (s, 1H), 9.42 (s, 1H), 8.41 (s, 1H), 7.81 (s, 1H), 7.60 (dd, 4H), 7.15 (s, 1H), 4.18 (t, 2H), 3.95 (s, 3H), 3.61 (m, 4H), 2.79 (m, 1H), 2.50 (t, 2H), 2.38 (m, 4H), 1.95 (t, 2H), 1.82 (m, 2H), 1.71 (m, 4H), 1.55 (m, 2H):
MS (+ve ESI): 506 (M+H)$^+$.

EXAMPLE 119

Preparation of Compound No. 119 in Table 4

An analogous reaction to that described in example 103, but starting with cyclohexylacetic acid (71 mg, 0.50 mmol), yielded the title compound (139 mg, 52% yield) as an off-white solid:
$^1$H-NMR (DMSO d$_6$): 9.86 (s, 1H), 9.42 (s, 1H), 8.39 (s, 1H), 7.84 (s, 1H), 7.62 (dd, 4H), 7.15 (s, 1H), 4.17 (t, 2H), 3.93 (s, 3H), 3.58 (m, 4H), 2.42 (t, 2H), 2.38 (m, 4H), 2.18 (d, 2H), 1.95 (m, 2H), 1.50-1.81 (m, 5H), 1.21 (m, 4H), 0.98 (m, 2H):
MS (+ve ESI): 534 (M+H)$^+$.

EXAMPLE 120

Preparation of Compound No. 120 in Table 4

An analogous reaction to that described in example 103, but starting with 4-methoxy-3-nitrobenzoic acid (99 mg, 0.50 mmol), yielded the title compound (172 mg, 59% yield) as an off-white solid:
$^1$H-NMR (DMSO d$_6$): 10.38 (s, 1H), 9.50 (s, 1H), 8.55 (d, 1H), 8.45 (s, 1H), 8.31 (dd, 1H), 7.87 (s, 1H), 7.78 (m, 4H), 7.53 (d, 1H), 7.18 (s, 1H), 4.21 (t, 2H), 4.02 (s, 3H), 3.97 (s, 3H), 3.58 (m, 4H), 2.46 (t, 2H), 2.40 (m, 4H), 1.95 (m, 2H):
MS (+ve ESI): 589 (M+H)$^+$.

EXAMPLE 121

Preparation of Compound No. 121 in Table 4

An analogous reaction to that described in example 103, but starting with tetrahydro 2-furoic acid (58 mg, 0.50 mmol), yielded the title compound (151 mg, 60% yield) as an off-white solid:
$^1$H-NMR (DMSO d$_6$): 9.68 (s, 1H), 9.5 (s, 1H), 8.41 (s, 1H), 7.82 (s, 1H), 7.69 (m, 4H), 7.15 (s, 1H), 4.39 (dd, 1H), 4.17 (t, 2H), 3.99 (dd, 1H), 3.94 (s, 3H), 3.84 (dd, 1H), 3.58 (m, 4H), 2.45 (t, 2H), 2.38 (m, 4H), 1.97 (m, 4H), 1.87 (m, 2H):
MS (+ve ESI): 508 (M+H)$^+$.

EXAMPLE 122

Preparation of Compound No. 122 in Table 4

An analogous reaction to that described in example 103, but starting with picolinic acid (62 mg, 0.50 mmol), yielded the title compound (133 mg, 52% yield) as an off-white solid:
$^1$H-NMR (DMSO d$_6$): 10.65 (s, 1H), 9.49 (s, 1H), 8.75 (d, 1H), 8.44 (s, 1H), 8.18 (d, 1H), 8.08 (m, 1H), 7.91 (d, 2H), 7.85 (s, 1H), 7.76 (d, 2H), 7.68 (m, 1H), 7.18 (s, 1H), 4.18 (t, 2H), 3.98 (s, 3H), 3.58 (m, 4H), 2.45 (t, 2H), 2.38 (m, 4H), 1.95 (t, 2H):
MS (+ve ESI): 515 (M+H)$^+$.

EXAMPLE 123

Preparation of Compound No. 123 in Table 4

An analogous reaction to that described in example 103, but starting with nicotinic acid (62 mg, 0.50 mmol), yielded the title compound (139 mg, 54% yield) as an off-white solid:

¹H-NMR (DMSO d₆): 10.45 (s, 1H), 9.46 (s, 1H), 9.10 (d, 1H), 8.78 (d, 1H), 8.43 (s, 1H), 8.31 (m, 1H), 7.85 (s, 1H), 7.78 (m, 4H), 7.57 (m, 1H), 7.18 (s, 1H), 4.18 (t, 2H), 3.95 (s, 3H), 3.58 (m, 4H), 2.45 (t, 2H), 2.35 (m, 4H), 1.95 (t, 2H):
MS (+ve ESI): 515 (M+H)$^+$.

EXAMPLE 124

Preparation of Compound No. 124 in Table 4

An analogous reaction to that described in example 103, but starting with 4-nitrocinnamic acid (96 mg, 0.50 mmol), yielded the title compound (176 mg, 60% yield) as an off-white solid:
¹H-NMR (DMSO d₆): 10.48 (s, 1H), 9.51 (s, 1H), 8.40 (s, 1H), 8.29 (d, 2H), 7.90 (d, 2H), 7.85 (s, 1H), 7.71 (m, 4H), 7.70 (d, 1H, J=16 Hz), 7.18 (s, 1H), 7.05 (d, 1H, J=16 Hz), 4.18 (t, 2H), 3.95 (s, 3H), 3.60 (m, 4H), 2.45 (t, 2H), 2.38 (m, 4H), 1.95 (t, 2H):
MS (+ve ESI): 585 (M+H)$^+$.

EXAMPLE 125

Preparation of Compound No. 125 in Table 4

An analogous reaction to that described in example 103, but starting with 2,4-dinitrobenzoic acid (106 mg, 0.50 mmol), yielded the title compound (181 mg, 60% yield) as an off-white solid:
¹H-NMR (DMSO d₆): 9.50 (s, 1H), 8.79 (d, 1H), 8.61 (dd, 1H), 8.41 (s, 1H), 8.10 (d, 1H), 7.85 (s, 1H), 7.75 (d, 2H), 7.64 (d, 2H), 7.16 (s, 1H), 4.19 (t, 2H), 3.95 (s, 3H), 3.58 (m, 4H), 2.47 (t, 2H), 2.40 (m, 4H), 1.95 (t, 2H):
MS (+ve ESI): 604 (M+H)$^+$.

EXAMPLE 126

Preparation of Compound No. 126 in Table 4

An analogous reaction to that described in example 103, but starting with 3-acetoxybenzoic acid (90 mg, 0.50 mmol), yielded the title compound (161 mg, 56% yield) as an off-white solid:
HPLC/LCMS (RT): 1.56 min:
MS (+ve ESI): 572 (M+H)$^+$.

EXAMPLE 127

Preparation of Compound No. 127 in Table 4

An analogous reaction to that described in example 103, but starting with 1,5-dimethyl-1H-pyrazole-3-carboxylic acid (70 mg, 0.50 mmol), yielded the title compound (146 mg, 55% yield) as an off-white solid:
¹H-NMR (DMSO d₆): 9.90 (s, 1H), 9.47 (s, 1H), 8.41 (s, 1H), 7.82 (s, 1H), 7.80 (d, 2H), 7.67 (d, 2H), 7.15 (s, 1H), 6.57 (s, 1H), 4.18 (t, 2H), 3.95 (s, 3H), 3.85 (s, 3H), 3.58 (m, 4H), 2.46 (t, 2H), 2.38 (m, 4H), 2.31 (s, 3H), 1.95 (t, 2H):
MS (+ve ESI): 532 (M+H)$^+$.

EXAMPLE 128

Preparation of Compound No. 128 in Table 4

An analogous reaction to that described in example 103, but starting with cyclobutane-carboxylic acid (40 mg, 0.40 mmol) and 4-(4-aminoanilino)-6-methoxy-7-(3-morpholinopropoxy)-quinazoline (143 mg, 0.35 mmol), yielded the title compound (12 mg, 7% yield) as a white solid:
¹H-NMR (DMSO d6): 9.71 (s, 1H), 9.42 (s, 1H), 8.40 (s, 1H), 7.82 (s, 1H), 7.68 (d, 2H, J=8 Hz), 7.62 (d, 2H, J=8 Hz), 7.15 (s, 1H), 4.18 (t, 2H, J=7 Hz), 3.95 (s, 3H), 3.58 (m, 4H), 3.22 (m, 1H), 2.46 (t, 2H, J=7 Hz), 2.38 (m, 4H), 2.23 (m, 2H), 2.11 (m, 2H), 1.95 (t, 2H, J=7 Hz), 1.95 (m, 1H), 1.82 (1H, m):
MS (+ve ESI): 492 (M+H)$^+$.

EXAMPLE 129

Preparation of Compound No. 129 in Table 4

An analogous reaction to that described in example 103, but starting with 2-methoxybenzoic acid (61 mg, 0.40 mmol) yielded the title compound (134 mg, 70% yield) as a white solid:
¹H-NMR (DMSO d₆): 9.71 (s, 1H), 9.48 (s, 1H), 8.42 (s, 1H), 7.84 (s, 1H), 7.74 (d, 2H, J=8 Hz), 7.72 (d, 2H, J=8 Hz), 7.68 (d, 1H, J=7 Hz), 7.52 (t, 1H, J=7 Hz), 7.18 (d, 1H, J=7 Hz), 7.15 (s, 1H), 7.08 (t, 1H, J=7 Hz), 4.20 (t, 2H, J=7 Hz), 3.97 (s, 3H), 3.92 (s, 3H), 3.60 (m, 4H), 2.46 (t, 2H, J=7 Hz), 2.38 (m, 4H), 1.95 (m, 2H):
MS (+ve ESI): 544 (M+H)$^+$.

EXAMPLE 130

Preparation of Compound No. 130 in Table 4

An analogous reaction to that described in example 103, but starting with 3-nitrobenzoic acid (67 mg, 0.40 mmol) yielded the title compound (153 mg, 78% yield) as a white solid:
HPLC/LCMS (RT): 3.31 min:
MS (+ve ESI): 559 (M+H)$^+$.

EXAMPLE 131

Preparation of Compound No. 131 in Table 4

An analogous reaction to that described in example 103, but starting with 4-nitrobenzoic acid (67 mg, 0.40 mmol) yielded the title compound (95 mg, 49% yield) as a white solid:
¹H-NMR (DMSO d₆): 9.71 (s, 1H), 9.50 (s, 1H), 8.45 (s, 1H), 8.41 (d, 2H, J=8 Hz), 8.22 (d, 2H, J=8 Hz), 7.83 (s, 1H), 7.80 (bs, 4H), 7.17 (s, 1H), 4.20 (t, 2H, J=7 Hz), 3.96 (s, 3H), 3.59 (m, 4H), 2.46 (t, 2H, J=7 Hz), 2.38 (m, 4H), 1.95 (m, 2H):
MS (+ve ESI): 559 (M+H)$^+$.

EXAMPLE 132

Preparation of Compound No. 132 in Table 4

An analogous reaction to that described in example 103, but starting with cyclohexane-carboxylic acid (51 mg, 0.40 mmol) yielded the title compound (102 mg, 56% yield) as a white solid:
¹H-NMR (DMSO d₆): 9.79 (s, 1H), 9.42 (s, 1H), 8.40 (s, 1H), 7.82 (s, 1H), 7.68 (d, 2H, J=8 Hz), 7.62 (d, 2H, J=8 Hz), 7.15 (s, 1H), 4.18 (t, 2H, J=7 Hz), 3.95 (s, 3H), 3.58 (m, 4H), 2.69 (m, 1H), 2.46 (t, 2H, J=7 Hz), 2.38 (m, 4H), 1.95 (t, 2H, J=7 Hz), 1.80 (m, 4H), 1.65 (m, 1H), 1.42 (m, 2H), 1.15-1.33 (m, 3H):
MS (+ve ESI): 520 (M+H)$^+$.

EXAMPLE 133

Preparation of Compound No. 133 in Table 4

An analogous reaction to that described in example 103, but starting with 4-nitropyrrole-2-carboxylic acid (62 mg, 0.40 mmol) yielded the title compound (97 mg, 51% yield) as a white solid:
$^1$H-NMR (DMSO d$_6$): 9.51 (s, 1H), 8.44 (s, 1H), 7.99 (s, 1H), 7.83 (s, 1H), 7.75 (m, 5H), 7.71 (s, 1H), 7.17 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):
MS (+ve ESI): 548 (M+H)$^+$.

EXAMPLE 134

Preparation of Compound No. 134 in Table 4

An analogous reaction to that described in example 103, but starting with 4-methyl-3-nitro-benzoic acid (72 mg, 0.40 mmol) yielded the title compound (162 mg, 81% yield) as a white solid:
$^1$H-NMR (DMSO d$_6$): 8.59 (s, 1H), 8.41 (s, 1H), 8.21 (d, 1H), 7.82 (s, 1H), 7.79 (bs, 4H), 7.63 (d, 1H), 7.15 (s, 1H), 4.19 (t, 3H), 3.95 (s, 3H), 3.60 (m, 4H), 2.59 (s, 3H), 2.43-2.33 (m, 6H), 1.85 (m, 2H):
MS (+ve ESI): 573 (M+H)$^+$.

EXAMPLE 135

Preparation of Compound No. 135 in Table 4

An analogous reaction to that described in example 103, but starting with 4-fluoro-3-nitro-benzoic acid (74 mg, 0.40 mmol) yielded the title compound (96 mg, 48% yield) as a white solid:
$^1$H-NMR (DMSO d$_6$): 9.52 (s, 1H), 8.79 (d, 1H, J=7 Hz), 8.43 (s, 1H), 8.40 (m, 1H), 7.85 (s, 1H), 7.78 (m, 5H), 7.18 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):
MS (+ve ESI): 577 (M+H)$^+$.

EXAMPLE 136

Preparation of Compound No. 136 in Table 4

An analogous reaction to that described in example 103, but starting with thiophene-3-acetic acid (57 mg, 0.40 mmol) yielded the title compound (148 mg, 79% yield) as a white solid:
$^1$H-NMR (DMSO d$_6$): 9.42 (s, 1H), 8.40 (s, 1H), 7.83 (s, 1H), 7.68 (d, 2H, J=8 Hz), 7.60 (d, 2H, J=8 Hz), 7.50 (m, 1H), 7.33 (d, 1H, J=2 Hz), 7.15 (s, 1H), 7.11 (d, 1H, J=5 Hz), 4.18 (t, 2H, J=7 Hz), 3.95 (s, 3H), 3.58 (m, 4H), 2.46 (t, 2H, J=7 Hz), 2.38 (m, 4H), 1.95 (m, 2H):
MS (+ve ESI): 534 (M+H)$^+$.

EXAMPLE 137

Preparation of Compound No. 137 in Table 4

An analogous reaction to that described in example 103, but starting with 3-chlorobenzothiophene-2-carboxylic acid (85 mg, 0.40 mmol) yielded the title compound (189 mg, 89% yield) as a white solid:
$^1$H-NMR (DMSO d$_6$): 9.52 (s, 1H), 8.44 (s, 1H), 8.19 (m, 1H), 7.95 (m, 1H), 7.84 (s, 1H), 7.81 (d, 2H, J=8 Hz), 7.75 (d, 2H, J=8 Hz), 7.63 (m, 2H), 7.19 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):
MS (+ve ESI): 603 (M+H)$^+$.

EXAMPLE 138

Preparation of Compound No. 138 in Table 4

An analogous reaction to that described in example 103, but starting with 5-chloro indole-2-carboxylic acid (78 mg, 0.40 mmol) yielded the title compound (167 mg, 81% yield) as a white solid:
$^1$H-NMR (DMSO d$_6$): 9.52 (s, 1H), 8.44 (s, 1H), 7.95 (m, 1H), 7.84 (s, 1H), 7.81 (d, 2H, J=8 Hz), 7.76 (d, 2H, J=8 Hz), 7.49 (d, 1H, J=7 Hz), 7.42 (s, 1H), 7.24 (d, 1H, J=7 Hz), 7.19 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):
MS (+ve ESI): 587 (M+H)$^+$.

EXAMPLE 139

Preparation of Compound No. 139 in Table 4

An analogous reaction to that described in example 103, but starting with 1-piperidine propanoic acid (63 mg, 0.40 mmol) yielded the title compound (68 mg, 35% yield) as a white solid:
$^1$H-NMR (DMSO d$_6$): 9.71 (s, 1H), 9.42 (s, 1H), 8.40 (s, 1H), 7.82 (s, 1H); 7.68 (d, 2H, J=8 Hz), 7.62 (d, 2H, J=8 Hz), 7.15 (s, 1H), 4.18 (t, 2H, J=7 Hz), 3.95 (s, 3H), 3.58 (m, 4H), 2.60 (m, 4H), 2.46 (m, 4H), 2.38 (m, 4H), 1.95 (t, 2H, J=7 Hz), 1.51 (m, 4H), 1.40 (m, 2H):
MS (+ve ESI): 549 (M+H)$^+$.

EXAMPLE 140

Preparation of Compound No. 140 in Table 4

An analogous reaction to that described in example 103, but starting with 3,4-methylenedioxybenzoic acid (66 mg, 0.40 mmol) yielded the title compound (119 mg, 61% yield) as a white solid:
HPLC/LCMS (RT): 3.21 min:
MS (+ve ESI): 558 (M+H)$^+$.

EXAMPLE 141

Preparation of Compound No. 141 in Table 4

An analogous reaction to that described in example 103, but starting with 3-butynoic acid (39 mg, 0.40 mmol) yielded the title compound (119 mg, 69% yield) as a white solid:
HPLC/LCMS (RT): 2.82 min:
MS (+ve ESI): 490 (M+H)$^+$.

EXAMPLE 142

Preparation of Compound No. 142 in Table 4

An analogous reaction to that described in example 103, but starting with 3-cyanobenzoic acid (59 mg, 0.40 mmol) yielded the title compound (156 mg, 83% yield) as a white solid:
HPLC/LCMS (RT): 3.18 min:
MS (+ve ESI): 539 (M+H)$^+$.

EXAMPLE 143

Preparation of Compound No. 143 in Table 4

An analogous reaction to that described in example 103, but starting with N-acetyl 3-aminopropanoic acid (52 mg, 0.40 mmol) yielded the title compound (55 mg, 30% yield) as a white solid:

$^1$H-NMR (DMSO d$_6$): 9.95 (s, 1H), 9.42 (s, 1H), 8.40 (s, 1H), 7.95 (m, 1H), 7.82 (s, 1H), 7.68 (d, 2H, J=8 Hz), 7.61 (d, 2H, J=8 Hz), 7.15 (s, 1H), 4.18 (t, 2H, J=7 Hz), 3.95 (s, 3H), 3.58 (m, 4H), 2.46 (m, 6H), 2.38 (m, 4H), 1.95 (m, 2H), 1.80 (s, 3H):

MS (+ve ESI): 523 (M+H)$^+$.

EXAMPLE 144

Preparation of Compound No. 144 in Table 4

An analogous reaction to that described in example 103, but starting with 4-(trifluoromethyl)-benzoic acid (76 mg, 0.40 mmol) yielded the title compound (153 mg, 75% yield) as a white solid:

$^1$H-NMR (DMSO d$_6$): 9.50 (s, 1H), 8.45 (s, 1H), 8.18 (2H, d, J=7 Hz), 7.93 (2H, d, J=7 Hz), 7.84 (s, 1H), 7.80 (m, 4H), 7.18 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):

MS (+ve ESI): 582 (M+H)$^+$.

EXAMPLE 145

Preparation of Compound No. 145 in Table 4

An analogous reaction to that described in example 103, but starting with 3-chloro-4-fluoro-benzoic acid (70 mg, 0.40 mmol) yielded the title compound (98 mg, 49% yield) as a white solid:

$^1$H-NMR (DMSO d$_6$): 9.50 (s, 1H), 8.44 (s, 1H), 8.22 (m, 1H), 8.02 (m, 1H), 7.85 (s, 1H), 7.78 (m, 4H), 7.61 (t, 1H, J=7 Hz), 7.17 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):

MS (+ve ESI): 566 (M+H)$^+$.

EXAMPLE 146

Preparation of Compound No. 146 in Table 4

An analogous reaction to that described in example 103, but starting with 4-fluoro-3-(trifluoromethyl)benzoic acid (83 mg, 0.40 mmol) yielded the title compound (188 mg, 89% yield) as a white solid:

HPLC/LCMS (RT): 3.85 min:

MS (−ve ESI): 598 (M−H)$^−$.

EXAMPLE 147

Preparation of Compound No. 147 in Table 4

An analogous reaction to that described in example 103, but starting with 4-fluorobenzoic acid (56 mg, 0.40 mmol) yielded the title compound (146 mg, 78% yield) as a white solid:

$^1$H-NMR (DMSO d$_6$): 9.52 (s, 1H), 8.43 (s, 1H), 8.03 (d, 2H, J=8 Hz), 7.85 (s, 1H), 7.77 (m, 4H), 7.38 (t, 2H, J=8 Hz), 7.18 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):

MS (+ve ESI): 532 (M+H)$^+$.

EXAMPLE 148

Preparation of Compound No. 148 in Table 4

An analogous reaction to that described in example 103, but starting with 5-bromo thiophene-2-carboxylic acid (83 mg, 0.40 mmol) yielded the title compound (203 mg, 97% yield) as a white solid:

$^1$H-NMR (DMSO d$_6$): 9.52 (s, 1H), 8.43 (s, 1H), 7.89 (d, 1H, J=5 Hz), 7.85 (s, 1H), 7.79 (d, 2H, J=8 Hz), 7.71 (d, 2H, J=8 Hz), 7.38 (d, 2H, J=1 Hz), 7.18 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (m, 2H):

MS (+ve ESI): 600 (M+H)$^+$.

EXAMPLE 149

Preparation of Compound No. 149 in Table 4

An analogous reaction to that described in example 128, but starting with 4-methoxybenzoic acid (61 mg, 0.40 mmol) yielded the title compound (143 mg, 75% yield) as a white solid $^1$H-NMR (DMSO d$_6$): 9.71 (s, 1H), 9.46 (s, 1H), 8.43 (s, 1H), 7.98 (d, 1H, J=8 Hz), 7.85 (s, 1H), 7.78 (d, 2H, J=8 Hz), 7.71 (d, 2H, J=8 Hz), 7.18 (s, 1H), 7.08 (d, 2H, J=8 Hz), 4.18 (t, 2H, J=7 Hz), 3.95 (s, 3H), 3.85 (s, 3H), 3.58 (m, 4H), 2.46 (t, 2H, J=7 Hz), 2.38 (m, 4H), 1.95 (m, 2H):

MS (+ve ESI): 544 (M+H)$^+$.

EXAMPLE 150

Preparation of Compound No. 150 in Table 4

An analogous reaction to that described in example 103, but starting with 6-methylnicotinic acid (55 mg, 0.40 mmol) yielded the title compound (104 mg, 56% yield) as a white solid:

$^1$H-NMR (DMSO d$_6$): 9.71 (s, 1H), 9.50 (s, 1H), 9.02 (d, 1H, J=2 Hz), 8.45 (s, 1H), 8.23 (dd, 1H, J=2, 7 Hz), 7.85 (s, 1H), 7.77 (s, 4H), 7.42 (d, 1H, J=8 Hz), 7.18 (s, 1H), 4.18 (t, 2H, J=7 Hz), 3.95 (s, 3H), 3.58 (m, 4H), 2.57 (s, 3H), 2.46 (t, 2H, J=7 Hz), 2.38 (m, 4H), 1.95 (t, 2H, J=7 Hz):

MS (+ve ESI): 529 (M+H)$^+$.

EXAMPLE 151

Preparation of Compound No. 151 in Table 4

An analogous reaction to that described in example 103, but starting with 5-nitro-2-furoic acid (63 mg, 0.40 mmol) yielded the title compound (158 mg, 83% yield) as a white solid:

HPLC/LCMS (RT): 3.10 min:

MS (−ve ESI): 548 (M−H)$^−$.

EXAMPLE 152

Preparation of Compound No. 152 in Table 4

An analogous reaction to that described in example 103, but starting with 2-nitrobenzoic acid (67 mg, 0.40 mmol) yielded the title compound (166 mg, 85% yield) as a white solid:

HPLC/LCMS (RT): 3.08 min:

MS (+ve ESI): 559 (M+H)$^+$.

EXAMPLE 153

Preparation of Compound No. 153 in Table 4

An analogous reaction to that described in example 103, but starting with 3-chlorocinnamic acid (73 mg, 0.40 mmol) yielded the title compound (81 mg, 41% yield) as a white solid:
HPLC/LCMS (RT): 3.87 min:
MS (+ve ESI): 574 (M+H)$^+$.

EXAMPLE 154

Preparation of Compound No. 154 in Table 4

An analogous reaction to that described in example 103, but starting with thiophene-2-carboxylic acid (51 mg, 0.40 mmol) yielded the title compound (121 mg, 66% yield) as a white solid:
HPLC/LCMS (RT): 3.14 min:
MS (+ve ESI): 520 (M+H)$^+$.

EXAMPLE 155

Preparation of Compound No. 155 in Table 4

An analogous reaction to that described in example 103, but starting with cyclopropane carboxylic acid (34 mg, 0.40 mmol) yielded the title compound (147 mg, 88% yield) as a white solid:
HPLC/LCMS (RT): 2.82 min:
MS (+ve ESI): 478 (M+H)$^+$.

EXAMPLE 156

Preparation of Compound No. 156 in Table 4

An analogous reaction to that described in example 103, but starting with 3-toluic acid (54 mg, 0.40 mmol) yielded the title compound (71 mg, 39% yield) as a white solid:
$^1$H-NMR (DMSO d$_6$): 9.71 (s, 1H), 9.42 (s, 1H), 8.40 (s, 1H), 7.85 (s, 1H), 7.73-7.83 (m, 6H), 7.43 (m, 2H), 7.17 (s, 1H), 4.20 (t, 2H, J=7 Hz), 3.95 (s, 3H), 3.58 (m, 4H), 2.46 (t, 2H, J=7 Hz), 2.40 (s, 3H), 2.36 (m, 4H), 1.95 (t, 2H, J=7 Hz):
MS (+ve ESI): 528 (M+H)$^+$.

EXAMPLE 157

Preparation of Compound No. 157 in Table 4

An analogous reaction to that described in example 103, but starting with 2-chlorobenzoic acid (63 mg, 0.40 mmol) yielded the title compound (134 mg, 70% yield) as a white solid:
$^1$H-NMR (DMSO d$_6$): 9.71 (s, 1H), 9.49 (s, 1H), 8.42 (s, 1H), 7.86 (s, 1H), 7.73 (m, 4H), 7.44-7.62 (m, 4H), 7.17 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (t, 2H, J=7 Hz):
MS (+ve ESI): 548 (M+H)$^+$.

EXAMPLE 158

Preparation of Compound No. 158 in Table 4

An analogous reaction to that described in example 103, but starting with 2-fluorobenzoic acid (56 mg, 0.40 mmol) yielded the title compound (138 mg, 74% yield) as a white solid:
HPLC/LCMS (RT): 3.21 min:
MS (+ve ESI): 532 (M+H)$^+$.

EXAMPLE 159

Preparation of Compound No. 159 in Table 4

An analogous reaction to that described in example 103, but starting with 2,5-dichlorobenzoic acid (76 mg, 0.40 mmol) yielded the title compound (191 mg, 94% yield) as a white solid:
HPLC/LCMS (RT): 3.57 min:
MS (+ve ESI): 582 (M+H)$^+$.

EXAMPLE 160

Preparation of Compound No. 160 in Table 4

An analogous reaction to that described in example 103, but starting with 3-fluorobenzoic acid (56 mg, 0.40 mmol) yielded the title compound (154 mg, 83% yield) as a white solid:
HPLC/LCMS (RT): 3.31 min:
MS (+ve ESI): 532 (M+H)$^+$.

EXAMPLE 161

Preparation of Compound No. 161 in Table 4

An analogous reaction to that described in example 103, but starting with 6-chloronicotinic acid (63 mg, 0.40 mmol) yielded the title compound (70 mg, 36% yield) as a white solid:
$^1$H-NMR (DMSO d$_6$): 9.71 (s, 1H), 9.50 (s, 1H), 8.94 (d, 1H, J=2 Hz), 8.43 (s, 1H), 8.38 (dd, 1H, J=2, 7 Hz), 7.84 (s, 1H), 7.80 (s, 4H), 7.72 (m, 1H), 7.17 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (t, 2H, J=7 Hz):
MS (+ve ESI): 549 (M+H)$^+$.

EXAMPLE 162

Preparation of Compound No. 162 in Table 4

An analogous reaction to that described in example 103, but starting with 5-bromo-2-furoic acid (76 mg, 0.40 mmol) yielded the title compound (192 mg, 94% yield) as a white solid:
$^1$H-NMR (DMSO d$_6$): 9.50 (s, 1H), 8.42 (s, 1H), 7.84 (s, 1H), 7.74 (m, 4H), 7.38 (d, 1H, J=5 Hz), 7.15 (s, 1H), 6.83 (d, 1H, J=5 Hz), 4.18 (t, 2H, J=7 Hz), 3.95 (s, 3H), 3.58 (m, 4H), 2.46 (t, 2H, J=7 Hz), 2.38 (m, 4H), 1.95 (m, 2H):
MS (+ve ESI): 584 (M+H)$^+$.

EXAMPLE 163

Preparation of Compound No. 163 in Table 4

An analogous reaction to that described in example 103, but starting with 2-methyl-3-nitro-benzoic acid (72 mg, 0.40 mmol) yielded the title compound (141 mg, 71% yield) as a white solid:
HPLC/LCMS (RT): 3.32 min:
MS (+ve ESI): 573 (M+H)$^+$.

EXAMPLE 164

Preparation of Compound No. 164 in Table 4

An analogous reaction to that described in example 103, but starting with 3-chlorobenzoic acid (63 mg, 0.40 mmol) yielded the title compound (46 mg, 24% yield) as a white solid:

$^1$H-NMR (DMSO d$_6$): 9.50 (s, 1H), 8.44 (s, 1H), 8.04 (s, 1H), 7.94 (d, 1H, J=7 Hz), 7.86 (s, 1H), 7.78 (m, 4H), 7.62 (d, 1H, J=7 Hz), 7.58 (t, 1H, J=7 Hz), 7.15 (s, 1H), 4.18 (t, 2H, J=7 Hz), 3.95 (s, 3H), 3.58 (m, 4H), 2.46 (t, 2H, J=7 Hz), 2.38 (m, 4H), 1.95 (t, 2H, J=7 Hz):

MS (+ve ESI): 548 (M+H)$^+$.

EXAMPLE 165

Preparation of Compound No. 165 in Table 5

An analogous reaction to that described in example 1, but starting with 4-chloro-6-methoxy-7-(2,2,2-trifluoroethoxy)quinazoline (400 mg, 1.37 mmol) and N-benzoyl 4-aminoaniline (290 mg, 1.37 mmol) in isopropanol (100 ml), yielded the title compound (553 mg, 86% yield) as an off-white solid:

$^1$H-NMR (DMSO d$_6$): 10.62 (s, 1H), 10.29 (s, 1H), 8.65 (s, 1H), 8.05 (s, 1H), 7.90 (d, 2H), 7.81 (d, 2H), 7.60 (d, 2H), 7.51 (m, 3H), 7.32 (s, 1H), 5.0 (dd, 2H), 3.95 (s, 3H):

MS (−ve ESI): 467 (M−H)$^−$,
MS (+ve ESI): 469 (M+H)$^+$.

4-Chloro-6-methoxy-7-(2,2,2-trifluoroethoxy)quinazoline, used as starting material was obtained as follows:

a) Potassium carbonate (62.2 g, 450 mmol) was added to a solution of ethyl vanillate (58.9 g, 300 mmol) in dimethylformamide (400 ml) and the reaction heated to 120° C. 2,2,2-Trifluoroethyl methanesulphonate (63.4 g, 360 mmol) was added over 15 minutes and the reaction heated at 120° C. for 15 hours. The reaction was cooled to ambient temperature, diethyl ether (400 ml) was added and the reaction was filtered. The filtrate was evaporated in vacuo and the residue was taken up in a mixture of diethyl ether (375 ml) and isohexane (375 ml). The organic layer was concentrated in vacuo to a total volume of 250 ml and the solid which crystallised out was collected by suction filtration. Drying of the solid in vacuo yielded ethyl 4-(2,2,2-trifluoroethoxy)-3-methoxybenzoate (43.0 g, 52% yield) as a white crystalline solid:

$^1$H-NMR (DMSO d$_6$): 7.57 (dd, 1H, J=2, 8 Hz), 7.49 (d, 1H, J=2 Hz), 7.18 (d, 1H, J=8 Hz), 5.81 (q, 2H, J=7 Hz), 5.29 (q, 2H, J=7 Hz), 3.82 (s, 3H), 1.30 (t, 3H, J=7 Hz):

MS (+ve ESI): 279 (M+H)$^+$.

b) Concentrated sulphuric acid (64 ml) and concentrated nitric acid (10.0 ml, 0.152 mol) were added cautiously, over 1 hour, to a two-phase system containing a stirred solution of ethyl 4-(2,2,2-trifluoroethoxy)-3-methoxybenzoate (35.3 g, 0.127 mol) in dichloromethane (340 ml), acetic acid (173 ml) and water (40 ml) at 5° C. The reaction was allowed to warm to ambient temperature over 60 hours (with vigorous mechanical stirring), the aqueous phase was separated, and the organic phase washed with water (6×250 ml). The organic phase was concentrated to a total volume of ~200 ml, isohexane (150 ml) was added and the solid which precipitated out was collected by suction filtration. Drying of the solid in vacuo yielded ethyl 3-methoxy-4-(2,2,2-trifluoroethoxy)-6-nitrobenzoate (21.7 g, 52% yield) as a yellow solid. The mother liquors contained a mixture of product (28%) and starting material (72%) which was recycled in a latter reaction:

$^1$H-NMR (DMSO d$_6$): 7.80 (s, 1H), 7.42 (s, 1H), 4.90 (q, 2H, J=7 Hz), 4.20-4.35 (m, 2H), 4.00 (s, 3H), 1.32 (t, 3H, J=7 Hz):

MS (+ve ESI): 324 (M+H)$^+$.

c) A suspension of ethyl 3-methoxy-4-(2,2,2-trifluoroethoxy)-6-nitrobenzoate (24.0 g, 74.3 mmol) and 10% palladium on carbon (3.0 g) in a mixture of ethanol (100 ml) and ethyl acetate (750 ml) was stirred under an atmosphere of hydrogen for 18 hours. Removal of the catalyst by filtration, followed by solvent evaporation in vacuo yielded ethyl 3-methoxy-4-(2,2,2-trifluoroethoxy)-6-aminobenzoate (20.2 g, 93% yield) as a pale brown solid:

$^1$H-NMR (DMSO d$_6$): 7.20 (s, 1H), 6.45 (s, 1H), 6.40 (s, 2H), 5.70 (q, 2H, J=7 Hz), 4.20 (q, 2H, J=7 Hz), 3.65 (s, 3H), 1.32 (t, 3H, J=7 Hz):

MS (−ve ESI): 292 (M−H)$^−$,
MS (+ve ESI): 294 (M+H)$^+$.

d) A mixture of ethyl 2-amino-4-(2,2,2-trifluoroethoxy)-5-methoxybenzoate (20.2 g, 69.1 mmol) and formamide (50 ml) was heated at 175° C. for 6 hours. The mixture was allowed to cool to ambient temperature, ethanol (150 ml) was added and the reaction allowed to stand for 18 hours. Collection of the solid which had precipitated by suction filtration, followed by washing with ethanol (2×50 ml) and drying in vacuo, yielded 6-methoxy-7-(2,2,2-trifluoroethoxy)-3,4-dihydroquinazolin-4-one (15.8 g, 84% yield) as a pale brown crystalline solid:

$^1$H-NMR (DMSO d$_6$): 12.10 (s, 1H), 8.00 (s, 1H), 7.51 (s, 1H), 7.30 (s, 1H), 4.90 (q, 2H, J=7 Hz), 3.90 (s, 3H):

MS (−ve ESI): 273 (M−H),
MS (+ve ESI): 275 (M+H)$^+$.

e) Dimethylformamide (0.1 ml) was added dropwise to a solution of 6-methoxy-7-(2,2,2-trifluoroethoxy)-3,4-dihydroquinazolin-4-one (15.8 g, 57.7 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6-methoxy-7-(2,2,2-trifluoroethoxy)quinazoline (16.3 g, 97% yield) as a cream solid:

$^1$H-NMR (DMSO d$_6$): 8.95 (s, 1H), 7.65 (s, 1H), 7.25 (s, 1H), 5.05 (q, 2H, J=7 Hz), 4.00 (s, 3H):

MS (+ve ESI): 293, 295 (M+H)$^+$.

EXAMPLE 166

Preparation of Compound No. 166 in Table 5

An analogous reaction to that described in example 103, but starting with 4-(4-aminoanilino)-6-methoxy-7-(2,2,2-trifluoroethoxy)quinazoline (91 mg, 0.25 mmol), and 2-chloro-3-nitrobenzoic acid (54 mg, 0.27 mmol), yielded the title compound (82 mg, 60% yield) as a yellow solid:

$^1$H-NMR (DMSO d$_6$): 10.69 (s, 1H), 9.61 (s, 1H), 8.42 (m, 2H), 8.35 (dd, 1H), 7.90 (m, 2H), 7.75 (dd, 4H), 7.40 (s, 1H), 4.95 (q, 2H), 4.00 (s, 3H):

MS (−ve ESI): 546, 548 (M−H)$^−$,
MS (+ve ESI): 548, 550 (M+H)$^+$.

4-(4-Aminoanilino)-6-methoxy-7-(2,2,2-trifluoroethoxy)quinazoline, used as the starting material was obtained as follows:

a) A solution of 4-chloro-6-methoxy-7-(2,2,2-trifluoroethoxy)quinazoline (4.50 g, 15.4 mmol) and N-(t-butoxycarbonyl)-1,4-phenylenediamine (3.21 g, 15.4 mmol) in isopropanol (150 ml) was heated at reflux for 3.5 hours before the reaction was allowed to cool to ambient temperature and the reaction was poured into diethyl ether (200 ml). Collection of the precipitated solid by suction filtration and drying in vacuo yielded of 4-(4-(N-Boc-amino)anilino)-6-methoxy-7-(3-morpholinopropoxy)quinazoline dihydrochloride (7.50 g, 76% yield) as a pale yellow solid:
$^1$H-NMR (DMSO d$_6$): 11.11 (s, 1H), 9.45 (s, 1H), 8.76 (s, 1H), 8.20 (s, 1H), 7.55 (s, 4H), 7.35 (s, 1H), 5.11 (q, 2H), 4.00 (s, 3H), 1.50 (s, 9H):
MS (−ve ESI): 463 (M−H)$^−$,
MS (+ve ESI): 465 (M+H)$^+$.

b) Trifluoroacetic acid (20.0 ml, 260 mmol) was added to a suspension of 4-(4-(N-Boc-amino)anilino)-6-methoxy-7-(2,2,2-trifluoroethoxy)quinazoline (7.50 g, 11.7 mmol) in dichloromethane (80 ml) and the reaction stirred for 45 minutes at ambient temperature. The solvents were removed in vacuo, the residue was suspended in water (50 ml) and saturated aqueous sodium bicarbonate solution was added. The aqueous phase was extracted with ethyl acetate (3×100 ml) and the combined organic layers were washed with brine (100 ml) and evaporated in vacuo. Drying of the solid in vacuo yielded 4-(4-aminoanilino)-6-methoxy-7-(3-morpholinopropoxy)quinazoline (5.62 g, 100% yield) as a yellow solid:
$^1$H-NMR (DMSO d$_6$): 9.30 (s, 1H), 8.35 (s, 1H), 7.85 (s, 1H), 7.20-7.35 (m, 3H), 6.62 (d, 2H), 5.20 (s, 2H), 4.85-5.00 (m, 2H), 3.91 (s, 3H):
MS (−ve ESI): 363 (M−H)$^−$,
MS (+ve ESI): 365 (M+H)$^+$.

EXAMPLE 167

Preparation of Compound No. 167 in Table 5

An analogous reaction to that described in example 103, but starting with 4-(4-aminoanilino)-6-methoxy-7-(2,2,2-trifluoroethoxy)quinazoline (163 mg, 0.45 mmol) and cyclopentanecarboxylic acid (57 mg, 0.50 mmol), yielded the title compound (56 mg, 25% yield) as an off-white solid:
HPLC/LCMS (RT): 2.25 min:
MS (+ve ESI): 461 (M+H)$^+$.

EXAMPLE 168

Preparation of Compound No. 168 in Table 5

An analogous reaction to that described in example 103, but starting with cyclohexylacetic acid (71 mg, 0.50 mmol), yielded the title compound (65 mg, 27% yield) as an off-white solid:
$^1$H-NMR (DMSO d$_6$): 9.81 (s, 1H), 9.48 (s, 1H), 8.41 (s, 1H), 7.89 (s, 1H), 7.55-7.68 (m, 4H), 7.34 (s, 1H), 4.94 (q, 2H), 3.97 (s, 3H), 2.57 (d, 2H), 0.80-1.85 (m, 1H):
MS (+ve ESI): 489 (M+1)$^+$.

EXAMPLE 169

Preparation of Compound No. 169 in Table 5

An analogous reaction to that described in example 103, but starting with 4-methoxy-3-nitro-benzoic acid (99 mg, 0.50 mmol), yielded the title compound (65 mg, 24% yield) as a white solid:
$^1$H-NMR (DMSO d$_6$): 10.34 (s, 1H), 9.54 (s, 1H), 8.53 (d, 1H), 8.45 (s, 1H), 8.30 (dd, 1H), 8.27 (s, 1H), 7.91 (s, 4H), 7.52 (d, 1H), 7.36 (s, 1H), 4.95 (q, 2H), 4.01 (s, 3H), 3.98 (s, 3H):
MS (+ve ESI): 544 (M+H)$^+$.

EXAMPLE 170

Preparation of Compound No. 170 in Table 5

An analogous reaction to that described in example 103, but starting with octanoic acid (72 mg, 0.50 mmol), yielded the title compound (104 mg, 43% yield) as an off-white solid:
$^1$H-NMR (DMSO d$_6$): 9.82 (s, 1H), 9.48 (s, 1H), 8.41 (s, 1H), 7.89 (s, 1H), 7.52-7.68 (m, 4H), 7.34 (s, 1H), 4.94 (q, 2H), 3.97 (s, 3H), 2.29 (t, 2H), 1.50-1.65 (m, 2H), 1.08-1.56 (m, 8H), 0.86 (t, 3H):
MS (+ve ESI): 491 (M+H)$^+$.

EXAMPLE 171

Preparation of Compound No. 171 in Table 5

An analogous reaction to that described in example 103, but starting with furan-2-carboxylic acid (56 mg, 0.50 mmol), yielded the title compound (132 mg, 58% yield) as an off-white solid:
$^1$H-NMR (DMSO d$_6$): 10.16 (s, 1H), 9.53 (s, 1H), 8.44 (s, 1H), 7.92 (m, 2H), 7.69 (m, 4H), 7.36 (s, 1H), 7.32 (dd, 1H), 6.69 (dd, 1H), 4.95 (q, 2H), 3.98 (s, 3H):
MS (+ve ESI): 459 (M+H)$^+$.

EXAMPLE 172

Preparation of Compound No. 172 in Table 5

An analogous reaction to that described in example 103, but starting with 3-furoic acid (56 mg, 0.50 mmol), yielded the title compound (80 mg, 35% yield) as an off-white solid:
$^1$H-NMR (DMSO d$_6$): 9.91 (s, 1H), 9.52 (s, 1H), 8.44 (s, 1H), 8.36 (s, 1H), 7.91 (s, 1H), 7.78 (d, 1H), 7.76-7.76 (m, 4H), 7.35 (s, 1H), 6.99 (s, 1H), 4.95 (q, 2H), 3.98 (s, 3H):
MS (+ve ESI): 459 (M+H)$^+$.

EXAMPLE 173

Preparation of Compound No. 173 in Table 5

An analogous reaction to that described in example 103, but starting with 2-thiopheneacetic acid (71 mg, 0.50 mmol), yielded the title compound (64 mg, 26% yield) as an off-white solid:
HPLC/LCMS (RT): 2.17 min:
MS (+ve ESI): 489 (M+H)$^+$.

EXAMPLE 174

Preparation of Compound No. 174 in Table 5

An analogous reaction to that described in example 103, but starting with indole-2-carboxylic acid (80 mg, 0.50 mmol), yielded the title compound (8 mg, 3% yield) as an off-white solid:
HPLC/LCMS (RT): 2.41 min:
MS (+ve ESI): 508 (M+H)$^+$.

EXAMPLE 175

Preparation of Compound No. 175 in Table 5

An analogous reaction to that described in example 103, but starting with tetrahydro 2-furoic acid (58 mg, 0.50 mmol), yielded the title compound (71 mg, 31% yield) as an off-white solid:

$^1$H-NMR (DMSO d$_6$): 9.62 (s, 1H), 9.49 (s, 1H), 8.43 (s, 1H), 7.90 (s, 1H), 7.68 (s, 4H), 7.35 (s, 1H), 4.95 (q, 2H), 4.38 (dd, 1H), 3.94-4.03 (m, 1H), 3.97 (s, 3H), 3.82 (dd, 1H), 1.78-2.27 (m, 4H):

MS (+ve ESI): 463 (M+H)$^+$.

EXAMPLE 176

Preparation of Compound No. 176 in Table 5

An analogous reaction to that described in example 103, but starting with picolinic acid (62 mg, 0.50 mmol), yielded the title compound (28 mg, 12% yield) as an off-white solid:

$^1$H-NMR (DMSO d$_6$): 10.61 (s, 1H), 9.55 (s, 1H), 8.74 (m, 1H), 8.45 (s, 1H), 8.12-8.19 (m, 1H), 8.02-8.09 (m, 1H), 7.92 (d, 2H), 7.91 (s, 1H), 7.74 (d, 2H), 7.63-7.69 (m, 1H), 7.36 (s, 1H), 4.95 (q, 2H), 3.99 (s, 3H):

MS (+ve ESI): 470 (M+H)$^+$.

EXAMPLE 177

Preparation of Compound No. 177 in Table 5

An analogous reaction to that described in example 103, but starting with nicotinic acid (62 mg, 0.50 mmol), yielded the title compound (14 mg, 6% yield) as an off-white solid:

$^1$H-NMR (DMSO d$_6$): 10.43 (s, 1H), 9.55 (s, 1H), 9.11 (d, 1H), 8.75 (dd, 1H), 8.45 (s, 1H), 8.25-8.33 (m, 1H), 7.92 (s, 1H), 7.77 (s, 4H), 7.56 (dd, 1H), 7.36 (s, 1H), 4.95 (q, 2H), 3.99 (s, 3H):

MS (+ve ESI): 470 (M+H)$^+$.

EXAMPLE 178

Preparation of Compound No. 178 in Table 5

An analogous reaction to that described in example 103, but starting with 2,4-dinitrobenzoic acid (106 mg, 0.50 mmol), yielded the title compound (17 mg, 6% yield) as an off-white solid:

HPLC/LCMS (RT): 2.36 min:

MS (+ve ESI): 559 (M+H)$^+$.

EXAMPLE 179

Preparation of Compound No. 179 in Table 5

An analogous reaction to that described in example 103, but starting with 2,4-difluorobenzoic acid (79 mg, 0.50 mmol), yielded the title compound (38 mg, 15% yield) as an off-white solid:

$^1$H-NMR (DMSO d$_6$): 10.38 (s, 1H), 9.54 (s, 1H), 8.44 (s, 1H), 7.91 (s, 1H), 7.70-7.76 (m, 4H), 7.40-7.45 (m, 1H), 7.36 (s, 1H), 7.22 (m, 1H), 4.91-5.00 (m, 2H); 3.98 (s, 3H):

MS (+ve ESI): 505 (M+H)$^+$.

EXAMPLE 180

Preparation of Compound No. 180 in Table 5

An analogous reaction to that described in example 103, but starting with 5-hexynoic acid (56 mg, 0.50 mmol), yielded the title compound (39 mg, 17% yield) as an off-white solid:

$^1$H-NMR (DMSO d$_6$): 9.90 (s, 1H), 9.47 (s, 1H), 8.42 (s, 1H), 7.89 (s, 1H), 7.66 (d, 2H), 7.58 (d, 2H), 7.34 (s, 1H), 4.90-5.00 (m, 2H), 3.97 (s, 3H), 2.78 (m, 1H), 2.40 (t, 2H), 2.20-2.25 (m, 2H), 1.78 (m, 2H):

MS (+ve ESI): 459 (M+H)$^+$.

EXAMPLE 181

Preparation of Compound No. 181 in Table 5

An analogous reaction to that described in example 103, but starting with 3-sulpholanyl acetic acid (89 mg, 0.50 mmol), yielded the title compound (58 mg, 22% yield) as an off-white solid:

HPLC/LCMS (RT): 1.86 min:

MS (+ve ESI): 525 (M+H)$^+$.

EXAMPLE 182

Preparation of Compound No. 182 in Table 5

An analogous reaction to that described in example 103, but starting with 3-methoxy-propionic acid (52 mg, 0.50 mmol), yielded the title compound (14 mg, 6% yield) as an off-white solid:

HPLC/LCMS (RT): 1.84 min:

MS (+ve ESI): 451 (M+H)$^+$.

EXAMPLE 183

Preparation of Compound No. 183 in Table 5

An analogous reaction to that described in example 103, but starting with 2-fluoro-5-nitro-benzoic acid (92 mg, 0.50 mmol), yielded the title compound (115 mg, 43% yield) as an off-white solid:

$^1$H-NMR (DMSO d$_6$): 10.64 (s, 1H), 9.56 (s, 1H), 8.50-8.55 (m, 1H), 8.40-8.47 (m, 2H), 7.91 (s, 1H), 7.64-7.79 (m, 5H), 7.36 (s, 1H), 4.90-5.00 (m, 2H), 3.99 (s, 3H):

MS (+ve ESI): 532 (M+H)$^+$.

EXAMPLE 184

Preparation of Compound No. 184 in Table 5

An analogous reaction to that described in example 103, but starting with 3-methoxy-2-nitrobenzoic acid (99 mg, 0.50 mmol), yielded the title compound (42 mg, 16% yield) as an off-white solid:

$^1$H-NMR (DMSO d$_6$): 10.65 (s, 1H), 9.55 (s, 1H), 8.45 (s, 1H), 7.91 (s, 1H), 7.77 (d, 2H), 7.66 (d, 2H), 7.50 (d, 1H), 7.45 (d, 1H), 7.35 (s, 1H), 4.90-5.00 (m, 2H) 3.98 (s, 3H), 3.93 (s, 3H):

MS (+ve ESI): 544 (M+H)$^+$.

EXAMPLE 185

Preparation of Compound No. 185 in Table 5

An analogous reaction to that described in example 103, but starting with 2-(methylthio)benzoic acid (84 mg, 0.50 mmol), yielded the title compound (67 mg, 26% yield) as an off-white solid:

$^1$H-NMR (DMSO d$_6$): 10.35 (s, 1H), 9.58 (s, 1H), 8.45 (s, 1H), 7.93 (s, 1H), 7.73 (m, 4H), 7.50 (m, 2H), 7.42 (t, 1H), 7.35 (s, 1H), 7.25 (t, 1H), 4.98 (dd, 2H), 4.00 (s, 3H), 2.45 (s, 3H):

MS (+ve ESI) 515 (M+H)$^+$.

EXAMPLE 186

Preparation of Compound No. 186 in Table 5

An analogous reaction to that described in example 103, but starting with 2-methylpyrazine-5-carboxylic acid (69 mg, 0.50 mmol), yielded the title compound (198 mg, 82% yield) as an off-white solid:

$^1$H-NMR (DMSO d$_6$): 10.64 (s, 1H), 9.55 (s, 1H), 9.16 (s, 1H), 8.69 (s, 1H), 8.45 (s, 1H), 7.89-7.92 (m, 3H), 7.76 (d, 2H), 7.36 (s, 1H), 4.90-5.00 (m, 2H) 3.98 (s, 3H), 2.63 (s, 3H):

MS (+ve ESI): 485 (M+H)$^+$.

EXAMPLE 187

Preparation of Compound No. 187 in Table 5

An analogous reaction to that described in example 103, but starting with 6-heptynoic acid (63 mg, 0.50 mmol), yielded the title compound (29 mg, 12% yield) as an off-white solid:

HPLC/LCMS (RT): 2.19 min:

MS (+ve ESI): 473 (M+H)$^+$.

EXAMPLE 188

Preparation of Compound No. 188 in Table 5

An analogous reaction to that described in example 103, but starting with 3-acetoxybenzoic acid (90 mg, 0.50 mmol), yielded the title compound (39 mg, 15% yield) as an off-white solid:

$^1$H-NMR (DMSO d$_6$): 10.23 (s, 1H), 9.54 (s, 1H), 8.45 (s, 1H), 7.86-7.91 (m, 2H), 7.70-7.80 (m, 5H), 7.55-7.60 (m, 1H), 7.35-7.40 (m, 2H), 4.90-5.00 (m, 2H) 3.98 (s, 3H), 2.31 (s, 3H):

MS (+ve ESI): 527 (M+H)$^+$.

EXAMPLE 189

Preparation of Compound No. 189 in Table 5

An analogous reaction to that described in example 103, but starting with 1,5-dimethyl-1H-pyrazole-3-carboxylic acid (70 mg, 0.50 mmol), yielded the title compound (43 mg, 18% yield) as an off-white solid:

$^1$H-NMR (DMSO d$_6$): 9.87 (s, 1H), 9.51 (s, 1H), 8.43 (s, 1H), 7.90 (s, 1H), 7.81 (d, 2H), 7.67 (d, 2H), 7.35 (s, 1H), 6.54 (s, 1H), 4.90-5.00 (m, 2H), 3.98 (s, 3H), 3.83 (s, 3H), 2.30 (s, 3H):

MS (+ve ESI): 487 (M+H)$^+$.

EXAMPLE 190

Preparation of Compound No. 190 in Table 6

An analogous reaction to that described in example 1, but starting with 4-chloro-6-acetoxy-7-methoxyquinazoline hydrochloride (2.52 g, 8.75 mmol) yielded the title compound (4.09 g, 100% yield) as a white solid:

$^1$H-NMR (DMSO d$_6$): 11.30 (s, 1H), 10.40 (s, 1H), 8.85 (s, 1H), 8.70 (s, 1H), 7.95 (d, 2H), 7.85 (d, 2H), 7.65 (d, 2H), 7.50 (m, 3H), 7.48 (s, 1H), 4.00 (s, 3H), 2.35 (s, 3H):

MS (−ve ESI): 427 (M−H)$^-$,

MS (+ve ESI): 429 (M+H)$^+$.

4-chloro-6-acetoxy-7-methoxyquinazoline, used as the starting material, was obtained as follows:

a) A mixture of 6,7-dimethoxy-3,4-dihydro-quinazolin-4-one (20.0 g, 97 mmol) and racemic methionine (21.7 g, 146 mmol) in methanesulphonic acid (150 ml) were heated at 100° C. for 5.5 hours and then allowed to cool to ambient temperature over 18 hours. The reaction was poured into cold water (750 ml), the pH of the aqueous solution was adjusted to pH 6 (by addition of 2.0N aqueous sodium hydroxide solution) and the solid which formed was collected by suction filtration. The solid was dried in vacuo and then dissolved in a mixture of pyridine (20 ml) and acetic anhydride (150 ml). The solution was heated at 100° C. for 1 hour, cooled and poured into cold water (1050 ml). Collection of the resultant solid by suction filtration, followed by drying in vacuo, yielded 6-acetoxy-7-methoxy-3,4-dihydro-quinazolin-4-one (13.9 g, 57% yield) as a pale-brown solid:

$^1$H-NMR (DMSO d$_6$): 12.16 (s, 1H), 8.05 (s, 1H), 7.75 (s, 1H), 3.90 (s, 3H), 2.25 (s, 3H):

MS (−ve ESI): 233 (M−H)$^-$, b) Dimethylformamide (0.25 ml) was added dropwise to a solution of 6-acetoxy-7-methoxy-3,4-dihydroquinazolin-4-one (13.8 g, 59.0 mmol) in thionyl chloride (150 ml) and the reaction was heated at reflux for 1.5 hours. The reaction was cooled, excess thionyl chloride was removed in vacuo and the residue was azeotroped with toluene (2×50 ml) to remove the last of the thionyl chloride. Drying in vacuo yielded 4-chloro-6,7-dimethoxyquinazoline hydrochloride (14.7 g, 87% yield) as a beige solid, which was used without further purification:

$^1$H-NMR (DMSO d$_6$): 9.00 (s, 1H), 8.00 (s, 1H), 7.60 (s, 1H), 4.00 (s, 3H), 2.35 (s, 3H):

MS (+ve ESI): 253 (M+H)$^+$.

EXAMPLE 191

Preparation of Compound No. 191 in Table 6

An analogous reaction to that described in example 1, but starting with 4-chloro-6,7-di(2-methoxyethoxy)quinazoline (200 mg, 0.64 mmol) yielded the title compound (285 mg, 91% yield) as a pale yellow solid:

$^1$H-NMR (DMSO d$_6$): 11.29 (s, 1H), 10.40 (s, 1H), 8.79 (s, 1H), 8.30 (s, 1H), 7.97 (d, 2H, J=7 Hz), 7.88 (d, 2H, J=7 Hz), 7.65 (d, 2H, J=7 Hz), 7.50-7.60 (m, 3H), 7.37 (s, 1H), 4.35 (m, 4H), 3.77 (m, 4H), 3.36 (s, 6H):

MS (+ve ESI): 489.5 (M+H)$^+$.

4-Chloro-6,7-di(2-methoxyethoxy)quinazoline, used as the starting material was obtained in an analogous reaction to that described in example 1 b), starting with 6,7-di(2-methoxyethoxy)-3,4-dihydroquinazolin-4-one (prepared according to U.S. Pat. No. 5,747,498).

$^1$H-NMR (DMSO d$_6$): 8.83 (s, 1H), 7.43 (s, 1H), 7.39 (s, 1H), 4.35 (m, 4H), 3.75 (m, 4H), 3.36 (s, 6H):

MS (+ve ESI): 313 (M+H)$^+$.

EXAMPLE 192

Preparation of Compound No. 192 in Table 6

A solution of 4-chloro-6-methoxy-7-benzyloxyquinazoline (2.40 g, 8.00 mmol) and N-benzoyl 4-aminoaniline (1.70 g, 8.00 mmol) in isopropanol (100 ml) was heated at reflux for 3 hours before the reaction was allowed to cool to ambient temperature. The solid which had precipitated was collected by suction filtration and washed with diethyl ether (2×50 ml). Drying of this material yielded the title compound (3.81 g, 100% yield) as an off-white solid:

$^1$H-NMR (DMSO d$_6$): 11.34 (s, 1H), 10.39 (s, 1H), 8.80 (s, 1H), 8.30 (s, 1H), 8.00 (d, 2H), 7.90 (d, 2H), 7.65 (d, 2H), 7.50 (m, 5H), 7.40 (m, 4H), 5.35 (s, 2H), 4.00 (s, 3H):

MS (−ve ESI): 475 (M−H)$^−$,
MS (+ve ESI): 477 (M+H)$^+$.

4-Chloro-6-methoxy-7-benzyloxyquinazoline, used as the starting material, was obtained as follows:

a) A mixture of 2-amino-4-benzyloxy-5-methoxybenzamide (10 g, 0.04 mol—prepared according to *J. Med. Chem.* 1977, 20, 146-149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid yielded 7-benzyloxy-6-methoxy-3,4-dihydroquinazolin-4-one (8.7 g, 84% yield) as a white solid.

b) Dimethylformamide (0.2 ml) was added dropwise to a solution of 6-methoxy-7-benzyloxy-3,4-dihydroquinazolin-4-one (5.00 g, 17.9 mmol) in thionyl chloride (100 ml) and the reaction was heated at reflux for 1 hour. The reaction was cooled, excess thionyl chloride was removed in vacuo and the residue was azeotroped with toluene (3×50 ml) to remove the last of the thionyl chloride. The residue was taken up in dichloromethane (550 ml), the solution was washed with saturated aqueous sodium hydrogen carbonate solution (100 ml) and water (100 ml) and the organic phase was dried over magnesium sulphate. Solvent evaporation in vacuo yielded 4-chloro-6,7-dimethoxyquinazoline (4.80 g, 90% yield) as a pale brown solid:

$^1$H-NMR (DMSO d$_6$): 8.85 (s, 1H), 7.58 (s, 1H), 7.50 (d, 2H), 7.40 (m, 4H), 5.35 (s, 2H), 4.00 (s, 3H):

MS (+ve ESI): 301 (M+H)$^+$.

EXAMPLE 193

Preparation of Compound No. 193 in Table 6

An analogous reaction to that described in example 1, but starting with 4-chloro-6-methoxy-7-((1-methyl-4-piperazinyl)methoxy)quinazoline (100 mg, 0.31 mmol), yielded the title compound (21 mg, 14% yield) as a white solid, after purification by flash chromatography on silica gel, eluting with 2-6% 2.0 N ammonia in methanolic dichloromethane (5:95):

$^1$H-NMR (DMSO d$_6$): 10.23 (s, 1H), 9.43 (s, 1H), 8.42 (s, 1H), 7.95 (d, 2H, J=7 Hz), 7.83 (s, 1H), 7.69-7.80 (m, 4H), 7.46-7.64 (m, 3H), 7.15 (s, 1H), 3.98 (d, 2H), 3.95 (s, 3H), 2.72-2.82 (m, 2H), 2.15 (s, 3H), 1.70-1.92 (m, 5H), 1.25-1.45 (m, 2H):

MS (+ve ESI): 498.5 (M+H)$^+$.

4-Chloro-6-methoxy-7-((1-methyl-4-piperazinyl)methoxy) quinazoline, used as the starting material was obtained as follows:

a) A solution of di-tert-butyl dicarbonate (41.7 g, 0.19 mol) in ethyl acetate (75 ml) was added dropwise to a solution of ethyl 4-piperidinecarboxylate (30 g, 0.19 mol) in ethyl acetate (150 ml) while maintaining the temperature in the range 0-5° C. The reaction was stirred at ambient temperature for 48 hours, poured onto water (300 ml) and the organic layer was separated and washed with i) water (200 ml), ii) 0.1N aqueous hydrochloric acid (200 ml), iii) saturated sodium hydrogen carbonate (200 ml) and iv) brine (200 ml). Evaporation and drying in vacuo yielded ethyl 4-(1-tert-butyloxycarbonyl-piperidine)carboxylate (48 g, 98% yield) as a white solid:

$^1$H NMR (CDCl$_3$): 4.15 (q, 2H), 3.91-4.10 (s, 2H), 2.70-2.95 (t, 2H), 2.35-2.50 (m, 1H), 1.80-2.00 (d, 2H), 1.55-1.70 (m, 2H), 1.45 (s, 9H), 1.25 (t, 3H).

b) A solution of 1.0N lithium aluminium hydride in tetrahydrofuran (133 ml, 0.133 mol) was added dropwise to a solution of ethyl 4-(1-tert-butyloxycarbonyl-piperidine)carboxylate (48 g, 0.19 mol) in dry tetrahydrofuran (180 ml) at 0° C. The reaction was stirred at 0° C. for 2 hours, water (30 ml) and 2.0N sodium hydroxide (10 ml) were added and the precipitate was filtered through diatomaceous earth and washed with ethyl acetate. The filtrate was washed with water and brine before being evaporated to yield 4-hydroxymethyl-1-tert-butyloxycarbonylpiperidine (36.3 g, 89% yield) as a white solid:

$^1$H NMR (CDCl$_3$): 4.10 (s, 2H), 3.40-3.60 (t, 2H), 2.60-2.80 (t, 2H), 1.60-1.80 (m, 2H), 1.35-1.55 (m, 10H), 1.05-1.20 (m, 2H):

MS (+ve E1): 215 (M+H)$^+$.

c) 1,4-Diazabicyclo[2.2.2]octane (42.4 g, 0.378 mol) was added to a solution of 4-hydroxymethyl-1-tert-butyloxycarbonylpiperidine (52.5 g, 0.244 mol) in tert-butyl methyl ether (525 ml) and the reaction stirred at ambient temperature for 15 minutes. The reaction was cooled to 5° C. and a solution of 4-toluenesulphonyl chloride (62.8 g, 0.33 mmol) in tert-butyl methyl ether (525 ml) was added dropwise over 2 hours while maintaining the temperature at 0° C. The reaction was stirred at ambient temperature for 1 hour, isohexane was added and the resultant precipitate was collected by suction filtration. Solvent evaporation in vacuo afforded a solid which was dissolved in diethyl ether (250 ml) and washed successively with 0.5N aqueous hydrochloric acid (2×500 ml), water, saturated sodium hydrogen carbonate and brine. Solvent evaporation and drying in vacuo yielded 4-(4-methylphenylsulphonyloxy-methyl)-1-tert-butyloxy-carbonylpiperidine (76.7 g, 85% yield) as a white solid:

$^1$H NMR (CDCl$_3$): 7.80 (d, 2H), 7.35 (d, 2H), 4.00-4.20 (s, 2H), 3.85 (d, 1H), 2.55-2.75 (m, 2H), 2.45 (s, 3H), 1.75-1.90 (m, 2H), 1.65 (d, 2H), 1.45 (s, 9H), 1.00-1.20 (m, 2H):

MS (+ve ESI): 392 (M+Na)$^+$.

d) 4-(4-Methylphenylsulphonyloxymethyl)-1-tert-butyloxycarbonylpiperidine (40 g, 0.1 mmol) was added to a suspension of ethyl 3-methoxy-4-hydroxybenzoate (19.6 g, 0.1 mol) and potassium carbonate (28 g, 0.2 mol) in dry dimethylformamide (200 ml) and the reaction was heated at 95° C. for 2.5 hours. The reaction was cooled to ambient temperature, partitioned between water and ethyl acetate/diethyl ether, before the organic layer was washed with water and brine. Solvent evaporation in vacuo afforded a clear oil which crystallised on standing. Collection of the solid by suction filtration followed by washing with isohexane and drying in vacuo yielded ethyl 3-methoxy-4-(1-tert-butyloxycarbonylpiperidin-4-yl-methoxy)benzoate (35 g, 89%) as a white solid:

m.p. 81-83° C.:

$^1$H NMR Spectrum: (CDCl$_3$) 7.65 (d, 1H), 7.55 (s, 1H), 6.85 (d, 1H), 4.35 (q, 2H), 4.05-4.25 (s, 2H), 3.95 (s, 3H), 3.90 (d, 2H), 2.75 (t, 2H), 2.00-2.15 (m, 2H), 1.80-1.90 (d, 2H), 1.48 (s, 9H), 1.40 (t, 3H), 1.20-1.35 (m, 2H):

MS (+ve ESI): 416 (M+Na)$^+$.

e) Formaldehyde (35 ml of a 37% solution in water, 420 mmol) was added to a solution of ethyl 3-methoxy-4-(1-tert-butyloxycarbonylpiperidin-4-ylmethoxy)benzoate (35 g, 89 mmol) in formic acid (35 ml) and the reaction was heated at 95° C. for 3 hours. The reaction was cooled, the volatiles we re removed in vacuo and the residue was dissolved in dichloromethane. 3.0N Hydrogen chloride in diethyl ether (40 ml, 120 mmol) was added, together with a little diethyl ether and a solid was precipitated. Collection of the solid by suction filtration followed by drying in vacuo yielded ethyl 3-methoxy-4-(1-methylpiperidin-4-ylmethoxy)benzoate (30.6 g, 100% yield) as a white solid:

$^1$H NMR (DMSOd$_6$): 7.60 (d, 1H), 7.48 (s, 1H), 7.10 (d, 1H), 4.30 (q, 2H), 3.90-4.05 (s, 2H), 3.85 (s, 3H), 3.35-3.50 (s, 2H), 2.90-3.10 (m, 2H), 2.72 (s, 3H), 2.00-2.15 (s, 1H), 1.95 (d, 2H), 1.50-1.70 (m, 2H), 1.29 (t, 3H):

MS (+ve ESI): 308 (M+H)$^+$.

f) Trifluoroacetic acid (37.5 ml) was added to a solution of ethyl 3-methoxy-4-(1-methylpiperidin-4-ylmethoxy)benzoate (30.6 g, 89 mmol) in dichloromethane (75 ml) at 0-5° C. before dropwise addition of a solution of fuming nitric acid (7.42 ml, 178 mmol) in dichloromethane (15 ml) over 15 minutes. The reaction was stirred at ambient temperature for 2 hours, the volatiles were removed in vacuo and the residue was dissolved in dichloromethane (50 ml). The solution was cooled to 0-5° C., diethyl ether was added (50 ml) and the resultant precipitate was collected by suction filtration, and dried in vacuo. The solid was taken up in dichloromethane (500 ml), 3.0N hydrogen chloride in diethyl ether (30 ml) was added followed by diethyl ether (500 ml) which cause precipitation of a solid. Collection of the solid by suction filtration followed by drying in vacuo yielded ethyl 3-methoxy-4-(1-methylpiperidin-4-ylmethoxy)-6-nitrobenzoate (28.4 g, 82% yield) as a white solid:

$^1$H NMR (DMSO-d$_6$): 7.66 (s, 1H), 7.32 (s, 1H), 4.30 (q, 2H), 4.05 (d, 2H), 3.95 (s, 3H), 3.40-3.50 (d, 2H), 2.90-3.05 (m, 2H), 2.75 (s, 3H), 1.75-2.10 (m, 3H), 1.45-1.65 (m, 2H), 1.30 (t, 3H):

MS (+ve ESI): 353 (M+H)$^+$.

g) A suspension of ethyl 3-methoxy-4-(1-methylpiperidin-4-ylmethoxy)-6-nitrobenzoate (3.89 g, 10 mmol) in methanol (80 ml) containing 10% platinum on activated carbon (50% wet) (389 mg) was hydrogenated at 1.8 atmospheres pressure until uptake of hydrogen ceased. The reaction was filtered through celite, the filtrate was evaporated and the residue was taken up in water (30 ml) and adjusted to pH10 with a saturated solution of sodium hydrogen carbonate. The mixture was diluted with ethyl acetate/diethyl ether (1:1) and the organic layer was separated. The aqueous layer was further extracted with ethyl acetate/ether and the organic layers were combined prior to washing with water and brine. Solvent evaporation in vacuo, followed by trituration with a mixture of diethyl ether/isohexane yielded ethyl 6-amino-3-methoxy-4-(1-methylpiperidin-4-ylmethoxy)benzoate (2.58 g, 80% yield) as a white solid after drying in vacuo:

m.p. 111-112° C.:

$^1$H NMR (CDCl$_3$): 7.33 (s, 1H), 6.13 (s, 1H), 5.55 (s, 2H), 4.30 (q, 2H), 3.85 (d, 2H), 3.80 (s, 3H), 2.90 (d, 2H); 2.29 (s, 3H), 1.95 (t, 2H), 1.85 (m, 3H), 1.40-1.50 (m, 2H), 1.35 (t, 3H):

MS (+ve ESI): 323 (M+H)$^+$.

h) A solution of ethyl 6-amino-3-methoxy-4-(1-methylpiperidin-4-ylmethoxy)benzoate (16.1 g, 50 mmol) in 2-methoxyethanol (160 ml) containing formamidine acetate (5.2 g, 50 mmol) was heated at 115° C. for 2 hours. Formamidine acetate (10.4 g, 100 mmol) was added in portions every 30 minutes over a period of 4 hours and the reaction was heated for 30 minutes after the last addition. The reaction was cooled, the volatiles were removed in vacuo, and the residue was dissolved in ethanol (100 ml) and dichloromethane (50 ml). The reaction was filtered and the filtrate was concentrated to a final volume of 100 ml. Collection of the precipitated solid by suction filtration (at 5° C.) followed by drying in vacuo yielded 6-methoxy-7-((1-methylpiperidin-4-yl) methoxy)-3,4-dihydroquinazolin-4-one (12.7 g, 70% yield) as a white solid:

$^1$H NMR (DMSO-d$_6$): 7.97 (s, 1H), 7.44 (s, 1H), 7.11 (s, 1H), 4.00 (d, 2H), 3.90 (s, 3H), 2.80 (d, 2H), 2.16 (s, 2H), 1.90 (s, 3H), 1.90 (t, 1H), 1.75 (d, 2H), 1.25-1.40 (m, 2H):

MS (+ve ESI): 304 (M+H)$^+$.

i) A solution of 6-methoxy-7-((1-methylpiperidin-4-yl)methoxy)-3,4-dihydroquinazolin-4-one (2.8 g, 9.24 mmol) in thionyl chloride (28 ml) containing dimethylformamide (0.28 ml) was heated at reflux for 1 hour. The reaction was cooled, the volatiles were removed in vacuo and the resultant solid was triturated with diethyl ether, filtered, washed with diethyl ether and dried in vacuo. The solid was dissolved in dichloromethane and washed with saturated aqueous sodium hydrogen carbonate, water and brine. Evaporation of the solvent and drying in vacuo yielded 4-chloro-6-methoxy-7-((1-methylpiperidin-4-yl)methoxy)quinazoline (2.9 g, 98% yield):

$^1$H NMR (DMSO-d$_6$): 8.90 (s, 1H), 7.46 (s, 1H), 7.41 (s, 1H), 4.12 (d, 2H), 4.02 (s, 3H), 2.85 (d, 2H), 2.25 (s, 3H), 2.00 (t, 1H), 1.75-1.90 (m, 3H), 1.30-1.50 (m, 2H):

MS (+ve ESI): 322 (M+H)$^+$.

EXAMPLE 194

Preparation of Compound No. 194 in Table 6

An analogous reaction to that described in example 1, but starting with 2-(1-morpholino)-4-chloro-6,7-dimethoxyquinazoline (90 mg, 0.29 mmol), yielded the title compound (123 mg, 81% yield) as an off-white solid:

$^1$H-NMR (DMSO d$_6$): 10.76 (s, 1H), 10.36 (s, 1H), 8.86 (d, 2H, J=8 Hz), 8.09 (s, 1H), 7.95 (d, 2H, J=8 Hz), 7.63 (d, 2H, J=8 Hz), 7.52 (d, 2H, J=8 Hz), 7.45-7.61 (m, 2H), 3.93 (s, 3H), 3.90 (s, 3H), 3.80 (m, 4H), 3.70 (m, 4H):

MS (+ve ESI): 484.5 (M–H)$^+$.

2-(1-Morpholino)-4-chloro-6,7-dimethoxyquinazoline, used as the starting material was obtained as follows:

A solution of 2,4-dichloro-6,7-dimethoxyquinazoline (1.55 g, 6.00 mmol) and N-methylmorpholine (1.32 ml, 12.0 mmol) in dioxan (30 ml) was heated at reflux for 24 hours under an inert atmosphere. The reaction was cooled and stirred with saturated aqueous sodium bicarbonate solution (40 ml) for 15 minutes before being extracted with ethyl acetate (2×50 ml). Washing of the combined organic layers with brine (50 ml) followed by solvent evaporation in vacuo yielded 2-(1-morpholino)-4-chloro-6,7-dimethoxyquinazoline (1.67 g, 90% yield) as a white solid:

$^1$H-NMR (DMSO d$_6$): 7.15 (s, 1H), 6.95 (s, 1H), 3.95 (s, 3H), 3.85 (s, 3H), 3.60-3.79 (m, 8H):

MS (+ve ESI): 310 (M+H)$^+$.

EXAMPLE 195

Preparation of Compound No. 195 in Table 6

4-((4-(N-Benzoyl)amino)anilino)-6-acetoxy-7-methoxyquinazoline hydrochloride (4.40 g, 9.48 mmol) was taken up in a mixture of methanol (100 ml) and concentrated aqueous ammonia solution (50 ml) and the solution heated at 50° C. for 2 hours. The solvents were evaporated in vacuo, the resultant white paste was filtered off and was then triturated with methanol (75 ml). The solid was stirred with 5.0 N hydrochloric acid (150 ml) and the solid hydrochloride salt collected by suction filtration. Drying in vacuo yielded the title compound (3.74 g, 93% yield) as a pale yellow solid:

$^1$H-NMR (DMSO d$_6$): 10.94 (s, 1H), 10.39 (s, 1H), 10.34 (s, 1H), 8.70 (s, 1H), 8.00 (s, 1H), 7.90 (d, 2H), 7.80 (d, 2H), 7.60 (d, 2H), 7.50 (m, 3H), 7.30 (s, 1H), 3.95 (s, 3H):

MS (−ve ESI): 385 (M−H)$^−$,
MS (+ve ESI): 387 (M+H)$^+$.

EXAMPLE 196

Preparation of Compound No. 196 in Table 6

A solution of 4-((4-(N-benzoyl)amino)anilino)-6-methoxy-7-benzyloxyquinazoline (3.70 g, 7.20 mmol) in trifluoroacetic acid (50 ml) was heated at reflux for 2 hours. The reaction was cooled, evaporated in vacuo and the residue so formed was triturated with diethyl ether (3×25 ml). Drying of this material yielded the title compound (3.84 g, 100% yield) as a pale-yellow solid:

$^1$H-NMR (DMSO d$_6$): 10.97 (s, 1H), 10.37 (s, 1H), 8.75 (s, 1H), 8.05 (s, 1H), 7.95 (d, 2H), 7.90 (d, 2H), 7.60 (m, 5H), 7.20 (s, 1H), 4.00 (s, 3H):

MS (−ve ESI): 385 (M−H)$^−$,
MS (+ve ESI): 387 (M+H)$^+$.

EXAMPLE 197

Preparation of Compound No. 197 in Table 7

Diethyl azodicarboxylate (0.06 ml, 0.33 mmol) was added to a stirred suspension of 4-((4-(N-benzoyl)amino)anilino)-6-hydroxy-7-methoxyquinazoline (106 mg, 0.25 mmol), triethylamine (0.036 ml, 0.27 mmol), N-(3-hydroxyethyl)morpholine (65 mg, 0.50 mmol) and triphenylphosphine (65 mg, 0.33 mmol) in dichloromethane (10 ml). The reaction was stirred at ambient temperature for 15 minutes, additional triphenylphosphine and diethyl azodicarboxylate were added (quantities as before) and after an additional 2 hours stirring, further triphenylphosphine and diethyl azodicarboxylate were added (quantities as before). The reaction mixture was poured onto an SCX column which was washed through with 0-10% methanol in dichloromethane before the product was eluted with a mixture of 3% ammonia in 20% methanolic dichloromethane. Purification of the crude product by flash chromatography on silica gel, eluting with 0-20% methanol in dichloromethane, yielded the title compound (32 mg, 26% yield) as a white solid:

$^1$H-NMR (DMSO d$_6$): 10.22 (s, 1H), 9.40 (s, 1H), 8.40 (s, 1H), 7.95 (d, 2H), 7.85 (s, 1H), 7.75 (dd, 4H), 7.50 (m, 3H), 7.15 (s, 1H), 4.25 (t, 2H), 3.90 (s, 3H), 3.60 (t, 4H), 2.80 (t, 2H), 2.55 (t, 4H):

MS (−ve ESI): 498 (M−H)$^−$,
MS (+ve ESI): 500 (M+H)$^+$.

EXAMPLE 198

Preparation of Compound No. 198 in Table 7

An analogous reaction to that described in example 197, but starting with 4-((4-(N-benzoyl)-amino)anilino)-6-hydroxy-7-methoxyquinazoline (164 mg, 0.389 mmol) and N-(3-hydroxypropyl)-morpholine (113 mg, 0.78 mmol), yielded the title compound (43 mg, 21% yield) as a white solid:

$^1$H-NMR (DMSO d$_6$): 10.22 (s, 1H), 9.45 (s, 1H), 8.40 (s, 1H), 7.95 (d, 2H), 7.85 (s, 1H), 7.75 (dd, 4H), 7.55 (m, 3H), 7.15 (s, 1H), 4.20 (t, 2H), 3.90 (s, 3H), 3.60 (t, 4H), 2.45 (m, 2H), 2.39 (m, 4H), 2.00 (m, 2H):

MS (−ve ESI): 512 (M−H)$^−$,
MS (+ve ESI): 514 (M+H)$^+$.

EXAMPLE 199

Preparation of Compound No. 199 in Table 7

An analogous reaction to that described in example 197, but starting with 4-((4-(N-benzoyl)-amino)anilino)-6-hydroxy-7-methoxyquinazoline (164 mg, 0.389 mmol) and 4-(3-hydroxypropyl)-thiomorpholine-1,1-dioxide (96 mg, 0.50 mmol), yielded the title compound (30 mg, 14% yield) as a white solid:

$^1$H-NMR (DMSO d$_6$): 10.23 (s, 1H), 9.45 (s, 1H), 8.40 (s, 1H), 8.00 (d, 2H), 7.85 (s, 1H), 7.75 (dd, 4H), 7.60 (m, 3H), 7.20 (s, 1H), 4.20 (t, 2H), 3.90 (s, 3H), 3.10 (m, 4H), 2.95 (m, 4H), 2.70 (t, 2H), 2.00 (m, 2H):

MS (−ve ESI): 560 (M−H)$^−$,
MS (+ve ESI): 562 (M+H)$^+$.

EXAMPLE 200

Preparation of Compound No. 200 in Table 7

An analogous reaction to that described in example 197, but starting with 4-((4-(N-benzoyl)-amino)anilino)-6-hydroxy-7-methoxyquinazoline hydrochloride (100 mg, 0.236 mmol) and 3-hydroxypropyl methylsulphone (55 mg, 0.40 mmol), yielded the title compound (41 mg, 41% yield) as a pale yellow solid:

$^1$H-NMR (DMSO d$_6$): 10.24 (bs, 1H), 9.47 (s, 1H), 8.43 (s, 1H), 7.97 (d, 2H, J=7 Hz), 7.88 (s, 1H), 7.69-7.82 (m, 4H), 7.49-7.62 (m, 3H), 7.19 (s, 1H), 4.28 (t, 2H, J=6 Hz), 3.95 (s, 3H), 3.25-3.38 (m, 2H), 3.04 (s, 3H), 2.20-2.33 (m, 2H)

MS (+ve ESI): 507 (M+H)$^+$.

EXAMPLE 201

Preparation of Compound No. 201 in Table 7

An analogous reaction to that described in example 197, but starting with 4-((4-(N-benzoyl)-amino)anilino)-6-hydroxy-7-methoxyquinazoline hydrochloride (165 mg, 0.39 mmol) and 1-(2-hydroxyethyl)-1,2,4-triazole (88 mg, 0.78 mmol), yielded the title compound (30 mg, 16% yield) as a pale yellow solid:

$^1$H-NMR (DMSO d$_6$): 10.23 (bs, 1H), 9.42 (s, 1H), 8.59 (s, 1H), 8.42 (s, 1H), 8.01 (s, 1H), 7.97 (d, 2H, J=7 Hz), 7.89 (s, 1H), 7.79 (d, 2H, J=8 Hz), 7.74 (d, 2H, J=8 Hz), 7.50-7.61 (m, 3H), 7.18 (s, 1H), 4.70 (t, 2H, J=7 Hz), 4.51 (t, 2H, J=7 Hz), 3.92 (s, 3H):

MS (+ve ESI): 482 (M+H)$^+$.

EXAMPLE 202

Preparation of Compound No. 202 in Table 7

Tributylphosphine (0.193 ml, 0.78 mmol) and N,N-dimethylethanolamine (0.052 ml, 0.52 mmol) were added to a solution of 4-((4-(N-benzoyl)amino)anilino)-6-hydroxy-7-methoxyquinazoline (100 mg, 0.26 mmol) in tetrahydrofuran under an inert atmosphere at ambient temperature. After 5 minutes, 1,1'-(azodicarbonyl)dipiperidine (196 mg, 0.78 mmol) was slowly added over 10 minutes and the reaction was allowed to stir for a further 2 hours. Additional tributylphosphine and 1,1'-(azodicarbonyl)dipiperidine (quantities as before) were added and the reaction was allowed to stir for 40 minutes. The reaction mixture was poured onto an SCX column which was washed through with 0-10% methanol in dichloromethane before the product was eluted with a mixture of 3% ammonia in 20% methanolic dichloromethane. Purification of the crude product by flash chromatography on silica gel, eluting with 5-10% methanol in dichloromethane, yielded the title compound (42 mg, 36% yield) as a white solid:

$^1$H-NMR (DMSO d$_6$): 10.23 (s, 1H), 9.41 (s, 1H), 8.42 (s, 1H), 7.95 (d, 2H, J=8 Hz), 7.84 (s, 1H), 7.75 (m, 4H), 7.50-7.61 (m, 3H), 7.16 (s, 1H), 4.20 (t, 2H, J=7 Hz), 3.93 (s, 3H), 2.75 (t, 2H, J=7 Hz), 2.27 (s, 6H):

MS (+ve ESI): 458 (M+H)$^+$.

EXAMPLE 203

Preparation of Compound No. 203 in Table 7

Sodium hydride (60% dispersion in mineral oil: 26 mg, 0.65 mmol) and benzyl triethylammonium bromide (104 mg, 0.45 mmol) were added to a suspension of with 4-((4-(N-benzoyl)amino)anilino)-6-hydroxy-7-methoxyquinazoline (164 mg, 0.389 mmol) at ambient temperature. 3-Picolyl chloride hydrochloride (85 mg, 0.52 mmol) was added and the reaction stirred for 3 hours. Sodium hydride (10.0 mg, 0.25 mmol) and dimethylformamide (3.0 ml) were added and the reaction heated at 50° C. for 3 hours. The reaction was cooled, diethyl ether (10 ml) was added and the solid which precipitated was collected by suction filtration. Purification by reverse phase preparative high pressure chromatography (hplc), eluting with 5-95% acetonitrile in water, yielded the title compound (25 mg, 20% yield) as a yellow-brown solid:

$^1$H-NMR (DMSO d$_6$): 10.24 (bs, 1H), 9.49 (s, 1H), 8.77 (d, 1H, J=1 Hz), 8.60 (d, 1H, J=5 Hz), 8.45 (s, 1H), 8.06 (s, 1H), 7.94-8.00 (m, 3H), 7.72-7.83 (m, 4H), 7.43-7.63 (m, 4H), 7.21 (s, 1H), 5.29 (s, 2H), 3.93 (s, 3H):

MS (+ve ESI): 478 (M+H)$^+$.

EXAMPLE 204

Preparation of Compound No. 204 in Table 7

An analogous reaction to that described in example 203, but starting with 4-((4-(N-benzoyl)amino)anilino)-6-hydroxy-7-methoxyquinazoline (100 mg, 0.25 mmol) and methyl 2-chloroethyl ether (0.024 ml, 0.26 mmol), and heating the reaction at 80° C. for 18 hours, yielded the title compound (32 mg, 28% yield) as a white solid:

$^1$H-NMR (DMSO d$_6$): 10.23 (s, 1H), 9.43 (s, 1H), 8.43 (s, 1H), 7.97 (d, 2H, J=7 Hz), 7.86 (s, 1H), 7.70-7.82 (m, 4H), 7.49-7.62 (m, 3H), 7.18 (s, 1H), 4.24-4.31 (m, 2H), 3.94 (s, 3H), 3.73-3.81 (m, 2H), 3.36 (s, 3H):

MS (+ve ESI): 445 (M+H)$^+$.

EXAMPLE 205

Preparation of Compound No. 205 in Table 7

An analogous reaction to that described in example 203, but starting with 4-((4-(N-benzoyl)amino)anilino)-6-hydroxy-7-methoxyquinazoline (100 mg, 0.25 mmol) and 3-(dimethylamino)-1-chloropropane hydrochloride (41 mg, 0.26 mmol), and heating the reaction at 150° C. for 2.5 hours, yielded the title compound (53 mg, 43% yield) as a pale brown solid:

$^1$H-NMR (DMSO d$_6$): 10.23 (bs, 1H), 9.48 (s, 1H), 8.42 (s, 1H), 7.97 (d, 2H, J=7 Hz), 7.86 (s, 1H), 7.69-7.81 (m, 4H), 7.47-7.63 (m, 3H), 7.16 (s, 1H), 4.18 (t, 2H, J=7 Hz), 3.92 (s, 3H), 2.46 (t, 2H, J=7 Hz), 2.19 (s, 6H), 1.90-2.01 (m, 2H):

MS (+ve ESI): 472 (M+H)$^+$.

EXAMPLE 206

Preparation of Compound No. 206 in Table 5

Potassium carbonate (178 mg, 1.29 mmol) and benzyl tributylammonium bromide (46 mg, 0.13 mmol) were added to a suspension of with 4-((4-(N-benzoyl)amino)anilino)-6-hydroxy-7-methoxy-quinazoline (50 mg, 0.13 mmol) in dimethylformamide (5 ml) at ambient temperature. Benzyl bromide (22 mg, 0.13 mmol) was added and the reaction heated at 50° C. for 3 hours. The reaction was cooled, poured into water (10 ml) and the solid which precipitated was collected by suction filtration. Purification by flash chromatography on silica gel, eluting with ethyl acetate, yielded the title compound (8 mg, 13% yield) as a yellow solid:

$^1$H-NMR (DMSO d$_6$): 10.23 (s, 1H), 9.47 (s, 1H), 8.45 (s, 1H), 8.05 (s, 1H), 7.95 (d, 2H, J=8 Hz), 7.78 (d, 2H, J=8 Hz), 7.72 (d, 2H, J=8 Hz), 7.48-7.59 (m, 5H), 7.37 (t, 2H, J=7 Hz), 7.34 (m, 1H), 5.22 (s, 2H), 3.92 (s, 3H):

MS (+ve ESI): 477 (M+H)$^+$.

EXAMPLE 207

Preparation of Compound No. 207 in Table 5

An analogous reaction to that described in example 206, but starting with 4-((4-(N-benzoyl)amino)anilino)-6-hydroxy-7-methoxyquinazoline (154 mg, 0.40 mmol) and 2-bromoethanol (0.031 ml, 0.44 mmol), and heating the reaction at 80° C. for 4.5 hours, yielded the title compound (73 mg, 42% yield) as a white solid:

$^1$H-NMR (DMSO d$_6$): 10.23 (s, 1H), 9.44 (s, 1H), 8.43 (s, 1H), 7.95 (d, 2H, J=8 Hz), 7.83 (s, 1H), 7.71-7.78 (m, 4H), 7.48-7.59 (m, 3H), 7.18 (s, 1H), 4.95 (t, 1H, J=7 Hz), 4.19 (t, 2H, J=7 Hz), 3.92 (s, 3H), 3.82 (m, 2H):

MS (+ve ESI): 431 (M+H)$^+$.

EXAMPLE 208

Preparation of Compound No. 208 in Table 8

An analogous reaction to that described in example 197, but starting with 4-(3-hydroxypropyl)thiomorpholine-1,1-dioxide (96 mg, 0.50 mmol) yielded the title compound (106 mg, 76% yield) as a white solid:
$^1$H-NMR (DMSO d$_6$): 10.22 (s, 1H), 9.45 (s, 1H), 8.40 (s, 1H), 7.95 (d, 2H), 7.85 (s, 1H), 7.75 (m, 4H), 7.55 (m, 3H), 7.20 (s, 1H), 4.20 (t, 2H), 3.95 (s, 3H), 3.10 (m, 4H), 2.90 (m, 4H), 2.60 (t, 2H), 1.95 (t, 2H):
MS (−ve ESI): 560 (M−H)$^−$,
MS (+ve ESI): 562 (M+H)$^+$.

EXAMPLE 209

Preparation of Compound No. 209 in Table 8

An analogous reaction to that described in example 197, but starting with 3-(dimethylamino)-propanol (47 mg, 0.40 mmol), yielded the title compound (39 mg, 41% yield) as a pale yellow solid:
$^1$H-NMR (DMSO d$_6$): 10.23 (s, 1H), 9.45 (s, 1H), 8.42 (s, 1H), 7.97 (d, 2H, J=7 Hz), 7.84 (s, 1H), 7.70-7.82 (m, 4H), 7.48-7.63 (m, 3H), 7.14 (s, 1H), 4.16 (t, 2H, J=7 Hz), 3.97 (s, 3H), 2.41 (t, 2H, J=7 Hz), 2.18 (6H, s), 1.86-1.99 (2H, m):
MS (+ve ESI): 472 (M+H)$^+$.

EXAMPLE 210

Preparation of Compound No. 210 in Table 8

Diethyl azodicarboxylate (DEAD) (0.118 ml, 0.75 mmol) was added to a suspension of 4-((4-(N-benzoyl)amino)anilino)-6-methoxy-7-hydroxyquinazoline trifluoroacetate (125 mg, 0.25 mmol), triethylamine (0.036 ml, 0.275 mmol), triphenylphosphine (196 mg, 0.75 mmol) and N-(2-hydroxyethyl)morpholine (0.061 ml, 0.50 mmol) in dichloromethane (10 ml). The reaction was stirred for 18 hours at ambient temperature and then more diethyl azodicarboxylate (0.118 ml, 0.75 mmol), triphenylphosphine (196 mg, 0.75 mmol) and N-(2-hydroxyethyl)morpholine (0.061 ml, 0.50 mmol) were added and the reaction stirred for 30 minutes. The reaction mixture was transferred to an SCX column and purified by chromatography, eluting with i) dichloromethane, ii) 10% methanol in dichloromethane and iii) 2% ammonia 10% methanol in dichloromethane. Evaporation of the product fractions in vacuo yielded the title compound (75 mg, 60% yield) as a white solid:
$^1$H-NMR (DMSO d$_6$): 10.24 (s, 1H), 9.58 (s, 1H), 8.45 (s, 1H), 7.95 (d, 2H), 7.85 (s, 1H), 7.75 (dd, 4H), 7.5 (m, 3H), 7.20 (s, 1H), 4.35 (m, 2H), 3.95 (s, 3H), 3.65 (m, 4H), 3.05 (m, 2H), 2.75 (m, 4H):
MS (−ve ESI): 498 (M−H)$^−$,
MS (+ve ESI): 500 (M+H)$^+$.

EXAMPLE 211

Preparation of Compound No. 211 in Table 8

An analogous reaction to that described in example 210, but starting with 2-(dimethylamino)-ethanol (0.40 ml, 0.40 mmol), yielded the title compound (17 mg, 19% yield) as a pale yellow solid:
$^1$H-NMR (DMSO d$_6$): 10.23 (s, 1H), 9.46 (s, 1H), 8.42 (s, 1H), 7.97 (d, 2H, J=7 Hz), 7.85 (s, 1H), 7.70-7.81 (m, 4H), 7.47-7.62 (m, 3H), 7.20 (s, 1H), 4.23 (t, 2H, J=5.5 Hz), 3.96 (s, 3H), 2.75 (t, 2H, J=5.5 Hz), 2.27 (s, 6H):
MS (+ve ESI): 458 (M+H)$^+$.

EXAMPLE 212

Preparation of Compound No. 212 in Table 8

An analogous reaction to that described in example 210, but starting with 1-(2-hydroxyethyl)-1,2,4-triazole (57 mg, 0.50 mmol) yielded the title compound (21 mg, 18% yield) as a white solid:
$^1$H-NMR (DMSO d$_6$): 10.23 (s, 1H), 9.45 (s, 1H), 8.59 (s, 1H), 8.45 (s, 1H), 8.00 (s, 1H), 7.95 (d, 2H), 7.85 (s, 1H), 7.75 (dd, 4H), 7.55 (m, 3H), 7.20 (s, 1H), 4.65 (t, 2H), 4.55 (t, 2H), 3.90 (s, 3H):
MS (+ve ESI): 482 (M+H)$^+$.

EXAMPLE 213

Preparation of Compound No. 213 in Table 8

Triethylamine (0.031 ml, 0.22 mmol), tributylphosphine (0.149 ml, 0.60 mmol) and 3-hydroxypropyl methylsulphone (55 mg, 0.40 mmol) were added to a suspension of 4-((4-(N-benzoyl)amino)anilino)-6-methoxy-7-hydroxyquinazoline trifluoroacetate (100 mg, 0.200 mmol) in dichloromethane (10 ml) at ambient temperature. The reaction was stirred for 5 minutes before addition of 1,1'-(azodicarbonyl)dipiperidine (151 mg, 0.60 mmol) and then stirred for a further 15 minutes. Tributylphosphine (0.149 ml, 0.60 mmol) and 1,1'-(azodicarbonyl)dipiperidine (151 mg, 0.60 mmol) were added and the reaction stirred for 2 hours at ambient temperature. The reaction mixture was transferred to an SCX column which was eluted with 0-5% methanol in dichloromethane before the product was eluted with 3% ammonium hydroxide/20% methanol in dichloromethane. Evaporation of the desired fractions in vacuo, followed by trituration of the solid product with ethyl acetate, yielded the title compound (45 mg, 44% yield) as a white solid, after drying in vacuo:
$^1$H-NMR (DMSO d$_6$): 10.24 (bs, 1H), 9.47 (s, 1H), 8.43 (s, 1H), 7.97 (d, 2H, J=7 Hz), 7.88 (s, 1H), 7.69-7.82 (m, 4H), 7.49-7.63 (m, 3H), 7.19 (s, 1H), 4.29 (t, 2H, J=6 Hz), 3.99 (s, 3H), 3.23-3.38 (m, 2H), 3.05 (s, 3H), 2.15-2.31 (m, 2H):
MS (+ve ESI): 507 (M+H)$^+$.

EXAMPLE 214

Preparation of Compound No. 214 in Table 8

An analogous reaction to that described in example 213, but starting with 4-((4-(N-benzoyl)-amino)anilino)-6-methoxy-7-hydroxyquinazoline (100 mg, 0.26 mmol) and N-(tert-butoxycarbonyl)-ethanolamine (0.08 ml, 0.78 mmol) yielded the title compound (130 mg, 54% yield) as a white solid, after purification by flash chromatography on silica gel, eluting with 2-3.5% methanol in dichloromethane:
$^1$H-NMR (DMSO d$_6$): 10.23 (s, 1H), 9.45 (s, 1H), 8.42 (s, 1H), 7.96 (d, 2H), 7.84 (s, 1H), 7.70-7.81 (m, 4H), 7.48-7.63 (m, 3H), 7.17 (s, 1H), 6.98 (s, 1H), 4.53 (t, 2H), 3.95 (s, 3H), 3.31-3.41 (m, 2H), 1.38 (s, 9H):
MS (+ve ESI): 530 (M+H)$^+$.

EXAMPLE 215

Preparation of Compound No. 215 in Table 8

A solution of 4-((4-(N-benzoyl)amino)anilino)-6-methoxy-7-benzyloxyquinazoline trifluoroacetate (250 mg, 0.50 mmol), 3-picolyl chloride hydrochloride (90 mg, 0.55 mmol) and potassium carbonate (230 mg, 1.65 mmol) in dimethylacetamide (2.0 ml) was heated at 100° C. for 2 hours under an inert atmosphere. The reaction was cooled to ambient temperature, diluted with water (7.0 ml) and the solid which precipitated was collected by suction filtration. The solid was taken up in a small volume of dimethylacetamide and purified by chromatography on an SCX column, eluting with i) dichloromethane, ii) 10% methanol in dichloromethane and iii) 2% ammonia/10% methanol in dichloromethane. Evaporation of the product fractions in vacuo yielded the title compound (130 mg, 54% yield) as a white solid:

$^1$H-NMR (DMSO d$_6$): 10.23 (s, 1H), 9.45 (s, 1H), 8.75 (d, 1H), 8.59 (d, 1H), 8.42 (s, 1H), 7.9 (m, 4H), 7.75 (dd, 4H), 7.50 (m, 4H), 7.30 (s, 1H), 5.30 (s, 2H), 3.95 (s, 3H):

MS (–ve ESI): 476 (M–H)$^-$,
MS (+ve ESI): 478 (M+H)$^+$.

EXAMPLE 216

Preparation of Compound No. 216 in Table 8

An analogous reaction to that described in example 215, but starting with (2-chloroethyl)methyl ether (0.050 ml, 0.55 mmol) yielded the title compound (156 mg, 70% yield) as a white solid:

$^1$H-NMR (DMSO d$_6$): 11.39 (s, 1H), 10.40 (s, 1H), 8.80 (s, 1H), 8.30 (s, 1H), 8.00 (d, 2H), 7.90 (d, 2H), 7.65 (d, 2H), 7.55 (m, 3H), 7.40 (s, 1H), 4.30 (m, 2H), 4.00 (s, 3H), 3.75 (m, 2H), 3.30 (s, 3H):

MS (–ve ESI): 443 (M–H)$^-$,
MS (+ve ESI): 445 (M+H)$^+$.

EXAMPLE 217

Preparation of Compound No. 217 in Table 8

An analogous reaction to that described in example 215, but starting with acetic anhydride (0.10 ml, 1.06 mmol) yielded the title compound (65 mg, 49% yield) as a white solid:

$^1$H-NMR (DMSO d$_6$): 10.25 (s, 1H), 9.65 (s, 1H), 8.45 (s, 1H), 8.05 (s, 1H), 7.99 (d, 2H), 7.75 (dd, 4H), 7.55 (m, 3H), 7.50 (s, 1H), 3.99 (s, 3H), 2.30 (s, 3H):

MS (–ve ESI): 427 (M–H)$^-$,
MS (+ve ESI): 429 (M+H)$^+$.

EXAMPLE 218

Preparation of Compound No. 218 in Table 8

An analogous reaction to that described in example 215, but starting with 3,4,5-trifluorobenzyl bromide (27 mg, 0.12 mmol) and heating the reaction in dimethylformamide at ambient temperature for 2.5 hours, yielded the title compound (25 mg, 39% yield) as a white solid:

$^1$H-NMR (DMSO d$_6$): 10.28 (s, 1H), 10.02 (bs, 1H), 8.56 (s, 1H), 7.93-8.00 (m, 3H), 7.83 (d, 2H, J=8 Hz), 7.70 (d, 2H, J=8 Hz), 7.42-7.63 (m, 5H), 7.27 (s, 1H), 5.28 (s, 2H), 3.99 (s, 3H):

MS (+ve ESI): 531 (M+H)$^+$.

EXAMPLE 219

Preparation of Compound No. 219 in Table 8

An analogous reaction to that described in example 215, but starting with 1-(3-bromopropyl)-4,5-dihydroimidazole (327 mg, 0.97 mmol) and heating the reaction at 60° C. for 24 hours, yielded the title compound (84 mg, 26% yield) as a white solid, after purification by flash chromatography on silica gel, eluting with 5-15% methanol in dichloromethane:

$^1$HNMR (DMSO-d$_6$, TFA): 8.87 (s, 1H), 8.51 (s, 1H), 8.13 (s, 1H), 7.98 (d, 2H), 7.93 (d, 2H), 7.63 (m, 3H), 7.56 (t, 2H), 7.35 (s, 1H), 4.30 (t, 2H), 4.02 (s, 3H), 3.91 (s, 4H), 3.69 (t, 2H), 2.22 (t, 2H):

MS ES$^+$: 497 [M$^+$H]$^+$ 1-(3-bromopropyl)-4,5-dihydroimidazole, used as the starting material was obtained as below:—

A solution of 1-(3-hydroxypropyl)-4,5-dihydroimidazole (1.0 g, 3.65 mmol) in tetrahydrofuran (15 ml) was reacted with carbon tetrabromide (1.43 g, 5.47 mmol) and triphenylphosphine (1.43 g, 5.47 mmol) at ambient temperature for 18 hours. Solvent evaporation in vacuo and purification by flash chromatography on silica gel, eluting with 10% methanol in dichloromethane, yielded 1-(3-bromopropyl)-4,5-dihydroimidazole (429 mg, 35% yield) as a white solid:

$^1$H-NMR (DMSO d$_6$): 8.45 (s, 1H), 3.83 (m, 4H), 3.57 (m, 4H), 2.14 (q, 2H):

EXAMPLE 220

Preparation of Compound No. 220 in Table 8 cis-1,4-Dichloro-2-butene (0.138 ml, 1.29 mmol) was added to a stirred suspension of potassium carbonate (178 mg, 1.29 mmol) and 4-((4-(N-benzoyl)amino)anilino)-6-methoxy-7-hydroxyquinazoline (100 mg, 0.26 mmol) in dimethylacetamide (5 ml) and the reaction was stirred for 8 hours at ambient temperature. Pyrrolidine (0.42 ml, 5.05 mmol) was added, the reaction was stirred for 16 hours at ambient temperature, poured into water and the resultant yellow solid collected by suction filtration. Purification by flash chromatography on silica gel, eluting with 5% methanol in dichloromethane, yielded the title compound (18 mg, 17% yield) as a pale yellow solid:

$^1$H-NMR (DMSO d$_6$): 10.23 (s, 1H), 9.44 (s, 1H), 8.41 (s, 1H), 7.97 (d, 2H, J=8 Hz), 7.83 (s, 1H), 7.77 (m, 4H), 7.51-7.59 (m, 3H), 7.20 (s, 1H), 5.78 (m, 2H), 4.81 (m, 2H), 3.97 (s, 3H), 3.34 (m, 4H), 3.22 (m, 2H), 1.62 (m, 4H):

MS (–ve ESI): 508 (M–H)$^-$.

EXAMPLE 221

Preparation of Compound No. 221 in Table 8 trans-1,4-Dichloro-2-butene (0.138 ml, 1.29 mmol) was added to a stirred suspension of potassium carbonate (178 mg, 1.29 mmol) and 4-((4-(N-benzoyl)amino)anilino)-6-methoxy-7-hydroxyquinazoline (125 mg, 0.32 mmol) in dimethylacetamide (6 ml) and the reaction was stirred for 18 hours at ambient temperature. Additional potassium carbonate (134 mg, 0.97 mmol) and trans-1,4-dichloro-2-butene (0.102 ml, 0.97 mmol) were added, the reaction was stirred for a further 5 hours and pyrrolidine (0.673 ml, 8.10 mmol) was added. After 16 hours stirring at ambient temperature, the reaction was poured into water, the aqueous was extracted with ethyl acetate and the combined organic layers were dried over magnesium sulphate. Solvent evaporation in vacuo yielded the title compound (46 mg, 28% yield) as a white solid:

$^1$H-NMR (DMSO d$_6$): 10.22 (s, 1H), 9.47 (s, 1H), 8.41 (s, 1H), 7.94 (d, 2H, J=8 Hz), 7.83 (s, 1H), 7.76 (m, 4H), 7.48-

7.59 (m, 3H), 7.17 (s, 1H), 4.71 (d, 2H, J=6 Hz), 3.96 (s, 3H), 3.09 (d, 2H, J=7 Hz), 2.40 (m, 4H), 1.64 (m, 4H):

MS (+ve ESI): 510 (M+H)$^+$.

EXAMPLE 222

Preparation of Compound No. 222 in Table 8

An analogous reaction to that described in example 221, but starting with piperidine (0.80 ml, 8.10 mmol) yielded the title compound (45 mg, 27% yield) as a white solid, after purification by reverse phase hplc:

$^1$H-NMR (DMSO d$_6$): 10.23 (s, 1H), 9.45 (s, 1H), 8.40 (s, 1H), 7.98 (d, 2H, J=8 Hz), 7.84 (s, 1H), 7.77 (m, 4H), 7.51-7.59 (m, 3H), 7.17 (s, 1H), 5.86 (m, 2H), 4.72 (d, 2H, J=6 Hz), 3.96 (s, 3H), 2.93 (m, 2H), 2.30 (m, 2H), 1.46 (m, 2H), 1.37 (m, 2H):

MS (+ve ESI): 522 (M+H)$^+$.

EXAMPLE 223

Preparation of Compound No. 223 in Table 8

An analogous reaction to that described in example 221, but starting with morpholine (0.70 ml, 8.10 mmol) yielded the title compound (39 mg, 23% yield) as a white solid, after purification by reverse phase hplc:

$^1$H-NMR (DMSO d$_6$): 10.23 (s, 1H), 9.43 (s, 1H), 8.40 (s, 1H), 7.95 (d, 2H, J=8 Hz), 7.82 (s, 1H), 7.77 (m, 4H), 7.51-7.60 (m, 3H), 7.18 (s, 1H), 5.86 (m, 2H), 4.71 (s, 2H), 3.96 (s, 3H), 3.56 (m, 4H), 2.96 (m, 2H), 2.32 (m, 4H):

MS (+ve ESI): 526 (M+H)$^+$.

EXAMPLE 224

Preparation of Compound No. 224 in Table 8

An analogous reaction to that described in example 221, but starting with N-methylpiperidine (0.844 ml, 8.10 mmol) yielded the title compound (23 mg, 13% yield) as a white solid, after purification by reverse phase hplc:

$^1$H-NMR (DMSO d$_6$): 10.22 (s, 1H), 9.43 (s, 1H), 8.40 (s, 1H), 7.95 (d, 2H, J=8 Hz), 7.82 (s, 1H), 7.77 (m, 4H), 7.51-7.59 (m, 3H), 7.17 (s, 1H), 5.85 (m, 2H), 4.71 (m, 2H), 3.96 (s, 3H), 2.95 (m, 2H), 2.21-2.28 (m, 8H), 2.11 (s, 3H):

MS (+ve ESI): 539 (M+H)$^+$.

EXAMPLE 225

Preparation of Compound No. 225 in Table 8

2-Bromoethanol (0.031 ml, 0.44 mmol) was added to a stirred suspension of potassium carbonate (276 mg, 2.00 mmol) and 4-((4-(N-benzoyl)amino)anilino)-6-methoxy-7-hydroxy-quinazoline trifluoroacetate (200 mg, 0.40 mmol) in dimethylformamide (1 ml) and the reaction was stirred for 3.5 hours at 85°. 2-Bromoethanol (0.031 ml, 0.44 mmol) was added, the reaction was stirred for a further 1 hour, was then poured into water (10 ml) and the solid product was collected by suction filtration. Purification by flash chromatography on silica gel, eluting with 4-6% methanol in dichloromethane yielded the title compound (37 mg, 21% yield) as a white solid:

$^1$H-NMR (DMSO d$_6$): 10.20 (s, 1H), 9.41 (s, 1H), 8.39 (s, 1H), 7.88 (d, 2H, J=7 Hz), 7.80 (s, 1H), 7.73 (d, 2H, J=8 Hz), 7.69 (d, 2H, J=8 Hz), 7.42-7.54 (m, 3H), 7.12 (s, 1H), 4.88 (t, 1H, J=7 Hz), 4.10 (m, 2H), 3.92 (s, 3H), 3.72 (m, 2H):

MS (+ve ESI): 432 (M+H)$^+$.

EXAMPLE 226

Preparation of Compound No. 226 in Table 8

An analogous reaction to that described in example 225, but starting with 3-chloro-1-bromo-propane (0.256 ml, 2.59 mmol) yielded the title compound (897 mg, 75% yield) as a white solid:

$^1$H-NMR (DMSO d$_6$): 10.06 (s, 1H), 9.28 (s, 1H), 8.29 (s, 1H), 7.80 (d, 2H, J=7 Hz), 7.70 (s, 1H), 7.62 (d, 2H, J=8 Hz), 7.58 (d, 2H, J=8 Hz), 7.30-7.41 (m, 3H), 7.00 (s, 1H), 4.08 (t, 2H, J=7 Hz), 3.79 (s, 3H), 3.59 (t, 2H, J=7 Hz), 2.04 (t, 2H, J=7 Hz):

MS (+ve ESI): 464 (M+H)$^+$.

EXAMPLE 227

Preparation of Compound No. 227 in Table 8

(2S)-(+)-glycidyl tosylate (5.00 g, 21.9 mmol) was added to a stirred suspension of potassium carbonate (7.26 g, 52.6 mmol) and 4-((4-(N-benzoyl)amino)anilino)-6-methoxy-7-hydroxyquinazoline (6.77 g, 17.5 mmol) in dimethylformamide (350 ml) and the reaction was stirred for 3.5 hours at 60° C. Additional (2S)-(+)-glycidyl tosylate (0.30 g, 1.1 mmol) was added and the reaction was stirred for a further 3 hours at 60° C. The dimethylformamide was evaporated in vacuo and the residue was triturated with methanol and then saturated aqueous sodium hydrogen carbonate solution. Trituration with dichloromethane caused the residue to solidify and the solid was then collected by suction filtration. Drying in vacuo yielded the title compound (4.87 g, 63% yield) as a pale yellow solid:

$^1$H-NMR (DMSO d$_6$): 10.24 (s, 1H), 9.46 (s, 1H), 8.42 (s, 1H), 7.96 (d, 2H), 7.85 (s, 1H), 7.68-7.82 (m, 4H), 7.44-7.63 (m, 3H), 7.19 (s, 1H), 4.52 (dd, 1H), 3.92-4.03 (m, 1H), 3.97 (s, 3H), 3.35-3.45 (m, 1H), 2.87 (t, 1H), 2.75 (m, 1H):

MS (+ve ESI): 443 (M+H)$^+$.

EXAMPLE 228

Preparation of Compound No. 228 in Table 8

An analogous reaction to that described in example 225, but starting with N-(tert-butoxycarbonyl)-3-hydroxypyrrolidine methanesulphonate (21 mg, 0.079 mmol), and using caesium carbonate (108 mg, 0.33 mmol), in preference to potassium carbonate, yielded the title compound (30 mg, 82% yield) as a white solid:

$^1$H-NMR (DMSO d$_6$): 10.22 (s, 1H), 9.46 (s, 1H), 8.41 (m, 1H), 7.97 (d, 2H, J=8 Hz), 7.84 (s, 1H), 7.77 (m, 4H), 7.50-7.58 (m, 3H), 7.18 (s, 1H), 5.21 (m, 1H), 3.95 (s, 3H), 3.64 (m, 1H), 3.30-3.50 (m, 3H), 2.10-2.25 (m, 2H), 1.38 (s, 9H):

MS (+ve ESI): 556 (M+H)$^+$.

N-(tert-Butoxycarbonyl)-3-hydroxypyrrolidine methanesulphonate, used as the starting material was obtained as follows:

Triethylamine (4.5 ml, 32.0 mmol) was added to a stirred solution of, N-(tert-butoxy-carbonyl)-3-hydroxypyrrolidine (2.00 g, 10.7 mmol) in diethyl ether (100 ml) and the reaction was cooled to 0° C. before addition of methanesulphonyl chloride (1.65 ml, 21.4 mmol) and stirring for 2 hours, warming from 0° C. to ambient temperature. The reaction was filtered, the filtrate was washed with 1.0 N hydrochloric acid

EXAMPLE 229

Preparation of Compound No. 229 in Table 8

An analogous reaction to that described in example 210, but starting with N-isopropyl-3-hydroxyazetidine (100 mg, 0.87 mmol) yielded the title compound (21 mg, 10% yield) as an off-white solid, after purification by reverse phase hplc:
$^1$H-NMR (DMSO d$_6$): 10.22 (s, 1H), 9.45 (s, 1H), 8.41 (m, 1H), 7.97 (d, 2H, J=8 Hz), 7.82 (s, 1H), 7.75 (m, 4H), 7.50-7.62 (m, 3H), 7.04 (s, 1H), 5.02 (m, 1H), 3.96 (s, 3H), 3.42 (t, 2H, J=7 Hz), 3.21 (s, 3H), 2.89 (m, 1H), 2.78 (m, 2H), 2.60 (m, 2H), 2.30-2.45 (m, 2H), 1.81 (m, 1H):
MS (−ve ESI): 482 (M−H)$^−$.

EXAMPLE 230

Preparation of Compound No. 230 in Table 8

An analogous reaction to that described in example 227, but starting with (2R)-(−)-glycidyl tosylate (4.87 g, 21.3 mmol), yielded the title compound (5.15 g mg, 60% yield) as a white solid:
$^1$H-NMR (DMSO d$_6$): 10.23 (s, 1H), 9.46 (s, 1H), 8.42 (s, 1H), 7.95 (d, 2H), 7.85 (s, 1H), 7.64-7.82 (m, 4H), 7.46-7.63 (m, 3H), 7.19 (s, 1H), 4.53 (dd, 1H), 3.93-4.02 (m, 1H), 3.97 (s, 3H), 3.34-3.45 (m, 1H), 2.87 (t, 1H), 2.70-2.80 (m, 1H):
MS (+ve ESI): 443 (M+H)$^+$.

EXAMPLE 231

Preparation of Compound No. 231 in Table 9

An analogous reaction to that described in example 210, but starting with 4-((4-(N-benzoyl)-amino)anilino)-6-methoxy-7-(2-hydroxyethoxy)quinazoline (60 mg, 0.14 mmol) and 2,2,2-trifluoroethanol (0.104 ml, 0.417 mmol), yielded the title compound (14 mg, 20% yield) as a white solid, after purification by flash chromatography on an SCX column, eluting with 0-20% methanol in dichloromethane:
$^1$H-NMR (DMSO d$_6$) 10.23 (s, 1H), 9.45 (s, 1H), 8.42 (s, 1H), 7.95 (d, 2H), 7.85 (s, 1H), 7.64-7.82 (m, 4H), 7.46-7.63 (m, 3H), 7.19 (s, 1H), 4.25-4.35 (m, 2H), 4.19 (t, 2H), 3.98-4.05 (m, 2H), 3.96 (s, 3H):
MS (−ve ESI): 443 (M−H)$^−$.

EXAMPLE 232

Preparation of Compound No. 232 in Table 9

Trifluororacetic acid (1.5 ml) was added to a stirred solution of with 4-((4-(N-benzoyl)-amino)anilino)-6-methoxy-7-((N-tert-butoxycarbonyl)-2-aminoethoxy)quinazoline (35 mg, 0.066 mmol) and the reaction stirred for 1 hour at ambient temperature. The volatiles were removed in vacuo, water (1 ml) was added and then the reaction was neutralised by addition of saturated aqueous sodium hydrogen carbonate solution. The solid which precipitated was collected by suction filtration and washed with diethyl ether and water. Drying in vacuo yielded the title compound as an off-white solid (25 mg, 88% yield):
$^1$H-NMR (DMSO d$_6$): 10.20 (s, 1H), 9.40 (s, 1H), 8.39 (s, 1H), 7.92 (d, 2H, J=7 Hz), 7.79 (s, 1H), 7.73 (d, 2H, J=8 Hz), 7.67 (d, 2H, J=8 Hz), 7.46-7.56 (m, 3H), 7.11 (s, 1H), 4.04 (t, 2H, J=7 Hz), 3.91 (s, 3H), 2.90 (m, 2H), 1.55-1.72 (m, 2H):
MS (+ve ESI): 431 (M+H)$^+$.

EXAMPLE 233

Preparation of Compound No. 233 in Table 9

An analogous reaction to that described in example 232, but starting with 4-((4-(N-benzoyl)-amino)anilino)-6-methoxy-7-((N-tert-butoxycarbonyl)-3-pyrrolidinoxy)quinazoline (20 mg, 0.036 mmol), yielded the title compound (20 mg, 98% yield) as an off-white solid:
$^1$H-NMR (DMSO d$_6$): 10.34 (s, 1H), 9.18 (m, 1H), 8.72 (s, 1H), 8.05 (s, 1H), 7.97 (d, 2H, J=8 Hz), 7.85 (d, 2H, J=8 Hz), 7.63 (d, 2H, J=8 Hz), 7.50-7.59 (m, 3H), 7.38 (s, 1H), 5.35 (m, 1H), 3.99 (s, 3H), 3.24-3.64 (m, 5H), 2.21 (m, 2H):
MS (+ve ESI): 456 (M+H)$^+$.

EXAMPLE 234

Preparation of Compound No. 234 in Table 9

An analogous reaction to that described in example 232, but starting with 4-((4-(N-benzoyl)-amino)anilino)-6-methoxy-7-(((N-tert-butoxycarbonyl)-2-pyrrolidine)methoxy)quinazoline (453 mg, 0.79 mmol), yielded the title compound (515 mg, 93% yield) as an off-white solid:
$^1$H-NMR (DMSO d$_6$): 10.36 (s, 1H), 9.30 (m, 1H), 8.90 (s, 1H), 8.76 (s, 1H), 8.10 (s, 1H), 7.98 (d, 2H, J=8 Hz), 7.86 (d, 2H, J=8 Hz), 7.63 (d, 2H, J=8 Hz), 7.51-7.60 (m, 3H), 7.34 (s, 1H), 4.44 (m, 1H), 4.36 (m, 1H), 4.09 (m, 1H), 4.00 (s, 3H), 3.24 (m, 2H), 1.80-2.21 (m, 4H):
MS (+ve ESI): 470 (M+H)$^+$.

EXAMPLE 235

Preparation of Compound No. 235 in Table 9

An analogous reaction to that described in example 232, but starting with 4-((4-(N-benzoyl)-amino)anilino)-6-methoxy-7-(((N-tert-butoxycarbonyl)-4-piperidine)methoxy)quinazoline (1.53 g, 3.19 mmol), yielded the title compound (1.00 g, 54% yield) as an off-white solid:
$^1$H-NMR (DMSO d$_6$): 10.36 (s, 1H), 8.78 (s, 1H), 8.62 (m, 1H), 8.35 (m, 1H), 8.07 (s, 1H), 7.98 (d, 2H, J=8 Hz), 7.88 (d, 2H, J=8 Hz), 7.50-7.65 (m, 5H), 7.32 (s, 1H), 4.10 (d, 2H, J=8 Hz), 3.98 (s, 3H), 3.37 (m, 2H), 2.95 (m, 2H), 2.18 (m, 1H), 1.92 (m, 2H), 1.50 (m, 2H):
MS (+ve ESI): 482 (M+H)$^+$.

EXAMPLE 236

Preparation of Compound No. 236 in Table 9

An aqueous solution of paraformaldehyde (1 ml of a 40% w/v solution) was added to a stirred solution of 4-((4-(N-benzoyl)amino)anilino)-6-methoxy-7-(4-piperidinoxy)quinazoline (100 mg, 0.143 mmol) in formic acid (2 ml) and the reaction was stirred for 16 hours at ambient temperature. The reaction was heated to 95° C. for 45 minutes, then cooled and absorbed onto silica gel. Purification by flash chromatography on silica gel, eluting with 0-6% methanol in dichloromethane, yielded the title compound (32 mg, 48% yield) as an off-white solid:

$^1$H-NMR (DMSO d$_6$): 10.22 (s, 1H), 9.42 (s, 1H), 8.40 (m, 1H), 7.97 (d, 2H, J=8 Hz), 7.83 (s, 1H), 7.77 (m, 4H), 7.50-7.58 (m, 3H), 7.19 (s, 1H), 3.98 (s, 3H), 3.96 (m, 1H), 2.68 (s, 3H), 2.23 (m, 2H), 2.00 (m, 2H), 1.69 (m, 2H):

MS (+ve ESI): 484 (M+H)$^+$.

EXAMPLE 237

Preparation of Compound No. 237 in Table 9

An analogous reaction to that described in example 236, but starting with 4-((4-(N-benzoyl)-amino)anilino)-6-methoxy-7-(2-pyrrolidinomethoxy)quinazoline (310 mg, 0.54 mmol), yielded the title compound (47 mg, 18% yield) as a yellow solid:

$^1$H-NMR (DMSO d$_6$): 10.22 (s, 1H), 9.44 (s, 1H), 8.41 (m, 1H), 7.97 (d, 2H, J=8 Hz), 7.82 (s, 1H), 7.75 (m, 4H), 7.50-7.58 (m, 3H), 7.18 (s, 1H), 4.06 (q, 1H, J=7 Hz), 4.01 (q, 1H, J=7 Hz), 3.95 (s, 3H), 3.00 (s, 3H), 2.95 (m, 1H), 2.65 (m, 2H), 2.21 (m, 1H), 1.98 (m, 1H), 1.62-1.75 (m, 2H):

MS (+ve ESI): 484 (M+H)$^+$.

EXAMPLE 238

Preparation of Compound No. 238 in Table 9

An analogous reaction to that described in example 236, but starting with 4-((4-(N-benzoyl)-amino)anilino)-6-methoxy-7-(3-pyrrolidinoxy)quinazoline (100 mg, 0.146 mmol), yielded the title compound (32 mg, 48% yield) as a yellow solid:

$^1$H-NMR (DMSO d$_6$): 10.22 (s, 1H), 9.44 (s, 1H), 8.41 (m, 1H), 7.97 (d, 2H, J=8 Hz), 7.82 (s, 1H), 7.75 (m, 4H), 7.50-7.59 (m, 3H), 7.05 (s, 1H), 5.02 (m, 1H), 3.95 (s, 3H), 2.70-2.83 (m, 3H), 2.39 (m, 2H), 2.30 (s, 3H), 1.83 (m, 1H):

MS (+ve ESI): 470 (M+H)$^+$.

EXAMPLE 239

Preparation of Compound No. 239 in Table 9

Methane sulphonyl chloride (27 mg, 0.24 mmol) was added to a stirred solution of 2-methoxyethanol (18 mg, 0.24 mmol) and triethylamine (33 mg, 0.33 mmol) in tetrahydrofuran (1 ml) and the reaction was stirred at 0° C. for 1 hour. A solution of 4-((4-(N-benzoyl)-amino)anilino)-6-methoxy-7-(N-methyl-3-aminopropoxy)quinazoline (100 mg, 0.22 mmol) in dimethylacetamide (1 ml) was added and the reaction was stirred at 60° C. for 16 hours. After cooling to ambient temperature, saturated aqueous sodium hydrogen carbonate solution (5 ml) was added and the organic material was extracted into ethyl acetate (3×10 ml). After solvent evaporation in vacuo, purification by flash chromatography on silica gel, eluting with 5-10% methanol in dichloromethane yielded the title compound (26 mg, 23% yield) as a pale yellow solid:

$^1$H-NMR (DMSO d$_6$): 10.20 (s, 1H), 9.40 (s, 1H), 8.40 (s, 1H), 8.00 (d, 2H), 7.81 (s, 1H), 7.60-7.70 (m, 4H), 7.40-7.50 (m, 3H), 7.10 (s, 1H), 4.20 (t, 2H), 3.98 (s, 3H), 3.30-3.40 (m, 2H), 3.10 (s, 3H), 2.52 (m, 4H), 2.20 (s, 3H), 1.90 (t, 2H):

MS (+ve ESI): 516 (M+H)$^+$,
MS (−ve ESI): 514 (M−H)$^-$.

EXAMPLE 240

Preparation of Compound No. 240 in Table 9

Acetyl chloride (38 mg, 0.48 mmol) was added to a stirred solution of 4-((4-(N-benzoyl)-amino)anilino)-6-methoxy-7-(N-methyl-3-aminopropoxy)quinazoline (100 mg, 0.22 mmol) and triethylamine (49 mg, 0.48 mmol) in dimethylacetamide (1 ml) and the reaction was stirred at ambient temperature for 16 hours. Brine (10 ml) was added, the resultant precipitate was collected by suction filtration and taken up in methanol (0.5 ml). Addition of diethyl ether (5 ml) caused a solid to precipitate and drying of this solid in vacuo yielded the title compound (80 mg, 73% yield) as a pale yellow solid:

$^1$H-NMR (DMSO d$_6$): 10.65 (s, 1H), 10.00 (s, 1H), 8.25 (s, 1H), 8.00 (d, 2H), 7.80 (dd, 4H); 7.45-7.60 (m, 3H), 7.30 (s, 1H), 4.30 (t, 2H), 4.0 (s, 3H), 3.50 (t, 2H), 2.00-2.20 (m, 2H), 1.90 (s, 3H):

MS (+ve ESI): 500 (M+H)$^+$
MS (−ve ESI): 498 (M−H)$^-$.

EXAMPLE 241

Preparation of Compound No. 241 in Table 9

An analogous reaction to that described in example 240, but starting with N,N-dimethyl-carbamoyl chloride (0.044 ml, 0.048 mmol), yielded the title compound (55 mg, 48% yield) as a white solid, after purification by flash chromatography on silica gel, eluting with 5-10% methanol in dichloromethane:

$^1$H-NMR (DMSO d$_6$): 10.22 (s, 1H), 9.40 (s, 1H), 8.40 (s, 1H), 8.0 (d, 2H), 7.81 (s, 1H), 7.75 (dd, 4H); 7.50-7.60 (m, 3H), 7.10 (s, 1H), 4.20 (t, 2H), 3.98 (s, 3H), 3.20-3.30 (m, 2H), 2.80 (s, 3H), 2.70 (s, 6H), 1.90-2.10 (m, 2H):

MS (+ve ESI): 529 (M+H)$^+$
MS (−ve ESI): 527 (M−H)$^-$.

EXAMPLE 242

Preparation of Compound No. 242 in Table 9

An analogous reaction to that described in example 225, but starting with 2-bromoethanol (0.031 ml, 0.44 mmol), and using sodium iodide (66 mg, 0.44 mmol) as a catalyst, yielded the title compound (17 mg, 23% yield) as a pale yellow solid:

$^1$H-NMR (DMSO d$_6$): 10.22 (s, 1H), 9.45 (s, 1H), 8.41 (s, 1H), 7.97 (d, 2H, J=8 Hz), 7.84 (s, 1H), 7.76 (m, 4H), 7.50-7.58 (m, 3H), 7.07 (s, 1H), 5.06 (m, 1H), 4.55 (m, 1H), 3.96 (s, 3H), 3.51 (q, 2H, J=7 Hz), 3.03 (m, 1H), 2.83-2.97 (m, 2H), 2.38-2.67 (m, 4H), 1.82-1.90 (m, 1H):

MS (−ve ESI): 498 (M−H)$^-$

EXAMPLE 243

Preparation of Compound No. 243 in Table 9

An analogous reaction to that described in example 225, but starting with 2-bromoethyl ethyl ether (0.012 ml, 0.13 mmol), yielded the title compound (23 mg, 13% yield) as a white solid, after purification by flash chromatography on silica gel, eluting with 5% methanol in dichloromethane:

$^1$H-NMR (DMSO d$_6$): 10.22 (s, 1H), 9.45 (s, 1H), 8.41 (s, 1H), 7.97 (d, 2H, J=8 Hz), 7.83 (s, 1H), 7.76 (m, 4H), 7.50-7.60 (m, 3H), 6.91 (s, 1H), 4.90 (m, 1H), 3.96 (s, 3H), 3.73 (m, 2H), 3.04 (m, 2H), 2.34 (m, 1H), 0.87 (d, 6H, J=7 Hz):

MS (−ve ESI): 512 (M−H)$^-$

EXAMPLE 244

Preparation of Compound No. 244 in Table 9

An analogous reaction to that described in example 225, but starting with bromoacetonitrile (0.024 ml, 0.35 mmol) yielded the title compound (9 mg, 16% yield) as a white solid, after purification by reverse phase hplc:
$^1$H-NMR (DMSO d$_6$): 10.22 (s, 1H), 9.45 (s, 1H), 8.41 (s, 1H), 7.96 (d, 2H, J=8 Hz), 7.83 (s, 1H), 7.76 (m, 4H), 7.49-7.59 (m, 3H), 7.09 (s, 1H), 5.12 (m, 1H), 3.95 (s, 3H), 3.87 (s, 2H), 2.98 (m, 1H), 2.84 (m, 2H), 2.40-2.58 (m, 2H), 1.87-1.94 (m, 1H):
MS (+ve ESI): 495 (M+H)$^+$

EXAMPLE 245

Preparation of Compound No. 245 in Table 9

An analogous reaction to that described in example 225, but starting with 2-bromoethyl methyl ether (0.009 ml, 0.09 mmol) yielded the title compound (10 mg, 22% yield) as a white solid:
$^1$H-NMR (DMSO d$_6$): 10.22 (s, 1H), 9.45 (s, 1H), 8.41 (s, 1H), 7.96 (d, 2H, J=8 Hz), 7.82 (s, 1H), 7.77 (m, 4H), 7.50-7.58 (m, 3H), 7.21 (s, 1H), 4.60 (m, 1H), 3.95 (s, 3H), 3.47 (m, 2H), 3.24 (s, 3H), 2.82 (m, 2H), 2.35-2.69 (m, 4H), 2.03 (m, 2H), 1.70 (m, 2H):
MS (−ve ESI): 526 (M−H)$^-$

EXAMPLE 246

Preparation of Compound No. 246 in Table 9

An analogous reaction to that described in example 225, but starting with bromoacetonitrile (0.009 ml, 0.09 mmol), yielded the title compound (25 mg, 55% yield) as an off-white solid:
$^1$H-NMR (DMSO d$_6$): 10.22 (s, 1H), 9.43 (s, 1H), 8.41 (s, 1H), 7.96 (d, 2H), 7.82 (s, 1H), 7.76 (m, 4H), 7.49-7.58 (m, 3H), 7.24 (s, 1H), 4.66 (m, 1H), 3.96 (s, 3H), 3.74 (s, 3H), 2.77 (m, 2H), 2.45 (m, 2H), 2.09 (m, 2H), 1.74 (m, 2H):
MS (+ve ESI): 509 (M+H)+.

EXAMPLE 247

Preparation of Compound No. 247 in Table 9

An analogous reaction to that described in example 225, but starting with cyclopropylmethyl bromide (0.042 ml, 0.43 mmol), yielded the title compound (25 mg, 33% yield) as an off-white solid, after purification by reverse phase hplc:
$^1$H-NMR (DMSO d$_6$): 10.13 (s, 1H), 9.34 (s, 1H), 8.32 (s, 1H), 7.96 (d, 2H), 7.75 (s, 1H), 7.64 (m, 4H), 7.40-7.49 (m, 3H), 7.05 (s, 1H), 3.98 (m, 1H), 3.94 (s, 3H), 3.09 (m, 1H), 2.81 (m, 1H), 2.72 (m, 1H), 2.10-2.24 (m, 2H), 1.84 (m, 1H), 1.56-1.69 (m, 3H), 0.79 (m, 1H), 0.32 (m, 2H), 0.01 (m, 2H):
MS (+ve ESI): 524 (M+H)+.

EXAMPLE 248

Preparation of Compound No. 248 in Table 9

An analogous reaction to that described in example 225, but starting with cyclobutylmethyl bromide (0.048 ml, 0.43 mmol), yielded the title compound (39 mg, 51% yield) as an off-white solid, after purification by reverse phase hplc:
$^1$H-NMR (DMSO d$_6$): 10.22 (s, 1H), 9.43 (s, 1H), 8.42 (s, 1H), 7.96 (d, 2H), 7.84 (s, 1H), 7.70-7.80 (m, 4H), 7.48-7.63 (m, 3H), 7.15 (s, 1H), 3.90-4.07 (m, 2H), 3.95 (s, 3H), 2.92-3.05 (m, 2H), 2.80-2.92 (m, 1H), 2.31-2.50 (m, 2H), 2.12-2.27 (m, 1H), 1.53-2.08 (m, 10H):
MS (+ve ESI): 538 (M+H)+.

EXAMPLE 249

Preparation of Compound No. 249 in Table 9

An analogous reaction to that described in example 225, but starting with bromoethanol (0.030 ml, 0.43 mmol), yielded the title compound (16 mg, 22% yield) as an off-white solid, after purification by reverse phase hplc:
$^1$H-NMR (DMSO d$_6$): 10.22 (s, 1H), 9.43 (s, 1H), 8.41 (s, 1H), 7.97 (d, 2H), 7.82 (s, 1H), 7.76 (m, 4H), 7.48-7.61 (m, 3H), 7.17 (s, 1H), 4.38 (m, 2H), 4.06 (m, 1H), 3.96 (s, 3H), 3.50 (m, 2H), 2.91-3.11 (m, 1H), 2.27-2.40 (m, 2H), 1.92 (m, 1H), 1.60-1.78 (m, 3H):
MS (+ve ESI): 514 (M+H)+.

EXAMPLE 250

Preparation of Compound No. 250 in Table 9

An analogous reaction to that described in example 225, but starting with (2-chloroethyl)ethyl sulphide (0.050 ml, 0.43 mmol), yielded the title compound (32 mg, 40% yield) as an off-white solid, after purification by reverse phase hplc:
$^1$H-NMR (DMSO d$_6$): 10.22 (s, 1H), 9.43 (s, 1H), 8.41 (s, 1H), 7.97 (d, 2H), 7.82 (s, 1H), 7.77 (m, 4H), 7.50-7.59 (m, 3H), 7.16 (s, 1H), 4.00 (m, 2H), 3.95 (s, 3H), 3.05-3.15 (m, 2H), 2.98 (m, 1H), 2.50 (m, 2H), 2.46 (s, 3H), 2.30 (m, 1H), 1.94 (m, 1H), 1.59-1.75 (m, 3H), 1.15 (t, 3H, J=7 Hz):
MS (+ve ESI): 558 (M+H)+.

EXAMPLE 251

Preparation of Compound No. 251 in Table 9

An analogous reaction to that described in example 225, but starting with cyclopropylmethyl bromide (0.063 ml, 0.64 mmol), yielded the title compound (6 mg, 6% yield) as an off-white solid, after purification by reverse phase hplc:
$^1$H-NMR (DMSO d$_6$): 10.18 (s, 1H), 9.39 (s, 1H), 8.36 (s, 1H), 7.91 (d, 2H), 7.78 (s, 1H), 7.64-7.75 (m, 4H), 7.41-7.57 (m, 3H), 7.08 (s, 1H), 3.95 (d, 2H), 3.91 (s, 3H), 2.87-2.99 (m, 2H), 2.11 (d, 2H), 1.82-1.95 (m, 2H), 1.64-1.82 (m, 3H), 1.21-1.39 (m, 2H), 0.70-0.85 (m, 1H), 0.34-0.45 (m, 2H), 0.00 (m, 2H):
MS (−ve ESI): 536 (M−H)$^-$.

EXAMPLE 252

Preparation of Compound No. 252 in Table 9

An analogous reaction to that described in example 225, but starting with 2-bromoethanol (0.046 ml, 0.64 mmol), yielded the title compound (38 mg, 33% yield) as an off-white solid:
$^1$H-NMR (DMSO d$_6$): 10.22 (s, 1H), 9.44 (s, 1H), 8.41 (s, 1H), 7.95 (d, 2H), 7.83 (s, 1H), 7.70-7.81 (m, 4H), 7.48-7.62 (m, 3H), 7.13 (s, 1H), 4.30 (t, 1H), 3.98 (d, 2H), 3.95 (s, 3H), 3.47 (q, 2H), 2.84-2.94 (m, 2H), 2.37 (t, 2H), 1.90-2.03 (m, 2H), 1.69-1.86 (m, 3H), 1.20-1.45 (m, 2H):
MS (+ve ESI): 528 (M+H)+.

EXAMPLE 253

Preparation of Compound No. 253 in Table 9

An analogous reaction to that described in example 225, but starting with (2-bromoethyl)-ethyl ether (0.061 ml, 0.64 mmol), yielded the title compound (73 mg, 62% yield) as a white solid:

$^1$H-NMR (DMSO d$_6$): 10.22 (s, 1H), 9.44 (s, 1H), 8.42 (s, 1H), 7.95 (d, 2H), 7.84 (s, 1H), 7.70-7.82 (m, 4H), 7.47-7.62 (m, 3H), 7.13 (s, 1H), 3.98 (d, 2H), 3.95 (s, 3H), 3.42 (t, 2H), 3.22 (s, 3H), 2.85-2.95 (m, 2H), 2.39-2.55 (m, 2H), 1.92-2.05 (m, 2H), 1.68-1.87 (m, 3H), 1.23-1.43 (m, 2H):

MS (+ve ESI): 542 (M+H)+.

EXAMPLE 254

Preparation of Compound No. 254 in Table 9

An analogous reaction to that described in example 225, but starting with bromoacetonitrile (0.045 ml, 0.64 mmol), yielded the title compound (38 mg, 35% yield) as an off-white solid:

$^1$H-NMR (DMSO d$_6$): 10.31 (s, 1H), 8.63 (s, 1H), 7.97 (s, 1H), 7.95 (d, 2H), 7.84 (d, 2H), 7.67 (d, 2H), 7.48-7.63 (m, 3H), 7.20 (s, 1H), 4.05 (d, 2H), 3.97 (s, 3H), 3.70 (s, 2H), 2.79-2.90 (m, 2H), 2.13-2.28 (m, 2H), 1.74-1.92 (m, 3H), 1.30-1.50 (m, 2H):

MS (−ve ESI): 521 (M−H)−.

EXAMPLE 255

Preparation of Compound No. 255 in Table 9

4-(Methylthio)-6-methoxy-7-((4,5-dihydro-2-imidazolyl) methoxy)quinazoline (56 mg, 0.181 mmol) was heated with 4-aminobenzanilide (192 mg, 0.905 mmol) in presence of paratoluenesulphonic acid (192 mg, 0.905 mmol) at 140° C. for 2 hours before solvent evaporation in vacuo. Purification by flash chromatography on silica gel, eluting with 10% methanol in dichloromethane yielded the title compound (12 mg, 14% yield) as a white solid:

$^1$H-NMR (DMSO d$_6$): 9.53 (s, 1H), 8.45 (s, 1H), 8.09 (t, 1H), 7.99 (d, 2H), 7.91 (s, 1H), 7.82 (d, 2H), 7.76 (d, 2H), 7.61 (dd, 1H), 7.56 (t, 2H), 7.12 (s, 1H), 4.71 (s, 2H), 4.01 (s, 3H), 3.18 (q, 2H), 2.65 (t, 2H):

MS (−ve ESI): 468 (M−H)−.

4-(Methylthio)-6-methoxy-7-((4,5-dihydro-2-imidazolyl) methoxy)quinaline, used as the starting material, was obtained as follows:

a) A solution of 4-(methylthio)-6-methoxy-7-hydroxyquinazoline (250 mg, 1.126 mmol) in acetone (5 ml) was heated with bromoacetonitrile (0.12 ml, 1.69 mmol) in the presence of potassium carbonate (233 mg, 1.69 mmol) at reflux for 16 hours. Water was added to the reaction mixture, which was extracted with ethyl acetate, the organic phase was washed with saturated brine, dried over magnesium sulphate, filtered, evaporated. Purification by flash chromatography on silica gel, eluting with 5% methanol in dichloromethane yielded 4-(methylthio)-6-methoxy-7-hydroxyquinazoline (261 mg, 89%) as a white solid:

$^1$H-NMR (DMSO d$_6$): 8.90 (s, 1H), 7.53 (s, 1H), 7.27 (s, 1H), 5.43 (s, 2H), 3.98 (s, 3H), 2.69 (s, 3H).

b) Excess anhydrous hydrochloric acid in ethanol (1 ml) was added to a solution of 4-(methylthio)-6-methoxy-7-(cyanomethoxy)quinazoline (300 mg, 1.15 mmol) in dichloromethane (20 ml) and the reaction was stirred for 20 hours at 4° C. The solvent was evaporated, ethylene diamine (280 mg, 8.15 mmol) in ethanol (10 ml) was added to the residue, and the mixture was refluxed for 2 hours. Solvent evaporation in vacuo and purification by flash chromatography on silica gel, eluting with 5% methanol in dichloromethane, yielded 4-(methylthio)-6-methoxy-7-((4,5-dihydro-2-imidazolyl) methoxy)quinazoline (56 mg, 22% yield) as a white solid:

$^1$H-NMR (DMSO d$_6$): 8.86 (s, 1H), 8.09 (t, 1H), 7.24 (s, 2H), 4.76 (s, 2H), 3.99 (s, 3H), 3.14 (q, 2H), 2.69 (s, 3H), 2.61 (t, 2H).

EXAMPLE 256

Preparation of Compound No. 256 in Table 10

4-((4-(N-benzoyl)-amino)anilino)-6-methoxy-7-(2-bromoethoxy)quinazoline (99 mg, 0.2 mmol) was added to a stirred solution of thiophene-2-methylamine (113 mg, 1.00 mmol) in dimethyacetamide (5 ml) and the reaction was heated at 60° C. for 16 hours. After cooling to ambient temperature, the crude reaction mixture was adsorbed onto silica gel. Purification by flash chromatography, eluting with 0-10% methanol in dichloromethane, yielded the title compound (45.2 mg, 37% yield) as an off-white solid:

$^1$H-NMR (DMSO d$_6$): 10.02 (s, 1H), 9.22 (s, 1H), 8.20 (s, 1H), 7.73 (d, 2H, J=7 Hz), 7.64 (s, 1H), 7.57 (d, 2H, J=7 Hz), 7.51 (d, 2H, J=7 Hz), 7.29-7.38 (m, 3H), 7.19 (d, 1H, J=5 Hz), 6.80 (m, 1H), 6.75 (m, 1H), 3.99 (m, 2H), 3.79 (s, 2H), 3.74 (s, 3H), 2.79 (s, 2H):

MS (+ve ESI): 526 (M+H)+.

4-((4-(N-benzoyl)-amino)anilino)-6-methoxy-7-(2-bromoethoxy)quinazoline, used as the starting material was obtained as follows:

A mixture of potassium carbonate (1.67 g, 12.1 mmol), 1,2-dibromoethane (2.33 ml, 25.9 mmol) and 4-((4-(N-benzoyl)amino)anilino)-6-methoxy-7-hydroxyquinazoline (1.0 g, 2.59 mmol) in dimethylformamide (85 ml) was heated for 18 hours at 85° C. The reaction was cooled, filtered and the residue evaporated in vacuo. Trituration of the residue with methanol/diethyl ether yielded 4-((4-(N-benzoyl)-amino) anilino)-6-methoxy-7-(2-bromoethoxy)quinazoline (1.15 g, 91% yield) as a white solid:

$^1$H-NMR (DMSO d$_6$): 10.24 (s, 1H), 9.47 (s, 1H), 8.43 (s, 1H), 8.00 (m, 2H), 7.85 (s, 1H), 7.76 (d, 2H, J=7 Hz), 7.72 (d, 2H, J=7 Hz), 7.55-7.64 (m, 3H), 7.18 (s, 1H), 4.20 (t, 2H, J=7 Hz), 3.99 (s, 3H), 3.14 (m, 2H), 3.00 (m, 2H), 2.67 (m, 2H), 1.81 (s, 3H):

MS (+ve ESI): 493 (M+H)+.

EXAMPLE 257

Preparation of Compound No. 257 in Table 10

An analogous reaction to that described in example 256, but starting with N-acetyl ethylene-diamine (102 mg, 1.00 mmol), yielded the title compound (69.4 mg, 58% yield) as a white solid:

$^1$H-NMR (DMSO d$_6$): 10.25 (s, 1H), 9.47 (s, 1H), 8.42 (s, 1H), 7.96 (m, 2H), 7.88 (s, 1H), 7.74 (m, 4H), 7.48-7.57 (m, 3H), 7.20 (s, 1H), 4.48 (t, 2H, J=7 Hz), 3.98 (s, 3H), 3.87 (t, 2H, J=7 Hz):

MS (+ve ESI): 515 (M+H)+.

EXAMPLE 258

Preparation of Compound No. 258 in Table 10

An analogous reaction to that described in example 256, but starting with N,N-diisopropyl-ethylenediamine (144 mg, 1.00 mmol), yielded the title compound (124.3 mg, 97% yield) as a white solid:

$^1$H-NMR (DMSO d$_6$) 10.18 (s, 1H), 9.37 (s, 1H), 8.35 (s, 1H), 7.90 (d, 2H, J=7 Hz), 7.80 (s, 1H), 7.73 (d, 2H, J=7 Hz), 7.68 (d, 2H, J=7 Hz), 7.45-7.55 (m, 3H), 7.10 (s, 1H), 4.12 (m, 2H), 3.88 (s, 3H), 2.82-2.95 (m, 6H), 2.44-2.61 (m, 2H), 0.88 (m, 2H):

MS (+ve ESI): 557 (M+H)+.

EXAMPLE 259

Preparation of Compound No. 259 in Table 10

An analogous reaction to that described in example 256, but starting with 2-(methylthio)-ethylamine (91 mg, 1.00 mmol), yielded the title compound (81 mg, 69% yield) as a white solid:

$^1$H-NMR (DMSO d$_6$): 10.26 (s, 1H), 9.49 (s, 1H), 8.45 (s, 1H), 8.00 (d, 2H, J=8 Hz), 7.89 (s, 1H), 7.82 (d, 2H, J=8 Hz), 7.78 (d, 2H, J=8 Hz), 7.45-7.55 (m, 3H), 7.21 (s, 1H), 4.24 (m, 2H), 3.99 (s, 3H), 3.09 (m, 2H), 2.92 (t, 2H, J=7 Hz), 2.65 (t, 2H, J=7 Hz), 2.10 (s, 3H):

MS (+ve ESI): 504 (M+H)+.

EXAMPLE 260

Preparation of Compound No. 260 in Table 10

An analogous reaction to that described in example 256, but starting with L-alaninamide hydrochloride (88 mg, 1.00 mmol), yielded the title compound (15.9 mg, 14% yield) as a white solid:

HPLC/LCMS (RT): 5.29 min:

MS (+ve ESI): 501 (M+H)+.

EXAMPLE 261

Preparation of Compound No. 261 in Table 10

An analogous reaction to that described in example 256, but starting with cyclopropyl-amine (57 mg, 1.00 mmol), yielded the title compound (32.3 mg, 29% yield) as an off-white solid:

$^1$H-NMR (DMSO d6): 10.05 (s, 1H), 9.24 (s, 1H), 8.21 (s, 1H), 7.75 (d, 2H, J=8 Hz), 7.62 (s, 1H), 7.58 (d, 2H, J=8 Hz), 7.53 (d, 2H, J=8 Hz), 7.30-7.39 (m, 3H), 6.97 (s, 1H), 3.98 (m, 2H), 3.75 (s, 3H), 2.86 (m, 2H), 2.02 (m, 1H), 0.20 (m, 2H), 0.07 (m, 2H):

MS (+ve ESI): 470 (M+H)+.

EXAMPLE 262

Preparation of Compound No. 262 in Table 10

An analogous reaction to that described in example 256, but starting with cyclopropane-methylamine (71 mg, 1.00 mmol), yielded the title compound (71.4 mg, 63% yield) as an off-white solid:

$^1$H-NMR (DMSO d$_6$): 10.09 (s, 1H), 9.30 (s, 1H), 8.25 (s, 1H), 7.79 (d, 2H, J=8 Hz), 7.69 (s, 1H), 7.60 (d, 2H, J=8 Hz), 7.55 (d, 2H, J=8 Hz), 7.32-7.41 (m, 3H), 7.04 (s, 1H), 4.08 (m, 2H), 3.80 (s, 3H), 2.92 (m, 2H), 2.40 (d, 2H, J=7 Hz), 0.78 (m, 1H), 0.29 (m, 2H), 0.02 (m, 2H):

MS (+ve ESI): 484 (M+H)+.

EXAMPLE 263

Preparation of Compound No. 263 in Table 10

An analogous reaction to that described in example 256, but starting with cyclobutylamine (71 mg, 1.00 mmol), yielded the title compound (59.1 mg, 52% yield) as an off-white solid:

$^1$H-NMR (DMSO d$_6$): 10.27 (s, 1H), 9.50 (s, 1H), 8.49 (s, 1H), 8.01 (d, 2H, J=8 Hz), 7.89 (s, 1H), 7.82 (d, 2H, J=8 Hz), 7.77 (d, 2H, J=8 Hz), 7.54-7.63 (m, 3H), 7.21 (s, 1H), 4.24 (m, 2H), 4.00 (s, 3H), 3.42 (m, 1H), 3.04 (m, 2H), 2.18 (m, 2H), 1.81 (m, 2H), 1.59-1.76 (m, 4H):

MS (+ve ESI): 484 (M+H)+.

EXAMPLE 264

Preparation of Compound No. 264 in Table 10

An analogous reaction to that described in example 256, but starting with cyclopentylamine (85 mg, 1.00 mmol), yielded the title compound (48.4 mg, 42% yield) as an off-white solid:

$^1$H-NMR (DMSO d$_6$): 10.28 (s, 1H), 9.50 (s, 1H), 8.46 (s, 1H), 7.96 (d, 2H, J=8 Hz), 7.89 (s, 1H), 7.82 (d, 2H, J=8 Hz), 7.77 (d, 2H, J=8 Hz), 7.52-7.63 (m, 3H), 7.23 (s, 1H), 4.25 (t, 2H, J=7 Hz), 3.98 (s, 3H), 3.25 (m, 1H), 3.09 (m, 2H), 1.83 (m, 2H), 1.69 (m, 2H), 1.54 (m, 2H), 1.40 (m, 2H):

MS (+ve ESI): 498 (M+H)+.

EXAMPLE 265

Preparation of Compound No. 265 in Table 10

An analogous reaction to that described in example 256, but starting with 1-(3-aminopropyl)-imidazole (125 mg, 1.00 mmol), yielded the title compound (96.4 mg, 78% yield) as an off-white solid:

$^1$H-NMR (DMSO d$_6$): 10.25 (s, 1H), 9.50 (s, 1H), 8.46 (s, 1H), 7.99 (d, 2H, J=8 Hz), 7.89 (s, 1H), 7.82 (d, 2H, J=8 Hz), 7.77 (d, 2H, J=8 Hz), 7.52-7.63 (m, 3H), 7.20 (s, 1H), 7.17 (d, 1H, J=7 Hz), 6.89 (s, 1H), 4.19 (t, 2H, J=7 Hz), 4.03 (m, 2H), 3.98 (s, 3H), 2.96 (m, 2H), 2.52 (m, 2H), 1.88 (m, 2H), 1.79 (m, 2H), 1.54 (m, 2H), 1.40 (m, 2H):

MS (+ve ESI): 538 (M+H)+.

EXAMPLE 266

Preparation of Compound No. 266 in Table 10

An analogous reaction to that described in example 256, but starting with cyclohexylamine (99 mg, 1.00 mmol), yielded the title compound (78.9 mg, 67% yield) as an off-white solid:

$^1$H-NMR (DMSO (6): 10.07 (s, 1H), 9.31 (s, 1H), 8.26 (s, 1H), 7.79 (d, 2H, J=8 Hz), 7.72 (s, 1H), 7.61 (d, 2H, J=8 Hz), 7.56 (d, 2H, J=8 Hz), 7.34-7.44 (m, 3H), 7.05 (s, 1H), 4.14 (m, 2H), 3.80 (s, 3H), 3.05 (m, 2H), 2.69 (m, 1H), 1.80 (m, 2H), 1.69 (m, 1H), 1.55 (m, 3H), 1.41 (m, 2H), 0.90-1.16 (m, 4H):

MS (+ve ESI): 512 (M+H)+.

EXAMPLE 267

Preparation of Compound No. 267 in Table 10

An analogous reaction to that described in example 256, but starting with 4-aminocyclo-hexanol (115 mg, 1.00 mmol), yielded the title compound (67.5 mg, 55% yield) as an off-white solid:
$^1$H-NMR (DMSO d$_6$): 10.26 (s, 1H), 9.47 (s, 1H), 8.44 (s, 1H), 7.98 (d, 2H, J=8 Hz), 7.86 (s, 1H), 7.83 (d, 2H, J=8 Hz), 7.79 (d, 2H, J=8 Hz), 7.54-7.63 (m, 3H), 7.20 (s, 1H), 4.19 (t, 2H, J=7 Hz), 3.99 (s, 3H), 3.37 (m, 1H), 3.01 (m, 2H), 2.57 (m, 1H), 1.80-1.94 (m, 2H), 1.41-1.66 (m, 4H), 1.19 (m, 1H), 1.06 (m, 1H):
MS (+ve ESI): 528 (M+H)+.

EXAMPLE 268

Preparation of Compound No. 268 in Table 1

An analogous reaction to that described in example 256, but starting with cyclohexane-methylamine (113 mg, 1.00 mmol), yielded the title compound (80.4 mg, 66% yield) as an off-white solid:
$^1$H-NMR (DMSO d$_6$): 10.07 (s, 1H), 9.30 (s, 1H), 8.26 (s, 1H), 7.81 (d, 2H, J=8 Hz), 7.69 (s, 1H), 7.64 (d, 2H, J=8 Hz), 7.59 (d, 2H, J=8 Hz), 7.33-7.43 (m, 3H), 7.00 (s, 1H), 4.02 (t, 2H, J=7 Hz), 3.79 (s, 3H), 2.80 (m, 2H), 2.29 (m, 2H), 1.40-1.60 (m, 5H), 1.24 (m, 1H), 1.01 (m, 3H), 0.72 (m, 2H):
MS (+ve ESI): 526 (M+H)+.

EXAMPLE 269

Preparation of Compound No. 269 in Table 1

An analogous reaction to that described in example 256, but starting with 2-amino-2-methyl-1,3-propanediol (105 mg, 1.00 mmol), yielded the title compound (54.9 mg, 46% yield) as an off-white solid:
$^1$H-NMR (DMSO d$_6$): 10.26 (s, 1H), 9.50 (s, 1H), 8.43 (s, 1H), 8.00 (d, 2H, J=8 Hz), 7.89 (s, 1H), 7.84 (d, 2H, J=8 Hz), 7.79 (d, 2H, J=8 Hz), 7.54-7.63 (m, 3H), 7.20 (s, 1H), 4.55 (m, 2H), 4.22 (m, 2H), 4.00 (s, 3H), 3.32 (m, 4H), 3.07 (m, 2H), 0.99 (s, 3H):
MS (+ve ESI): 518 (M+H)+.

EXAMPLE 270

Preparation of Compound No. 270 in Table 1

An analogous reaction to that described in example 256, but starting with tris-(hydroxy-methyl)methylamine (121 mg, 1.00 mmol), yielded the title compound (15.1 mg, 12% yield) as an off-white solid:
$^1$H-NMR (DMSO d$_6$): 10.05 (s, 1H), 9.29 (s, 1H), 8.23 (s, 1H), 7.79 (d, 2H, J=8 Hz), 7.69 (s, 1H), 7.57 (d, 2H, J=8 Hz), 7.52 (d, 2H, J=8 Hz), 7.34-7.40 (m, 3H), 7.00 (s, 1H), 4.10 (m, 2H), 3.78 (s, 3H), 3.30 (m, 6H):
MS (+ve ESI): 534 (M+H)+.

EXAMPLE 271

Preparation of Compound No. 271 in Table 10

An analogous reaction to that described in example 256, but starting with 2-amino-2-ethyl-1,3-propanediol (119 mg, 1.00 mmol), yielded the title compound (59.1 mg, 48% yield) as an off-white solid:
$^1$H-NMR (DMSO d$_6$): 10.27 (s, 1H), 9.49 (s, 1H), 8.45 (s, 1H), 8.00 (d, 2H, J=8 Hz), 7.89 (s, 1H), 7.83 (d, 2H, J=8 Hz), 7.78 (d, 2H, J=8 Hz), 7.55-7.64 (m, 3H), 7.20 (s, 1H), 5.10 (m, 1H), 4.33 (m, 2H), 4.19 (m, 2H), 3.96 (s, 3H), 3.30-3.45 (m, 4H), 2.95 (m, 2H), 1.52 (m, 1H), 1.36 (m, 1H), 0.83 (t, 3H, J=7 Hz):
MS (+ve ESI): 532 (M+H)+.

EXAMPLE 272

Preparation of Compound No. 272 in Table 10

An analogous reaction to that described in example 256, but starting with (S)-leucinol (117 mg, 1.00 mmol), yielded the title compound (109.9 mg, 90% yield) as an off-white solid:
$^1$H-NMR (DMSO d$_6$): 10.03 (s, 1H), 9.23 (s, 1H), 8.21 (s, 1H), 7.75 (d, 2H, J=8 Hz), 7.64 (s, 1H), 7.55 (d, 2H, J=8 Hz), 7.52 (d, 2H, J=8 Hz), 7.29-7.39 (m, 3H), 6.97 (s, 1H), 4.38 (m, 1H), 3.95 (t, 2H, J=7 Hz), 3.73 (s, 3H), 2.93 (m, 2H), 2.79 (m, 1H), 2.53 (m, 2H), 1.50 (m, 2H), 0.85-1.03 (m, 2H), 0.65 (d, 6H, J=7 Hz):
MS (+ve ESI): 530 (M+H)+.

EXAMPLE 273

Preparation of Compound No. 273 in Table 10

An analogous reaction to that described in example 256, but starting with 2-(aminomethyl)-1-ethylpyrrolidine (128 mg, 1.00 mmol), yielded the title compound (113.1 mg, 91% yield) as an off-white solid:
$^1$H-NMR (DMSO d$_6$): 10.27 (s, 1H), 9.49 (s, 1H), 8.44 (s, 1H), 7.98 (d, 2H, J=8 Hz), 7.88 (s, 1H), 7.81 (d, 2H, J=8 Hz), 7.76 (d, 2H, J=8 Hz), 7.52-7.63 (m, 3H), 7.21 (s, 1H), 4.20 (m, 2H), 3.99 (s, 3H), 3.05 (m, 2H), 2.79 (m, 2H), 2.40-2.65 (m, 2H), 2.05-2.22 (m, 2H), 1.82 (m, 3H), 1.55-1.68 (m, 2H), 1.01 (t, 3H, J=7 Hz):
MS (+ve ESI): 541 (M+H)+.

EXAMPLE 274

Preparation of Compound No. 274 in Table 1

An analogous reaction to that described in example 256, but starting with 1-(3-aminopropyl)-2-pyrrolidinone (142 mg, 1.00 mmol), yielded the title compound (127.2 mg, 100% yield) as an off-white solid:
$^1$H-NMR (DMSO d$_6$): 10.27 (s, 1H), 9.48 (s, 1H), 8.45 (s, 1H), 7.99 (d, 2H, J=8 Hz), 7.89 (s, 1H), 7.81 (d, 2H, J=8 Hz), 7.76 (d, 2H, J=8 Hz), 7.54-7.63 (m, 3H), 7.20 (s, 1H), 6.61 (m, 1H), 4.22 (t, 2H, J=7 Hz), 3.99 (s, 3H), 3.22 (t, 2H, J=7 Hz), 2.97 (m, 2H), 2.93 (m, 2H), 2.20 (m, 2H), 1.92 (m, 2H), 1.60 (m, 2H):
MS (+ve ESI): 555 (M+H)+.

EXAMPLE 275

Preparation of Compound No. 275 in Table 1

An analogous reaction to that described in example 256, but starting with tetrahydrofurfuryl-amine (101 mg, 1.00 mmol), yielded the title compound (87.4 mg, 74% yield) as an off-white solid:
$^1$H-NMR (DMSO d$_6$): 10.29 (s, 1H), 9.51 (s, 1H), 8.47 (s, 1H), 8.00 (d, 2H, J=8 Hz), 7.89 (s, 1H), 7.83 (d, 2H, J=8 Hz), 7.78 (d, 2H, J=8 Hz), 7.55-7.64 (m, 3H), 7.21 (s, 1H), 4.22 (t, 2H, J=7 Hz), 4.00 (s, 3H), 3.95 (m, 1H), 3.80 (m, 1H), 3.65 (m, 1H), 3.04 (m, 2H), 2.71 (m, 2H), 1.80-2.01 (m, 2H), 1.57 (m, 2H):

MS (+ve ESI): 514 (M+H)+.

EXAMPLE 276

Preparation of Compound No. 276 in Table 10

An analogous reaction to that described in example 256, but starting with isonipecotamide (128 mg, 1.00 mmol), yielded the title compound (76.4 mg, 61% yield) as an off-white solid:

$^1$H-NMR (DMSO d$_6$): 10.25 (s, 1H), 9.45 (s, 1H), 8.44 (s, 1H), 7.98 (d, 2H, J=8 Hz), 7.86 (s, 1H), 7.81 (d, 2H, J=8 Hz), 7.76 (d, 2H, J=8 Hz), 7.52-7.63 (m, 3H), 7.21 (s, 1H), 7.19 (s, 1H), 6.71 (s, 1H), 4.26 (t, 2H, J=7 Hz), 3.98 (s, 3H), 3.00 (m, 2H), 2.74 (m, 2H), 2.06 (m, 3H), 1.70 (m, 2H), 1.59 (m, 2H):

MS (+ve ESI): 541 (M+H)+.

EXAMPLE 277

Preparation of Compound No. 277 in Table 10

An analogous reaction to that described in example 256, but starting with 4-(2-aminoethyl)-morpholine (130 mg, 1.00 mmol), yielded the title compound (120.7 mg, 97% yield) as an off-white solid:

$^1$H-NMR (DMSO d$_6$): 10.25 (s, 1H), 9.47 (s, 1H), 8.42 (s, 1H), 7.97 (d, 2H, J=8 Hz), 7.85 (s, 1H), 7.81 (d, 2H, J=8 Hz), 7.76 (d, 2H, J=8 Hz), 7.52-7.63 (m, 3H), 7.20 (s, 1H), 6.50 (m, 1H), 4.21 (t, 2H, J=7 Hz), 3.96 (s, 3H), 3.55 (m, 4H), 2.95 (m, 2H), 2.70 (m, 4H), 2.36 (m, 4H):

MS (+ve ESI): 543 (M+H)+.

EXAMPLE 278

Preparation of Compound No. 278 in Table 10

An analogous reaction to that described in example 256, but starting with 4-(3-aminopropyl)-morpholine (144 mg, 1.00 mmol), yielded the title compound (88.6 mg, 70% yield) as an off-white solid:

$^1$H-NMR (DMSO d$_6$): 10.22 (s, 1H), 9.43 (s, 1H), 8.42 (s, 1H), 7.97 (d, 2H, J=8 Hz), 7.85 (s, 1H), 7.79 (d, 2H, J=8 Hz), 7.73 (d, 2H, J=8 Hz), 7.52-7.62 (m, 3H), 7.16 (s, 1H), 4.21 (t, 2H, J=7 Hz), 3.95 (s, 3H), 3.54 (m, 4H), 3.02 (m, 2H), 2.73 (m, 2H), 2.28 (m, 6H), 1.60 (m, 2H):

MS (+ve ESI): 557 (M+H)+.

EXAMPLE 279

Preparation of Compound No. 279 in Table 10

An analogous reaction to that described in example 256, but starting with 2-piperidino-ethylamine (128 mg, 1.00 mmol), yielded the title compound (112.4 mg, 90% yield) as an off-white solid:

$^1$H-NMR (DMSO d$_6$): 10.21 (s, 1H), 9.43 (s, 1H), 8.41 (s, 1H), 7.98 (d, 2H, J=8 Hz), 7.86 (s, 1H), 7.78 (d, 2H, J=8 Hz), 7.73 (d, 2H, J=8 Hz), 7.52-7.62 (m, 3H), 7.16 (s, 1H), 4.20 (t, 2H, J=7 Hz), 3.96 (s, 3H), 2.96 (m, 2H), 2.67 (m, 4H), 2.28-2.39 (m, 4H), 1.50 (m, 4H), 1.40 (m, 2H):

MS (+ve ESI): 541 (M+H)+.

EXAMPLE 280

Preparation of Compound No. 280 in Table 10

An analogous reaction to that described in example 256, but starting with 1-(2-aminoethyl)-pyrrolidine (114 mg, 1.00 mmol), yielded the title compound (56.6 mg, 47% yield) as an off-white solid:

$^1$H-NMR (DMSO d$_6$): 10.21 (s, 1H), 9.45 (s, 1H), 8.43 (s, 1H), 7.98 (d, 2H, J=8 Hz), 7.86 (s, 1H), 7.79 (d, 2H, J=8 Hz), 7.73 (d, 2H, J=8 Hz), 7.52-7.62 (m, 3H), 7.18 (s, 1H), 4.19 (t, 2H, J=7 Hz), 3.94 (s, 3H), 3.00 (m, 2H), 2.73 (m, 2H), 2.42-2.59 (m, 2H), 1.67 (m, 4H):

MS (+ve ESI): 527 (M+H)+.

EXAMPLE 281

Preparation of Compound No. 281 in Table 10

An analogous reaction to that described in example 256, but starting with 2-amino-2-methyl-3-hexanol (131 mg, 1.00 mmol), yielded the title compound (123.8 mg, 99% yield) as an off-white solid:

$^1$H-NMR (DMSO d$_6$): 10.01 (s, 1H), 9.20 (s, 1H), 8.19 (s, 1H), 7.73 (d, 2H, J=8 Hz), 7.62 (s, 1H), 7.57 (d, 2H, J=8 Hz), 7.51 (d, 2H, J=8 Hz), 7.28-7.38 (m, 3H), 6.96 (s, 1H), 4.40 (m, 1H), 3.93 (t, 2H, J=7 Hz), 3.74 (s, 3H), 3.04 (m, 2H), 2.70 (m, 2H), 0.90-1.35 (m, 4H), 0.80 (s, 6H), 0.65 (t, 3H, J=7 Hz):

MS (+ve ESI): 544 (M+H)+.

EXAMPLE 282

Preparation of Compound No. 282 in Table 10

An analogous reaction to that described in example 256, but starting with 2-amino-2-methyl-1-propanol (89 mg, 1.00 mmol), yielded the title compound (62.6 mg, 54% yield) as an off-white solid:

$^1$H-NMR (DMSO d$_6$): 10.05 (s, 1H), 9.25 (s, 1H), 8.23 (s, 1H), 7.78 (d, 2H, J=8 Hz), 7.67 (s, 1H), 7.59 (d, 2H, J=8 Hz), 7.53 (d, 2H, J=8 Hz), 7.32-7.43 (m, 3H), 6.98 (s, 1H), 4.40 (m, 1H), 3.98 (t, 2H, J=7 Hz), 3.78 (s, 3H), 3.04 (m, 2H), 2.75 (m, 2H), 0.82 (s, 6H):

MS (+ve ESI): 502 (M+H)+.

EXAMPLE 283

Preparation of Compound No. 283 in Table 10

An analogous reaction to that described in example 256, but starting with 3-amino-3-methyl-1-butanol (103 mg, 1.00 mmol), yielded the title compound (51.8 mg, 43% yield) as an off-white solid:

$^1$H-NMR (DMSO d$_6$): 10.12 (s, 1H), 9.34 (s, 1H), 8.33 (s, 1H), 7.88 (d, 2H, J=8 Hz), 7.76 (s, 1H), 7.68 (d, 2H, J=8 Hz), 7.63 (d, 2H, J=8 Hz), 7.42-7.52 (m, 3H), 7.08 (s, 1H), 4.10 (t, 2H, J=7 Hz), 3.85 (s, 3H), 3.46 (t, 2H, J=7 Hz), 2.92 (m, 2H), 1.50 (t, 2H, J=7 Hz), 1.00 (s, 6H):

MS (+ve ESI): 516 (M+H)+.

EXAMPLE 284

Preparation of Compound No. 284 in Table 10

An analogous reaction to that described in example 256, but starting with isopropylamine (59 mg, 1.00 mmol), yielded the title compound (54.8 mg, 50% yield) as an off-white solid:

¹H-NMR (DMSO d₆): 10.24 (s, 1H), 9.46 (s, 1H), 8.43 (s, 1H), 7.98 (d, 2H, J=8 Hz), 7.86 (s, 1H), 7.78 (d, 2H, J=8 Hz), 7.73 (d, 2H, J=8 Hz), 7.52-7.62 (m, 3H), 7.19 (s, 1H), 4.20 (t, 2H, J=7 Hz), 3.96 (s, 3H), 2.99 (m, 1H), 1.03 (d, 6H, J=7 Hz):
MS (+ve ESI): 472 (M+H)+.

EXAMPLE 285

Preparation of Compound No. 285 in Table 10

An analogous reaction to that described in example 256, but starting with 2-amino-1-propanol (75 mg, 1.00 mmol), yielded the title compound (43.9 mg, 39% yield) as an off-white solid:
¹H-NMR (DMSO d₆): 10.27 (s, 1H), 9.48 (s, 1H), 8.45 (s, 1H), 7.98 (d, 2H, J=8 Hz), 7.86 (s, 1H), 7.82 (d, 2H, J=8 Hz), 7.77 (d, 2H, J=8 Hz), 7.62-7.72 (m, 3H), 7.20 (s, 1H), 4.58 (m, 1H), 4.37 (t, 2H, J=7 Hz), 4.21 (m, 2H), 3.96 (s, 3H), 3.25-3.37 (m, 2H), 2.95-3.06 (m, 2H), 2.73 (m, 1H), 0.95 (d, 3H, J=7 Hz):
MS (+ve ESI): 488 (M+H)+.

EXAMPLE 286

Preparation of Compound No. 286 in Table 10

An analogous reaction to that described in example 256, but starting with D-2-amino-1-butanol (89 mg, 1.00 mmol), yielded the title compound (77.2 mg, 66% yield) as an off-white solid:
HPLC/LCMS (RT): 1.41 min:
MS (+ve ESI): 502 (M+H)+.

EXAMPLE 287

Preparation of Compound No. 287 in Table 10

An analogous reaction to that described in example 256, but starting with 3-amino-1,2-propanediol (91 mg, 1.00 mmol), yielded the title compound (48.3 mg, 41% yield) as an off-white solid:
HPLC/LCMS (RT): 5.16 min:
MS (+ve ESI): 504 (M+H)+.

EXAMPLE 288

Preparation of Compound No. 288 in Table 10

An analogous reaction to that described in example 256, but starting with N,N-dimethyl-ethylenediamine (88 mg, 1.00 mmol), yielded the title compound (55.8 mg, 48% yield) as an off-white solid:
¹H-NMR (DMSO d₆): 10.08 (s, 1H), 9.30 (s, 1H), 8.28 (s, 1H), 7.82 (d, 2H, J=7 Hz), 7.71 (s, 1H), 7.65 (d, 2H, J=7 Hz), 7.60 (d, 2H, J=7 Hz), 7.35-7.45 (m, 3H), 7.03 (s, 1H), 4.06 (m, 2H), 3.81 (s, 3H), 2.84 (m, 2H), 2.58 (m, 2H), 2.25 (m, 2H), 2.01 (s, 6H):
MS (+ve ESI): 502 (M+H)+.

EXAMPLE 289

Preparation of Compound No. 289 in Table 10

An analogous reaction to that described in example 256, but starting with N,N-diethyl-ethylenediamine (116 mg, 1.00 mmol), yielded the title compound (86.5 mg, 71% yield) as an off-white solid:
¹H-NMR (DMSO d₆): 10.20 (s, 1H), 9.40 (s, 1H), 8.38 (s, 1H), 7.93 (d, 2H, J=7 Hz), 7.81 (s, 1H), 7.74 (d, 2H, J=7 Hz), 7.69 (d, 2H, J=7 Hz), 7.45-7.54 (m, 3H), 7.12 (s, 1H), 4.13 (m, 2H), 3.90 (s, 3H), 2.92 (t, 2H, J=7 Hz), 2.60 (t, 2H, J=7 Hz), 2.42 (m, 2H), 0.88 (t, 6H, J=7 Hz):
MS (+ve ESI): 529 (M+H)⁺.

EXAMPLE 290

Preparation of Compound No. 290 in Table 10

An analogous reaction to that described in example 256, but starting with 2-methoxyethyl-amine (75 mg, 1.00 mmol), yielded the title compound (70.7 mg, 62% yield) as an off-white solid:
¹H-NMR (DMSO d₆): 10.21 (s, 1H), 9.44 (s, 1H), 8.39 (s, 1H), 7.94 (d, 2H, J=7 Hz), 7.84 (s, 1H), 7.77 (d, 2H, J=7 Hz), 7.72 (d, 2H, J=7 Hz), 7.47-7.56 (m, 3H), 7.18 (s, 1H), 4.21 (m, 2H), 3.95 (s, 3H), 3.45 (m, 2H), 3.23 (s, 3H), 3.08 (m, 2H), 2.85 (m, 2H):
MS (+ve ESI): 488 (M+H)+.

EXAMPLE 291

Preparation of Compound No. 291 in Table 10

An analogous reaction to that described in example 256, but starting with 2-(2-amino-ethoxy)ethanol (105 mg, 1.00 mmol), yielded the title compound (70.3 mg, 59% yield) as an off-white solid:
¹H-NMR (DMSO d₆): 10.28 (s, 1H), 9.50 (s, 1H), 8.46 (s, 1H), 8.00 (d, 2H, J=7 Hz), 7.89 (s, 1H), 7.82 (d, 2H, J=7 Hz), 7.76 (d, 2H, J=7 Hz), 7.54-7.63 (m, 3H), 7.23 (s, 1H), 4.60 (s, 1H), 4.24 (m, 2H), 4.00 (s, 3H), 3.54 (m, 4H), 3.46 (m, 2H), 3.06 (m, 2H), 2.83 (m, 2H):
MS (+ve ESI): 518 (M+H)⁺.

EXAMPLE 292

Preparation of Compound No. 292 in Table 10

An analogous reaction to that described in example 256, but starting with ethanolamine (61 mg, 1.00 mmol), yielded the title compound (51.3 mg, 46% yield) as an off-white solid:
HPLC/LCMS (RT): 1.48 min:
MS (+ve ESI): 474 (M+H)+.

EXAMPLE 293

Preparation of Compound No. 293 in Table 10

An analogous reaction to that described in example 256, but starting with 2-mercapto-ethylamine hydrochloride (77 mg, 1.00 mmol), yielded the title compound (72.7 mg, 64% yield) as an off-white solid:
¹H-NMR (DMSO d₆): 10.03 (s, 1H), 9.26 (s, 1H), 8.21 (s, 1H), 7.76 (d, 2H, J=7 Hz), 7.64 (s, 1H), 7.58 (d, 2H, J=7 Hz), 7.53 (d, 2H, J=7 Hz), 7.30-7.39 (m, 3H), 7.00 (s, 1H), 4.10 (m, 2H), 3.76 (s, 3H), 2.77 (m, 2H), 2.55 (m, 2H), 2.50 (m, 2H):
MS (+ve ESI): 490 (M+H)+.

EXAMPLE 294

Preparation of Compound No. 294 in Table 10

An analogous reaction to that described in example 256, but starting with 2-(ethylthio)ethyl-amine (105 mg, 1.00 mmol), yielded the title compound (85.9 mg, 72% yield) as an off-white solid:

¹H-NMR (DMSO d₆): 10.03 (s, 1H), 9.24 (s, 1H), 8.21 (s, 1H), 7.76 (d, 2H, J=7 Hz), 7.64 (s, 1H), 7.58 (d, 2H, J=7 Hz), 7.53 (d, 2H, J=7 Hz), 7.30-7.39 (m, 3H), 7.00 (s, 1H), 4.00 (m, 2H), 3.75 (s, 3H), 2.80 (m, 2H), 2.61 (m, 2H), 2.44 (m, 2H), 2.27 (m, 2H), 0.97 (t, 3H, J=7 Hz):
MS (+ve ESI): 518 (M+H)+.

EXAMPLE 295

Preparation of Compound No. 295 in Table 10

An analogous reaction to that described in example 256, but starting with 3-ethoxypropyl-amine (103 mg, 1.00 mmol), yielded the title compound (67.1 mg, 56% yield) as an off-white solid:
¹H-NMR (DMSO d₆): 10.43 (s, 1H), 9.68 (s, 1H), 8.62 (s, 1H), 8.16 (d, 2H, J=7 Hz), 8.05 (s, 1H), 7.99 (d, 2H, J=7 Hz), 7.94 (d, 2H, J=7 Hz), 7.69-7.78 (m, 3H), 7.39 (s, 1H), 4.40 (m, 2H), 4.17 (s, 3H), 3.60 (m, 4H), 3.22 (m, 2H), 2.94 (s, 3H), 1.90 (m, 2H) 1.27 (t, 3H, J=7 Hz):
MS (+ve ESI): 516 (M+H)+.

EXAMPLE 296

Preparation of Compound No. 296 in Table 10

An analogous reaction to that described in example 256, but starting with 3-butoxypropyl-amine (131 mg, 1.00 mmol), yielded the title compound (51.9 mg, 42% yield) as an off-white solid:
¹H-NMR (DMSO d₆): 10.06 (s, 1H), 9.29 (s, 1H), 8.23 (s, 1H), 7.79 (d, 2H, J=7 Hz), 7.69 (s, 1H), 7.61 (d, 2H, J=7 Hz), 7.56 (d, 2H, J=7 Hz), 7.35-7.43 (m, 3H), 7.00 (s, 1H), 4.01 (m, 2H), 3.79 (s, 3H), 3.24 (t, 2H, J=7 Hz), 3.14 (m, 2H), 2.79 (m, 2H), 2.50 (m, 2H), 1.50 (m, 2H), 1.26 (m, 2H), 1.10 (m, 2H), 0.99 (t, 3H, J=7 Hz):
MS (+ve ESI): 544 (M+H)+.

EXAMPLE 297

Preparation of Compound No. 297 in Table 10

An analogous reaction to that described in example 256, but starting with 3-amino-1-propanol (75 mg, 1.00 mmol), yielded the title compound (58.1 mg, 51% yield) as an off-white solid:
¹H-NMR (DMSO d₆): 10.20 (s, 1H), 9.41 (s, 1H), 8.39 (s, 1H), 7.92 (d, 2H, J=7 Hz), 7.81 (s, 1H), 7.76 (d, 2H, J=7 Hz), 7.70 (d, 2H, J=7 Hz), 7.48-7.57 (m, 3H), 7.16 (s, 1H), 4.17 (m, 2H), 3.91 (s, 3H), 3.41 (t, 2H, J=7 Hz), 2.95 (m, 2H), 2.69 (m, 2H), 1.56 (m, 2H):
MS (+ve ESI): 488 (M+H)+.

EXAMPLE 298

Preparation of Compound No. 298 in Table 10

An analogous reaction to that described in example 256, but starting with 5-amino-1-pentanol (103 mg, 1.00 mmol), yielded the title compound (66 mg, 55% yield) as an off-white solid:
¹H-NMR (DMSO d₆): 10.28 (s, 1H), 9.48 (s, 1H), 8.43 (s, 1H), 7.99 (d, 2H, J=7 Hz), 7.86 (s, 1H), 7.80 (d, 2H, J=7 Hz), 7.75 (d, 2H, J=7 Hz), 7.52-7.60 (m, 3H), 7.19 (s, 1H), 4.20 (m, 2H), 3.99 (s, 3H), 3.40 (t, 2H, J=7 Hz), 3.00 (m, 2H), 2.65 (m, 2H), 1.47 (m, 4H), 1.33 (m, 2H):
MS (+ve ESI): 516 (M+H)+.

EXAMPLE 299

Preparation of Compound No. 299 in Table 10

An analogous reaction to that described in example 256, but starting with 2-amino-1-methoxypropane (89 mg, 1.00 mmol), yielded the title compound (30.8 mg, 26% yield) as an off-white solid:
¹H-NMR (DMSO d₆): 10.20 (s, 1H), 9.43 (s, 1H), 8.38 (s, 1H), 7.92 (d, 2H, J=7 Hz), 7.83 (s, 1H), 7.75 (d, 2H, J=7 Hz), 7.70 (d, 2H, J=7 Hz), 7.46-7.56 (m, 3H), 7.19 (s, 1H), 4.21 (m, 2H), 3.93 (s, 3H), 3.20-3.35 (m, 5H), 3.07 (m, 2H), 1.00 (d, 3H, J=7 Hz):
MS (+ve ESI): 502 (M+H)+.

EXAMPLE 300

Preparation of Compound No. 300 in Table 10

An analogous reaction to that described in example 256, but starting with 4-amino-1-butanol (89 mg, 1.00 mmol), yielded the title compound (58.4 mg, 50% yield) as an off-white solid:
¹H-NMR (DMSO d₆): 10.47 (s, 1H), 9.69 (s, 1H), 8.65 (s, 1H), 8.20 (d, 2H, J=7 Hz), 8.08 (s, 1H), 8.01 (d, 2H, J=7 Hz), 7.97 (d, 2H, J=7 Hz), 7.73-7.82 (m, 3H), 7.40 (s, 1H), 4.39 (m, 2H), 4.20 (s, 3H), 3.62 (m, 2H), 3.20 (m, 2H), 2.85 (m, 2H), 1.69 (m, 4H):
MS (+ve ESI): 502 (M+H)+.

EXAMPLE 301

Preparation of Compound No. 301 in Table 10

An analogous reaction to that described in example 256, but starting with 3-amino-5-methyl-pyrazole (97 mg, 1.00 mmol), yielded the title compound (40.6 mg, 34% yield) as an off-white solid:
HPLC/LCMS (RT): 5.63 min:
MS (+ve ESI): 510 (M+H)+.

EXAMPLE 302

Preparation of Compound No. 302 in Table 10

An analogous reaction to that described in example 256, but starting with 1-(3-aminopropyl)-4-methylpiperazine (157 mg, 1.00 mmol), yielded the title compound (58.6 mg, 45% yield) as an off-white solid:
¹H-NMR (DMSO d₆): 10.43 (s, 1H), 9.70 (s, 1H), 8.64 (s, 1H), 8.20 (d, 2H, J=7 Hz), 8.10 (s, 1H), 8.03 (d, 2H, J=7 Hz), 7.98 (d, 2H, J=7 Hz), 7.77-7.86 (m, 3H), 7.42 (s, 1H), 4.43 (m, 2H), 4.21 (s, 3H), 3.20 (m, 2H), 2.88 (m, 2H), 2.45-2.63 (m, 10H), 2.34 (s, 3H), 1.80 (m, 2H):
MS (+ve ESI): 570 (M+H)+.

EXAMPLE 303

Preparation of Compound No. 303 in Table 10

An analogous reaction to that described in example 256, but starting with ethyl-4-amino-1-piperidinecarboxylate (172 mg, 1.00 mmol), yielded the title compound (191.8 mg, 144% yield) as an off-white solid:

¹H-NMR (DMSO d₆): 9.65 (s, 1H), 8.59 (s, 1H), 8.14 (d, 2H, J=7 Hz), 8.02 (s, 1H), 7.96 (d, 2H, J=7 Hz), 7.91 (d, 2H, J=7 Hz), 7.67-7.76 (m, 3H), 7.35 (s, 1H), 4.34 (m, 2H), 4.19 (s, 3H), 4.14 (q, 2H, J=7 Hz), 4.05 (m, 2H), 3.17 (m, 2H), 2.95-3.10 (m, 3H), 1.99 (m, 2H), 1.85 (m, 2H), 1.32 (t, 3H, J=7 Hz):
MS (+ve ESI): 585 (M+H)+.

EXAMPLE 304

Preparation of Compound No. 304 in Table 10

An analogous reaction to that described in example 256, but starting with 2-dibutylamino-ethylamine (172 mg, 1.00 mmol), yielded the title compound (123.6 mg, 93% yield) as an off-white solid:
HPLC/LCMS (RT): 1.40 min:
MS (+ve ESI): 586 (M+H)+.

EXAMPLE 305

Preparation of Compound No. 305 in Table 10

An analogous reaction to that described in example 256, but starting with 2-di-n-propylaminoethylamine (144 mg, 1.00 mmol), yielded the title compound (123.4 mg, 97% yield) as an off-white solid:
¹H-NMR (DMSO d₆): 10.20 (s, 1H), 9.41 (s, 1H), 8.38 (s, 1H), 7.94 (d, 2H, J=7 Hz), 7.80 (s, 1H), 7.75 (d, 2H, J=7 Hz), 7.70 (d, 2H, J=7 Hz), 7.47-7.55 (m, 3H), 7.13 (s, 1H), 4.15 (m, 2H), 3.90 (s, 3H), 2.91 (m, 2H), 2.59 (m, 2H), 2.40 (m, 2H), 2.30 (m, 4H), 1.31 (m, 4H), 0.76 (t, 3H, J=7 Hz):
MS (+ve ESI): 557 (M+H)⁺.

EXAMPLE 306

Preparation of Compound No. 306 in Table 10

An analogous reaction to that described in example 256, but starting with 1-aminomethyl-1-cyclohexanol hydrochloride (129 mg, 1.00 mmol), yielded the title compound (80 mg, 64% yield) as an off-white solid:
HPLC/LCMS (RT): 1.61 min:
MS (+ve ESI): 542 (M+H)+.

EXAMPLE 307

Preparation of Compound No. 307 in Table 10

An analogous reaction to that described in example 256, but starting with 2-thiophene ethylamine (127 mg, 1.00 mmol), yielded the title compound (107.9 mg, 87% yield) as an off-white solid:
¹H-NMR (DMSO d₆): 10.28 (s, 1H), 9.46 (s, 1H), 8.47 (s, 1H), 8.01 (d, 2H, J=7 Hz), 7.89 (s, 1H), 7.81 (d, 2H, J=8 Hz), 7.77 (d, 2H, J=8 Hz), 7.53-7.63 (m, 3H), 7.34 (d, 1H, J=5 Hz), 7.21 (s, 1H), 6.92-7.00 (m, 2H), 4.20 (t, 2H, J=7 Hz), 2.89-3.00 (m, 6H):
MS (+ve ESI): 540 (M+H)+.

EXAMPLE 308

Preparation of Compound No. 308 in Table 10

An analogous reaction to that described in example 256, but starting with 2-amino-1-hexanol (117 mg, 1.00 mmol), yielded the title compound (115.2 mg, 94% yield) as an off-white solid:
¹H-NMR (DMSO d₆): 10.30 (s, 1H), 9.49 (s, 1H), 8.45 (s, 1H), 7.99 (d, 2H, J=7 Hz), 7.88 (s, 1H), 7.80 (d, 2H, J=8 Hz), 7.77 (d, 2H, J=8 Hz), 7.50-7.60 (m, 3H), 7.20 (s, 1H), 4.52 (m, 1H), 4.19 (t, 2H, J=7 Hz), 3.97 (s, 3H), 3.13 (m, 2H), 2.64 (m, 3H), 1.10-1.46 (m, 6H), 0.90 (t, 3H, J=7 Hz):
MS (+ve ESI): 530 (M+H)+.

EXAMPLE 309

Preparation of Compound No. 309 in Table 10

An analogous reaction to that described in example 256, but starting with 1-methioninol (135 mg, 1.00 mmol), yielded the title compound (111.7 mg, 89% yield) as an off-white solid:
HPLC/LCMS (RT): 1.53 min:
MS (+ve ESI): 548 (M+H)+.

EXAMPLE 310

Preparation of Compound No. 310 in Table 10

An analogous reaction to that described in example 256, but starting with 2-(2-aminoethyl)-1-methylpyrrolidine (128 mg, 1.00 mmol), yielded the title compound (65.2 mg, 52% yield) as an off-white solid:
HPLC/LCMS (RT): 5.04 min:
MS (+ve ESI): 541 (M+H)+.

EXAMPLE 311

Preparation of Compound No. 311 in Table 10

An analogous reaction to that described in example 256, but starting with 5-methyl-2-furanmethanamine (111 mg, 1.00 mmol), yielded the title compound (61.1 mg, 51% yield) as an off-white solid:
¹H-NMR (DMSO d₆): 10.16 (s, 1H), 9.39 (s, 1H), 8.35 (s, 1H), 7.87 (d, 2H, J=7 Hz), 7.79 (s, 1H), 7.71 (d, 2H, J=8 Hz), 7.66 (d, 2H, J=8 Hz), 7.42-7.52 (m, 3H), 7.10 (s, 1H), 6.29 (d, 1H, J=2 Hz), 5.99 (d, 1H, J=2 Hz), 4.10 (t, 2H, J=7 Hz), 3.90 (s, 3H), 3.71 (s, 2H), 2.96 (t, 2H, J=7 Hz), 2.19 (s, 3H):
MS (+ve ESI): 524 (M+H)+.

EXAMPLE 312

Preparation of Compound No. 312 in Table 10

An analogous reaction to that described in example 256, but starting with tetrahydro-3-thiophenamine 1,1-dioxide (135 mg, 1.00 mmol), yielded the title compound (53.7 mg, 43% yield) as an off-white solid:
HPLC/LCMS (RT): 1.45 min:
MS (+ve ESI): 548 (M+H)+.

EXAMPLE 313

Preparation of Compound No. 313 in Table 10

An analogous reaction to that described in example 256, but starting with 3-amino-2,2-dimethyl-1-propanol (103 mg, 1.00 mmol), yielded the title compound (69.2 mg, 58% yield) as an off-white solid:
¹H-NMR (DMSO d₆): 10.10 (s, 1H), 9.30 (s, 1H), 8.29 (s, 1H), 7.82 (d, 2H, J=7 Hz), 7.71 (s, 1H), 7.66 (d, 2H, J=8 Hz), 7.62 (d, 2H, J=8 Hz), 7.39-7.48 (m, 3H), 7.04 (s, 1H), 4.05 (t, 2H, J=7 Hz), 3.82 (s, 3H), 3.07 (d, 2H, J=7 Hz), 2.80 (t, 2H, J=7 Hz), 0.70 (s, 3H), 0.69 (s, 3H):
MS (+ve ESI): 516 (M+H)+.

EXAMPLE 314

Preparation of Compound No. 314 in Table 10

An analogous reaction to that described in example 256, but starting with 3-(aminomethyl)-thiophene dihydrochloride (113 mg, 1.00 mmol), yielded the title compound (122.5 mg, 100% yield) as an off-white solid:
HPLC/LCMS (RT): 1.56 min:
MS (+ve ESI): 526 (M+H)+.

EXAMPLE 315

Preparation of Compound No. 315 in Table 10

An analogous reaction to that described in example 256, but starting with thiomorpholine (0.10 ml, 1.0 mmol), yielded the title compound (21 mg, 20% yield) as a white solid:
$^1$H-NMR (DMSO d$_6$): 10.27 (s, 1H), 9.80 (bs, 1H), 8.52 (s, 1H), 7.96 (d, 2H), 7.94 (s, 1H), 7.81 (d, 2H), 7.71 (d, 2H), 7.49-7.63 (m, 3H), 7.28 (s, 1H), 4.48 (m, 2H), 3.98 (s, 3H), 3.10-3.55 (m, 6H), 2.78-2.95 (m, 4H):
MS (+ve ESI): 515.7 (M+H)+.

EXAMPLE 316

Preparation of Compound No. 316 in Table 10

An analogous reaction to that described in example 256, but starting with N-(2-hydroxyethyl)-1-(2-aminoethyl)morpholine (50 mg, 0.26 mmol), yielded the title compound (59 mg, 49% yield) as a white solid.
$^1$H-NMR (DMSO d$_6$): 10.09 (s, 1H), 9.30 (s, 1H), 8.29 (s, 1H), 7.81 (d, 2H, J=7 Hz), 7.70 (s, 1H), 7.67 (d, 2H, J=8 Hz), 7.62 (d, 2H, J=8 Hz), 7.38-7.47 (m, 3H), 7.04 (s, 1H), 4.29 (m, 1H), 4.03 (t, 2H, J=7 Hz), 3.81 (s, 3H), 3.35-3.42 (m, 4H), 3.31 (m, 2H), 2.82 (t, 2H, J=7 Hz), 2.59 (t, 4H, J=7 Hz), 2.53 (m, 2H), 2.13-2.30 (m, 6H):
MS (-ve ESI): 585 (M-H)-.

EXAMPLE 317

Preparation of Compound No. 317 in Table 10

An analogous reaction to that described in example 256, but starting with diethanolamine (0.097 ml, 1.00 mmol), yielded the title compound (49 mg, 47% yield) as a white solid:
$^1$H-NMR (DMSO d$_6$): 10.31 (s, 1H), 9.53 (s, 1H), 8.51 (s, 1H), 8.06 (d, 2H, J=7 Hz), 7.93 (s, 1H), 7.86 (d, 2H, J=8 Hz), 7.81 (d, 2H, J=8 Hz), 7.60-7.70 (m, 3H), 7.26 (s, 1H), 4.37 (t, 2H, J=7 Hz), 4.25 (t, 2H, J=7 Hz), 4.03 (s, 3H), 3.52 (m, 4H), 3.08 (t, 2H, J=7 Hz), 2.79 (t, 4H, J=7 Hz):
MS (+ve ESI): 517.9 (M+H)+.

EXAMPLE 318

Preparation of Compound No. 318 in Table 10

An analogous reaction to that described in example 256, but starting with piperidine (0.10 ml, 1.00 mmol), yielded the title compound (34 mg, 68% yield) as a white solid, after purification by flash chromatography on silica gel, eluting with 0-5% methanol in dichloromethane containing 2% ammonia:
$^1$H-NMR (DMSO d$_6$): 9.50 (s, 1H), 8.47 (s, 1H), 7.99 (d, 2H, J=7 Hz), 7.88 (s, 1H), 7.82 (d, 2H, J=8 Hz), 7.76 (d, 2H, J=8 Hz), 7.54-7.64 (m, 3H), 7.22 (s, 1H), 4.26 (m, 2H), 3.99 (s, 3H), 3.32-3.45 (m, 4H), 2.76 (m, 2H), 1.54 (m, 4H), 1.42 (m, 2H):
MS (+ve ESI): 498 (M+H)+.
MS (-ve ESI): 496 (M-H)-.

EXAMPLE 319

Preparation of Compound No. 319 in Table 10

An analogous reaction to that described in example 256, but starting with 4-(aminomethyl)-pyridine (108 mg, 1.0 mmol), yielded the title compound (62.5 mg, 60% yield) as an off-white solid:
HPLC/LCMS (RT): 5.27 min:
MS (+ve ESI): 521 (M+H)+.

EXAMPLE 320

Preparation of Compound No. 320 in Table 10

An analogous reaction to that described in example 256, but starting with 2-amino-1,3-propanediol (91 mg, 1.00 mmol), yielded the title compound (45 mg, 45% yield) as a white solid:
$^1$H-NMR (DMSO d$_6$): 10.13 (s, 1H), 9.34 (s, 1H), 8.32 (s, 1H), 7.86 (d, 2H, J=7 Hz), 7.77 (s, 1H), 7.69 (d, 2H, J=8 Hz), 7.63 (d, 2H, J=8 Hz), 7.40-7.49 (m, 3H), 7.08 (s, 1H), 4.28 (t, 2H, J=7 Hz), 4.08 (t, 2H, J=7 Hz), 3.84 (s, 3H), 3.19-3.33 (m, 4H), 2.91 (t, 2H, J=7 Hz), 2.51 (m, 1H):
MS (+ve ESI): 504 (M+H)+.

EXAMPLE 321

Preparation of Compound No. 321 in Table 10

An analogous reaction to that described in example 256, but starting with a solution of methylamine in tetrahydrofuran (40.5 ml of a 2.0 N solution, 81 mmol), yielded the title compound (2.20 g, 61% yield) as a white solid, after purification by flash chromatography on silica gel, eluting with 1-5% methanol in dichloromethane:
$^1$H-NMR (DMSO d$_6$): 10.22 (s, 1H), 9.43 (s, 1H), 8.40 (s, 1H), 7.98 (d, 2H), 7.80 (s, 1H), 7.70-7.19 (m, 4H), 7.45-7.60 (m, 3H), 7.15 (s, 1H), 4.20 (t, 2H), 3.95 (s, 3H), 2.90 (t, 2H), 2.37 (s, 3H):
MS (+ve ESI): 444 (M+H)$^+$
MS (-ve ESI): 442 (M-H)$^-$

EXAMPLE 322

Preparation of Compound No. 322 in Table 10

Methansulphonyl chloride (58 mg, 0.51 mmol) was added to a stirred solution of 4-((4-(N-benzoyl)-amino)anilino)-6-methoxy-7-(N-methyl-3-aminoethoxy)quinazoline (150 mg, 0.34 mmol) and triethylamine (34 mg, 0.34 mmol) in dimethylacetamide (0.5 ml) and the reaction was stirred at ambient temperature for 3 hours. 2.0 N Hydrochloric acid (10 ml) was added, the resultant precipitate was collected by suction filtration and washed with i) water (10 ml), ii) saturated sodium hydrogen carbonate solution (10 ml) and iii) brine (10 ml) before being adsorbed onto silica gel. Purification by flash chromatography on silica gel, eluting with 5-10% methanol in dichloromethane yielded the title compound (76 mg, 43% yield) as a pale yellow solid:
$^1$H-NMR (DMSO d$_6$): 10.23 (s, 1H), 9.42 (s, 1H), 8.40 (s, 1H), 7.90 (d, 2H), 7.81 (s, 1H), 7.70-7.80 (m, 4H); 7.45-7.60 (m, 3H), 7.20 (s, 1H), 4.30 (t, 2H), 3.95 (s, 3H), 3.60 (t, 2H), 3.0 (s, 3H), 2.90 (t, 3H):
MS (+ve ESI): 522 (M+H)$^+$
MS (−ve ESI): 520 (M−H)$^-$

EXAMPLE 323

Preparation of Compound No. 323 in Table 10

An analogous reaction to that described in example 256, but starting with diethylamine (73 mg, 1.00 mmol), yielded the title compound (28 mg, 29% yield) as an off-white solid:
HPLC/LCMS (RT): 3.27 min:
MS (+ve ESI): 486 (M+H)+.

EXAMPLE 324

Preparation of Compound No. 324 in Table 10

An analogous reaction to that described in example 256, but starting with hexamethylene-imine (99 mg, 1.00 mmol), yielded the title compound (50 mg, 49% yield) as an off-white solid:
HPLC/LCMS (RT): 3.41 min:
MS (+ve ESI): 512 (M+H)+.

EXAMPLE 325

Preparation of Compound No. 325 in Table 10

An analogous reaction to that described in example 256, but starting with N-methyl ethanolamine (75 mg, 1.00 mmol), yielded the title compound (45 mg, 46% yield) as an off-white solid:
HPLC/LCMS (RT): 3.13 min:
MS (+ve ESI) 488 (M+H)+.

EXAMPLE 326

Preparation of Compound No. 326 in Table 10

An analogous reaction to that described in example 256, but starting with 3-pyrroline (69 mg, 1.00 mmol), yielded the title compound (16 mg, 16% yield) as an off-white solid:
$^1$H-NMR (DMSO d$_6$): 10.26 (s, 1H), 9.48 (s, 1H), 8.44 (s, 1H), 7.97 (d, 2H, J=7 Hz), 7.86 (s, 1H), 7.77 (d, 2H, J=8 Hz), 7.59 (d, 2H, J=8 Hz), 7.53-7.60 (m, 3H), 7.20 (s, 1H), 5.82 (s, 2H), 4.22 (m, 2H), 3.97 (s, 3H), 3.55 (s, 4H), 3.07 (t, 2H, J=6 Hz):
MS (+ve ESI): 482 (M+H)+.

EXAMPLE 327

Preparation of Compound No. 327 in Table 10

An analogous reaction to that described in example 256, but starting with N,N,N'-trimethyl ethylenediamine (102 mg, 1.00 mmol), yielded the title compound (41 mg, 40% yield) as an off-white solid:
HPLC/LCMS (RT): 3.04 min:
MS (+ve ESI): 515 (M+H)+.

EXAMPLE 328

Preparation of Compound No. 328 in Table 10

An analogous reaction to that described in example 256, but starting with N-methyl piperazine (100 mg, 1.00 mmol), yielded the title compound (43 mg, 42% yield) as a white solid:
HPLC/LCMS (RT): 3.11 min:
MS (+ve ESI): 513 (M+H)+.

EXAMPLE 329

Preparation of Compound No. 329 in Table 10

An analogous reaction to that described in example 256, but starting with N-cyclopropyl piperazine (126 mg, 1.00 mmol), yielded the title compound (16 mg, 14% yield) as a white solid:
HPLC/LCMS (RT): 3.24 min:
MS (+ve ESI): 539 (M+H)+.

EXAMPLE 330

Preparation of Compound No. 330 in Table 10

An analogous reaction to that described in example 256, but starting with S-prolinol (101 mg, 1.00 mmol), yielded the title compound (56 mg, 55% yield) as an off-white solid:
HPLC/LCMS (RT): 3.21 min:
MS (+ve ESI): 514 (M+H)+.

EXAMPLE 331

Preparation of Compound No. 331 in Table 10

An analogous reaction to that described in example 256, but starting with 4-hydroxy piperidine (101 mg, 1.00 mmol), yielded the title compound (61 mg, 59% yield) as a white solid:
$^1$H-NMR (DMSO d$_6$): 9.50 (s, 1H), 8.45 (s, 1H), 8.01 (d, 2H, J=7 Hz), 7.86 (s, 1H), 7.81 (d, 2H, J=8 Hz), 7.76 (d, 2H, J=8 Hz), 7.54-7.64 (m, 3H), 7.22 (s, 1H), 4.59 (m, 1H), 4.26 (m, 2H), 4.00 (s, 3H), 3.49 (m, 1H), 2.87 (m, 2H), 2.80 (m, 2H), 2.20 (m, 2H), 1.75 (m 2H), 1.42 (m, 2H):
MS (+ve ESI): 514 (M+H)+.

EXAMPLE 332

Preparation of Compound No. 332 in Table 10

An analogous reaction to that described in example 256, but starting with N-(2-(1-morpholino)ethyl)piperazine (199 mg, 1.00 mmol), yielded the title compound (19 mg, 16% yield) as an off-white solid:
HPLC/LCMS (RT): 3.09 min:
MS (+ve ESI): 612 (M+H)+.

EXAMPLE 333

Preparation of Compound No. 333 in Table 10

An analogous reaction to that described in example 256, but starting with N-(3-hydroxy-propyl)piperazine (144 mg, 1.00 mmol), yielded the title compound (53 mg, 48% yield) as an off-white solid:
HPLC/LCMS (RT): 3.11 min:
MS (+ve ESI): 557 (M+H)+.

EXAMPLE 334

Preparation of Compound No. 334 in Table 10

An analogous reaction to that described in example 256, but starting with N-ethyl ethanolamine (89 mg, 1.00 mmol), yielded the title compound (36 mg, 36% yield) as an off-white solid:
HPLC/LCMS (RT): 3.20 min:
MS (+ve ESI): 502 (M+H)+.

EXAMPLE 335

Preparation of Compound No. 335 in Table 10

An analogous reaction to that described in example 256, but starting with 3-hydroxy pyrrolidine (87 mg, 1.00 mmol), yielded the title compound (35 mg, 35% yield) as a white solid:
$^1$H-NMR (DMSO d$_6$): 10.26 (s, 1H), 9.48 (s, 1H), 8.44 (s, 1H), 7.97 (d, 2H, J=7 Hz), 7.85 (s, 1H), 7.80 (d, 2H, J=8 Hz), 7.75 (d, 2H, J=8 Hz), 7.53-7.60 (m, 3H), 7.19 (s, 1H), 4.74 (s, 1H), 4.23 (m, 2H), 3.97 (s, 3H), 2.68-2.92 (m, 5H), 2.00 (m, 2H), 1.55 (m, 2H):
MS (+ve ESI): 500 (M+H)+.

EXAMPLE 336

Preparation of Compound No. 336 in Table 10

An analogous reaction to that described in example 256, but starting with N-methyl 2-cyano-ethylamine (84 mg, 1.00 mmol), yielded the title compound (75 mg, 75% yield) as an off-white solid:
$^1$H-NMR (DMSO d$_6$): 9.50 (s, 1H), 8.45 (s, 1H), 8.00 (d, 2H, J=7 Hz), 7.86 (s, 1H), 7.81 (d, 2H, J=8 Hz), 7.76 (d, 2H, J=8 Hz), 7.54-7.64 (m, 3H), 7.22 (s, 1H), 4.26 (m, 2H), 3.99 (s, 3H), 2.93 (t, 2H, J=7 Hz), 2.81 (m, 2H), 2.72 (m, 2H), 2.38 (s, 3H):
MS (+ve ESI): 497 (M+H)+.

EXAMPLE 337

Preparation of Compound No. 337 in Table 10

An analogous reaction to that described in example 256, but starting with 4-piperidino-piperidine (168 mg, 1.00 mmol), yielded the title compound (57 mg, 49% yield) as a white solid:
HPLC/LCMS (RT): 3.13 min:
MS (+ve ESI): 581 (M+H)+.

EXAMPLE 338

Preparation of Compound No. 338 in Table 10

An analogous reaction to that described in example 256, but starting with 2,6-dimethyl morpholine (115 mg, 1.00 mmol), yielded the title compound (37 mg, 35% yield) as a white solid:
HPLC/LCMS (RT): 3.36 min:
MS (+ve ESI): 528 (M+H)+.

EXAMPLE 339

Preparation of Compound No. 339 in Table 10

An analogous reaction to that described in example 256, but starting with N-acetyl piperazine (128 mg, 1.00 mmol), yielded the title compound (60 mg, 55% yield) as a white solid:
HPLC/LCMS (RT): 3.16 min:
MS (+ve ESI): 541 (M+H)+.

EXAMPLE 340

Preparation of Compound No. 340 in Table 10

An analogous reaction to that described in example 256, but starting with N-methyl allylamine (71 mg, 1.00 mmol), yielded the title compound (38 mg, 39% yield) as an off-white solid:
HPLC/LCMS (RT): 3.29 min:
MS (+ve ESI): 484 (M+H)+.

EXAMPLE 341

Preparation of Compound No. 341 in Table 10

An analogous reaction to that described in example 256, but starting with 2-methyl-pyrrolidine (85 mg, 1.00 mmol), yielded the title compound (80 mg, 80% yield) as a white solid:
HPLC/LCMS (RT): 3.31 min:
MS (+ve ESI): 498 (M+H)+.

EXAMPLE 342

Preparation of Compound No. 342 in Table 10

An analogous reaction to that described in example 256, but starting with N-ethyl isopropylamine (87 mg, 1.00 mmol), yielded the title compound (29 mg, 29% yield) as an off-white solid:
HPLC/LCMS (RT): 3.36 min:
MS (+ve ESI): 500 (M+H)+.

EXAMPLE 343

Preparation of Compound No. 343 in Table 10

An analogous reaction to that described in example 256, but starting with N-ethyl 2-cyano-ethylamine (98 mg, 1.00 mmol), yielded the title compound (51 mg, 50% yield) as an off-white solid:
HPLC/LCMS (RT): 3.27 min:
MS (+ve ESI): 511 (M+H)+.

EXAMPLE 344

Preparation of Compound No. 344 in Table 10

An analogous reaction to that described in example 256, but starting with N-methyl 2-methyl-propylamine (87 mg, 1.00 mmol), yielded the title compound (25 mg, 25% yield) as an off-white solid:
HPLC/LCMS (RT): 3.44 min:
MS (+ve ESI): 500 (M+H)+.

EXAMPLE 345

Preparation of Compound No. 345 in Table 10

An analogous reaction to that described in example 256, but starting with N-ethylpiperazine (114 mg, 1.00 mmol), yielded the title compound (91 mg, 86% yield) as an off-white solid:
$^1$H-NMR (DMSO $d_6$): 9.50 (s, 1H), 8.44 (s, 1H), 8.00 (d, 2H, J=7 Hz), 7.86 (s, 1H), 7.82 (d, 2H, J=8 Hz), 7.77 (d, 2H, J=8 Hz), 7.53-7.63 (m, 3H), 7.22 (s, 1H), 4.25 (m, 2H), 3.99 (s, 3H), 2.79 (m, 2H), 2.30-2.65 (m, 8H), 2.31 (q, 2H, J=7 Hz), 1.00 (t, 3H, J=7 Hz):
MS (+ve ESI): 527 (M+H)+.

EXAMPLE 346

Preparation of Compound No. 346 in Table 10

An analogous reaction to that described in example 256, but starting with N-(4-fluorophenyl)piperazine (180 mg, 1.00 mmol), yielded the title compound (87 mg, 72% yield) as an off-white solid:
$^1$H-NMR (DMSO $d_6$): 9.48 (s, 1H), 8.43 (s, 1H), 7.96 (d, 2H, J=7 Hz), 7.83 (s, 1H), 7.78 (d, 2H, J=8 Hz), 7.72 (d, 2H, J=8 Hz), 7.50-7.61 (m, 3H), 7.20 (s, 1H), 7.03 (m, 2H), 6.93 (m, 2H), 4.28 (m, 2H), 3.96 (s, 3H), 3.08 (m, 4H), 2.85 (m, 2H), 2.67 (m, 4H):
MS (+ve ESI): 593 (M+H)+.

EXAMPLE 347

Preparation of Compound No. 347 in Table 10

An analogous reaction to that described in example 256, but starting with thiazoline-2-carboxylic acid (133 mg, 1.00 mmol), yielded the title compound (48 mg, 44% yield) as an off-white solid:
HPLC/LCMS (RT): 3.39 min:
MS (+ve ESI): 546 (M+H)+.

EXAMPLE 348

Preparation of Compound No. 348 in Table 10

An analogous reaction to that described in example 256, but starting with 4-(2-hydroxyethyl)-piperidine (129 mg, 1.00 mmol), yielded the title compound (75 mg, 69% yield) as an off-white solid:
$^1$H-NMR (DMSO $d_6$): 9.50 (s, 1H), 8.45 (s, 1H), 8.00 (d, 2H, J=7 Hz), 7.88 (s, 1H), 7.82 (d, 2H, J=8 Hz), 7.76 (d, 2H, J=8 Hz), 7.54-7.64 (m, 3H), 7.22 (s, 1H), 4.35 (m, 1H), 4.26 (m, 2H), 3.99 (s, 3H), 3.40-3.48 (m, 2H), 2.99 (m, 2H), 2.79 (m, 2H), 2.05 (m, 2H)), 1.65 (m, 2H), 1.39 (m, 3H), 1.19 (m, 2H):
MS (+ve ESI): 542 (M+H)+.

EXAMPLE 349

Preparation of Compound No. 349 in Table 10

An analogous reaction to that described in example 256, but starting with N-methyl 3-(aminomethyl)pyridine (122 mg, 1.00 mmol), yielded the title compound (21 mg, 20% yield) as an off-white solid:
HPLC/LCMS (RT): 3.13 min:
MS (+ve ESI): 535 (M+H)+.

EXAMPLE 350

Preparation of Compound No. 350 in Table 10

An analogous reaction to that described in example 256, but starting with N-methyl 2-(aminomethyl)pyridine (122 mg, 1.00 mmol), yielded the title compound (62 mg, 58% yield) as an off-white solid:
$^1$H-NMR (DMSO $d_6$): 9.50 (s, 1H), 8.50 (d, 1H, J=5 Hz), 8.45 (s, 1H), 8.00 (d, 2H, J=7 Hz), 7.89 (s, 1H), 7.75-7.84 (m, 5H), 7.53-7.64 (m, 4H), 7.27 (m, 1H), 7.23 (s, 1H), 4.31 (m, 2H), 4.00 (s, 3H), 3.79 (s, 2H), 2.90 (t, 2H, J=7 Hz), 2.36 (s, 3H):
MS (+ve ESI): 535 (M+H)+.

EXAMPLE 351

Preparation of Compound No. 351 in Table 10

An analogous reaction to that described in example 256, but starting with 2,5-dimethyl-pyrrolidine (99 mg, 1.00 mmol), yielded the title compound (36 mg, 35% yield) as a white solid:
HPLC/LCMS (RT): 3.39 min:
MS (+ve ESI): 512 (M+H)+.

EXAMPLE 352

Preparation of Compound No. 352 in Table 10

An analogous reaction to that described in example 256, but starting with 1,2,3,6-tetrahydro-piperidine (183 mg, 1.00 mmol), yielded the title compound (29 mg, 29% yield) as a white solid:
HPLC/LCMS (RT): 3.27 min:
MS (+ve ESI): 496 (M+H)+.

EXAMPLE 353

Preparation of Compound No. 353 in Table 10

An analogous reaction to that described in example 256, but starting with 4-methylpiperidine (99 mg, 1.00 mmol), yielded the title compound (15 mg, 14% yield) as an off-white solid:
HPLC/LCMS (RT): 3.46 min:
MS (+ve ESI): 512 (M+H)+.

EXAMPLE 354

Preparation of Compound No. 354 in Table 10

An analogous reaction to that described in example 256, but starting with N-(2-hydroxyethyl)-piperazine (130 mg, 1.00 mmol), yielded the title compound (75 mg, 70% yield) as an off-white solid:
$^1$H-NMR (DMSO $d_6$): 9.50 (s, 1H), 8.46 (s, 1H), 7.99 (d, 2H, J=7 Hz), 7.87 (s, 1H), 7.80 (d, 2H, J=8 Hz), 7.74 (d, 2H, J=8 Hz), 7.54-7.64 (m, 3H), 7.24 (s, 1H), 4.44 (s, 1H), 4.26 (m, 2H), 3.98 (s, 3H), 3.54 (m, 2H), 2.80 (t, 2H, J=7 Hz), 2.40-2.70 (m, 10H):
MS (+ve ESI): 484 (M+H)+.

EXAMPLE 355

Preparation of Compound No. 355 in Table 10

An analogous reaction to that described in example 256, but starting with 2-(2-hydroxyethyl)-piperidine (129 mg, 1.00 mmol), yielded the title compound (48 mg, 44% yield) as an off-white solid:

HPLC/LCMS (RT): 3.30 min:
MS (+ve ESI): 542 (M+H)+.

EXAMPLE 356

Preparation of Compound No. 356 in Table 10

4-((4-(N-Benzoyl)amino)anilino)-6-methoxy-7-(2-bromoethoxy)quinazoline (100 mg, 0.202 mmol) in DMF (5 ml) was heated with excess 2-ethylimidazoline in the presence of potassium carbonate (56 mg, 0.405 mmol) at 100° C. for 2 hours. The solvent was evaporated in vacuo, water was added to the reaction mixture, the pH adjusted to 4 with hydrochloric acid (2.0 N), the solid was collected by suction filtration. Purification by flash chromatography on silica gel, eluting with 5% methanol in dichloromethane, yielded the title compound (48 mg, 46% yield) as a white solid:

$^1$H-NMR (DMSO d$_6$, TFA): 8.89 (s, 1H), 8.15 (s, 1H), 7.99 (d, 2H), 7.94 (d, 2H), 7.65 (d, 2H), 7.63 (d, 1H), 7.56 (t, 2H), 7.33 (s, 1H), 4.44 (t, 2H), 4.01 (m, 7H), 3.81 (t, 2H), 2.80 (q, 2H), 1.26 (t, 3H):

MS (+ve ESI): 511 (M+H)+.

EXAMPLE 357

Preparation of Compound No. 357 in Table 10

An analogous reaction to that described for the synthesis of compound 356, but starting with imidazoline (460 mg, 2.13 mmol) and heating at 80° C. for 2 hours, yielded the title compound (150 mg, 44% yield) as a white solid:

$^1$H-NMR (DMSO d$_6$): 9.47 (s, 1H), 8.42 (s, 1H), 7.95 (d, 2H), 7.85 (s, 1H), 7.78 (d, 2H), 7.73 (d, 2H), 7.57 (d, 1H) 7.52 (t, 2H), 7.20 (s, 1H), 6.37 (s, 1H), 4.24 (t, 2H), 3.95 (s, 3H), 3.60 (t, 2H), 3.53 (t, 2H), 3.27 (t, 2H):

MS (+ve ESI): 483 (M+H)+.

EXAMPLE 358

Preparation of Compound No. 358 in Table 11

A solution of 4-((4-(N-benzoyl)amino)anilino)-6-methoxy-7-(3-chloropropoxy)quinazoline (92.5 mg, 0.20 mmol) in dimethylacetamide (2.0 ml) was sodium iodide (15.0 mg, 0.10 mmol) and N-acetylethylenediamine (102 mg, 1.00 mmol) and the reaction heated at 100° C. for 24 hours. The reaction was allowed to cool, methanol (0.50 ml) was added and the reaction mixtures were absorbed onto normal phase silica gel. Purification by flash chromatography on silica gel, eluting with 0-20% methanol in dichloromethane (containing 1% aqueous ammonia), yielded the title compound (45.6 mg, 43% yield) as a white solid:

HPLC/LCMS (RT): 5.21 min:
MS (+ve ESI): 529.4 (M+H)+.

EXAMPLE 359

Preparation of Compound No. 359 in Table 11

An analogous reaction to that described in example 358 but starting with L-alaninamide hydrochloride (88 mg, 1.0 mmol), yielded the title compound (18.7 mg, 18% yield) as a white solid:

HPLC/LCMS (RT): 5.27 min:
MS (+ve ESI): 515.4 (M+H)+.

EXAMPLE 360

Preparation of Compound No. 360 in Table 11

An analogous reaction to that described in example 358 but starting with cyclopropylamine (57 mg, 1.00 mmol), yielded the title compound (15.5 mg, 16% yield) as a white solid:

HPLC/LCMS (RT): 5.42 min:
MS (+ve ESI): 484.3 (M+H)+.

EXAMPLE 361

Preparation of Compound No. 361 in Table 11

An analogous reaction to that described in example 358 but starting with cyclopropane-methylamine (71 mg, 1.00 mmol), yielded the title compound (64.3 mg, 65% yield) as a white solid:

HPLC/LCMS (RT): 5.56 min:
MS (+ve ESI): 498.4 (M+H)+.

EXAMPLE 362

Preparation of Compound No. 362 in Table 11

An analogous reaction to that described in example 358 but starting with cyclobutylamine (71 mg, 1.00 mmol), yielded the title compound (17.5 mg, 18% yield) as a white solid:

HPLC/LCMS (RT): 5.40 min:
MS (+ve ESI): 498.4 (M+H)+.

EXAMPLE 363

Preparation of Compound No. 363 in Table 111

An analogous reaction to that described in example 358 but starting with cyclopentylamine (85 mg, 1.00 mmol), yielded the title compound (15.7 mg, 15% yield) as a white solid:

HPLC/LCMS (RT): 5.58 min:
MS (+ve ESI): 512.4 (M+H)+.

EXAMPLE 364

Preparation of Compound No. 364 in Table 11

An analogous reaction to that described in example 358 but starting with 1-(3-aminopropyl)-imidazole (125 mg, 1.0 mmol), yielded the title compound (113.8 mg, 103% yield) as a white solid:

HPLC/LCMS (RT): 4.90 min:
MS (+ve ESI): 552.7 (M+H)+.

EXAMPLE 365

Preparation of Compound No. 365 in Table 11

An analogous reaction to that described in example 358 but starting with cyclohexylamine (99 mg, 1.00 mmol), yielded the title compound (158.2 mg, 150% yield) as a white solid:
HPLC/LCMS (RT): 5.55 min:
MS (+ve ESI): 526.4 (M+H)+.

EXAMPLE 366

Preparation of Compound No. 366 in Table 11

An analogous reaction to that described in example 358 but starting with 4-aminocyclo-hexanol (115 mg, 1.00 mmol), yielded the title compound (52.6 mg, 49% yield) as a white solid:
HPLC/LCMS (RT): 5.24 min:
MS (+ve ESI): 542.4 (M+H)+.

EXAMPLE 367

Preparation of Compound No. 367 in Table 11

An analogous reaction to that described in example 358 but starting with cyclohexane-methylamine (113 mg, 1.00 mmol), yielded the title compound (126.5 mg, 117% yield) as a white solid:
HPLC/LCMS (RT): 5.76 min:
MS (+ve ESI): 540.4 (M+H)+.

EXAMPLE 368

Preparation of Compound No. 368 in Table 11

An analogous reaction to that described in example 358 but starting with 2-amino-2-methyl-1,3-propanediol (105 mg, 1.00 mmol), yielded the title compound (52 mg, 49% yield) as a white solid:
HPLC/LCMS (RT): 5.21 min:
MS (+ve ESI): 532.3 (M+H)+.

EXAMPLE 369

Preparation of Compound No. 369 in Table 11

An analogous reaction to that described in example 358 but starting with tris-(hydroxymethyl)-methylamine (121 mg, 1.00 mmol), yielded the title compound (27 mg, 25% yield) as a white solid:
HPLC/LCMS (RT): 5.14 min:
MS (+ve ESI): 548.3 (M+H)+.

EXAMPLE 370

Preparation of Compound No. 370 in Table 11

An analogous reaction to that described in example 358 but starting with 2-amino-2-ethyl-1,3-propanediol (119 mg, 1.00 mmol), yielded the title compound (55.5 mg, 51% yield) as a white solid:
HPLC/LCMS (RT): 5.20 min:
MS (+ve ESI): 546.4 (M+H)+.

EXAMPLE 371

Preparation of Compound No. 371 in Table 11

An analogous reaction to that described in example 358 but starting with (S)-leucinol (117 mg, 1.00 mmol), yielded the title compound (75 mg, 69% yield) as a white solid:
HPLC/LCMS (RT): 5.46 min:
MS (+ve ESI): 544.4 (M+H)+.

EXAMPLE 372

Preparation of Compound No. 372 in Table 11

An analogous reaction to that described in example 358 but starting with tetrahydrofurfuryl-amine (101 mg, 1.00 mmol), yielded the title compound (73.8 mg, 70% yield) as a white solid:
HPLC/LCMS (RT): 5.43 min:
MS (+ve ESI): 528.4 (M+H)+.

EXAMPLE 373

Preparation of Compound No. 373 in Table 11

An analogous reaction to that described in example 358 but starting with isonipecotamide (128 mg, 1.00 mmol), yielded the title compound (109.8 mg, 99% yield) as a white solid:
HPLC/LCMS (RT): 5.18 min:
MS (+ve ESI): 555.4 (M+H)+.

EXAMPLE 374

Preparation of Compound No. 374 in Table 11

An analogous reaction to that described in example 358 but starting with 4-(2-aminoethyl)-morpholine (130 mg, 1.00 mmol), yielded the title compound (79.4 mg, 71% yield) as a white solid:
HPLC/LCMS (RT): 5.08 min:
MS (+ve ESI): 557.4 (M+H)+.

EXAMPLE 375

Preparation of Compound No. 375 in Table 11

An analogous reaction to that described in example 358 but starting with 2-amino-2-methyl-1-propanol (89 mg, 1.00 mmol), yielded the title compound (59.2 mg, 57% yield) as a white solid:
HPLC/LCMS (RT): 5.33 min:
MS (+ve ESI): 516.4 (M+H)+.

EXAMPLE 376

Preparation of Compound No. 376 in Table 11

An analogous reaction to that described in example 358 but starting with 3-amino-3-methyl-1-butanol (103 mg, 1.00 mmol), yielded the title compound (47.7 mg, 45% yield) as a white solid:
HPLC/LCMS (RT): 5.27 min:
MS (+ve ESI): 530.4 (M+H)+.

EXAMPLE 377

Preparation of Compound No. 377 in Table 11

An analogous reaction to that described in example 358 but starting with isopropylamine (59 mg, 1.00 mmol), yielded the title compound (65.4 mg, 67% yield) as a white solid:
HPLC/LCMS (RT): 5.32 min:
MS (+ve ESI): 486.3 (M+H)+.

EXAMPLE 378

Preparation of Compound No. 378 in Table 11

An analogous reaction to that described in example 358 but starting with 2-amino-1-propanol (75 mg, 1.00 mmol), yielded the title compound (63.8 mg, 64% yield) as a white solid:
HPLC/LCMS (RT): 5.18 min:
MS (+ve ESI): 502.4 (M+H)+.

EXAMPLE 379

Preparation of Compound No. 379 in Table 11

An analogous reaction to that described in example 358 but starting with D-2-amino-1-butanol (89 mg, 1.00 mmol), yielded the title compound (70.7 mg, 69% yield) as a white solid:
HPLC/LCMS (RT): 5.22 min:
MS (+ve ESI): 516.4 (M+H)+.

EXAMPLE 380

Preparation of Compound No. 380 in Table 11

An analogous reaction to that described in example 358 but starting with 3-amino-1,2-propanediol (91 mg, 1.00 mmol), yielded the title compound (22.1 mg, 21% yield) as a white solid:
HPLC/LCMS (RT): 1.66 min:
MS (+ve ESI): 518.4 (M+H)+.

EXAMPLE 381

Preparation of Compound No. 381 in Table 11

An analogous reaction to that described in example 358 but starting with 2-methoxyethyl-amine (75 mg, 1.00 mmol), yielded the title compound (67.1 mg, 67% yield) as a white solid:
HPLC/LCMS (RT): 5.47 min:
MS (+ve ESI): 502.4 (M+H)+.

EXAMPLE 382

Preparation of Compound No. 382 in Table 11

An analogous reaction to that described in example 358 but starting with 2-(2-aminoethoxy)-ethanol (105 mg, 1.00 mmol), yielded the title compound (75.8 mg, 71% yield) as a white solid:
HPLC/LCMS (RT): 5.24 min:
MS (+ve ESI): 532.4 (M+H)+.

EXAMPLE 383

Preparation of Compound No. 383 in Table 11

An analogous reaction to that described in example 358 but starting with 2-mercaptoethyl-amine hydrochloride (77 mg, 1.00 mmol), yielded the title compound (31.8 mg, 33% yield) as a white solid:
HPLC/LCMS (RT): 1.81 min:
MS (+ve ESI): 488.3 (M+H)+.

EXAMPLE 384

Preparation of Compound No. 384 in Table 11

An analogous reaction to that described in example 358 but starting with 2-(ethylthio)ethyl-amine (105 mg, 1.00 mmol), yielded the title compound (194.4 mg, 193% yield) as a white solid:
HPLC/LCMS (RT): 1.92 min:
MS (+ve ESI): 504.3 (M+H)+.

EXAMPLE 385

Preparation of Compound No. 385 in Table 11

An analogous reaction to that described in example 358 but starting with 3-diethylamino-propylamine (130 mg, 1.0 mmol), yielded the title compound (25.3 mg, 24% yield) as a white solid:
HPLC/LCMS (RT): 5.02 min:
MS (+ve ESI): 532.2 (M+H)+.

EXAMPLE 386

Preparation of Compound No. 386 in Table 11

An analogous reaction to that described in example 358 but starting with 3-ethoxypropylamine (103 mg, 1.00 mmol), yielded the title compound (15.9 mg, 14% yield) as a white solid:
HPLC/LCMS (RT): 5.44 min:
MS (+ve ESI): 557.4 (M+H)+.

EXAMPLE 387

Preparation of Compound No. 387 in Table 11

An analogous reaction to that described in example 358 but starting with 3-amino-1-propanol (75 mg, 1.00 mmol), yielded the title compound (112.7 mg, 106% yield) as a white solid:
HPLC/LCMS (RT): 5.23 min:
MS (+ve ESI): 530.4 (M+H)+.

EXAMPLE 388

Preparation of Compound No. 388 in Table 11

An analogous reaction to that described in example 358 but starting with 5-amino-1-pentanol (103 mg, 1.00 mmol), yielded the title compound (11.9 mg, 12% yield) as a white solid:
HPLC/LCMS (RT): 5.37 min:
MS (+ve ESI): 502.4 (M+H)+.

EXAMPLE 389

Preparation of Compound No. 389 in Table 11

An analogous reaction to that described in example 358 but starting with D-prolinamide (114 mg, 1.00 mmol), yielded the title compound (15.4 mg, 15% yield) as a white solid:
HPLC/LCMS (RT) 5.34 min:
MS (+ve ESI): 530.4 (M+H)+.

EXAMPLE 390

Preparation of Compound No. 390 in Table 11

An analogous reaction to that described in example 358 but starting with 3-amino-5-methylpyrazole (97 mg, 1.00 mmol), yielded the title compound (150.6 mg, 139% yield) as a white solid:
HPLC/LCMS (RT): 5.52 min:
MS (+ve ESI): 541.3 (M+H)+.

EXAMPLE 391

Preparation of Compound No. 391 in Table 11

An analogous reaction to that described in example 358 but starting with 1-aminomethyl-1-cyclohexanol hydrochloride (129 mg, 1.00 mmol), yielded the title compound (153.9 mg, 147% yield) as a white solid:
HPLC/LCMS (RT): 5.54 min:
MS (+ve ESI): 524.4 (M+H)+.

EXAMPLE 392

Preparation of Compound No. 392 in Table 11

An analogous reaction to that described in example 358 but starting with 2-amino-1-hexanol (117 mg, 1.00 mmol), yielded the title compound (52.6 mg, 47% yield) as a white solid:
HPLC/LCMS (RT): 5.53 min:
MS (+ve ESI): 556.7 (M+H)+.

EXAMPLE 393

Preparation of Compound No. 393 in Table 11

An analogous reaction to that described in example 358 but starting with 5-methyl-2-furanmethanamine (111 mg, 1.00 mmol), yielded the title compound (63.1 mg, 58% yield) as a white solid:
HPLC/LCMS (RT): 5.58 min:
MS (+ve ESI): 544.4 (M+H)+.

EXAMPLE 394

Preparation of Compound No. 394 in Table 11

An analogous reaction to that described in example 358 but starting with 3-amino-2,2-dimethyl-1-propanol (103 mg, 1.00 mmol), yielded the title compound (151 mg, 140% yield) as a white solid:
HPLC/LCMS (RT): 5.38 min:
MS (+ve ESI): 538.3 (M+H)+.

EXAMPLE 395

Preparation of Compound No. 395 in Table 11

An analogous reaction to that described in example 358 but starting with 3-aminomethyl-thiophene dihydrochloride (113 mg, 1.00 mmol), yielded the title compound (113.4 mg, 107% yield) as a white solid:
HPLC/LCMS (RT): 5.64 min:
MS (+ve ESI): 530.4 (M+H)+.

EXAMPLE 396

Preparation of Compound No. 396 in Table 11

An analogous reaction to that described in example 358 but starting with ethanolamine (61 mg, 1.00 mmol), yielded the title compound (46.1 mg, 43% yield) as a white solid:
HPLC/LCMS (RT): 5.19 min:
MS (+ve ESI): 540.3 (M+H)+.

EXAMPLE 397

Preparation of Compound No. 397 in Table 11

An analogous reaction to that described in example 358 but starting with thiophene-2-methylamine (113 mg, 1.0 mmol), yielded the title compound (10.8 mg, 10% yield) as a white solid:
HPLC/LCMS (RT): 5.64 min:
MS (+ve ESI): 540.3 (M+H)+.

EXAMPLE 398

Preparation of Compound No. 398 in Table 11

An analogous reaction to that described in example 358 but starting with piperidine (0.11 ml, 1.1 mmol), and omitting the sodium iodide catalyst, yielded the title compound (18.7 mg, 18% yield) as a white solid:
$^1$H-NMR (DMSO $d_6$): 10.23 (s, 1H), 9.44 (s, 1H), 8.41 (s, 1H), 7.95 (d, 2H), 7.83 (s, 1H), 7.67-7.82 (m, 4H), 7.45-7.63 (m, 3H), 7.15 (s, 1H), 4.15 (t, 2H), 3.96 (s, 3H), 2.26-2.47 (m, 6H), 1.85-2.00 (m, 2H), 1.44-1.56 (m, 4H), 1.30-1.44 (m, 2H):
MS (+ve ESI): 512.6 (M+H)+.

EXAMPLE 399

Preparation of Compound No. 399 in Table 11

An analogous reaction to that described in example 358 but starting with pyrrolidine (0.09 ml, 1.1 mmol), yielded the title compound (38 mg, 36% yield) as a white solid:
$^1$H-NMR (DMSO $d_6$): 10.23 (s, 1H), 9.44 (s, 1H), 8.42 (s, 1H), 7.97 (d, 2H), 7.84 (s, 1H), 7.68-7.82 (m, 4H), 7.46-7.63 (m, 3H), 7.14 (s, 1H), 4.17 (t, 2H), 3.95 (s, 3H), 2.40-2.63 (m, 6H), 1.89-2.02 (m, 2H), 1.60-1.77 (m, 2H):
MS (+ve ESI): 498.6 (M+H)+.

EXAMPLE 400

Preparation of Compound No. 400 in Table 11

An analogous reaction to that described in example 358 but starting with N-methyl piperazine (0.12 ml, 1.1 mmol), yielded the title compound (47 mg, 41% yield) as a white solid:

¹H-NMR (DMSO d₆): 10.23 (1H, s), 9.44 (s, 1H), 8.42 (s, 1H), 7.96 (d, 2H), 7.84 (s, 1H), 7.68-7.82 (m, 4H), 7.47-7.62 (m, 3H), 7.14 (s, 1H), 4.15 (t, 2H), 3.95 (s, 3H), 2.22-2.50 (m, 10H), 2.14 (s, 3H), 1.85-1.99 (m, 2H):
MS (+ve ESI): 527.6 (M+H)+.

EXAMPLE 401

Preparation of Compound No. 401 in Table 11

An analogous reaction to that described in example 358 but starting with diethylamine (0.11 ml, 1.1 mmol), yielded the title compound (49 mg, 43% yield) as a white solid:
¹H-NMR (DMSO d₆): 10.23 (s, 1H), 9.44 (s, 1H), 8.42 (s, 1H), 7.95 (d, 2H), 7.84 (s, 1H), 7.70-7.81 (m, 4H), 7.46-7.62 (m, 3H), 7.14 (s, 1H), 4.16 (t, 2H), 3.95 (s, 3H), 2.56 (t, 2H), 2.50 (q, 4H), 1.82-1.94 (m, 2H), 0.95 (t, 6H):
MS (+ve ESI): 500.6 (M+H)+.

EXAMPLE 402

Preparation of Compound No. 402 in Table 11

An analogous reaction to that described in example 358 but starting with diethanolamine (0.10 ml, 1.1-mmol), yielded the title compound (24 mg, 27% yield) as a white solid:
¹H-NMR (DMSO d₆): 10.23 (s, 1H), 9.44 (s, 1H), 8.41 (s, 1H), 7.96 (d, 2H), 7.84 (s, 1H), 7.68-7.82 (m, 4H), 7.46-7.63 (m, 3H), 7.16 (s, 1H), 4.30 (t, 2H), 4.18 (t, 2H), 3.95 (s, 3H), 3.34-3.49 (m, 4H), 2.64 (t, 2H), 2.44-2.60 (m, 4H), 1.82-1.95 (m, 2H):
MS (+ve ESI): 532.6 (M+H)+.

EXAMPLE 403

Preparation of Compound No. 403 in Table 11

An analogous reaction to that described in example 358 but starting with N,N'-dimethyl-3-aminopyrrolidine (114 mg, 1.0 mmol), yielded the title compound (85 mg, 78% yield) as a white solid:
HPLC/LCMS (RT): 5.08 min:
MS (+ve ESI): 541 (M+H)+.

EXAMPLE 404

Preparation of Compound No. 404 in Table 11

An analogous reaction to that described in example 358 but starting with 2-(N-methylamino) N-methylacetamide (102 mg, 1.0 mmol), yielded the title compound (30 mg, 28% yield) as a white solid:
HPLC/LCMS (RT): 5.44 min:
MS (+ve ESI): 529 (M+H)+.

EXAMPLE 405

Preparation of Compound No. 405 in Table 11

An analogous reaction to that described in example 358 but starting with 2-oxopiperazine (100 mg, 1.0 mmol), yielded the title compound (80 mg, 76% yield) as a white solid:
HPLC/LCMS (RT): 5.35 min:
MS (+ve ESI): 527 (M+H)+.

EXAMPLE 406

Preparation of Compound No. 406 in Table 11

An analogous reaction to that described in example 358 but starting with 3-amino-4-hydroxy tetrahydrofuran (103 mg, 1.0 mmol), yielded the title compound (18 mg, 17% yield) as a white solid:
HPLC/LCMS (RT): 5.30 min:
MS (+ve ESI): 530 (M+H)+.

EXAMPLE 407

Preparation of Compound No. 407 in Table 11

An analogous reaction to that described in example 358 but starting with 4-methylpiperidine (99 mg, 1.0 mmol), yielded the title compound (96 mg, 91% yield) as a white solid:
HPLC/LCMS (RT): 5.59 min:
MS (+ve ESI): 526 (M+H)+.

EXAMPLE 408

Preparation of Compound No. 408 in Table 11

An analogous reaction to that described in example 358 but starting with 3,5-dimethyl-piperidine (113 mg, 1.0 μmmol), yielded the title compound (85 mg, 79% yield) as a white solid:
HPLC/LCMS (RT): 5.68 min:
MS (+ve ESI): 540 (M+H)+.

EXAMPLE 409

Preparation of Compound No. 409 in Table 11

An analogous reaction to that described in example 358 but starting with N-methyl 3-amino-4-hydroxy-4-methyl tetrahydropyran (145 mg, 1.0 mmol), yielded the title compound (11 mg, 10% yield) as a white solid:
HPLC/LCMS (RT): 5.52 min:
MS (+ve ESI): 572 (M+H)+.

EXAMPLE 410

Preparation of Compound No. 410 in Table 11

An analogous reaction to that described in example 358 but starting with 3-aminocyclopent-1-ene (83 mg, 1.0 mmol), yielded the title compound (76 mg, 75% yield) as a white solid:
HPLC/LCMS (RT): 5.64 min:
MS (+ve ESI): 510 (M+H)+.

EXAMPLE 411

Preparation of Compound No. 411 in Table 11

An analogous reaction to that described in example 358 but starting with (2S, 4R)-2-(hydroxymethyl)-4-hydroxypyrrolidine (117 mg, 1.0 mmol), yielded the title compound (80 mg, 74% yield) as a white solid:
HPLC/LCMS (RT): 5.26 min:
MS (+ve ESI): 544 (M+H)+.

EXAMPLE 412

Preparation of Compound No. 412 in Table 11

An analogous reaction to that described in example 358 but starting with trans-N-methyl-3-hydroxy-4-amino-tetrahydropyran (131 mg, 1.0 mmol), yielded the title compound (58 mg, 52% yield) as a white solid:
HPLC/LCMS (RT): 5.38 min:
MS (+ve ESI): 558 (M+H)+.

EXAMPLE 413

Preparation of Compound No. 413 in Table 11

An analogous reaction to that described in example 358 but starting with N-methyl cyclobutylmethylamine (99 mg, 1.0 mmol), yielded the title compound (83 mg, 79% yield) as a white solid:
HPLC/LCMS (RT): 5.60 min:
MS (+ve ESI): 526 (M+H)+.

EXAMPLE 414

Preparation of Compound No. 414 in Table 11

An analogous reaction to that described in example 358 but starting with 3-hydroxy azetidine (73 mg, 1.0 mmol), yielded the title compound (19 mg, 19% yield) as a white solid:
HPLC/LCMS (RT): 5.40 min:
MS (+ve ESI): 500 (M+H)+.

EXAMPLE 415

Preparation of Compound No. 415 in Table 11

An analogous reaction to that described in example 358 but starting with N-methyl 3-cyano-methylamine (84 mg, 1.0 mmol), yielded the title compound (63 mg, 62% yield) as a white solid:
HPLC/LCMS (RT): 5.33 min:
MS (+ve ESI): 511 (M+H)+.

EXAMPLE 416

Preparation of Compound No. 416 in Table 11

An analogous reaction to that described in example 358 but starting with N-methyl 1-(2-aminoethyl)morpholine (144 mg, 1.0 mmol), yielded the title compound (91 mg, 80% yield) as a white solid:
HPLC/LCMS (RT): 5.38 min:
MS (+ve ESI): 571 (M+H)+.

EXAMPLE 417

Preparation of Compound No. 417 in Table 11

An analogous reaction to that described in example 358 but starting with 1-(2-methoxy-ethyl)piperazine (144 mg, 1.0 mmol), yielded the title compound (52 mg, 46% yield) as a white solid:
HPLC/LCMS (RT): 5.44 min:
MS (+ve ESI): 571 (M+H)+.

EXAMPLE 418

Preparation of Compound No. 418 in Table 11

An analogous reaction to that described in example 358 but starting with 2,6-dimethyl-morpholine (115 mg, 1.0 mmol), yielded the title compound (38 mg, 35% yield) as a white solid:
HPLC/LCMS (RT): 5.47 min:
MS (+ve ESI): 542 (M+H)+.

EXAMPLE 419

Preparation of Compound No. 419 in Table 11

An analogous reaction to that described in example 358 but starting with thiomorpholine (103 mg, 1.0 mmol), yielded the title compound (69 mg, 65% yield) as a white solid:
HPLC/LCMS (RT): 5.52 min:
MS (+ve ESI): 530 (M+H)+.

EXAMPLE 420

Preparation of Compound No. 420 in Table 11

An analogous reaction to that described in example 358 but starting with 2-methylpiperidine (99 mg, 1.0 mmol), yielded the title compound (103 mg, 98% yield) as a white solid:
HPLC/LCMS (RT): 5.46 min:
MS (+ve ESI): 526 (M+H)+.

EXAMPLE 421

Preparation of Compound No. 421 in Table 11

An analogous reaction to that described in example 358 but starting with 2,6-dimethyl-piperidine (113 mg, 1.0 mmol), yielded the title compound (69 mg, 64% yield) as a white solid:
HPLC/LCMS (RT): 5.60 min:
MS (+ve ESI): 540 (M+H)+.

EXAMPLE 422

Preparation of Compound No. 422 in Table 11

An analogous reaction to that described in example 358 but starting with 2-piperidine-methanol (115 mg, 1.0 mmol), yielded the title compound (66 mg, 61% yield) as a white solid:
HPLC/LCMS (RT): 5.46 min:
MS (+ve ESI): 542 (M+H)+.

EXAMPLE 423

Preparation of Compound No. 423 in Table 11

An analogous reaction to that described in example 358 but starting with 3-hydroxy-piperidine (101 mg, 1.0 mmol), yielded the title compound (89 mg, 84% yield) as a white solid:
HPLC/LCMS (RT): 5.31 min:
MS (+ye ESI): 528 (M+H)+.

EXAMPLE 424

Preparation of Compound No. 424 in Table 11

An analogous reaction to that described in example 358 but starting with 3-pyrroline (69 mg, 1.0 mmol), yielded the title compound (33 mg, 33% yield) as a white solid:
HPLC/LCMS (RT): 6.46 min:
MS (+ve ESI): 494 (M+H)+.

EXAMPLE 425

Preparation of Compound No. 425 in Table 11

An analogous reaction to that described in example 358 but starting with bis-(2-methoxy-ethyl)amine (133 mg, 1.0 mmol), yielded the title compound (43 mg, 38% yield) as a white solid:
HPLC/LCMS (RT): 5.50 min:
MS (+ve ESI): 560 (M+1)+.

EXAMPLE 426

Preparation of Compound No. 426 in Table 11

An analogous reaction to that described in example 358 but starting with 4-hydroxy-piperidine (101 mg, 1.0 mmol), yielded the title compound (90 mg, 85% yield) as a white solid:
HPLC/LCMS (RT): 5.25 min:
MS (+ve ESI): 528 (M+H)+.

EXAMPLE 427

Preparation of Compound No. 427 in Table 11

An analogous reaction to that described in example 358 but starting with L-prolinamide (114 mg, 1.0 mmol), yielded the title compound (87 mg, 81% yield) as a white solid:
HPLC/LCMS (RT): 5.40 min:
MS (+ve ESI): 541 (M+H)+.

EXAMPLE 428

Preparation of Compound No. 428 in Table 11

An analogous reaction to that described in example 358 but starting with 1-isopropyl-piperazine (128 mg, 1.0 mmol), yielded the title compound (22 mg, 20% yield) as a white solid:
HPLC/LCMS (RT): 5.44 min:
MS (+ve ESI): 555 (M+H)+.

EXAMPLE 429

Preparation of Compound No. 429 in Table 11

An analogous reaction to that described in example 358 but starting with N-methyl tetrahydrofurfurylamine (115 mg, 1.0 mmol), yielded the title compound (106 mg, 98% yield) as a white solid:
HPLC/LCMS (RT): 5.52 min:
MS (+ve ESI): 542 (M+H)+.

EXAMPLE 430

Preparation of Compound No. 430 in Table 11

An analogous reaction to that described in example 358 but starting with 4-acetyl piperidine hydrochloride (163 mg, 1.0 mmol), yielded the title compound (55 mg, 50% yield) as a white solid:
HPLC/LCMS (RT): 5.59 min:
MS (+ve ESI): 554 (M+H)+.

EXAMPLE 431

Preparation of Compound No. 431 in Table 11

An analogous reaction to that described in example 358 but starting with (R)-3-pyridinoyl (87 mg, 1.0 mmol), yielded the title compound (100 mg, 97% yield) as a white solid:
HPLC/LCMS (RT): 5.34 min:
MS (+ve ESI): 514 (M+H)+.

EXAMPLE 432

Preparation of Compound No. 432 in Table 11

An analogous reaction to that described in example 358 but starting with 1-methyl-4-(methylamino)piperidine (128 mg; 1.0 mmol), yielded the title compound (83 mg, 75% yield) as a white solid:
HPLC/LCMS (RT): 5.10 min:
MS (+ve ESI): 555 (M+H)+.

EXAMPLE 433

Preparation of Compound No. 433 in Table 11

An analogous reaction to that described in example 358 but starting with 4-(1-pyrrolidinyl)-piperidine (154 mg, 1.0 mmol), yielded the title compound (103 mg, 89% yield) as a white solid:
HPLC/LCMS (RT): 5.07 min:
MS (+ve ESI): 581 (M+H)+.

EXAMPLE 434

Preparation of Compound No. 434 in Table 11

An analogous reaction to that described in example 358 but starting with 1-methyl homo-piperazine (114 mg, 1.0 mmol), yielded the title compound (63 mg, 58% yield) as a white solid:
HPLC/LCMS (RT): 5.03 min:
MS (+ve ESI): 541 (M+H)+.

EXAMPLE 435

Preparation of Compound No. 435 in Table 11

An analogous reaction to that described in example 358 but starting with 4-amino-2,2-dimethyltetrahydropyran (126 mg, 1.0 mmol), yielded the title compound (63 mg, 57% yield) as a white solid:
HPLC/LCMS (RT): 5.44 min:
MS (+ve ESI): 556 (M+H)+.

EXAMPLE 436

Preparation of Compound No. 436 in Table 11

An analogous reaction to that described in example 358 but starting with N-(2-hydroxyethyl)piperazine (128 mg, 1.0 mmol), yielded the title compound (91 mg, 82% yield) as a white solid:
HPLC/LCMS (RT): 5.25 min:
MS (+ve ESI): 557 (M+H)+.

EXAMPLE 437

Preparation of Compound No. 437 in Table 11

An analogous reaction to that described in example 358 but starting with 2-(methylamino)-ethanol (75 mg, 1.0 mmol), yielded the title compound (81 mg, 81% yield) as a white solid:
HPLC/LCMS (RT): 5.24 min:
MS (+ve ESI): 502 (M+H)+.

EXAMPLE 438

Preparation of Compound No. 438 in Table 11

An analogous reaction to that described in example 358 but starting with (S)-pyrrolidine-methanol (101 mg, 1.0 mmol), yielded the title compound (87 mg, 83% yield) as a white solid:
HPLC/LCMS (RT): 5.39 min:
MS (+ve ESI): 528 (M+H)+.

EXAMPLE 439

Preparation of Compound No. 439 in Table 11

An analogous reaction to that described in example 358 but starting with 3-piperidine-methanol (115 mg, 1.0 mmol), yielded the title compound (105 mg, 97% yield) as a white solid:
HPLC/LCMS (RT): 5.34 min:
MS (+ve ESI): 542 (M+H)+.

EXAMPLE 440

Preparation of Compound No. 440 in Table 11

An analogous reaction to that described in example 358 but starting with cis-2,5-dimethyl-piperazine (114 mg, 1.0 mmol), yielded the title compound (91 mg, 84% yield) as a white solid:
HPLC/LCMS (RT): 5.16 min:
MS (+ve ESI): 541 (M+H)+.

EXAMPLE 441

Preparation of Compound No. 441 in Table 11

An analogous reaction to that described in example 358 but starting with a solution of methylamine in tetrahydrofuran (60 ml of a 2.0N solution, 120 mmol), yielded the title compound (2.6 g, 38% yield) as a white solid, after purification by flash chromatography on silica gel, eluting with 5-10% methanol in dichloromethane:
$^1$H-NMR (DMSO $d_6$): 10.30 (s, 1H), 9.42 (s, 1H), 8.40 (s, 1H), 7.98 (d, 2H), 7.82 (s, 1H), 7.70-7.80 (m, 4H); 7.45-7.60 (m, 3H), 7.15 (s, 1H), 4.20 (t, 2H), 3.98 (s, 3H), 2.62 (t, 2H), 2.30 (s, 3H), 1.82-1.98 (m, 2H):
MS (−ve ESI): 456 (M−1)$^-$

EXAMPLE 442

Preparation of Compound No. 442 in Table 12

(R)-4-((4-(N-benzoyl)amino)anilino)-6-methoxy-7-(glycidyl)quinazoline (88 mg, 0.2 mmol) was added to a stirred solution of N,N-dimethylethylenediamine (88 mg, 1.00 mmol) in dimethylacetamide (2 ml) and the reaction was stirred at 50° C. for 24 hours. The reactions were allowed to cool to ambient temperature, diluted with methanol (5 ml) and adsorbed onto silica for chromatography. Purification by flash chromatography on silica gel, eluting with 0-10% methanol in dichloromethane yielded the title compound (36 mg, 34% yield) as an off-white solid:
HPLC/LCMS (RT): 4.93 min:
MS (+ve ESI): 531 (M+H)$^+$.

EXAMPLE 443

Preparation of Compound No. 443 in Table 12

An analogous reaction to that described in example 442, but starting with N,N-diethyl-ethylenediamine (116 mg, 1.00 mmol) and the S enantiomer of the starting epoxide, yielded the title compound (102 mg, 91% yield) as an off-white solid:
HPLC/LCMS (RT): 4.98 min:
MS (+ve ESI): 559 (M+H)$^+$.

EXAMPLE 444

Preparation of Compound No. 444 in Table 12

An analogous reaction to that described in example 442, but starting with 2-(2-aminoethoxy)-ethanol (105 mg, 1.00 mmol), yielded the title compound (71 mg, 67% yield) as an off-white solid:
HPLC/LCMS (RT): 5.17 min:
MS (+ve ESI): 548 (M+H)$^+$.

EXAMPLE 445

Preparation of Compound No. 445 in Table 12

An analogous reaction to that described in example 442, but starting with ethanolamine (62 mg, 1.00 mmol), yielded the title compound (33 mg, 33% yield) as an off-white solid:
HPLC/LCMS (RT): 5.18 min:
$^1$H-NMR (DMSO $d_6$):
MS (+ve ESI): 504 (M+H)$^+$.

EXAMPLE 446

Preparation of Compound No. 446 in Table 12

An analogous reaction to that described in example 442, but starting with 2-(ethylthio)ethylamine (106 mg, 1.00 mmol), yielded the title compound (28 mg, 26% yield) as an off-white solid:
HPLC/LCMS (RT): 5.51 min:
MS (+ve ESI): 548 (M+H)$^+$.

EXAMPLE 447

Preparation of Compound No. 447 in Table 12

An analogous reaction to that described in example 442, but starting with 3-(diethylamino)-propylamine (130 mg, 1.00 mmol), yielded the title compound (29 mg, 26% yield) as an off-white solid:
HPLC/LCMS (RT): 4.97 min:
MS (+ve ESI): 573 (M+H)$^+$.

EXAMPLE 448

Preparation of Compound No. 448 in Table 12

An analogous reaction to that described in example 442, but starting with 3-ethoxypropyl-amine (104 mg, 1.00 mmol), yielded the title compound (68 mg, 62% yield) as an off-white solid:
HPLC/LCMS (RT): 5.41 min:
MS (+ve ESI): 546 (M+H)$^+$.

EXAMPLE 449

Preparation of Compound No. 449 in Table 12

An analogous reaction to that described in example 442, but starting with 3-amino-1-propyl-amine (75 mg, 1.00 mmol), yielded the title compound (35 mg, 34% yield) as an off-white solid:
HPLC/LCMS (RT): 5.20 min:
MS (+ve ESI): 518 (M+H)$^+$.

EXAMPLE 450

Preparation of Compound No. 450 in Table 12

An analogous reaction to that described in example 442, but starting with 5-amino-1-pentyl-amine (103 mg, 1.00 mmol), yielded the title compound (67 mg, 62% yield) as an off-white solid:
HPLC/LCMS (RT): 5.26 min:
MS (+ve ESI): 546 (M+H)$^+$.

EXAMPLE 451

Preparation of Compound No. 451 in Table 12

An analogous reaction to that described in example 442, but starting with 4-amino-1-butanol (89 mg, 1.00 mmol), yielded the title compound (47 mg, 44% yield) as an off-white solid:
HPLC/LCMS (RT): 5.16 min:
MS (+ve ESI): 532 (M+H)$^+$.

EXAMPLE 452

Preparation of Compound No. 452 in Table 12

An analogous reaction to that described in example 442, but starting with 3-amino-5-methyl-pyrazole (98 mg, 1.00 mmol), yielded the title compound (35 mg, 32% yield) as an off-white solid:
HPLC/LCMS (RT): 5.44 min:
MS (+ve ESI): 540 (M+H)$^+$.

EXAMPLE 453

Preparation of Compound No. 453 in Table 12

An analogous reaction to that described in example 442, but starting with 1-(aminomethyl)-1-cyclohexanol hydrochloride (167 mg, 1.00 mmol), yielded the title compound (36 mg, 32% yield) as an off-white solid:
HPLC/LCMS (RT): 5.50 min:
MS (+ve ESI): 572 (M+H)$^+$.

EXAMPLE 454

Preparation of Compound No. 454 in Table 12

An analogous reaction to that described in example 442, but starting with thiophene-2-ethyl-amine (128 mg, 1.00 mmol), yielded the title compound (24 mg, 21% yield) as an off-white solid:
HPLC/LCMS (RT): 5.68 min:
$^1$H-NMR (DMSO d$_6$):
MS (+ve ESI): 570 (M+H)$^+$.

EXAMPLE 455

Preparation of Compound No. 455 in Table 12

An analogous reaction to that described in example 442, but starting with 2-amino-1-hexanol (118 mg, 1.00 mmol), yielded the title compound (66 mg, 59% yield) as an off-white solid:
HPLC/LCMS (RT): 5.55 min:
MS (+ve ESI): 560 (M+H)$^+$.

EXAMPLE 456

Preparation of Compound No. 456 in Table 12

An analogous reaction to that described in example 442, but starting with 2-(2-aminoethyl)-1-methylpyrrolidine (128 mg, 1.00 mmol), yielded the title compound (46 mg, 41% yield) as an off-white solid:
HPLC/LCMS (RT): 5.05 min:
MS (+ve ESI): 571 (M+H)$^+$.

EXAMPLE 457

Preparation of Compound No. 457 in Table 12

An analogous reaction to that described in example 442, but starting with 5-methyl-2-furan-methylamine (112 mg, 1.00 mmol), yielded the title compound (27 mg, 24% yield) as an off-white solid:
HPLC/LCMS (RT): 5.56 min:
MS (+ve ESI): 554 (M+H)$^+$.

EXAMPLE 458

Preparation of Compound No. 458 in Table 12

An analogous reaction to that described in example 442, but starting with 3-amino-2,2-dimethyl-1-propanol (104 mg, 1.00 mmol), yielded the title compound (106 mg, 95% yield) as an off-white solid:
HPLC/LCMS (RT): 5.34 min:
MS (+ve ESI): 546 (M+H)$^+$.

EXAMPLE 459

Preparation of Compound No. 459 in Table 12

An analogous reaction to that described in example 443, but starting with 3-aminomethyl-thiophene hydrochloride (150 mg, 1.00 mmol), yielded the title compound (55 mg, 50% yield) as an off-white solid:
HPLC/LCMS (RT): 5.54 min:
MS (+ve ESI): 556 (M+H)$^+$.

EXAMPLE 460

Preparation of Compound No. 460 in Table 12

An analogous reaction to that described in example 443, but starting with 3-aminopropane-1,2-diol (91 mg, 1.00 mmol), yielded the title compound (11 mg, 10% yield) as an off-white solid:
HPLC/LCMS (RT): 5.16 min:
MS (+ve ESI): 534 (M+H)$^+$.

EXAMPLE 461

Preparation of Compound No. 461 in Table 12

An analogous reaction to that described in example 443, but starting with cyclobutylamine (72 mg, 1.00 mmol), yielded the title compound (58 mg, 56% yield) as an off-white solid:
HPLC/LCMS (RT): 5.34 min:
MS (+ve ESI): 514 (M+H)$^+$.

EXAMPLE 462

Preparation of Compound No. 462 in Table 12

An analogous reaction to that described in example 443, but starting with cyclopentylamine (86 mg, 1.00 mmol), yielded the title compound (74 mg, 71% yield) as an off-white solid:
HPLC/LCMS (RT): 5.34 min:
MS (+ve ESI): 528 (M+H)$^+$.

EXAMPLE 463

Preparation of Compound No. 463 in Table 12

An analogous reaction to that described in example 443, but starting with 1-(3-aminopropyl)-imidazole (125 mg, 1.00 mmol), yielded the title compound (92 mg, 81% yield) as an off-white solid:
HPLC/LCMS (RT): 4.92 min:
MS (+ve ESI): 568 (M+H)$^+$.

EXAMPLE 464

Preparation of Compound No. 464 in Table 12

An analogous reaction to that described in example 442, but starting with cyclohexylamine (100 mg, 1.00 mmol), yielded the title compound (58 mg, 53% yield) as an off-white solid:
HPLC/LCMS (RT): 5.51 min:
MS (+ve ESI): 542 (M+H)$^+$.

EXAMPLE 465

Preparation of Compound No. 465 in Table 12

An analogous reaction to that described in example 442, but starting with 4-aminocyclo-hexanol (116 mg, 1.00 mmol), yielded the title compound (56 mg, 51% yield) as an off-white solid:
HPLC/LCMS (RT): 5.17 min:
MS (+ve ESI): 558 (M+H)$^+$.

EXAMPLE 466

Preparation of Compound No. 466 in Table 12

An analogous reaction to that described in example 442, but starting with cyclohexanemethyl-amine (114 mg, 1.00 mmol), yielded the title compound (68 mg, 62% yield) as an off-white solid:
HPLC/LCMS (RT): 5.77 min:
MS (+ve ESI): 556 (M+H)$^+$.

EXAMPLE 467

Preparation of Compound No. 467 in Table 12

An analogous reaction to that described in example 442, but starting with 2-amino-2-methyl-1,3-propanediol (106 mg, 1.00 mmol), yielded the title compound (66 mg, 60% yield) as an off-white solid:
HPLC/LCMS (RT): 5.25 min:
MS (+ve ESI): 548 (M+H)$^+$.

EXAMPLE 468

Preparation of Compound No. 468 in Table 12

An analogous reaction to that described in example 443, but starting with 2-amino-2-(hydroxymethyl)-1,3-propanediol (122 mg, 1.00 mmol), yielded the title compound (18 mg, 16% yield) as an off-white solid:
HPLC/LCMS (RT): 5.21 min:
MS (+ve ESI): 564 (M+H)$^+$.

EXAMPLE 469

Preparation of Compound No. 469 in Table 12

An analogous reaction to that described in example 442, but starting with 2-amino-2-ethyl-1,3-propanediol (120 mg, 1.00 mmol), yielded the title compound (56 mg, 49% yield) as an off-white solid:
HPLC/LCMS (RT): 5.26 min:
MS (+ve ESI): 562 (M+H)$^+$.

EXAMPLE 470

Preparation of Compound No. 470 in Table 12

An analogous reaction to that described in example 442, but starting with 2-(aminoethyl)-1-ethylpyrrolidine (128 mg, 1.00 mmol), yielded the title compound (74 mg, 65% yield) as an off-white solid:
HPLC/LCMS (RT): 5.01 min:
MS (+ve ESI): 571 (M+H)$^+$.

EXAMPLE 471

Preparation of Compound No. 471 in Table 12

An analogous reaction to that described in example 442, but starting with tetrahydrofurfuryl-amine (102 mg, 1.00 mmol), yielded the title compound (73 mg, 67% yield) as an off-white solid:
HPLC/LCMS (RT): 5.41 min:
MS (+ve ESI): 544 (M+H)$^+$.

EXAMPLE 472

Preparation of Compound No. 472 in Table 12

An analogous reaction to that described in example 442, but starting with isonipecotamide (128 mg, 1.00 mmol), yielded the title compound (86 mg, 75% yield) as an off-white solid:
HPLC/LCMS (RT): 5.18 min:
MS (+ve ESI): 571 (M+H)$^+$.

EXAMPLE 473

Preparation of Compound No. 473 in Table 12

An analogous reaction to that described in example 442, but starting with 4-(2-aminoethyl)-morpholine (130 mg, 1.00 mmol), yielded the title compound (112 mg, 98% yield) as an off-white solid:
HPLC/LCMS (RT): 5.04 min:
MS (+ve ESI): 573 (M+H)$^+$.

EXAMPLE 474

Preparation of Compound No. 474 in Table 12

An analogous reaction to that described in example 442, but starting with 2-amino-2-methyl-1-propanol (89 mg, 1.00 mmol), yielded the title compound (75 mg, 71% yield) as an off-white solid:
HPLC/LCMS (RT): 5.22 min:
MS (+ve ESI): 532 (M+H)$^+$.

EXAMPLE 475

Preparation of Compound No. 475 in Table 12

An analogous reaction to that described in example 442, but starting with 3-amino-3-methyl-1-butanol (103 mg, 1.00 mmol), yielded the title compound (48 mg, 44% yield) as an off-white solid:
HPLC/LCMS (RT): 5.28 min:
MS (+ve ESI): 546 (M+H)$^+$.

EXAMPLE 476

Preparation of Compound No. 476 in Table 12

An analogous reaction to that described in example 442, but starting with isopropylamine (59 mg, 1.00 mmol), yielded the title compound (73 mg, 73% yield) as an off-white solid:
HPLC/LCMS (RT): 5.17 min:
MS (+ve ESI): 502 (M+H)$^+$.

EXAMPLE 477

Preparation of Compound No. 477 in Table 12

An analogous reaction to that described in example 442, but starting with 2-amino-1-propanol (75 mg, 1.00 mmol), yielded the title compound (59 mg, 57% yield) as an off-white solid:
HPLC/LCMS (RT): 5.18 min:
MS (+ve ESI): 518 (M+H)$^+$.

EXAMPLE 478

Preparation of Compound No. 478 in Table 12

An analogous reaction to that described in example 442, but starting with cyclopropylamine (57 mg, 1.00 mmol), yielded the title compound (59 mg, 59% yield) as an off-white solid:
HPLC/LCMS (RT): 5.24 min:
MS (+ve ESI): 500 (M+H)$^+$.

EXAMPLE 479

Preparation of Compound No. 479 in Table 12

An analogous reaction to that described in example 442, but starting with thiophene-2-methylamine (113 mg, 1.00 mmol), yielded the title compound (14 mg, 13% yield) as an off-white solid:
HPLC/LCMS (RT): 5.50 min:
MS (+ve ESI): 556 (M+H)$^+$.

EXAMPLE 480

Preparation of Compound No. 480 in Table 12

An analogous reaction to that described in example 442, but starting with N-acetylethylene-diamine (102 mg, 1.00 mmol), yielded the title compound (73 mg, 67% yield) as an off-white solid:
HPLC/LCMS (RT): 5.21 min:
MS (+ve ESI): 545 (M+H)$^+$.

EXAMPLE 481

Preparation of Compound No. 481 in Table 12

An analogous reaction to that described in example 442, but starting with 2-(methylthio)ethylamine (92 mg, 1.00 mmol), yielded the title compound (51 mg, 48% yield) as an off-white solid:
HPLC/LCMS (RT): 5.34 min:
MS (+ve ESI): 534 (M+H)$^+$.

EXAMPLE 482

Preparation of Compound No. 482 in Table 12

An analogous reaction to that described in example 442, but starting with N-(2-aminoethyl)-piperidine (128 mg, 1.00 mmol), yielded the title compound (99 mg, 87% yield) as an off-white solid:
HPLC/LCMS (RT): 4.92 min:
MS (+ve ESI): 571 (M+H)$^+$.

EXAMPLE 483

Preparation of Compound No. 483 in Table 12

An analogous reaction to that described in example 443, but starting with L-prolinamide (114 mg, 1.00 mmol), yielded the title compound (112 mg, 99% yield) as an off-white solid:
HPLC/LCMS (RT): 5.38 min:
MS (+ve ESI): 557 (M+H)$^+$.

EXAMPLE 484

Preparation of Compound No. 484 in Table 12

An analogous reaction to that described in example 443, but starting with S-leucinol (117 mg, 1.00 mmol), yielded the title compound (76 mg, 68% yield) as an off-white solid:
HPLC/LCMS (RT): 5.44 min:
MS (+ve ESI): 560 (M+H)$^+$.

EXAMPLE 485

Preparation of Compound No. 485 in Table 12

An analogous reaction to that described in example 443, but starting with D-2-amino-1-butanol (75 mg, 1.00 mmol), yielded the title compound (78 mg, 73% yield) as an off-white solid:
HPLC/LCMS (RT): 5.27 min:
MS (+ve ESI): 532 (M+H)$^+$.

EXAMPLE 486

Preparation of Compound No. 486 in Table 12

An analogous reaction to that described in example 442, but starting with L-prolinamide (114 mg, 1.00 mmol), yielded the title compound (109 mg, 96% yield) as an off-white solid:
HPLC/LCMS (RT): 5.28 min:
MS (+ve ESI): 557 (M+H)$^+$.

EXAMPLE 487

Preparation of Compound No. 487 in Table 12

An analogous reaction to that described in example 442, but starting with S-leucinol (117 mg, 1.00 mmol), yielded the title compound (71 mg, 64% yield) as an off-white solid:
HPLC/LCMS (RT): 5.26 min:
MS (+ve ESI) 560 (M+H)$^+$.

EXAMPLE 488

Preparation of Compound No. 488 in Table 12

An analogous reaction to that described in example 442, but starting with D-2-amino-1-butanol (75 mg, 1.00 mmol), yielded the title compound (59 mg, 57% yield) as an off-white solid:
HPLC/LCMS (RT): 5.24 min:
MS (+ve ESI): 518 (M+H)$^+$.

EXAMPLE 489

Preparation of Compound No. 489 in Table 12

An analogous reaction to that described in example 443, but starting with N,N-dimethyl-ethylenediamine (88 mg, 1.00 mmol), yielded the title compound (38 mg, 36% yield) as an off-white solid:
HPLC/LCMS (RT): 4.92 min:
MS (+ve ESI): 531 (M+H)$^+$.

EXAMPLE 490

Preparation of Compound No. 490 in Table 12

An analogous reaction to that described in example 443, but starting with 2-(2-aminoethoxy)-ethanol (105 mg, 1.00 mmol), yielded the title compound (73 mg, 67% yield) as an off-white solid:
HPLC/LCMS (RT): 5.19 min:
MS (+ve ESI): 548 (M+H)$^+$.

EXAMPLE 491

Preparation of Compound No. 491 in Table 12

An analogous reaction to that described in example 443, but starting with ethanolamine (61 mg, 1.00 mmol), yielded the title compound (63 mg, 63% yield) as an off-white solid:
HPLC/LCMS (RT): 5.17 min:
MS (+ve ESI): 504 (M+H)$^+$.

EXAMPLE 492

Preparation of Compound No. 492 in Table 12

An analogous reaction to that described in example 443, but starting with 2-(ethylthio)ethyl-amine (105 mg, 1.00 mmol), yielded the title compound (28 mg, 25% yield) as an off-white solid:
HPLC/LCMS (RT): 5.53 min:
MS (+ve ESI): 548 (M+H)$^+$.

EXAMPLE 493

Preparation of Compound No. 493 in Table 12

An analogous reaction to that described in example 443, but starting with 3-(diethylamino)-propylamine (130 mg, 1.00 mmol), yielded the title compound (40 mg, 35% yield) as an off-white solid:
HPLC/LCMS (RT): 5.02 min:
MS (+ve ESI): 573 (M+H)$^+$.

EXAMPLE 494

Preparation of Compound No. 494 in Table 12

An analogous reaction to that described in example 443, but starting with 3-ethoxypropyl-amine (103 mg, 1.00 mmol), yielded the title compound (84 mg, 77% yield) as an off-white solid:
HPLC/LCMS (RT): 5.43 min:
MS (+ve ESI): 546 (M+H)$^+$.

EXAMPLE 495

Preparation of Compound No. 495 in Table 12

An analogous reaction to that described in example 443, but starting with 3-amino-1-propanol (75 mg, 1.00 mmol), yielded the title compound (61 mg, 59% yield) as an off-white solid:
HPLC/LCMS (RT): 5.16 min:
MS (+ve ESI): 518 (M+H)$^+$.

EXAMPLE 496

Preparation of Compound No. 496 in Table 12

An analogous reaction to that described in example 443, but starting with 5-amino-1-pentanol (103 mg, 1.00 mmol), yielded the title compound (65 mg, 60% yield) as an off-white solid:
HPLC/LCMS (RT): 5.21 min:
MS (+ve ESI): 546 (M+H)$^+$.

EXAMPLE 497

Preparation of Compound No. 497 in Table 12

An analogous reaction to that described in example 443, but starting with 4-amino-1-butanol (89 mg, 1.00 mmol), yielded the title compound (45 mg, 42% yield) as an off-white solid:
HPLC/LCMS (RT): 5.24 min:
MS (+ve ESI): 532 (M+H)$^+$.

EXAMPLE 498

Preparation of Compound No. 498 in Table 12

An analogous reaction to that described in example 443, but starting with 3-amino-5-methyl-pyrazole (98 mg, 1.00 mmol), yielded the title compound (38 mg, 35% yield) as an off-white solid:
HPLC/LCMS (RT): 5.48 min:
MS (+ve ESI): 540 (M+H)$^+$.

EXAMPLE 499

Preparation of Compound No. 499 in Table 12

An analogous reaction to that described in example 443, but starting with 1-(aminomethyl)-1-cyclohexanol (129 mg, 1.00 mmol), yielded the title compound (108 mg, 95% yield) as an off-white solid:
HPLC/LCMS (RT): 5.52 min:
MS (+ve ESI): 572 (M+H)$^+$.

EXAMPLE 500

Preparation of Compound No. 500 in Table 12

An analogous reaction to that described in example 443, but starting with thiophene-2-ethyl-amine (127 mg, 1.00 mmol), yielded the title compound (62 mg, 54% yield) as an off-white solid:
HPLC/LCMS (RT): 5.70 min:
MS (+ve ESI): 570 (M+H)$^+$.

EXAMPLE 501

Preparation of Compound No. 501 in Table 12

An analogous reaction to that described in example 443, but starting with 2-amino-1-hexanol (117 mg, 1.00 mmol), yielded the title compound (88 mg, 79% yield) as an off-white solid:
HPLC/LCMS (RT): 5.56 min:
MS (+ve ESI): 560 (M+H)$^+$.

EXAMPLE 502

Preparation of Compound No. 502 in Table 12

An analogous reaction to that described in example 443, but starting with 2-(2-aminoethyl)-1-methylpyrrolidine (128 mg, 1.00 mmol), yielded the title compound (108 mg, 95% yield) as an off-white solid:
HPLC/LCMS (RT): 4.98 min:
MS (+ve ESI): 571 (M+H)$^+$.

EXAMPLE 503

Preparation of Compound No. 503 in Table 12

An analogous reaction to that described in example 443, but starting with 5-methyl-2-furanmethylamine (111 mg, 1.00 mmol), yielded the title compound (55 mg, 50% yield) as an off-white solid:
HPLC/LCMS (RT): 5.51 min:
MS (+ve ESI): 554 (M+H)$^+$.

EXAMPLE 504

Preparation of Compound No. 504 in Table 12

An analogous reaction to that described in example 443, but starting with 3-amino-2,2-dimethyl-1-propanol (103 mg, 1.00 mmol), yielded the title compound (56 mg, 50% yield) as an off-white solid:
HPLC/LCMS (RT): 5.48 mm:
MS (+ve ESI): 556 (M+H)$^+$.

EXAMPLE 505

Preparation of Compound No. 505 in Table 12

An analogous reaction to that described in example 442, but starting with 3-aminomethylthiophene hydrochloride (150 mg, 1.00 mmol), yielded the title compound (105 mg, 97% yield) as an off-white solid:
HPLC/LCMS (RT): 5.34 min:
MS (+ve ESI): 546 (M+H)$^+$.

EXAMPLE 506

Preparation of Compound No. 506 in Table 12

An analogous reaction to that described in example 442, but starting with cyclobutylamine (71 mg, 1.00 mmol), yielded the title compound (80 mg, 78% yield) as an off-white solid:
HPLC/LCMS (RT): 5.36 min:
MS (+ve ESI): 514 (M+H)$^+$.

EXAMPLE 507

Preparation of Compound No. 507 in Table 12

An analogous reaction to that described in example 442, but starting with cyclopentylamine (85 mg, 1.00 mmol), yielded the title compound (83 mg, 78% yield) as an off-white solid:
HPLC/LCMS (RT): 5.37 min:
MS (+ve ESI): 528 (M+H)$^+$.

EXAMPLE 508

Preparation of Compound No. 508 in Table 12

An analogous reaction to that described in example 443, but starting with cyclohexylamine (99 mg, 1.00 mmol), yielded the title compound (77 mg, 71% yield) as an off-white solid:
HPLC/LCMS (RT): 5.50 min:
MS (+ve ESI): 542 (M+H)$^+$.

EXAMPLE 509

Preparation of Compound No. 509 in Table 12

An analogous reaction to that described in example 443, but starting with 4-aminocyclo-hexanol (115 mg, 1.00 mmol), yielded the title compound (35 mg, 31% yield) as an off-white solid:
HPLC/LCMS (RT): 5.35 min:
MS (+ve ESI): 558 (M+H)$^+$.

EXAMPLE 510

Preparation of Compound No. 510 in Table 12

An analogous reaction to that described in example 443, but starting with cyclohexanemethyl-amine (113 mg, 1.00 mmol), yielded the title compound (97 mg, 87% yield) as an off-white solid:
HPLC/LCMS (RT): 5.66 min:
MS (+ve ESI): 556 (M+H)$^+$.

EXAMPLE 511

Preparation of Compound No. 511 in Table 12

An analogous reaction to that described in example 443, but starting with 2-amino-2-methyl-1,3-propanediol (105 mg, 1.00 mmol), yielded the title compound (105 mg, 96% yield) as an off-white solid:
HPLC/LCMS (RT): 5.17 min:
MS (+ve ESI): 548 (M+H)$^+$.

EXAMPLE 512

Preparation of Compound No. 512 in Table 12

An analogous reaction to that described in example 443, but starting with 2-amino-2-ethyl-1,3-propanediol (119 mg, 1.00 mmol), yielded the title compound (112 mg, 99% yield) as an off-white solid:
HPLC/LCMS (RT): 5.24 min:
MS (+ve ESI): 562 (M+H)$^+$.

EXAMPLE 513

Preparation of Compound No. 513 in Table 12

An analogous reaction to that described in example 443, but starting with 2-(aminomethyl)-1-ethylpyrrolidine (128 mg, 1.00 mmol), yielded the title compound (108 mg, 95% yield) as an off-white solid:
HPLC/LCMS (RT): 4.95 min:
MS (+ve ESI): 571 (M+H)$^+$.

EXAMPLE 514

Preparation of Compound No. 514 in Table 12

An analogous reaction to that described in example 443, but starting with tetrahydrofurfuryl-amine (102 mg, 1.00 mmol), yielded the title compound (92 mg, 84% yield) as an off-white solid:
HPLC/LCMS (RT): 5.44 min:
MS (+ve ESI): 544 (M+H)$^+$.

EXAMPLE 515

Preparation of Compound No. 515 in Table 12

An analogous reaction to that described in example 443, but starting with isonepecotamide (128 mg, 1.00 mmol), yielded the title compound (94 mg, 82% yield) as an off-white solid:
HPLC/LCMS (RT): 5.24 min:
MS (+ve ESI): 571 (M+H)$^+$.

EXAMPLE 516

Preparation of Compound No. 516 in Table 12

An analogous reaction to that described in example 443, but starting with 4-(2-aminoethyl)morpholine (128 mg, 1.00 mmol), yielded the title compound (77 mg, 67% yield) as an off-white solid:
HPLC/LCMS (RT): 5.02 min:
MS (+ve ESI): 573 (M+H)$^+$.

EXAMPLE 517

Preparation of Compound No. 517 in Table 12

An analogous reaction to that described in example 443, but starting with 2-amino-2-methyl-1-propanol (89 mg, 1.00 mmol), yielded the title compound (71 mg, 67% yield) as an off-white solid:
HPLC/LCMS (RT): 5.21 min:
MS (+ve ESI): 532 (M+H)$^+$.

EXAMPLE 518

Preparation of Compound No. 518 in Table 12

An analogous reaction to that described in example 443, but starting with 3-amino-3-methyl-1-butanol (103 mg, 1.00 mmol), yielded the title compound (68 mg, 62% yield) as an off-white solid:
HPLC/LCMS (RT): 5.26 min:
MS (+ve ESI): 546 (M+H)$^+$.

EXAMPLE 519

Preparation of Compound No. 519 in Table 12

An analogous reaction to that described in example 443, but starting with isopropylamine (59 mg, 1.00 mmol), yielded the title compound (76 mg, 76% yield) as an off-white solid:
HPLC/LCMS (RT): 5.26 min:
MS (+ve ESI): 502 (M+H)$^+$.

EXAMPLE 520

Preparation of Compound No. 520 in Table 12

An analogous reaction to that described in example 443, but starting with 2-amino-1-propanol (75 mg, 1.00 mmol), yielded the title compound (56 mg, 54% yield) as an off-white solid:
HPLC/LCMS (RT): 5.17 min:
MS (+ve ESI): 518 (M+H)$^+$.

EXAMPLE 521

Preparation of Compound No. 521 in Table 12

An analogous reaction to that described in example 443, but starting with cyclopropylamine (57 mg, 1.00 mmol), yielded the title compound (58 mg, 58% yield) as an off-white solid:
HPLC/LCMS (RT): 5.26 min:
MS (+ve ESI): 500 (M+H)$^+$.

EXAMPLE 522

Preparation of Compound No. 522 in Table 12

An analogous reaction to that described in example 443, but starting with thiophene-2-methylamine (114 mg, 1.00 mmol), yielded the title compound (55 mg, 50% yield) as an off-white solid:
HPLC/LCMS (RT): 5.48 min:
MS (+ve ESI): 556 (M+H)$^+$.

EXAMPLE 523

Preparation of Compound No. 523 in Table 12

An analogous reaction to that described in example 443, but starting with N-acetylethylene-diamine (102 mg, 1.00 mmol), yielded the title compound (98 mg, 90% yield) as an off-white solid:
HPLC/LCMS (RT): 5.21 min:
MS (+ve ESI): 545 (M+H)$^+$.

EXAMPLE 524

Preparation of Compound No. 524 in Table 12

An analogous reaction to that described in example 443, but starting with 2-(methylthio)-ethylamine (92 mg, 1.00 mmol), yielded the title compound (76 mg, 71% yield) as an off-white solid:
HPLC/LCMS (RT): 5.32 min:
MS (+ve ESI): 534 (M+H)$^+$.

EXAMPLE 525

Preparation of Compound No. 525 in Table 12

An analogous reaction to that described in example 442, but starting with diethanolamine (0.5 ml), yielded the title compound (16 mg, 16% yield) as an off-white solid:
$^1$H-NMR (DMSO d$_6$): 10.23 (s, 1H), 9.45 (s, 1H), 8.42 (s, 1H), 7.95 (d, 2H), 7.85 (s, 1H), 7.66-7.82 (m, 4H), 7.46-7.63 (m, 3H), 7.18 (s, 1H), 4.85 (s, 1H), 4.39 (s, 2H), 4.17 (m, 1H), 3.99-4.07 (m, 2H), 3.96 (s, 3H), 3.39-3.50 (m, 4H), 2.51-2.71 (m, 6H):
MS (+ve ESI): 548 (M+H)$^+$.

EXAMPLE 526

Preparation of Compound No. 526 in Table 13

Di-tert-butyl-N,N-diethylphosphoramide (0.42 ml, 1.51 mmol) was added dropwise over 2 minutes to a suspension of 4-((4-(N-benzoyl)amino)anilino)-6-methoxy-7-(2-hydroxyethoxy)quinazoline (500 mg, 1.16 mmol) and tetrazole (244 mg, 0.348 mmol) in tetrahydrofuran (16 ml) at ambient temperature. The reaction was stirred for 1 hour at ambient temperature before addition of more di-tert-buty; —N,N-diethylphosphoramide (0.42 ml, 1.51 mmol) and a further stirring for 5 hours. Meta-chlorobenzoic acid (0.572 g of 70% activity, 2.32 mmol) was added, the reaction was stirred at ambient temperature for 30 minutes and then poured into water. Extraction of the aqueous phase with dichloromethane (3×25 ml) followed by solvent evaporation in vacuo and trituration of the resultant yellow solid with diethyl ether yielded the title compound (163 mg, 23% yield) as a pale yellow solid:
$^1$H-NMR (DMSO d$_6$): 10.23 (s, 1H), 9.45 (s, 1H), 8.42 (s, 1H), 7.96 (d, 2H), 7.85 (s, 1H), 7.70-7.81 (m, 4H), 7.48-7.62 (m, 3H), 7.19 (s, 1H), 4.30-4.38 (m, 2H), 4.18-4.28 (m, 2H), 3.95 (s, 3H), 1.42 (s, 18H):
MS (+ve ESI): 623 (M+H)$^+$.

EXAMPLE 527

Preparation of Compound No. 527 in Table 13

An analogous reaction to that described in example 526, but starting with di-benzyl-N,N-diethylphosphoramide (0.27 ml, 0.91 mmol), yielded the title compound (69 mg, 14% yield) as a pale yellow solid:
$^1$H-NMR (DMSO d$_6$): 10.23 (s, 1H), 9.46 (s, 1H), 8.43 (s, 1H), 7.96 (d, 2H), 7.84 (s, 1H), 7.70-7.82 (m, 4H), 7.47-7.63 (m, 3H), 7.25-7.42 (m, 10H), 7.20 (s, 1H), 5.08 (s, 2H), 5.05 (s, 2H), 4.30-4.43 (m, 4H), 3.88 (s, 3H):
MS (+ve ESI): 691 (M+H)$^+$.

EXAMPLE 528

Preparation of Compound No. 528 in Table 13

Trimethylsilyl bromide (0.325 ml, 2.46 mmol) was added to a solution of 4-((4-(N-benzoyl)amino)anilino)-6-methoxy-7-(2-((di-benzyloxy)phosphono)ethoxy)quinazoline (170 mg, 0.246 mmol) in dichloromethane (30 ml) and the reaction was stirred at ambient temperature for 16 hours. The solvent was removed in vacuo, methanol (10 ml) was added and this was evaporated in vacuo. Trituration of the residue with diethyl ether yielded the title compound (125 mg, 100% yield) as a pale yellow solid, after prolonged drying in vacuo:
$^1$H-NMR (DMSO d$_6$): 11.04 (s, 1H), 10.37 (s, 1H), 8.81 (s, 1H), 8.10 (s, 1H), 7.97 (d, 2H), 7.90 (d, 2H), 7.48-7.67 (m, 5H), 7.24 (s, 1H), 4.34-4.43 (m, 2H), 4.19-4.29 (m, 2H), 4.00 (s, 3H):
MS (−ve ESI): 509 (M−H)$^−$.

EXAMPLE 529

Preparation of Compound No. 529 in Table 14

4-(Methylthio)-6-methoxy-7-(3-carbomethoxyprop-1-enyl))quinazoline (1 g, 3.45 mmol) was heated with 4-aminobenzanilide (3.66 g, 17.2 mmol), in the absence of solvent, at 140° C. for 2 hours. Purification of the residue by flash chromatography on silica gel, eluting with 5-10% methanol in dichloromethane, the title compound (850 mg, 54% yield) as a white solid:

$^1$H-NMR (DMSO d$_6$): 10.33 (s, 1H), 9.81 (s, 1H), 8.59 (s, 1H), 8.22 (s, 1H), 8.07 (m, 4H), 7.91 (d, 2H, J=7 Hz), 7.86 (d, 2H, J=8 Hz), 7.60-7.70 (m, 3H), 6.99 (d, 2H, J=17 Hz), 4.15 (s, 3H), 3.82 (s, 3H):

MS (+ve ESI): 456 (M+H)$^+$.

4-((4-(N-Benzoyl)amino)anilino)-6-methoxy-7-(3-carboxyprop-1-enyl))quinazoline, used as starting material was obtained as follows:

a) 4-((4-(N-Benzoyl)amino)anilino)-6-methoxy-7-(trifluoromethanesulphonyloxy)quinazoline (3.04 g, 8.21 mmol), methyl acrylate (1.48 ml, 16.4 mmol), 1,3-bis(diphenylphosphine)propane (95 mg, 0.23 mmol), triethylamine (1.26 ml, 9.03 mmol) and palladium acetate (46 mg, 0.2 mmol) were heated in dimethylformamide (36 ml) at 100° C. for 1.5 hour, under argon. The mixture was cooled, the solvents were evaporated in vacuo and hydrochloric acid (2.0 N) was added. The aqueous phase was extracted with dichloromethane, the organic phase was washed with brine and dried over magnesium sulphate before solvent evaporation in vacuo. Purification by flash chromatography on silica gel, eluting with 4% methanol in dichloromethane, yielded 4-(methylthio)-6-methoxy-7-(3-carbomethoxyprop-1-enyl))quinazoline (1.82 g, 76% yield) as a white solid:

$^1$H-NMR (DMSO d$_6$): 8.95 (s, 1H), 8.36 (s, 1H), 7.98 (d, 1H), 7.33 (s, 1H), 6.99 (d, 1H), 4.06 (s, 3H), 3.78 (s, 3H), 2.72 (s, 3H):

EXAMPLE 530

Preparation of Compound No. 530 in Table 14

A solution of sodium hydroxide (26 mg, 0.66 mmol) in water (0.5 ml) was added to a solution of 4-((4-(N-benzoyl)amino)anilino)-6-methoxy-7-(3 carbomethoxyprop-1-enyl)) quinazoline (150 mg, 0.33 mmol) in ethanol at 80° C. over 45 minutes. The solvent was evaporated in vacuo, water was added, and the mixture was acidified with hydrochloric acid (2.0N) to pH 2. Collection of the solid by suction filtration the title compound (135 mg, 93%) as a white solid:

$^1$H-NMR (DMSO d$_6$): 10.50 (s, 1H), 8.86 (s, 1H), 8.39 (s, 1H), 8.20 (s, 1H), 8.06 (d, 2H, J=8 Hz), 7.98 (m, 4H), 7.80 (d, 2H, J=8 Hz), 7.60-7.70 (m, 3H), 6.82 (d, 2H, J=17 Hz), 4.19 (s, 3H):

MS (+ve ESI): 442 (M+H)$^+$.

EXAMPLE 531

Preparation of Compound No. 531 in Table 14

4-(methylthio)-6-methoxy-7-(3-hydroxyprop-1-enyl) quinazoline (100 mg, 0.38 mmol) was heated with 4-aminobenzanilide (405 mg, 1.91 mmol), in the absence of solvent, at 140° C. for 1.5 hours. Purification of the residue by flash chromatography on silica gel, eluting with 5-10% methanol in dichloromethane, yielded the title compound (66 mg, 40% yield) as a white solid:

$^1$H-NMR (DMSO d$_6$): 9.64 (s, 1H), 8.47 (s, 1H), 7.99 (d, 2H), 7.90 (s, 1H), 7.82 (m, 5H), 7.58 (m, 3H), 6.97 (d, 1H), 6.68 (m, 1H), 5.01 (t, 1H), 4.20 (m, 2H), 4.03 (s, 3H):

MS (+ve ESI): 427 (M+H)$^+$.

4-(methylthio)-6-methoxy-7-(3-hydroxyprop-1-enyl) quinazoline, used as starting material was obtained as follows:

a) 6-methoxy-7-benzyloxy-3,4-dihydroquinazolin-4-one (50 g, 0.177 mol) in Pyridine (2 l) was reacted with phosphorous pentasulfide (95 g, 0.213 mol) at reflux for 8 hours. The mixture was cooled, poured in water (6000 ml), the solid filtered and washed with water. This solid was taken up in an aqueous solution of sodium hydroxyde (6N), the insoluble material was filtered off and the solution acidified with hydrochloric acid (6N) to pH 2. The precipitate was filtered, washed with water and methanol, and dried under vacuum over phosphorus pentoxide, to give 6-methoxy-7-benzyloxy-3,4-dihydroquinazolin-4-thione (42.8 g, 81% yield).

$^1$H-NMR (DMSO d$_6$, TFA): 8.25 (s, 1H), 7.95 (s, 1H), 7.50 (d, 2H), 7.43 (t, 2H), 7.38 (d, 1H), 7.30 (s, 1H), 5.32 (s, 2H), 3.93 (s, 3H):

MS (+ve EI): 298 (M+H)$^+$.

b) Sodium hydroxide (1.0 N, 200 ml) was added to a solution of 6-methoxy-7-benzyloxy-3,4-dihydroquinazolin-4-thione (30 g, 0.1 mol) in tetrahydrofuran (100 ml) and then methyl iodide (7.5 ml, 0.12 mol) was slowly added at ambient temperature over 30 minutes. The pH of the solution was then adjusted to 7 with hydrochloric acid (2.0 N), the reaction was diluted with water and the solid was recovered by suction filtration. Drying in vacuo yielded 4-(methylthio)-6-methoxy-7-benzyloxyquinazoline (29.5 g, 94% yield):

$^1$H-NMR (DMSO d$_6$, TFA): 9.17 (s, 1H), 7.53 (d, 2H), 7.51 (s, 1H), 7.45 (t, 2H), 7.41 (d, 1H), 7.37 (s, 1H), 5.39 (s, 2H), 4.02 (s, 3H), 2.80 (s, 3H):

MS (+ve ESI): 283 (M+H)$^+$.

c) A solution of 4-(methylthio)-6-methoxy-7-benzyloxyquinazoline (29.5 g, 0.095 mol) in trifluoroacetic acid (250 ml) was heated at reflux for 3 hours. The mixture was cooled, water was added, and the pH adjusted to pH 5 with sodium hydroxide (2.0 N). The solid was filtered, washed with water and diethyl ether and dried in vacuo. The solid was redissolved in methanol (2000 ml) and water (500 ml), the pH was adjusted to 7 with sodium hydroxyde (2.0 N) and the precipitated solid was collected by suction filtration. Drying in vacuo yielded 4-(methylthio)-6-methoxy-7-hydroxy-quinazoline (19.18 g, 91% yield):

$^1$H-NMR (DMSO d$_6$, TFA): 9.26 (s, 1H), 7.39 (s, 1H), 7.36 (s, 1H), 4.04 (s, 3H), 2.87 (s, 3H):

MS (+ve ESI): 223 (M+H)$^+$.

d) A solution of 4-(methylthio)-6-methoxy-7-hydroxyquinazoline (2.28 g, 10.3 mmol) and pyridine (0.91 ml) in dichloromethane (20 ml) was slowly added to a solution of triflic anhydride (1.9 ml, 11.3 mmol) in dichloromethane (20 ml) at 0° C. The mixture was stirred at 0° C. for 40 minutes, hydrochloric acid (0.5 N, 50 ml) was then added, and the mixture was extracted with ethyl acetate. The organic phase was washed with brine, dried over magnesium sulphate and evaporated in vacuo. Purification by flash chromatography on silica gel, eluting with 1:1 isohexane:ethyl acetate, yielded 4-(methylthio)-6-methoxy-7-(trifluoromethanesulphonyloxy)-quinazoline (3.04 g, 80% yield):

$^1$H-NMR (DMSO d$_6$): 9.02 (s, 1H), 8.15 (s, 1H), 7.58 (s, 1H), 4.11 (s, 3H), 2.74 (s, 3H).

e) A suspension of 4-(methylthio)-6-methoxy-7-(trifluoromethanesulphonyloxy)quinazoline (1.1 g, 3.1 mmol), E-3-(tributylstannyl)-2-propen-1-ol (1.12 g, 3.23 mmol), bis-dichloro(triphenylphosphine)palladium (44 mg, 0.06 mmol) and lithium chloride (395 mg, 9.32 mmol) in dimethylformamide (14 ml) was heated at 65° C. for 3 hours. The mixture was cooled to ambient temperature, the solid was recovered by suction filtration and washed with ether. Drying in vacuo yielded 4-(methylthio)-6-methoxy-7-(3-hydroxyprop-1-enyl)quinazoline (355 mg, 44% yield):

$^1$H-NMR (DMSO d$_6$): 8.89 (s, 1H), 8.01 (s, 1H), 7.25 (s, 1H), 6.98 (d, 1H), 6.75 (m, 1H), 5.04 (t, 1H), 4.21 (m, 2H), 4.01 (s, 3H), 2.71 (s, 3H).

EXAMPLE 532

Preparation of Compound No. 532 in Table 14

Diisopropylethylamine (0.07 ml, 0.38 mmol) was added to a suspension of 4-((4-(N-benzoyl)amino)anilino)-6-methoxy-7-(3-carboxyprop-1-enyl))quinazoline (120 mg, 0.27 mmol, 1-(2-aminoethyl)piperidine (0.039 ml, 0.27 mmol) and 1-(3-dimethylaminopropyl)-3-ethylcarbodiimide hydrochloride (73 mg, 0.38 mmol) in dimethylformamide (4 ml), and the reaction stirred at ambient temperature for 16 hours. Solvent evaporation in vacuo yielded the title compound (60 mg, 40% yield), after purification by reverse phase hplc:

$^1$H-NMR (DMSO d$_6$, TFA): 8.91 (s, 1H), 8.25 (s, 1H), 8.00 (m, 5H), 7.80 (d, 1H), 7.68 (m, 2H), 7.58 (m, 3H), 6.34 (d, 1H), 4.10 (s, 3H), 3.57 (m, 4H), 3.21 (m, 2H), 2.97 (m, 2H), 1.82 (m, 1H), 1.70 (m, 4H), 1.40 (m, 1H):

MS (+ve ESI): 551 (M+H)$^+$.

EXAMPLE 533

Preparation of Compound No. 533 in Table 14

10% Palladium on carbon (30 mg) was added to a solution of 4-((4-(N-benzoyl)amino)-anilino)-6-methoxy-7-(3-hydroxyprop-1-enyl)quinazoline (120 mg, 0.28 mmol) in ethanol (10 ml), dimethylformamide (1 ml) and tetrahydrofuran (5 ml) and the reaction stirred under an atmosphere of hydrogen (50 psi) for 20 hours, before the catalyst was filtered off and the solvent evaporated in vacuo. Purification by flash chromatography on silica gel, eluting 15% methanol in dichloromethane, yielded the title compound (90 mg, 75% yield) as a white solid:

$^1$H-NMR (DMSO d$_6$): 9.58 (s, 1H), 8.45 (s, 1H), 7.98 (d, 2H), 7.84 (s, 1H), 7.81 (d, 2H), 7.78 (d, 2H), 7.57 (m, 4H), 4.53 (t, 1H), 3.99 (s, 3H), 3.46 (q, 2H), 2.77 (t, 2H), 1.77 (q, 2H):

MS (+ve ESI): 229 (M+H)$^+$.

EXAMPLE 534

Preparation of Compound No. 534 in Table 14

An analogous reaction to that described for the synthesis of compound 532, but starting with 1-(2-dimethylaminoethyl)piperazine (76 mg, 0.28 mmol), yielded the title compound (41 mg, 25% yield) as a white solid after purification by reverse phase preparative hplc:

$^1$H-NMR (DMSO d$_6$, TFA): 8.93 (s, 1H), 8.35 (s, 1H), 8.23 (s, 1H), 8.00 (m, 4H), 7.90 (d, 1H), 7.70 (m, 2H), 7.60 (m, 4H), 4.12 (s, 3H), 4.05 (m, 4H), 3.55 (m, 4H), 3.36 (m, 4H), 2.88 (s, 6H):

MS (+ve ESI): 580 (M+H)$^+$.

EXAMPLE 535

Preparation of Compound No. 535 in Table 14

4-(methylthio)-7-(3-hydroxy-3-methylbut-1-ynyl)quinazoline (240 mg, 0.93 mmol) was heated with 4-aminobenzanilide (1.38 g, 6.51 mmol), in the absence of solvent at 140° C. for 1.5 hours. Purification by flash chromatography on silica gel, eluting with 5-15% methanol in dichloromethane yielded the title compound (344 mg, 88% yield) as a white solid:

$^1$H-NMR (DMSO d$_6$): 9.88 (s, 1H), 8.58 (s, 1H), 8.54 (d, 1H), 7.97 (d, 2H), 7.80 (s, 4H), 7.72 (s, 1H), 7.57 (m, 4H), 5.59 (s, 1H), 1.52 (s, 6H):

MS (+ve ESI): 423 (M+H)$^+$.

4-(Methylthio)-7-(3-hydroxy-3-methylbut-1-ynyl)quinazoline, used as the starting material was obtained as follows:

a) Trifluoromethane sulfonic anhydride (0.96 ml, 5.73 mmol) and pyridine (0.46 ml, 5.73 mmol) were added to a solution of 7-benzyloxy-3,4-dihydroquinazolin-4-thione (1.0 g, 5.21 mmol) in methylene chloride (20 ml) at 0° C. for 1.5 hour. Hydrochloric acid (0.5 N) was then added to the mixture which was extracted with ethyl acetate. The organic phase was washed brine, dried over magnesium sulphate and the solvents were removed in vacuo. Purification by flash chromatography on silica gel, eluting with isohexane/ethyl acetate (1:4) yielded 4-(methylthio)-7-(trifluoromethanesulphonyloxy)quinazoline (800 mg, 50% yield):

$^1$H-NMR (DMSO d$_6$): 9.11 (s, 1H), 8.36 (d, 1H), 8.15 (s, 1H), 7.85 (d, 1H), 1.73 (s, 3H):

b) 4-(Methylthio)-7-(trifluoromethanesulphonyloxy)quinazoline (592 mg, 1.82 mmol) in dimethylformamide (20 ml) was reacted with 2-methyl-3-butyn-2-ol (0.53 ml, 0.54 mmol) in the presence of bis dichloro(triphenylphosphine)palladium (64 mg, 0.091 mmol), copper (I) iodide (20 mg) and triethylamine (1.1 ml, 0.8 mmol), at 90° C. for 2.5 hours. The solvent was removed in vacuo, aqueous hydrochloric acid (2N) was added, and the mixture was extracted with ethyl acetate. The organic phase was washed with brine, dried over magnesium sulphate and the solvents were evaporated in vacuo. Purification by flash chromatography on silica gel, eluting with isohexane/ethyl acetate (55:45), yielded, 4-(methylthio)-7-(3-hydroxy-3-methylbut-1-ynyl)quinazoline (243 mg, 51% yield):

$^1$H-NMR (DMSO d$_6$): 9.01 (s, 1H), 8.08 (d, 1H), 7.90 (s, 1H), 7.65 (d, 1H), 5.60 (s, 1H), 2.70 (s, 3H), 1.51 (s, 6H).

EXAMPLE 536

Preparation of Compound No. 536 in Table 14

4-(Methylthio)-6-methoxy-7-(3-hydroxyprop-1-ynyl)quinazoline (120 mg, 0.461 mmol) was heated with 4-aminobenzanilide (490 mg, 2.31 mmol), in the absence of solvent at 140° C. for 1.5 hours. Purification of the residue by flash chromatography on silica gel, eluting with 7.5% methanol in dichloromethane, yielded the title compound (42 mg, 21% yield) as a white solid:

$^1$H-NMR (DMSO d$_6$): 9.72 (s, 1H), 8.47 (s, 1H), 7.97 (d, 2H), 7.94 (s, 1H), 7.82 (d, 2H), 7.75 (m, 3H), 7.58 (d, 1H), 7.54 (t, 2H), 5.43 (t, 1H), 4.38 (d, 2H), 4.01 (s, 3H):

MS (+ve ESI): 425 (M+H)$^+$.

4-(methylthio)-6-methoxy-7-(3-hydroxyprop-1-ynyl)quinazoline, use as the starting material was obtained as follows:

4-(methylthio)-6-methoxy-7-(trifluoromethanesulphonyloxy)quinazoline (1.0 g, 2.82 mmol) in dimethylformamide (30 ml) was reacted with propargyl alcohol (0.51 ml, 8.75 mmol) in the presence of bisdichloro(triphenylphosphine)palladium (100 mg, 0.14 mmol) copper (I) iodide (40 mg) and triethylamine (1.7 ml, 0.0124 mmol) at 90° C. for 2.5 hours under argon. The solvent was evaporated in vacuo, water and hydrochloric acid (2.0 N) were added, and the mixture was extracted with ethyl acetate. Purification by flash chromatography on silica gel, eluting with 7.5% methanol in dichloromethane, yielded 4-(methylthio)-6-methoxy-7-(3-hydroxyprop-1-ynyl)quinazoline (122 mg, 17% yield):

$^1$H-NMR (DMSO $d_6$): 8.91 (s, 1H), 7.94 (s, 1H), 7.27 (s, 1H), 5.46 (t, 1H), 4.38 (d, 2H), 3.99 (s, 3H), 2.70 (s, 3H):

EXAMPLE 537

Preparation of Compound No. 537 in Table 14

Iron powder (325 mesh, 730 mg, 13 mmol) was added portionwise to a stirred solution of 4-((4-(N-benzoyl)amino)anilino)-7-nitroquinazoline (500 mg, 1.3 mmol) in ethanol (66 ml), water (33 ml) and acetic acid (1 ml) at reflux over 1 hour. The mixture was cooled to 50° C., and a solution of ammonia (28%, 5 ml) was added. The precipitate was collected by suction filtration, washed with warn ethanol and the solvent was evaporated in vacuo. Purification by flash chromatography on by silica gel, eluting with 5% methanol in dichloromethane, yielded 4-((4-(N-benzoyl)amino)anilino)-7-aminoquinazoline (461 mg, 100% yield):

$^1$H-NMR (DMSO $d_6$): 8.60 (s, 1H), 8.41 (d, 1H), 8.00 (d, 2H), 7.86 (d, 2H), 7.66 (d, 2H), 7.61 (d, 1H), 7.56 (t, 2H), 7.03 (dd, 1H), 6.90 (s, 2H), 6.76 (d, 1H):

MS (+ve ESI): 356 (M+H)$^+$.

4-((4-(N-benzoyl)amino)anilino)-7-nitroquinazoline, used as starting material was obtained as follows:

A solution of 4-chloro-7-nitroquinazoline (500 mg, 2.38 mmol) in isopropanol (15 ml) was reacted with 4-aminobenzanilide (607 mg, 2.86 mmol) at reflux, for 2 hours. Collection of the solid which precipitated on cooling, yielded 4-((4-(N-benzoyl)amino)anilino)-7-nitroquinazoline (920 mg, 100% yield):

$^1$H-NMR (DMSO $d_6$): 9.08 (d, 1H), 8.95 (s, 1H), 8.68 (d, 1H), 8.53 (dd, 1H), 8.03 (d, 2H), 7.92 (d, 2H), 7.80 (d, 2H), 7.63 (d, 1H), 7.57 (t, 2H).

EXAMPLE 538

Preparation of Compound No. 538 in Table 14

Isonicotinoyl chloride hydrochloride (95 mg, 0.507 mmol) was added to a solution of 4-((4-(N-benzoyl)amino)anilino)-7-aminoquinazoline (150 mg, 0.422 mmol) and triethylamine (0.5 ml) in pyridine (3 ml) and the reaction was stirred at ambient temperature for 3 hours. The solvent was evaporated, water was added to the residue and the precipitate was filtered, washed with water, and dried in vacuo. Trituration of the resulting solid with methanol in methanol yielded the title compound (66 mg, 33% yield) as a pale yellow solid:

$^1$H-NMR (DMSO $d_6$, TFA): 9.02 (d, 2H), 8.94 (d, 1H), 8.78 (d, 1H), 8.61 (s, 1H), 8.22 (d, 2H), 8.11 (d, 1H), 7.99 (d, 2H), 7.93 (dd, 2H), 7.72 (m, 2H), 7.61 (d, 1H), 7.56 (t, 2H):

MS (+ve ESI): 461 (M+H)$^+$.

EXAMPLE 539

Preparation of Compound No. 539 in Table 14

An analogous reaction to that described in example 538, but starting with 3-(1-piperidine)propionyl chloride (0.84 mmol) yielded title compound (18 mg, 9% yield), after purification by reverse phase preparative hplc:

$^1$H-NMR (DMSO $d_6$, TFA): 8.89 (s, 1H), 8.78 (d, 1H), 8.43 (d, 1H), 7.99 (d, 2H), 7.92 (dd, 2H), 7.71 (d, 1H), 7.69 (m, 2H), 7.61 (d, 1H), 7.55 (t, 2H), 3.42 (m, 4H), 3.05 (t, 2H), 2.96 (t, 2H), 1.80 (m, 5H), 1.43 (m, 1H):

MS (+ve ESI): 495 (M+H)$^+$.

EXAMPLE 540

Preparation of Compound No. 540 in Table 14

4-(Methylthio)-7-(N-2-acetoxyacetyl)quinazoline (78 mg, 0.268 mmol) was heated with 4-aminobenzanilide at 150° C. for 1.5 hours (without additional solvent). Purification by flash chromatography, on by silica gel, eluting with 5% methanol in dichloromethane, yielded the title compound (40 mg, 32% yield) as a white solid:

$^1$H-NMR (DMSO $d_6$): 9.71 (bs, 1H), 8.52 (s, 1H), 8.49 (d, 1H), 8.07 (d, 1H), 7.97 (d, 2H), 7.79 (d, 4H), 7.72 (dd, 1H), 7.57 (d, 1H), 7.54 (t, 2H), 4.73 (s, 2H), 2.15 (s, 3H):

MS (+ve ESI): 456 (M+H)$^+$.

4-(Methylthio)-7-(N-2-acetoxyacetyl)quinazoline used as starting material was obtained as follows:

a) Iron powder (325 mesh, 1.35 g, 52 mmol) was added portionwise to a stirred solution of 4-(methylthio)-7-nitroquinazoline (1.44 g, 6.52 mmol) in ethanol (130 ml), water (65 ml) and acetic acid (1.15 ml) at reflux over 1.5 hours. The mixture was cooled to 50° C., and a solution of ammonia (28%, 5 ml) was added. The precipitate was collected by suction filtration, washed with warm ethanol and the solvent was evaporated in vacuo. Purification by flash chromatography on by silica gel, eluting with 5% methanol in dichloromethane, yielded 4-(methylthio)-7-aminoquinazoline (1.17 g, 94% yield):

$^1$H-NMR (DMSO $d_6$): 8.65 (s, 1H), 7.74 (d, 1H), 7.00 (dd, 1H), 6.74 (d, 1H), 6.35 (s, 2H), 2.60 (s, 3H):

b) Acetoxyacetyl chloride (0.093 ml, 0.864 mmol) was added to a solution of 4-(methylthio)-7-aminoquinazoline (150 mg, 0.785 mmol) and triethylamine (150 mg, 1.49 mmol) in pyridine (4 ml) at 0° C. and the reaction stirred for 1 hour. The solvent was evaporated in vacuo, water was added to the residue and the mixture was extracted with dichloromethane and evaporated in vacuo. Purification by flash chromatography, on silica gel, eluting with 5% methanol in dichloromethane, yielded 4-(methylthio)-7-(N-2-acetoxyacetyl)quinazoline (78 mg, 34% yield) as a white solid:

$^1$H-NMR (DMSO $d_6$): 8.92 (s, 1H), 8.29 (d, 1H), 8.08 (d, 1H), 7.76 (dd, 1H), 4.74 (s, 2H), 2.67 (s, 3H), 2.14 (s, 3H).

EXAMPLE 541

Preparation of Compound No. 541 in Table 15

An analogous reaction to that described in example 99, but starting with N-(4-hydroxyphenyl)benzenesulphonamide (299 mg, 1.20 mmol), yielded the title compound (198 mg, 45% yield) as a beige solid:

$^1$H-NMR (DMSO $d_6$): 10.32 (s, 1H), 8.50 (s, 1H), 7.80 (d, 2H, J=8 Hz), 7.55-7.70 (m, 3H), 7.51 (s, 1H), 7.35 (s, 1H), 7.20 (s, 4H), 4.00 (s, 6H):

MS (−ve ESI): 436 (M−H)$^-$,
MS (+ve ESI): 438 (M+H)$^+$.

N-(4-Hydroxyphenyl)benzenesulphonamide, used as the starting material was obtained as follows:

A solution of benzenesulponyl chloride (2.54 ml, 20.0 mmol) in tetrahydrofuran (10 ml) was added dropwise to a solution of 4-aminophenol (1.09 g, 10.0 mmol) in pyridine (20 ml) at ambient temperature and the reaction allowed to stir for a further 18 hours. The reaction was poured into 2.0N hydrochloric acid (125 ml) and the aqueous phase was extracted with diethyl ether (3×50 ml). The combined organic layers were washed with saturated aqueous sodium hydrogen carbonate solution (100 ml), dried over magnesium sulphate and evaporated in vacuo. Drying in vacuo, yielded N-(4-hydroxyphenyl)benzenesulphonamide (694 mg, 28% yield) as a beige solid:

$^1$H-NMR (DMSO d$_6$): 9.70 (s, 1H), 9.25 (s, 1H), 7.62-7.69 (m, 2H), 7.45-7.55 (m, 3H), 6.80-6.85 (m, 2H), 6.50-6.60 (m, 2H):

MS (−ve ESI): 248 (M−H)$^−$,
MS (+ve ESI): 250 (M+H)$^+$.

EXAMPLE 542

Preparation of Compound No. 542 in Table 15

An analogous reaction to that described in example 1, but starting with N-(3-methoxy-4-aminophenyl)methanesulphonamide (128 mg, 0.59 mmol) and 4-chloro-6,7-dimethoxyquinazoline hydrochloride (154 mg, 0.59 mmol), yielded the title compound (122 mg, 51% yield) as an off-white solid:

$^1$H-NMR (DMSO d$_6$): 11.02 (s, 1H), 9.93 (s, 1H), 8.69 (s, 1H), 8.15 (s, 1H), 7.32 (d, 1H, J=8 Hz), 7.31 (s, 1H), 7.00 (d, 1H, J=2 Hz), 6.89 (dd, 2H, J=2, 8 Hz), 3.96 (s, 3H), 3.94 (s, 3H), 3.74 (s, 3H):

MS (−ve ESI): 403 (M−H)$^−$,
MS (+ve ESI): 405 (M+H)$^+$.

EXAMPLE 543

Preparation of Compound No. 543 in Table 16

A solution of n-butyl 4-aminobenzoate (103 mg, 0.535 mmol) in isopropanol (7 ml) was added to 4-chloro-6,7-dimethoxyquinazoline hydrochloride (140 mg, 0.535 mmol) and the reaction heated at 73° C. for 2 hours before being cooled to 5° C. The solid which precipitated was collected by suction filtration and washed with diethyl ether (2×5 ml). Drying of this material yielded the title compound (149 mg, 73% yield) as an off-white solid:

$^1$H-NMR (DMSO d$_6$): 11.40 (s, 1H), 8.87 (s, 1H), 8.32 (s, 1H), 8.04 (d, 2H, J=8 Hz), 7.93 (d, 2H, J=8 Hz), 7.36 (s, 1H), 4.28 (t, 2H), 4.02 (s, 3H), 3.99 (s, 3H), 1.70 (qu, 2H, J=7 Hz), 1.43 (m, 2H), 0.94 (t, 3H, J=7 Hz):

MS (−ve ESI): 380 (M−H)$^−$,
MS (+ve ESI): 382 (M+H)$^+$.

EXAMPLE 544

Preparation of Compound No. 544 in Table 16

An analogous reaction to that described in example 543, but starting with 4-aminobenzophenone (90 mg, 0.46 mmol) yielded the title compound (116 mg, 66% yield) as a white solid:

$^1$H-NMR (DMSO d$_6$) 11.40 (s, 1H), 8.89 (s, 1H), 8.33 (s, 1H), 7.97 (d, 2H, J=8 Hz), 7.85 (d, 2H, J=8 Hz), 7.75 (d, 2H, J=8 Hz), 7.67 (m, 1H), 7.58 (m, 2H), 7.35 (s, 1H), 4.03 (s, 3H), 4.00 (s, 3H):

MS (−ve ESI): 384 (M−H)$^−$,
MS (+ve ESI): 386 (M+H)$^+$.

EXAMPLE 545

Preparation of Compound No. 545 in Table 16

An analogous reaction to that described in example 543, but starting with sulphanilamide (104 mg, 0.60 mmol) yielded the title compound (122 mg, 56% yield) as a white solid:

$^1$H-NMR (DMSO d$_6$): 11.48 (s, 1H), 8.86 (s, 1H), 8.33 (s, 1H), 7.91 (s, 4H), 7.38 (s, 2H), 7.35 (s, 1H), 4.02 (s, 3H), 4.00 (s, 3H):

MS (+ve ESI): 361 (M+H)$^+$.

EXAMPLE 546

Preparation of Compound No. 546 in Table 16

An analogous reaction to that described in example 543, but starting with 4-nitrophenyl-sulphonyl aniline (164 mg, 0.59 mmol) yielded the title compound (146 mg, 53% yield) as a white solid:

$^1$H-NMR (DMSO d$_6$): 11.36 (s, 1H), 8.85 (s, 1H), 8.40 (d, 2H, J=8 Hz), 8.23-8.28 (m, 3H), 8.05-8.10 (m, 4H), 7.33 (s, 1H), 4.00 (s, 3H), 3.97 (s, 3H):

MS (+ve ESI): 467 (M+H)$^+$.

EXAMPLE 547

Preparation of Compound No. 547 in Table 16

An analogous reaction to that described in example 543, but starting with N-(2-cyanophenyl)-4-amino-2-chlorobenzamide (143 mg, 0.52 mmol) yielded the title compound (168 mg, 70% yield) as a white solid:

$^1$H-NMR (DMSO d$_6$): 11.32 (s, 1H), 8.90 (s, 1H), 8.28 (s, 1H), 8.07 (s, 1H), 7.88 (d, 2H, J=8 Hz), 7.74 (d, 2H, J=8 Hz), 7.65 (d, 1H, J=8 Hz), 7.43 (t, 1H, J=7 Hz), 7.35 (s, 1H), 4.03 (s, 3H), 4.00 (s, 3H):

MS (+ve ESI): 460 (M+H)$^+$.

N-(2-Cyanophenyl)-4-amino-2-chlorobenzamide, used as the starting material, was obtained as follows:

a) A solution of 2-chloro-4-nitrobenzoic acid (6.00 g, 29.8 mmol) in thionyl chloride (20 ml) was heated at reflux for 2.5 hours. The reaction was cooled, the excess thionyl chloride was evaporated in vacuo and the residue was azeotroped with toluene (2×25 ml). The residue was taken up in toluene (35 ml), 2-aminobenzonitrile (1.75 g, 14.8 mmol) was added and the reaction heated at reflux for 2 hours. The reaction was cooled, the solvent was removed in vacuo and the residue was absorbed onto silica gel. Purification by flash chromatography on silica gel, eluting with dichloromethane, yielded N-(2-cyanophenyl)-2-chloro-4-nitrobenzamide (1.30 g, 27% yield) as a pale yellow solid:

MS (+ve CI): 322 (M+H)$^+$.

b) N-(2-Cyanophenyl)-2-chloro-4-nitrobenzamide (1.30 g, 4.04 mmol) was added to a stirred suspension of tin (II) chloride dihydrate (4.42 g, 23 mmol) in hydrochloric acid (52 ml) at 0° C. The reaction was allowed to warm to ambient temperature over 2 hours and aqueous sodium hydroxide was added to take the reaction to pH 10. Extraction of the aqueous layer with dichloromethane (3×50 ml), followed by solvent evaporation in vacuo, yielded N-(2-cyanophenyl)-4-amino-2-chlorobenzamide (0.19 g, 16% yield) as a white solid:

MS (+ve CI): 292 (M+H)$^+$.

EXAMPLE 548

Preparation of Compound No. 548 in Table 16

An analogous reaction to that described in example 543, but starting with 4-amino-2,4'-difluorobenzophenone (438 mg, 2.00 mmol) and 4-chloro-6,7-dimethoxyquinazoline hydrochloride (458 mg, 2.00 mmol) yielded the title compound (389 mg, 46% yield) as a white solid:

$^1$H-NMR (DMSO $d_6$): 11.40 (s, 1H), 8.93 (s, 1H), 8.35 (s, 1H), 8.02 (d, 2H, J=8 Hz), 7.82-7.87 (m, 4H), 7.71 (t, 2H, J=8 Hz), 7.40 (t, 2H, J=8 Hz), 7.35 (s, 1H), 4.03 (s, 3H), 4.00 (s, 3H):

MS (−ve ESI): 420 (M−H)$^-$,
MS (+ve ESI): 422 (M+H)$^+$.

EXAMPLE 549

Preparation of Compound No. 549 in Table 16

An analogous reaction to that described in example 543, but starting with 4-amino-N-(4,5-dimethyl-2-oxazolyl)benzenesulphonamide (150 mg, 0.56 mmol) yielded the title compound (90 mg, 38% yield) as a white solid:

$^1$H-NMR (DMSO $d_6$): 11.35 (s, 1H), 8.84 (s, 1H), 8.28 (s, 1H), 7.87-7.94 (m, 4H), 7.33 (s, 1H), 4.01 (s, 3H), 3.99 (s, 3H), 2.05 (s, 3H), 1.94 (s, 3H):

MS (−ve ESI): 454 (M−H)$^-$,
MS (+ve ESI): 456 (M+H)$^+$.

EXAMPLE 550

Preparation of Compound No. 550 in Table 16

A solution of 4-chloro-6,7-dimethoxyquinazoline (224 mg, 1.00 mmol), potassium carbonate (152 mg, 1.10 mmol) and 4-hydroxybenzene-sulphonamide (87 mg, 0.50 mmol), in dimethylformamide (4 ml) was heated at 110° C. for 2 hours before the reaction was allowed to cool to ambient temperature. The reaction was poured into water and the solid which had precipitated was collected by suction filtration and washed with a mixture of diethyl ether (10 ml), ethyl acetate (10 ml) and isohexane (10 ml). Drying of this material yielded the title compound (48 mg, 26% yield) as a white solid:

$^1$H-NMR (DMSO $d_6$): 8.55 (s, 1H), 7.90 (d, 2H, J=8 Hz), 7.50-7.60 (m, 3H), 7.35-7.45 (m, 3H), 4.00 (s, 6H):

MS (−ve ESI): 360 (M−H)$^-$,
MS (+ve ESI): 362 (M+H)$^+$.

EXAMPLE 551

Preparation of Compound No. 551 in Table 16

4-Chloro-6,7-dimethoxyquinazoline (112 mg, 0.50 mmol) and potassium carbonate (69 mg, 0.50 mmol) were added sequentially to a stirred suspension of 4-hydroxy-2-methoxybenzaldehyde (76 mg, 0.50 mmol)) in dimethylformamide (3 ml). The reaction was heated at 100° C. for 4 hours then allowed to stir for a further 36 hours at ambient temperature. Brine (10 ml) was added and the reaction allowed to stand for 16 hours before the solid was collected by suction filtration (analogous reactions which failed to yield a solid precipitate were extracted with dichloromethane (2×5 ml) and the dichloromethane layer evaporated in vacuo to give a solid product). Drying in vacuo yielded the title compound (140 mg, 86% yield) as a white solid:

$^1$H-NMR (DMSO $d_6$): 10.35 (s, 1H), 8.61 (s, 1H), 7.83 (d, 1H), 7.57 (s, 1H), 7.42 (s, 1H), 7.28 (d, 1H), 7.07 (dd, 1H), 4.01 (s, 3H), 3.99 (s, 3H), 3.94 (s, 3H):

MS (+ve ESI): 341 (M+H)$^+$.

EXAMPLE 552

Preparation of Compound No. 552 in Table 16

An analogous reaction to that described in example 551, but starting with 4-(methylsulphonyl)-phenol (86 mg, 0.50 mmol) yielded the title compound (143 mg, 82% yield) as a white solid:

$^1$H-NMR (DMSO $d_6$): 8.60 (s, 1H), 8.07 (d, 2H), 7.65 (d, 2H), 7.60 (s, 1H), 7.42 (s, 1H), 4.01 (s, 3H), 3.99 (s, 3H), 3.30 (s, 3H):

MS (+ve ESI): 361 (M+H)$^+$.

EXAMPLE 553

Preparation of Compound No. 553 in Table 16

An analogous reaction to that described in example 551, but starting with 4-hydroxybenzophenone (99 mg, 0.50 mmol) yielded the title compound (156 mg, 81% yield) as a white solid:

$^1$H-NMR (DMSO $d_6$): 8.62 (s, 1H), 7.90 (d, 2H), 7.80 (d, 2H), 7.71 (t, 1H), 7.58-7.66 (m, 3H), 7.55 (d, 2H), 7.44 (s, 1H), 4.01 (s, 3H), 4.00 (s, 3H):

MS (+ve ESI): 387 (M+H)$^+$.

EXAMPLE 554

Preparation of Compound No. 554 in Table 16

An analogous reaction to that described in example 551, but starting with 3-ethoxy-4-hydroxybenzaldehyde (83 mg, 0.50 mmol) yielded the title compound (159 mg, 90% yield) as a white solid:

$^1$H-NMR (DMSO $d_6$): 10.02 (s, 1H), 8.53 (s, 1H), 7.64-7.70 (m, 2H), 7.58 (d, 1H), 7.57 (s, 1H), 7.41 (s, 1H), 4.06 (q, 2H), 4.00 (s, 3H), 3.99 (s, 3H), 1.00 (t, 3H):

MS (+ve ESI): 355 (M+H)$^+$.

EXAMPLE 555

Preparation of Compound No. 555 in Table 16

A mixture of 4-(4-carboxy)anilino)-6,7-dimethoxyquinazoline (100 mg, 0.28 mmol), 4-(dimethylamino)-pyridine (67 mg, 0.55 mmol), n-heptylamine (0.045 ml, 0.031 mmol) and 1-(3-dimethylaminopropyl)-3-ethylcarbodiimide hydrochloride (EDCI) (58 mg, 0.31 mmol) in dimethylacetamide (3.0 ml) was stirred at ambient temperature for 16 hours. The reaction was acidified by addition of 2.0H hydrochloric acid (7.0 ml, 14.0 mmol) and the precipitated solid collected by suction filtration. Drying in vacuo yielded the title compound (114 mg, 90% yield) as a white solid:

$^1$H-NMR (DMSO $d_6$): 11.54 (s, 1H), 8.85 (s, 1H), 8.45-8.50 (m, 1H), 8.40 (s, 1H), 7.90 (d, 2H), 7.80 (d, 2H), 7.40 (s, 1H), 4.05 (s, 3H), 3.95 (s, 3H), 3.25 (m, 2H), 1.45-1.60 (m, 2H), 1.20-1.40 (m, 8H), 0.80-0.90 (m, 3H):

MS (−ve ESI): 421 (M−H)$^-$,
MS (+ve ESI): 423 (M+H)$^+$.

4-(4-carboxy)anilino-6,7-dimethoxyquinazoline, used as the starting material, was obtained as follows:

a) A solution of methyl 4-aminobenzoate (151 mg, 1.00 mmol) and 4-chloro-6,7-dimethoxyquinazoline (224 mg, 1.00 mmol) in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded 4-(4-carbomethoxy)anilino)-6,7-dimethoxyquinazoline (363 mg, 97% yield) as a white solid:

$^1$H-NMR (DMSO $d_6$): 11.50 (s, 1H), 8.90 (s, 1H), 8.40 (s, 1H), 8.05 (d, 2H), 7.95 (d, 2H), 7.4 (s, 1H), 4.05 (s, 3H), 4.00 (s, 3H):

MS (−ve ESI): 338 (M−H)$^−$,

MS (+ve ESI): 340 (M+H)$^+$.

b) Aqueous sodium hydroxide solution (2.0N, 2.0 ml, 4.0 mmol) was added to a solution of 4-(4-carboethoxy)anilino)-6,7-dimethoxyquinazoline (325 mg, 0.87 mmol) in methanol (10 ml) and the reaction was heated at reflux for 4 hours. The reaction was allowed to cool to ambient temperature, acidified with 2.0N hydrochloric acid and the solid material collected by suction filtration. The solid was taken up in acetone (20 ml), precipitated by addition of diethyl ether (20 ml) and the solid collected by suction filtration. Drying in vacuo yielded 4-(4-(2-carboxy)ethenyl)anilino-6,7-dimethoxyquinazoline (296 mg, 94% yield) as a white solid:

$^1$H-NMR (DMSO $d_6$+NaOD) 7.70 (s, 1H), 7.60 (d, 3H), 7.00 (d, 2H), 6.72 (s, 1H), 3.85 (s, 6H):

MS (−ve ESI): 324 (M−H)$^−$,

MS (+ve ESI): 326 (M+H)$^+$.

EXAMPLE 556

Preparation of Compound No. 556 in Table 16

A solution of 1-(3-dimethylaminopropyl)-3-ethylcarbodiimide hydrochloride (EDCI) (63 mg, 0.33 mmol) and 4-(dimethylamino)pyridine (73 mg, 0.60 mmol) in dimethylacetamide (3.0 ml) was added to 3-methoxypropylamine (29 mg, 0.33 mmol) and 4-(4-carboxy)anilino)-6,7-dimethoxyquinazoline (108 mg, 0.30 mmol). The reaction was stirred at ambient temperature for 48 hours and then heated at 100° C. for 4 hours before being cooled to ambient temperature. Brine (10 ml) was added and the reaction allowed to stand for 16 hours before the solid was collected by suction filtration (analogous reactions which failed to yield a solid precipitate were extracted with dichloromethane (2×5 ml) and the dichloromethane layer evaporated in vacuo to give a solid product). Drying in vacuo yielded the title compound (66.3 mg, 56% yield) as a white solid:

$^1$H-NMR (DMSO $d_6$): 9.61 (s, 1H), 8.65 (s, 1H), 8.45 (t, 1H), 7.98 (d, 2H), 7.88-7.95 (m, 3H), 7.25 (s, 1H), 4.02 (s, 3H), 3.95 (s, 3H), 3.45 (t, 2H), 3.30-3.35 (m, 2H), 3.25 (s, 3H), 1.75-1.85 (m, 2H):

MS (+ve ESI): 397 (M+H)$^+$.

EXAMPLE 557

Preparation of Compound No. 557 in Table 16

An analogous reaction to that described in example 556, but starting with 4-fluorobenzylamine (41 mg, 0.33 mmol) yielded the title compound (117.6 mg, 91% yield) as a white solid:

$^1$H-NMR (DMSO $d_6$): 9.61 (s, 1H), 8.95 (t, 1H), 8.55 (s, 1H), 7.90-8.00 (m, 4H), 7.88 (s, 1H), 7.35-7.40 (m, 2H), 7.23 (s, 1H), 7.10-7.20 (m, 2H), 4.50 (d, 2H), 4.00 (s, 3H), 3.96 (s, 3H):

MS (+ve ESI): 433 (M+H)$^+$.

EXAMPLE 558

Preparation of Compound No. 558 in Table 16

An analogous reaction to that described in example 556, but starting with cyclohexenyl-ethylamine (41 mg, 0.33 mmol) yielded the title compound (127.7 mg, 98% yield) as a white solid:

$^1$H-NMR (DMSO $d_6$): 9.68 (s, 1H), 8.55 (s, 1H), 8.30 (t, 1H), 8.0 (d, 2H), 7.92 (s, 1H), 7.90 (d, 2H), 7.25 (s, 1H), 5.50 (t, 1H), 4.02 (s, 3H), 3.98 (s, 3H), 3.35-3.40 (m, 2H), 2.20-2.25 (m, 2H), 1.92-2.00 (m, 4H), 1.50-1.70 (m, 4H):

MS (+ve ESI): 433 (M+H)$^+$.

EXAMPLE 559

Preparation of Compound No. 559 in Table 16

An analogous reaction to that described in example 556, but starting with 2-(aminoethyl)-thiophene (42 mg, 0.33 mmol) yielded the title compound (114.2 mg, 88% yield) as a white solid:

$^1$H-NMR (DMSO $d_6$): 9.62 (s, 1H), 8.60 (s, 1H), 8.55 (t, 1H), 8.0 (d, 2H), 7.88-7.95 (m, 3H), 7.35 (d, 1H), 7.25 (s, 1H), 6.98-7.01 (m, 1H), 6.95-6.97 (m, 1H), 4.0 (s, 3H), 3.95 (s, 3H), 3.50-3.57 (m, 2H), 3.08-3.15 (m, 2H):

MS (+ve ESI): 435 (M+H)$^+$.

EXAMPLE 560

Preparation of Compound No. 560 in Table 16

An analogous reaction to that described in example 556, but starting with 2,2,2-trifluoroethyl-amine hydrochloride (33 mg, 0.33 mmol) yielded the title compound (115.7 mg, 95% yield) as a white solid:

$^1$H-NMR (DMSO $d_6$): 9.65 (s, 1H), 8.95 (s, 1H), 8.50 (s, 1H), 7.98 (d, 2H), 7.93 (d, 2H), 7.88 (s, 1H), 7.20 (s, 1H), 4.10 (m, 2H), 4.00 (s, 3H), 3.95 (s, 3H):

MS (+ve ESI): 407 (M+H)$^+$.

EXAMPLE 561

Preparation of Compound No. 561 in Table 16

An analogous reaction to that described in example 556, but starting with 2-(methylthio)-ethylamine (30 mg, 0.33 mmol) yielded the title compound (101.2 mg, 85% yield) as a white solid:

$^1$H-NMR (DMSO $d_6$): 9.60 (s, 1H), 8.57 (s, 1H), 8.50 (m, 1H), 7.95 (d, 2H), 7.88 (m, 3H), 7.23 (s, 1H), 4.00 (s, 3H), 3.98 (s, 3H), 3.50 (m, 2H), 2.70 (m, 2H), 2.15 (s, 3H):

MS (+ve ESI): 399 (M+H)$^+$.

EXAMPLE 562

Preparation of Compound No. 562 in Table 16

An analogous reaction to that described in example 556, but starting with 1-aminoindan (44 mg, 0.33 mmol) yielded the title compound (107 mg, 81% yield) as a white solid:

EXAMPLE 563

Preparation of Compound No. 563 in Table 16

An analogous reaction to that described in example 556, but starting with cyclohexylamine (33 mg, 0.33 mmol) yielded the title compound (81.8 mg, 67% yield) as a white solid:
$^1$H-NMR (DMSO $d_6$): 9.6 (s, 1H), 8.50 (s, 1H), 8.05 (d, 1H), 7.90 (m, 5H), 7.25 (s, 1H), 4.00 (s, 3H), 3.95 (s, 3H), 3.75 (m, 1H), 1.85 (m, 2H), 1.75 (m, 2H), 1.60 (m, 1H), 1.30 (m, 4H), 1.12 (m, 1H):
MS (+ve ESI): 407 (M+H)$^+$.

EXAMPLE 564

Preparation of Compound No. 564 in Table 16

An analogous reaction to that described in example 556, but starting with (aminomethyl)cyclohexane (37 mg, 0.33 mmol) yielded the title compound (96.7 mg, 77% yield) as a white solid:
$^1$H-NMR (DMSO $d_6$): 9.60 (s, 1H), 8.52 (s, 1H), 8.30 (m, 1H), 7.90 (m, 5H), 7.25 (s, 1H), 4.00 (s, 3H), 3.95 (s, 3H), 3.13 (m, 1H), 1.72 (m, 4H), 1.60 (m, 2H), 1.20 (m, 3H), 0.95 (m, 2H):
MS (+ve ESI): 421 (M+H)$^+$.

EXAMPLE 565

Preparation of Compound No. 565 in Table 16

An analogous reaction to that described in example 556, but starting with 5-amino-2-chloropyridine (42 mg, 0.33 mmol) yielded the title compound (120.8 mg, 92% yield) as a white solid:
$^1$H-NMR (DMSO $d_6$): 10.50 (s, 1H), 9.72 (s, 1H), 8.85 (d, 1H), 8.58 (s, 1H), 8.28 (d, 1H), 8.05 (m, 4H), 7.90 (s, 1H), 7.52 (d, 1H), 7.25 (s, 1H), 4.02 (s, 3H), 3.97 (s, 3H):
MS (+ve ESI): 436 (M+H)$^+$.

EXAMPLE 566

Preparation of Compound No. 566 in Table 16

An analogous reaction to that described in example 556, but starting with 4-nitrobenzylamine hydrochloride (50 mg, 0.33 mmol) yielded the title compound (134.4 mg, 98% yield) as a white solid:
$^1$H-NMR (DMSO $d_6$): 9.75 (s, 1H), 9.15 (m, 1H), 8.55 (s, 1H), 8.20 (d, 2H), 8.00 (m, 5H), 7.62 (d, 2H), 7.22 (s, 1H), 4.60 (d, 2H), 4.00 (s, 3H), 3.95 (s, 3H):
MS (+ve ESI): 460 (M+H)$^+$.

EXAMPLE 567

Preparation of Compound No. 567 in Table 16

An analogous reaction to that described in example 556, but starting with 2-amino-1,3,4-thiadiazole (33 mg, 0.33 mmol) yielded the title compound (112.9 mg, 92% yield) as a white solid:
$^1$H-NMR (DMSO $d_6$): 12.95 (s, 1H), 9.80 (s, 1H), 9.08 (s, 1H), 5.58 (s, 1H), 8.20 (d, 2H), 8.05 (d, 2H), 7.90 (s, 1H), 7.25 (s, 1H), 4.00 (s, 3H), 3.95 (s, 3H):
MS (+ve ESI): 409 (M+H)$^+$.

EXAMPLE 568

Preparation of Compound No. 568 in Table 16

An analogous reaction to that described in example 556, but starting with 2-aminopyridine (31 mg, 0.33 mmol) yielded the title compound (73.8 mg, 61% yield) as a white solid:
$^1$H-NMR (DMSO $d_6$): 10.62 (s, 1H), 9.70 (s, 1H), 8.60 (s, 1H), 8.40 (m, 1H), 8.22 (d, 1H), 8.10 (d, 2H), 8.05 (d, 2H), 7.90 (s, 1H), 7.85 (m, 1H), 7.25 (s, 1H), 7.15 (m, 1H), 4.00 (s, 3H), 3.96 (s, 3H):
MS (+ve ESI): 402 (M+H)$^+$.

EXAMPLE 569

Preparation of Compound No. 569 in Table 16

An analogous reaction to that described in example 556, but starting with 1-aminoisoquinoline (48 mg, 0.33 mmol) yielded the title compound (84.1 mg, 62% yield) as a white solid:
$^1$H-NMR (DMSO $d_6$): 10.86 (s, 1H), 9.75 (s, 1H), 8.57 (s, 1H), 8.42 (m, 1H), 8.16 (d, 2H, J=8 Hz), 8.07 (d, 2H, J=8 Hz), 8.04 (t, 2H, J=7 Hz), 7.93 (s, 1H), 7.68-7.88 (m, 3H), 7.25 (s, 1H), 4.02 (s, 3H), 3.96 (s, 3H):
MS (+ve ESI): 452 (M+H)$^+$.

EXAMPLE 570

Preparation of Compound No. 570 in Table 16

An analogous reaction to that described in example 556, but starting with 5-amino-2-nitrobenzotrifluoride (68 mg, 0.33 mmol) yielded the title compound (19.9 mg, 13% yield) as a white solid:
$^1$H-NMR (DMSO $d_6$): 10.90 (s, 1H), 9.75 (s, 1H), 8.60 (s, 1H), 8.50 (d, 1H), 8.39 (d, 1H), 8.25 (d, 1H), 8.10 (s, 4H), 7.90 (s, 1H), 7.25 (s, 1H), 4.02 (s, 3H), 3.95 (s, 3H):
MS (+ve ESI): 514 (M+H)$^+$.

EXAMPLE 571

Preparation of Compound No. 571 in Table 16

An analogous reaction to that described in example 556, but starting with 1,3-dimethylbutylamine (33 mg, 0.33 mmol) yielded the title compound (66.9 mg, 55% yield) as a white solid:
$^1$H-NMR (DMSO $d_6$): 9.65 (s, 1H), 8.52 (s, 1H), 8.02 (d, 1H), 7.90 (m, 5H), 7.21 (s, 1H), 4.15 (m, 1H), 4.00 (s, 3H), 3.95 (s, 3H), 1.65 (m, 1H), 1.55 (m, 1H), 1.25 (m, 1H), 1.12 (d, 3H), 0.90 (d, 6H):
MS (+ve ESI): 409 (M+H)$^+$.

EXAMPLE 572

Preparation of Compound No. 572 in Table 16

A solution of 4-chloro-6-methoxy-7-(3-morpholinopropoxy)quinazoline (6.90 g, 20.0 mmol) and 4-aminobenzoic acid (2.90 g, 21.2 mmol) in isopropanol (100 ml) was heated at reflux for 3 hours before the reaction was allowed to cool to ambient temperature. The solid which had precipitated was collected by suction filtration and washed with diethyl ether (2×50 ml). Drying of this material yielded the title compound (9.08 g, 89% yield) as a white solid:

$^1$H-NMR (DMSO d$_6$): 11.70 (s, 1H), 11.20 (s, 1H), 8.90 (s, 1H), 8.50 (s, 1H), 7.95 (dd, 4H), 7.55 (s, 1H), 4.30 (t, 2H), 4.05 (s, 3H), 4.00 (d, 2H), 3.85 (t, 2H), 3.50 (m, 2H), 3.30 (m, 2H), 3.10 (m, 2H), 2.35 (m, 2H):

MS (−ve ESI): 437 (M−H)$^−$,
MS (+ve ESI): 439 (M+H)$^+$.

EXAMPLE 573

Preparation of Compound No. 573 in Table 16

An analogous reaction to that described in example 543, but starting with sulphanilamide (86 mg, 0.50 mmol) and 4-chloro-6-methoxy-7-(3-morpholinopropoxy)quinazoline (168 g, 0.50 mmol), yielded the title compound (231 mg, 98% yield) as a white solid:

$^1$H-NMR (DMSO d$_6$): 8.80 (s, 1H), 8.25 (s, 1H), 7.90 (dd, 4H), 7.40 (s, 3H), 4.30 (t, 2H), 3.05 (s, 3H), 4.00 (m, 2H), 3.80 (m, 2H), 3.50 (m, 2H), 3.30 (m, 2H), 3.10 (m, 2H), 2.30 (m, 2H):

MS (+ve ESI): 437 (M+H)$^+$.

EXAMPLE 574

Preparation of Compound No. 574 in Table 16

An analogous reaction to that described in example 543, but starting with N-(5-methoxypyrimidin-2-yl)-4-aminobenzenesulphonamide (60 mg, 0.24 mmol) yielded the title compound (123 mg, 85% yield) as a white solid:

$^1$H-NMR (DMSO d$_6$): 8.81 (s, 1H), 8.27-8.32 (m, 3H), 7.94-8.05 (m, 4H), 7.37 (s, 1H), 4.30 (t, 2H), 4.02 (s, 3H), 3.91-4.02 (m, 2H), 3.70-3.85 (m, 2H), 3.79 (s, 3H), 3.00-3.58 (m, 6H), 2.22-2.37 (m, 2H);

MS (+ve ESI): 582 (M+H)$^+$.

EXAMPLE 575

Preparation of Compound No. 575 in Table 16

An analogous reaction to that described in example 543, but starting with N-(4,5-dimethyloxazin-2-yl)-4-aminobenzenesulphonamide (57 mg, 0.24 mmol) yielded the title compound (138 mg, 99% yield) as a white solid:

$^1$H-NMR (DMSO d$_6$): 11.81 (s, 1H), 8.81 (s, 1H), 8.31 (s, 1H), 7.92 (s, 4H), 7.37 (s, 1H), 4.30 (t, 2H), 4.02 (s, 3H), 3.73-4.02 (m, 4H), 3.02-3.57 (m, 6H), 2.23-2.38 (m, 2H), 2.05 (s, 3H), 1.95 (s, 3H);

MS (+ve ESI): 569 (M+H)$^+$.

EXAMPLE 576

Preparation of Compound No. 576 in Table 1

An analogous reaction to that described in example 543, but starting with N-(3,4-dimethylisoxazin-5-yl)-4-aminobenzenesulphonamide (57 mg, 0.24 mmol) yielded the title compound (45 mg, 36% yield) as a white solid:

$^1$H-NMR (DMSO d$_6$): 8.84 (s, 1H), 8.29 (s, 1H), 8.05 (d, 2H), 7.84 (d, 2H), 7.38 (s, 1H), 4.31 (t, 2H), 4.03 (s, 3H), 3.69-4.03 (m, 4H), 3.00-3.58 (m, 6H), 2.22-2.38 (m, 2H), 2.09 (s, 3H), 1.69 (s, 3H);

MS (+ve ESI): 569 (M+H)$^+$.

EXAMPLE 577

Preparation of Compound No. 577 in Table 16

A solution of 4-chloro-6-methoxy-7-benzyloxyquinazoline (150 mg, 0.50 mmol) and 4-aminobenzamide (68 mg, 0.50 mmol) in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded the title compound (196 mg, 90% yield) as an off-white solid:

$^1$H-NMR (DMSO d$_6$): 11.2 (s, 1H), 8.8 (s, 1H), 8.25 (s, 1H), 7.95 (d, 3H), 7.80 (d, 2H), 7.52 (d, 2H), 7.35-7.45 (m, 5H), 5.34 (s, 2H); 4.02 (s, 3H):

MS (+ve ESI): 401 (M+H)$^+$.

EXAMPLE 578

Preparation of Compound No. 578 in Table 16

A solution of 4-chloro-6-methoxy-7-benzyloxyquinazoline (see example 577) (150 mg, 0.50 mmol) and 4-aminobenzophenone (99 mg, 0.50 mmol) in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded the title compound (233 mg, 94% yield) as an off-white solid:

$^1$H-NMR (DMSO d$_6$): $^1$H-NMR (DMSO d$_6$): 11.22 (s, 1H), 8.86 (s, 1H), 8.28 (s, 1H), 7.98 (d, 2H), 7.87 (d, 2H), 7.74-7.77 (m, 2H), 7.65-7.69 (m, 1H), 7.50-7.60 (m, 4H), 7.40-7.45 (m, 4H), 5.35 (s, 2H), 4.03 (s, 3H):

MS (+ve ESI): 462 (M+H)$^+$.

EXAMPLE 579

Preparation of Compound No. 579 in Table 16

An analogous reaction to that described in example 543, but starting with 4-amino-2-chloro-4'-fluorobenzophenone (777 mg, 3.11 mmol) and 4-chloro-6-methoxy-7-(2,2,2-trifluoroethoxy)quinazoline (932 g, 2.83 mmol), yielded the title compound (1.10 g, 77% yield) as a white solid:

$^1$H-NMR (DMSO d$_6$): 11.40 (s, 1H), 8.90 (s, 1H), 8.37 (s, 1H), 8.16 (s, 1H), 7.96 (dd, 2H, J=2, 8 Hz), 7.81-7.86 (m, 4H), 7.63 (d, 1H, J=8 Hz), 7.38-7.43 (m, 3H), 5.07 (q, 2H, J=7 Hz), 4.07 (s, 3H):

MS (−ve ESI): 504 (M−H)$^−$,
MS (+ve ESI): 506 (M+H)$^+$.

EXAMPLE 580

Preparation of Compound No. 580 in Table 16

O-(7-Azabenzotriazol-1-yl)-N,N,N',N'-tetramethyluronium hexafluorophosphate (HATU) (192 mg, 0.50 mmol) was added to a suspension 4-(4-carboxyphenyl)-6-methoxy-7-(3-morpholinopropoxy)quinazoline (232 mg, 0.50 mmol) in dimethylformamide (4.5 ml). After 5 minutes, cyclopentylamine (42.8 mg, 0.50 mmol) was added and the reaction heated at 50° C. for 16 hours. The reaction was cooled, poured into water (10 ml) and diethyl ether (5 ml) was added. The solid which precipitated was collected by suction filtration and washed with water (10 ml) and diethyl ether (10 ml).

Drying of the solid in vacuo yielded the title compound (63.4 mg, 28% yield) as a white solid:

¹H-NMR (DMSO d₆): 9.57 (s, 1H), 8.49 (s, 1H), 8.13 (d, 1H), 7.82-7.95 (m, 5H), 7.20 (s, 1H), 4.13-4.28 (m, 1H), 4.19 (t, 2H), 3.97 (s, 3H), 3.53-3.61 (m, 4H), 2.46 (t, 2H), 2.31-2.40 (m, 4H), 1.46-2.03 (m, 10M):

MS (+ve ESI): 506 (M+H)⁺.

EXAMPLE 581

Preparation of Compound No. 581 in Table 16

An analogous reaction to that described in example 580, but starting with cyclohexylamine (49.8 mg, 0.50 mmol) yielded the title compound (65.8 mg, 28% yield) as a white solid:

¹H-NMR (DMSO d₆): 9.56 (s, 1H), 8.48 (s, 1H), 8.04 (d, 1H), 7.80-7.95 (m, 5H), 7.19 (s, 1H), 4.19 (t, 2H), 3.97 (s, 3H), 3.69-3.83 (m, 1H), 3.52-3.62 (m, 4H), 2.45 (t, 2H), 2.32-2.40 (m, 4H), 1.56-2.03 (m, 7H), 1.01-1.41 (m, 5H):

MS (+ve ESI): 520 (M+H)⁺.

EXAMPLE 582

Preparation of Compound No. 582 in Table 16

An analogous reaction to that described in example 580, but starting with cyclohexylmethyl-amine (56.9 mg, 0.50 mmol) yielded the title compound (158.8 mg, 66% yield) as a white solid:

¹H-NMR (DMSO d₆): 9.57 (s, 1H), 8.50 (s, 1H), 8.29 (t, 1H), 7.80-7.95 (m, 5H), 7.20 (s, 1H), 4.19 (t, 2H), 3.97 (s, 3H), 3.52-3.61 (m, 4H), 3.11 (t, 2H), 2.45 (t, 2H), 2.32-2.41 (m, 4H), 1.89-2.01 (m, 2H), 1.45-1.77 (m, 6H), 1.06-1.28 (m, 3H), 0.82-1.02 (m, 2H):

MS (+ve ESI): 534 (M+H)⁺.

EXAMPLE 583

Preparation of Compound No. 583 in Table 16

An analogous reaction to that described in example 580, but starting with 5-amino-2-chloropyridine (64.6 mg, 0.50 mmol) yielded the title compound (215 mg, 86% yield) as a white solid:

¹H-NMR (DMSO d₆): 10.47 (s, 1H), 9.68 (s, 1H), 8.81 (d, 1H), 8.54 (s, 1H), 8.27 (dd, 1H), 7.97-8.08 (m, 4H), 7.87 (s, 1H), 7.51 (d, 1H), 7.22 (s, 1H), 4.20 (t, 2H), 3.98 (s, 3H), 3.54-3.63 (m, 4H), 2.47 (t, 2H), 2.32-2.43 (m, 4H), 1.89-2.03 (m, 2H):

MS (+ve ESI): 549 (M+H)⁺.

EXAMPLE 584

Preparation of Compound No. 584 in Table 16

An analogous reaction to that described in example 580, but starting with furfurylamine (48.8 mg, 0.50 mmol) yielded the title compound (147 mg, 63% yield) as a white solid:

¹H-NMR (DMSO d₆): 9.59 (s, 1H), 8.86 (t, 1H), 8.51 (s, 1H), 7.86-7.98 (m, 4H), 7.85 (s, 1H), 7.56 (d, 1H), 7.20 (s, 1H), 6.40 (t, 1H), 6.27 (d, 1H), 4.47 (d, 2H), 4.19 (t, 2H), 3.97 (s, 3H), 3.54-3.62 (m, 4H), 2.45 (t, 2H), 2.33-2.40 (m, 4H), 1.89-2.03 (m, 2H):

MS (+ve ESI): 518 (M+H)⁺.

EXAMPLE 585

Preparation of Compound No. 585 in Table 16

An analogous reaction to that described in example 580, but starting with tetrahydrofurfurylamine (50.8 mg, 0.50 mmol) yielded the title compound (45.9 mg, 19% yield) as a white solid:

¹H-NMR (DMSO d₆): 9.58 (s, 1H), 8.51 (s, 1H), 8.39 (t, 1H), 7.84-7.97 (m, 4H), 7.85 (s, 1H), 7.20 (s, 1H), 4.19 (t, 2H), 3.92-4.05 (m, 1H), 3.97 (s, 3H), 3.73-3.85 (m, 1H), 3.55-3.67 (m, 1H), 3.53-3.61 (m, 4H), 3.23-3.38 (m, 2H), 2.45 (t, 2H), 2.33-2.42 (m, 4H), 1.52-2.03 (m, 6H):

MS (+ve ESI): 522 (M+H)⁺.

EXAMPLE 586

Preparation of Compound No. 586 in Table 16

An analogous reaction to that described in example 580, but starting with 2-aminopyridine (47.3 mg, 0.50 mmol) yielded the title compound (72.5 mg, 31% yield) as a white solid:

¹H-NMR (DMSO d₆): 10.61 (s, 1H), 9.65 (s, 1H), 8.55 (s, 1H), 8.39 (dd, 1H), 8.20 (d, 1H), 7.97-8.13 (m, 4H), 7.87 (s, 1H), 7.78-7.87 (m, 1H), 7.22 (s, 1H), 7.10-7.18 (m, 1H), 4.20 (t, 2H), 3.98 (s, 3H), 3.53-3.63 (m, 4H), 2.46 (t, 2H), 2.33-2.42 (m, 4H), 1.89-2.02 (m, 2H):

MS (+ve ESI): 515 (M+H)⁺.

EXAMPLE 587

Preparation of Compound No. 587 in Table 16

An analogous reaction to that described in example 580, but starting with 3-aminopyridine (47.3 mg, 0.50 mmol) yielded the title compound (204 mg, 88% yield) as a white solid:

¹H-NMR (DMSO d₆) 10.33 (s, 1H), 9.67 (s, 1H), 8.94 (d, 1H), 8.54 (s, 1H), 8.27-8.32 (m, 1H), 8.15-8.23 (m, 1H), 8.03 (s, 4H), 7.87 (s, 1H), 7.39 (dd, 1H), 7.22 (s, 1H), 4.20 (t, 2H), 3.98 (s, 3H), 3.54-3.62 (m, 4H), 2.46 (t, 2H), 2.33-2.42 (m, 4H), 1.89-2.03 (m, 2H):

MS (+ve ESI): 515 (M+H)⁺.

EXAMPLE 588

Preparation of Compound No. 588 in Table 16

An analogous reaction to that described in example 580, but starting with 1,3-dimethylbutylamine (50.9 mg, 0.50 mmol) yielded the title compound (32.2 mg, 14% yield) as a white solid:

¹H-NMR (DMSO d₆): 9.58 (s, 1H), 8.50 (s, 1H), 8.00 (d, 1H), 7.83-7.94 (m, 4H), 7.85 (s, 1H), 7.20 (s, 1H), 4.19 (t, 2H), 4.05-4.20 (m, 1H), 3.97 (s, 3H), 3.53-3.61 (m, 4H), 2.45 (t, 2H), 2.32-2.41 (m, 4H), 1.89-2.02 (m, 2H), 1.17-1.71 (m, 3H), 1.13 (d, 3H), 0.89 (d, 6H):

MS (+ve ESI): 522 (M+H)⁺.

EXAMPLE 589

Preparation of Compound No. 589 in Table 16

An analogous reaction to that described in example 580, but starting with 2,2,2-trifluoroethylamine hydrochloride (67.8 mg, 0.50 mmol) yielded the title compound (173.6 mg, 74% yield) as a white solid:
$^1$H-NMR (DMSO d$_6$): 9.63 (s, 1H), 8.95 (t, 1H), 8.53 (s, 1H), 7.89-8.02 (m, 4H), 7.86 (s, 1H), 7.21 (s, 1H), 4.19 (t, 2H), 4.01-4.17 (m, 2H), 3.97 (s, 3H), 3.53-3.63 (m, 4H), 2.45 (t, 2H), 2.33-2.42 (m, 4H), 1.89-2.02 (m, 2H):
MS (+ve ESI): 520 (M+H)$^+$.

EXAMPLE 590

Preparation of Compound No. 590 in Table 16

An analogous reaction to that described in example 580, but starting with 3-ethoxypropylamine (51.8 mg, 0.50 mmol) yielded the title compound (31.8 mg, 13% yield) as a white solid:
$^1$H-NMR (DMSO d$_6$): 9.57 (s, 1H), 8.50 (s, 1H), 8.32 (t, 1H), 7.82-7.96 (m, 4H), 7.85 (s, 1H), 7.20 (s, 1H), 4.19 (t, 2H), 3.97 (s, 3H), 3.53-3.62 (m, 4H), 3.25-3.47 (m, 6H), 2.45 (t, 2H), 2.33-2.42 (m, 4H), 1.89-2.02 (m, 2H), 1.70-1.82 (m, 2H), 1.11 (t, 3H):
MS (+ve ESI): 524 (M+H)$^+$.

EXAMPLE 591

Preparation of Compound No. 591 in Table 16

An analogous reaction to that described in example 580, but starting with 3-(methylthio)propylamine (52.9 mg, 0.50 mmol) yielded the title compound (143 mg, 60% yield) as a white solid:
$^1$H-NMR (DMSO d$_6$): 9.59 (s, 1H), 8.50 (s, 1H), 7.89 (m, 4H), 7.85 (s, 1H), 7.20 (s, 1H), 4.19 (t, 2H), 3.97 (s, 3H), 3.53-3.62 (m, 4H), 3.27-3.37 (m, 4H), 2.43 (t, 2H), 2.33-2.42 (m, 4H), 1.89-2.02 (m, 2H), 1.75-1.82 (m, 2H):
MS (+ve ESI): 526 (M+H)$^+$.

EXAMPLE 592

Preparation of Compound No. 592 in Table 16

An analogous reaction to that described in example 580, but starting with 2-amino-1-methoxypropane (44.8 mg, 0.50 mmol) yielded the title compound (11.8 mg, 5% yield) as a white solid:
$^1$H-NMR (DMSO d$_6$): 9.59 (s, 1H), 8.50 (s, 1H), 7.89 (m, 4H), 7.85 (s, 1H), 7.20 (s, 1H), 4.19 (m, 4H), 3.97 (s, 3H), 3.53-3.62 (m, 4H), 3.40 (m, 1H), 3.27 (s, 3H), 2.45 (t, 2H), 2.33-2.42 (m, 4H), 1.96 (m, 2H), 1.14 (d, 3H, J=7 Hz):
MS (+ve ESI): 510 (M+H)$^+$.

EXAMPLE 593

Preparation of Compound No. 593 in Table 16

An analogous reaction to that described in example 580, but starting with 3-methylcyclohexylamine (56.9 mg, 0.50 mmol) yielded the title compound (160 mg, 66% yield) as a white solid:
$^1$H-NMR (DMSO d$_6$): 9.57 (s, 1H), 8.50 (s, 1H), 8.06 (d, 1H), 7.83-7.95 (m, 4H), 7.85 (s, 1H), 7.20 (s, 1H), 4.19 (t, 2H), 3.97 (s, 3H), 3.70-3.87 (m, 1H), 3.53-3.63 (m, 4H), 2.45 (t, 2H), 2.33-2.42 (m, 4H), 0.72-2.02 (m, 1H), 0.92 (d, 3H):
MS (+ve ESI): 534 (M+H)$^+$.

EXAMPLE 594

Preparation of Compound No. 594 in Table 16

An analogous reaction to that described in example 580, but starting with 2-aminoindan (66.9 mg, 0.50 mmol) yielded the title compound (222 mg, 88% yield) as a white solid:
$^1$H-NMR (DMSO d$_6$): 9.58 (s, 1H), 8.53 (d, 1H), 8.50 (s, 1H), 7.86-7.97 (m, 4H), 7.85 (s, 1H), 7.09-7.27 (m, 5H), 4.63-4.79 (m, 1H), 4.19 (t, 2H), 3.97 (s, 3H), 3.53-3.62 (m, 4H), 3.19-3.32 (m, 2H), 2.91-3.03 (m, 2H), 2.45 (t, 2H), 2.32-2.42 (m, 4H), 1.88-2.02 (m, 2H):
MS (+ve ESI): 580 (M+H)$^+$.

EXAMPLE 595

Preparation of Compound No. 595 in Table 16

An analogous reaction to that described in example 580, but starting with cyclohexenyl-ethylamine (62.9 mg, 0.50 mmol) yielded the title compound (120 mg, 48% yield) as a white solid:
$^1$H-NMR (DMSO d$_6$): 9.57 (s, 1H), 8.50 (s, 1H), 8.28 (t, 1H), 7.79-7.95-7.79 (m, 5H), 7.20 (s, 1H), 5.43 (s, 1H), 4.19 (t, 2H), 3.97 (s, 3H), 3.53-3.63 (m, 4H), 3.23-3.39 (m, 2H), 2.45 (t, 2H), 2.33-2.42 (m, 4H), 2.16 (t, 2H), 1.88-2.03 (m, 6H), 1.63-1.43 (m, 4H):
MS (+ve ESI): 546 (M+H)$^+$.

EXAMPLE 596

Preparation of Compound No. 596 in Table 16

An analogous reaction to that described in example 580, but starting with 2-thiophene ethylamine (63.9 mg, 0.50 mmol) yielded the title compound (207 mg, 83% yield) as a white solid:
$^1$H-NMR (DMSO d$_6$): 9.58 (s, 1H), 8.52 (t, 1H), 8.51 (s, 1H), 7.82-7.97 (m, 4H), 7.85 (s, 1H), 7.30-7.35 (m, 1H), 7.20 (s, 1H), 6.89-6.98 (m, 2H), 4.19 (t, 2H), 3.97 (s, 3H), 3.54-3.62 (m, 4H), 3.50 (q, 2H), 3.08 (t, 2H), 2.45 (t, 2H), 2.33-2.42 (m, 4H), 1.89-2.02 (m, 2H):
MS (+ve ESI): 548 (M+H)$^+$.

EXAMPLE 597

Preparation of Compound No. 597 in Table 1

An analogous reaction to that described in example 580, but starting with 5-methyl-2-(aminomethyl)furan (55.9 mg, 0.50 mmol) yielded the title compound (203 mg, 84% yield) as a white solid:
$^1$H-NMR (DMSO d$_6$): 9.59 (s, 1H), 8.79 (t, 1H), 8.51 (s, 1H), 7.87-7.98 (m, 4H), 7.85 (s, 1H), 7.20 (s, 1H), 6.13 (d, 1H), 5.99 (d, 1H), 4.41 (d, 2H), 4.19 (t, 2H), 3.97 (s, 3H), 3.53-3.62 (m, 4H), 2.45 (t, 2H), 2.33-2.42 (m, 4H), 2.23 (s, 3H), 1.89-2.02 (m, 2H):
MS (+ve ESI): 532 (M+H)$^+$.

EXAMPLE 598

Preparation of Compound No. 598 in Table 16

An analogous reaction to that described in example 580, but starting with 3-aminotetrahydrothiophene-S,S-dioxide dihydrochloride (104.5 mg, 0.50 mmol) yielded the title compound (217 mg, 86% yield) as a white solid:

$^1$H-NMR (DMSO d$_6$): 9.61 (s, 1H), 8.62 (m, 1H), 8.52 (s, 1H), 7.97 (d, 2H, J=8 Hz), 7.93 (d, 2H, J=8 Hz), 7.86 (s, 1H), 7.20 (s, 1H), 4.69 (m, 1H), 4.19 (t, 2H, J=7 Hz), 3.97 (s, 3H), 3.53-3.62 (m, 4H), 3.44-3.50 (m, 1H), 3.21-3.36 (m, 2H), 3.08-3.14 (m, 1H), 2.45 (t, 2H), 2.33-2.42 (m, 4H), 2.16-2.26 (m, 2H), 1.89-2.02 (m, 2H):

MS (+ve ESI): 556 (M+H)$^+$.

EXAMPLE 599

Preparation of Compound No. 599 in Table 16

An analogous reaction to that described in example 556, but starting with 2-methyl-pentylamine (33 mg, 0.33 mmol) yielded the title compound (59 mg, 43% yield) as a white solid:

$^1$H-NMR (DMSO d$_6$): 9.66 (s, 1H), 8.54 (s, 1H), 8.33 (t, 1H), 7.87-7.99 (m, 5H), 7.23 (s, 1H), 4.00 (s, 3H), 3.95 (s, 3H), 3.17-3.26 (m, 1H), 3.03-3.14 (m, 1H), 1.68-1.83 (m, 1H), 1.03-1.48 (m, 4H), 0.84-0.95 (m, 6H):

MS (+ve ESI): 409 (M+H)$^+$.

EXAMPLE 600

Preparation of Compound No. 600 in Table 16

An analogous reaction to that described in example 556, but starting with 3-ethoxypropyl-amine (34 mg, 0.33 mmol) yielded the title compound (95 mg, 70% yield) as a white solid:

$^1$H-NMR (DMSO d$_6$): 9.62 (s, 1H), 8.55 (s, 1H), 8.35 (t, 1H), 7.83-7.99 (m, 5H), 7.22 (s, 1H), 4.00 (s, 3H), 3.96 (s, 3H), 3.25-3.50 (m, 6H), 1.74-1.85 (m, 2H), 1.15 (t, 3H):

MS (+ve ESI): 411 (M+H)$^+$.

EXAMPLE 601

Preparation of Compound No. 601 in Table 16

An analogous reaction to that described in example 556, but starting with 3-(methylthio)propylamine (35 mg, 0.33 mmol) yielded the title compound (83 mg, 61% yield) as a white solid:

$^1$H-NMR (DMSO d$_6$): 9.62 (s, 1H), 8.56 (s, 1H), 8.40 (t, 1H), 7.87-7.99 (m, 5H), 7.23 (s, 1H), 4.00 (s, 3H), 3.96 (s, 3H), 3.27-3.43 (m, 2H), 2.55 (t, 2H), 2.09 (s, 3H), 1.78-1.88 (m, 2H):

MS (+ve ESI): 413 (M+H)$^+$.

EXAMPLE 602

Preparation of Compound No. 602 in Table 16

An analogous reaction to that described in example 556, but starting with hexylamine (33 mg, 0.33 mmol) yielded the title compound (74 mg, 54% yield) as a white solid:

$^1$H-NMR (DMSO d$_6$): 9.63 (s, 1H), 8.54 (s, 1H), 8.34 (t, 1H), 7.84-8.00 (m, 5H), 7.23 (s, 1H), 4.00 (s, 3H), 3.96 (s, 3H), 3.20-3.36 (m, 2H), 1.48-1.59 (m, 2H), 1.23-1.41 (m, 6H), 0.90 (t, 3H):

MS (+ve ESI): 409 (M+H)$^+$.

EXAMPLE 603

Preparation of Compound No. 603 in Table 16

A solution of 1.0N hydrochloric acid in ether (0.50 ml, 0.50 mmol) was added to a solution of 4-aminobenzamide (78 mg, 0.50 mmol) and 4-chloro-6-methoxy-7-(3-morpholinopropoxy)-quinazoline (168 mg, 0.50 mmol), in isopropanol (5.0 ml). The reaction was heated at 40° C. for 30 minutes and then at 83° C. for 12 hours. The reaction was allowed to cool to ambient temperature and the solid which had precipitated was collected by suction filtration and washed with diethyl ether (2×10 ml). Drying of this material yielded the title compound (222 mg, 94% yield) as a white solid:

$^1$H-NMR (DMSO d$_6$): 11.49 (s, 1H), 11.03 (s, 1H), 8.86 (s, 1H), 8.41 (s, 1H), 8.00 (m, 3H), 7.87 (d, 2H), 7.42 (s, 1H), 7.37 (s, 1H), 4.36 (t, 2H), 4.05 (s, 3H), 3.71-4.05 (m, 4H), 2.85-3.68 (m, 6H), 2.24-2.41 (m, 2H):

MS (+ve ESI): 438 (M+H)$^+$.

EXAMPLE 604

Preparation of Compound No. 604 in Table 16

An analogous reaction to that described in example 603, but starting with N-(4,5-dimethyloxazol-2-yl)sulphanilamide (135 mg, 0.50 mmol) yielded the title compound (279 mg, 92% yield) as a white solid:

$^1$H-NMR (DMSO d$_6$): 11.88 (s, 1H), 11.57 (s, 1H), 11.05 (s, 1H), 8.87 (s, 1H), 8.44 (s, 1H), 7.96 (s, 4H), 7.45 (s, 1H), 4.34 (t, 2H), 4.07 (s, 3H), 3.74-4.07 (m, 4H), 2.96-3.65 (m, 6H), 2.29-2.43 (m, 2H), 2.09 (s, 3H), 1.97 (s, 3H):

MS (−ve ESI): 569 (M−H)$^−$.

EXAMPLE 605

Preparation of Compound No. 605 in Table 16

An analogous reaction to that described in example 603, but starting with 4-amino-2,4'-dichlorobenzophenone (133 mg, 0.50 mmol) yielded the title compound (296 mg, 98% yield) as a white solid:

$^1$H-NMR (DMSO d$_6$): 11.52 (s, 1H), 10.94 (s, 1H), 8.93 (s, 1H), 8.48 (s, 1H), 8.24 (s, 1H), 8.05 (d, 1H), 7.79 (d, 2H), 7.69 (d, 2H), 7.65 (s, 1H), 7.44 (s, 1H), 4.35 (t, 2H), 4.09 (s, 3H), 3.76-4.09 (m, 4H), 2.90-3.72 (m, 6H), 2.28-2.42 (m, 2H):

MS (+ve ESI): 569 (M+H)$^+$.

EXAMPLE 606

Preparation of Compound No. 606 in Table 16

An analogous reaction to that described in example 603, but starting with sulphanilanilide (129 mg, 0.50 mmol) yielded the title compound (283 mg, 97% yield) as a white solid:

$^1$H-NMR (DMSO d$_6$): 11.49 (s, 1H), 11.00 (s, 1H), 10.32 (s, 1H), 8.85 (s, 1H), 8.41 (s, 1H), 8.00 (d, 2H), 7.85 (d, 2H), 7.43 (s, 1H), 7.27 (t, 2H), 7.15 (d, 2H), 7.05 (t, 1H), 4.34 (t, 2H), 4.04 (s, 3H), 3.75-4.04 (m, 4H), 2.87-3.70 (m, 6H), 2.25-2.39 (m, 2H):

MS (+ve ESI): 550 (M+H)$^+$.

EXAMPLE 607

Preparation of Compound No. 607 in Table 16

An analogous reaction to that described in example 603, but starting with 4-aminobenzophenone (99 mg, 0.50 mmol) yielded the title compound (244 mg, 91% yield) as a white solid:

$^1$H-NMR (DMSO d$_6$): 11.57 (s, 1H), 11.08 (s, 1H), 8.90 (s, 1H), 8.48 (s, 1H), 8.05 (d, 2H), 7.89 (d, 2H), 7.80 (d, 2H), 7.71 (t, 1H), 7.61 (t, 2H), 7.47 (s, 1H), 4.35 (t, 2H), 4.09 (s, 3H), 3.76-4.06 (m, 4H), 2.94-3.67 (m, 6H), 2.30-2.42 (m, 2H):

MS (+ve ESI): 499 (M+H)$^+$.

EXAMPLE 608

Preparation of Compound No. 608 in Table 16

An analogous reaction to that described in example 603, but starting with 4-(4-nitrophenylsulphonyl)aniline (139 mg, 0.50 mmol) yielded the title compound (289 mg, 94% yield) as a white solid:

$^1$H-NMR (DMSO d$_6$): 11.60 (s, 1H), 11.00 (s, 1H), 8.85 (s, 1H), 8.45 (s, 1H), 8.44 (s, 2H), 8.27 (d, 2H), 8.23 (m, 4H), 7.45 (s, 1H), 4.30 (t, 2H), 4.05 (s, 3H), 4.00 (m, 2H), 3.83 (m, 2H), 3.50 (m, 2H), 3.30 (m, 2H), 3.10 (m, 2H), 2.35 (m, 2H):

MS (+ve ESI): 580 (M+H)$^+$.

EXAMPLE 609

Preparation of Compound No. 609 in Table 16

A solution of 1-(3-dimethylaminopropyl)-3-ethylcarbodiimide hydrochloride (EDCI) (106 mg, 0.55 mmol) and 4-(dimethylamino)pyridine (190 mg, 1.55 mmol) in dimethylacetamide (5 ml) was added to a mixture of 4-(4-carboxyanilino)-6-methoxy-7-(3-morpholinopropoxy)quinazoline dihydrochloride (see example 29) (256 mg, 0.17 mmol) and 3-(trifluoromethyl)aniline (0.063 ml, 0.50 mmol) and the reaction stirred at ambient temperature for 18 hours. The reaction was poured into water (15 ml) and the solid material which precipitated was collected by suction filtration. Drying in vacuo yielded the title compound (247 mg, 85% yield) as a pale brown solid:

$^1$H-NMR (DMSO d$_6$): 9.65 (s, 1H), 8.55 (s, 1H), 8.25 (s, 1H), 8.05 (d, 1H), 8.00 (s, 4H), 7.85 (s, 1H), 7.60 (t, 1H), 7.45 (d, 1H), 7.20 (s, 1H), 4.20 (t, 2H), 4.00 (s, 3H), 3.60 (m, 4H), 2.45 (t, 2H), 2.40 (m, 4H), 1.95 (m, 2H):

MS (−ve ESI): 580 (M−H)$^−$,
MS (+ve ESI): 582 (M+H)$^+$.

EXAMPLE 610

Preparation of Compound No. 610 in Table 16

An analogous reaction to that described in example 581, but starting with 2-(methylthio)-ethylamine (40 mg, 0.44 mmol) and 4-((4-carboxy)anilino)-6-methoxy-7-(2,2,2-trifluoeoethoxy)-quinazoline (157 mg, 0.4 mmol), yielded the title compound (147 mg, 79% yield) as a white solid:

HPLC/LCMS (RT): 2.11 min:
MS (+ve ESI): 467 (M+H)$^+$.

4-((4-carboxy)anilino)-6-methoxy-7-(2,2,2-trifluoeoethoxy) quinazoline used as the starting material was obtained as follows:—

A mixture of 4-chloro-6-methoxy-7-(2,2,2-trifluoroethoxy)quinazoline (3.8 g, 13 mmol) and 4-aminobenzoic acid (1.78 g, 13 mmol) were heated in ethylene glycol dimethyl ether (DME) (75 ml) at 60° C. for 3 hours. The reaction was cooled and the pale yellow solid which precipitated was collected by suction filtration. Drying in vacuo yielded 4-((4-carboxy)anilino)-6-methoxy-7-(2,2,2-trifluoeoethoxy) quinazoline (5.37 g, 96% yield) as a pale yellow solid:

$^1$H-NMR (DMSO d$_6$): 8.85 (s, 1H), 8.45 (s, 1H), 8.00 (d, 2H), 7.95 (d, 2H), 7.45 (s, 1H), 5.05 (m, 2H), 4.05 (s, 3H):

MS (−ve ESI): 392 (M−H)$^−$,
MS (+ve ESI): 394 (M+H)$^+$.

EXAMPLE 611

Preparation of Compound No. 611 in Table 16

An analogous reaction to that described in example 610, but starting with cyclopentylamine (37 mg, 0.44 mmol) yielded the title compound (45 mg, 25% yield) as a white solid:

HPLC/LCMS (RT): 2.23 min:
MS (+ve ESI): 461 (M+H)$^+$.

EXAMPLE 612

Preparation of Compound No. 612 in Table 16

An analogous reaction to that described in example 610, but starting with cyclohexylamine (44 mg, 0.44 mmol) yielded the title compound (78 mg, 41% yield) as a white solid:

HPLC/LCMS (RT): 2.38 min:
MS (+ve ESI): 475 (M+H)$^+$.

EXAMPLE 613

Preparation of Compound No. 613 in Table 16

An analogous reaction to that described in example 610, but starting with 5-amino-2-chloropyridine (56 mg, 0.44 mmol) yielded the title compound (188 mg, 94% yield) as a white solid:

HPLC/LCMS (RT): 2.39 min:
MS (+ve ESI): 504 (M+H)$^+$.

EXAMPLE 614

Preparation of Compound No. 614 in Table 16

An analogous reaction to that described in example 610, but starting with tetrahydro-furfurylamine (44 mg, 0.44 mmol) yielded the title compound (140 mg, 74% yield) as a white solid:

HPLC/LCMS (RT): 1.98 min:
MS (+ve ESI): 477 (M+H)$^+$.

EXAMPLE 615

Preparation of Compound No. 615 in Table 16

An analogous reaction to that described in example 610, but starting with 4-(2-aminoethyl)-morpholine (57 mg, 0.44 mmol) yielded the title compound (169 mg, 84% yield) as a white solid:

HPLC/LCMS (RT): 1.51 min:
MS (+ve ESI): 506 (M+H)$^+$.

EXAMPLE 616

Preparation of Compound No. 616 in Table 16

An analogous reaction to that described in example 610, but starting with 2-aminopyridine (41 mg, 0.44 mmol) yielded the title compound (80 mg, 43% yield) as a white solid:
HPLC/LCMS (RT): 2.05 min:
MS (+ve ESI): 470 (M+H)$^+$.

EXAMPLE 617

Preparation of Compound No. 617 in Table 16

An analogous reaction to that described in example 610, but starting with 3-aminopyridine (41 mg, 0.44 mmol) yielded the title compound (173 mg, 92% yield) as a white solid:
HPLC/LCMS (RT): 1.83 min:
MS (+ve ESI): 470 (M+H)$^+$.

EXAMPLE 618

Preparation of Compound No. 618 in Table 16

An analogous reaction to that described in example 610, but starting with 1,3-dimethyl-butylamine (44 mg, 0.44 mmol) yielded the title compound (47 mg, 25% yield) as a white solid:
HPLC/LCMS (RT): 2.47 min:
MS (+ve ESI): 477 (M+H)$^+$.

EXAMPLE 19

Preparation of Compound No. 619 in Table 16

An analogous reaction to that described in example 610, but starting with 2,2,2-trifluoroethylamine hydrochloride (60 mg, 0.44 mmol) yielded the title compound (111 mg, 59% yield) as a white solid:
HPLC/LCMS (RT): 2.16 min:
MS (+ve ESI): 475 (M+H)$^+$.

EXAMPLE 620

Preparation of Compound No. 620 in Table 16

An analogous reaction to that described in example 610, but starting with 3-amino-1,2-propanediol (40 mg, 0.44 mmol) yielded the title compound (16 mg, 9% yield) as a white solid:
HPLC/LCMS (RT): 1.71 min:
MS (+ve ESI): 467 (M+H)$^+$.

EXAMPLE 621

Preparation of Compound No. 621 in Table 16

An analogous reaction to that described in example 610, but starting with 2-methyl-1-amylamine (40 mg, 0.44 mmol) yielded the title compound (78 mg, 41% yield) as a white solid:
HPLC/LCMS (RT): 2.53 min:
MS (+ve ESI): 477 (M+H)$^+$.

EXAMPLE 622

Preparation of Compound No. 622 in Table 16

An analogous reaction to that described in example 610, but starting with 3-dimethylamino-propylamine (45 mg, 0.44 mmol) yielded the title compound (14 mg, 8% yield) as a white solid:
HPLC/LCMS (RT): 1.49 min:
MS (+ve ESI): 478 (M+H)$^+$.

EXAMPLE 623

Preparation of Compound No. 623 in Table 16

An analogous reaction to that described in example 610, but starting with 3-ethoxypropyl-amine (45 mg, 0.44 mmol) yielded the title compound (116 mg, 61% yield) as a white solid:
HPLC/LCMS (RT): 2.16 min:
MS (+ve ESI): 479 (M+H)$^+$.

EXAMPLE 624

Preparation of Compound No. 624 in Table 16

An analogous reaction to that described in example 610, but starting with 3-methylcyclo-hexylamine (50 mg, 0.44 mmol) yielded the title compound (132 mg, 68% yield) as a white solid:
HPLC/LCMS (RT): 2.59 min: MS (+ve ESI): 489 (M+H)$^+$.

EXAMPLE 625

Preparation of Compound No. 625 in Table 16

An analogous reaction to that described in example 610, but starting with 2-aminoindan (59 mg, 0.44 mmol) yielded the title compound (193 mg, 95% yield) as a white solid:
HPLC/LCMS (RT): 2.53 min: MS (+ve ESI): 509 (M+H)$^+$.

EXAMPLE 626

Preparation of Compound No. 626 in Table 16

An analogous reaction to that described in example 610, but starting with cyclohexenylethyl-amine (55 mg, 0.44 mmol) yielded the title compound (180 mg, 90% yield) as a white solid:
HPLC/LCMS (RT): 2.67 min: MS (+ve ESI): 521 (M+H)$^+$.

EXAMPLE 627

Preparation of Compound No. 627 in Table 16

An analogous reaction to that described in example 610, but starting with 2-thiophene ethylamine (56 mg, 0.44 mmol) yielded the title compound (131 mg, 65% yield) as a white solid:
HPLC/LCMS (RT): 2.39 min: MS (+ve ESI): 503 (M+H)$^+$.

EXAMPLE 628

Preparation of Compound No. 628 in Table 16

An analogous reaction to that described in example 610, but starting with 2-(2-aminoethyl)-1-methylpyrrolidine (56 mg, 0.44 mmol) yielded the title compound (50 mg, 25% yield) as an off-white solid:

HPLC/LCMS (RT): 1.48 min: MS (+ve ESI): 504 (M+H)$^+$.

Biological Data

The compounds of the invention inhibit the serine/threonine kinase activity of the aurora2 kinase and thus inhibit the cell cycle and cell proliferation. These properties may be assessed, for example, using one or more of the procedures set out below:

(a) In Vitro Aurora2 Kinase Inhibition Test

This assay determines the ability of a test compound to inhibit serine/threonine kinase activity. DNA encoding aurora2 may be obtained by total gene synthesis or by cloning. This DNA may then be expressed in a suitable expression system to obtain polypeptide with serine/threonine kinase activity. In the case of aurora2, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the aurora2 coding sequence. This allowed the insertion of the aurora2 gene in frame with the 6 histidine residues, spacer region and rTEV protease cleavage site encoded by the pFastBac HTc vector. The 3' PCR primer replaced the aurora2 stop codon with additional coding sequence followed by a stop codon and a recognition sequence for the restriction endonuclease Not1. This additional coding sequence (5' TAC CCA TAC GAT GTT CCA GAT TAC GCT TCT TAA 3' (SEQ ID NO: 1)) encoded for the polypeptide sequence YPYDVPDYAS (SEQ ID NO: 2). This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged aurora2 protein. Details of the methods for the assembly of recombinant DNA molecules can be found in standard texts, for example Sambrook et al. 1989, Molecular Cloning—A Laboratory Manual, 2$^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora2 gene was transformed into *E. coli* DH10Bac cells containing the baculovirus genome (bacmid DNA) and via a transposition event in the cells, a region of the pFastBac vector containing gentamycin resistance gene and the aurora2 gene including the baculovirus polyhedrin promoter was transposed directly into the bacmid DNA. By selection on gentamycin, kanamycin, tetracycline and X-gal, resultant white colonies should contain recombinant bacmid DNA encoding aurora2. Bacmid DNA was extracted from a small scale culture of several BH10Bac white colonies and transfected into *Spodoptera frugiperda* Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing 1×10$^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant aurora2 protein.

For the large scale expression of aurora2 kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached 1.2×10$^6$ cells ml$^{-1}$ they were infected with plaque-pure aurora2 recombinant virus at a multiplicity of infection of 1 and harvested 48 hours later. All subsequent purification steps were performed at 4° C. Frozen insect cell pellets containing a total of 2.0×10$^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per 3×10$^7$ cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora2 protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora2 kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of aurora2 enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent & 20 µl of dilute enzyme is used for each assay well. Test compounds (at 10 mM in dimethylsulphoxide (DMSO)) were diluted with water & 10 µl of diluted compound was transferred to wells in the assay plates. "Total" & "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM MnCl$_2$, 6.25 mM ATP, 7.5 µM peptide substrate [biotin-LRRWSLGLRRWSLGLRRWSLGL-RRWSLG] (SEQ ID NO: 3)) containing 0.2 µCi [γ$^{33}$P]ATP (Amersham Pharmacia, specific activity ≧2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme and "total" (no compound) control values were used to determine the dilution range of test compound which gave 50% inhibition of enzyme activity.

In this test, compound 1 in Table 1 gave 50% inhibition of enzyme activity at a concentration of 0.374 µM and compound 101 in Table 4 gave 50% inhibition of enzyme activity at a concentration of 0.0193 µM. In this test, compound 557 in Table 16 gave 50% inhibition of enzyme activity at a concentration of 0.519 µM.

(b) In Vitro Cell Proliferation Assay

These and other assays can be used to determine the ability of a test compound to inhibit the growth of adherent mammalian cell lines, for example the human tumour cell line MCF7.

Assay 1: MCF-7 (ATCC HTB-22) or other adherent cells were typically seeded at $1 \times 10^3$ cells per well (excluding the peripheral wells) in DMEM (Sigma Aldrich) without phenol red, plus 10% foetal calf serum, 1% L-glutamine and 1% penicillin/streptomycin in 96 well tissue culture treated clear plates (Costar). The following day (day 1), the media was removed from a no treatment control plate and the plate stored at −80° C. The remaining plates were dosed with compound (diluted from 10 mM stock in DMSO using DMEM (without phenol red, 10% FCS, 1% L-glutamine, 1% penicillin/streptomycin). Untreated control wells were included on each plate. After 3 days in the presence/absence of compound (day 4) the media was removed and the plates stored at −80° C. Twenty four hours later the plates were thawed at room temperature and cell density determined using the CyQUANT cell proliferation assay kit (c-7026/c-7027 Molecular Probes Inc.) according to manufacturers directions. Briefly, 200 µl of a cell lysis/dye mixture (10 µl of 20× cell lysis buffer B, 190 µl of sterile water, 0.25 µl of CyQUANT GR dye) was added to each well and the plates incubated at room temperature for 5 minutes in the dark. The fluorescence of the wells was then measured using a fluorescence microplate reader (gain 70, 2 reads per well, 1 cycle with excitation 485 nm and emission 530 nm using a CytoFluor plate reader (PerSeptive Biosystems Inc.)). The values from day 1 and day 4 (compound treated) together with the values from the untreated cells were used to determine the dilution range of a test compound that gave 50% inhibition of cell proliferation. Compound no. 1 in Table 1 was effective in this test at 8.03 µM and compound no. 101 in Table 4 was effective in this test at 1.06 µM. Compound 557 in Table 16 was effective in this test at 1.57 µM. These values could also be used to calculate the dilution range of a test compound at which the cell density dropped below the day 1 control value. This indicates the cytotoxicity of the compound.

Assay 2: This assay determines the ability of at test compound to inhibit the incorporation of the thymidine analogue, 5'-bromo-2'-deoxy-uridine (BrdU) into cellular DNA. MCF-7 or other adherent cells were typically seeded at $0.8 \times 10^4$ cells per well in DMEM (Sigma Aldrich) without phenol red, plus 10% foetal calf serum, 1% L-glutamine and 1% penicillin/streptomycin (50 µl/well) in 96 well tissue culture treated 96 well plates (Costar) and allowed to adhere overnight. The following day the cells were dosed with compound (diluted from 10 mM stock in DMSO using DMEM (without phenol red, 10% FCS, 1% L-glutamine, 1% penicillin/streptomycin). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 µl of BrdU labelling reagent (diluted 1:100 in media—DMEM no phenol red, 10% FCS, 1% L-glutamine, 1% penicillin/streptomycin) was added to each well and the plate returned to a humidified (+5% $CO_2$) 37° C. incubator for 2 hours. After 2 hours the labelling reagent was removed by decanting and tapping the plate on a paper towel. FixDenat solution (50 µl per well) was added and the plates incubated at room temperature for 45mins with shaking. The FixDenat solution was removed by decanting and tapping the inverted plate on a paper towel. The plate was then washed once with phosphate buffered saline (PBS) and 100 µl/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 5 times with PBS before being blotted dry. TMB substrate solution was added (100 µl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. Compound 1 in Table 1 was effective in this test at 1.245 µM and Compound 101 in Table 4 was effective in at from 0.159-0.209 µM (c) In Vitro Cell Cycle Analysis Assay This assay determines the ability of a test compound to arrest cells in specific phases of the cell cycle. Many different mammalian cell lines could be used in this assay and MCF7 cells are included here as an example. MCF-7 cells were seeded at $3 \times 10^5$ cells per T25 flask (Costar) in 5 ml DMEM (no phenol red 10% FCS, 1% L-glutamine 1% penicillin/streptomycin). Flasks were then incubated overnight in a humidified 37° C. incubator with 5% $CO_2$. The following day 1 ml of DMEM (no phenol red 10% FCS, 1% L-glutamine 1% penicillin/streptomycin) carrying the appropriate concentration of test compound solubilised in DMSO was added to the flask. A no compound control treatments was also included (0.5% DMSO). The cells were then incubated for a defined time (usually 24 hours) with compound. After this time the media was aspirated from the cells and they were washed with 5 ml of prewarmed (37° C.) sterile PBSA, then detached from the flask by brief incubation with trypsin and followed by resuspension in 10 ml of 1% Bovine Serum Albumin (BSA, Sigma-Aldrich Co.) in sterile PBSA. The samples were then centrifuged at 2200 rpm for 10 min. The supernatant was aspirated and the cell pellet was resuspended in 200 µl of 0.1% (w/v) Tris sodium citrate, 0.0564% (w/v) NaCl, 0.03% (v/v) Nonidet NP40, [pH 7.6]. Propridium Iodide (Sigma Aldrich Co.) was added to 40 µg/ml and RNAase A (Sigma Aldrich Co.) to 100 µg/ml. The cells were then incubated at 37° C. for 30 minutes. The samples were centrifuged at 2200 rpm for 10 min, the supernatant removed and the remaining pellet (nuclei) resuspended in 200 µl of sterile PBSA. Each sample was then syringed 10 times using 21 gauge needle. The samples were then transferred to LPS tubes and DNA content per cell analysed by Fluorescence activated cell sorting (FACS) using a FACScan flow cytometer (Becton Dickinson). Typically 25000 events were counted and recorded using CellQuest v1.1 software (Verity Software). Cell cycle distribution of the population was calculated using Modfit software (Verity Software) and expressed as percentage of cells in G0/G1, S and G2/M phases of the cell cycle. Treating MCF7 cells with 25 µM Compound 1 in table 1 or 2.12 µM of Compound 101 in Table 4 for 24 hours produced the following changes in cell cycle distribution:

| Treatment | % Cells in G1 | % Cells in S | % Cells in G2/M |
|---|---|---|---|
| DMSO (control - Comp 1) | 49.9 | 39.2 | 10.9 |
| 25 μM Compound 1 | 25.82 | 17.71 | 56.47 |
| DMSO (control - Comp 101) | 57.5 | 31.95 | 10.55 |
| 2.12 μM Compound 101 | 19.69 | 12.4 | 68.21 |

The invention claimed is:

1. A compound of formula:

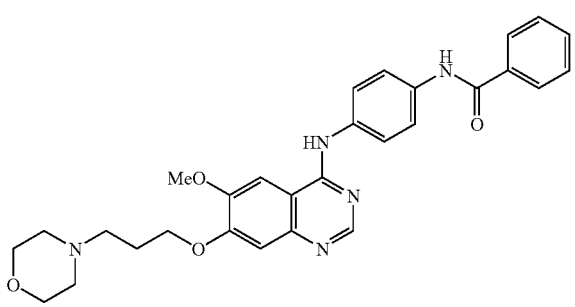

or a pharmaceutically acceptable salt thereof.

2. A pharmaceutical composition comprising a compound according to claim 1, or a pharmaceutically acceptable salt thereof, in combination with a pharmaceutically acceptable carrier.

3. A method of treating colorectal or breast cancer in a warm blooded animal in need of such treatment, which comprises administering to said animal an effective amount of a compound according to claim 1.

* * * * *

SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: Tag epitope sequence
<220> FEATURE:
<221> NAME/KEY: CDS
<222> LOCATION: (1)..(33)
<223> OTHER INFORMATION:

<400> SEQUENCE: 1 tac cca tac gat gtt cca gat tac gct tct taa      33
Tyr Pro Tyr Asp Val Pro Asp Tyr Ala Ser
1               5                  10

<210> SEQ ID NO 2
<211> LENGTH: 10
<212> TYPE: PRT
<213> ORGANISM: Artificial Sequence
<220> FEATURE:
<223> OTHER INFORMATION: Tag epitope sequence

<400> SEQUENCE: 2

Tyr Pro Tyr Asp Val Pro Asp Tyr Ala Ser
1               5                  10

<210> SEQ ID NO 3
<211> LENGTH: 28
<212> TYPE: PRT
<213> ORGANISM: Artificial Sequence
<220> FEATURE:
<223> OTHER INFORMATION: Peptide substrate

<400> SEQUENCE: 3

Leu Arg Arg Trp Ser Leu Gly Leu Arg Arg Trp Ser Leu Gly Leu Arg
1               5                  10                  15

Arg Trp Ser Leu Gly Leu Arg Arg Trp Ser Leu Gly
            20                  25